United States Patent
Im et al.

(10) Patent No.: US 11,357,777 B2
(45) Date of Patent: Jun. 14, 2022

(54) USE OF SGC STIMULATORS FOR THE TREATMENT OF NONALCOHOLIC STEATOHEPATITIS (NASH)

(71) Applicant: Cyclerion Therapeutics, Inc., Cambridge, MA (US)

(72) Inventors: G-Yoon Jamie Im, Cambridge, MA (US); Mark G. Currie, Boston, MA (US); James Edward Sheppeck, Newtown, PA (US); Paul Allan Renhowe, Sudbury, MA (US); Pei Ge, Arlington, MA (US); Jaime L. Masferrer, Cambridge, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 988 days.

(21) Appl. No.: 16/074,357

(22) PCT Filed: Jan. 31, 2017

(86) PCT No.: PCT/US2017/015749
§ 371 (c)(1),
(2) Date: Jul. 31, 2018

(87) PCT Pub. No.: WO2017/136309
PCT Pub. Date: Aug. 10, 2017

(65) Prior Publication Data
US 2021/0161893 A1    Jun. 3, 2021

Related U.S. Application Data

(60) Provisional application No. 62/398,872, filed on Sep. 23, 2016, provisional application No. 62/289,463, filed on Feb. 1, 2016.

(51) Int. Cl.
| | |
|---|---|
| *A61K 31/505* | (2006.01) |
| *A61P 1/16* | (2006.01) |
| *A61K 31/506* | (2006.01) |
| *A61K 31/197* | (2006.01) |
| *A61K 31/198* | (2006.01) |
| *A61K 31/5377* | (2006.01) |
| *A61K 31/575* | (2006.01) |
| *A61K 33/00* | (2006.01) |
| *A61K 35/20* | (2006.01) |
| *A61K 39/395* | (2006.01) |
| *A61K 45/06* | (2006.01) |
| *A61K 31/4985* | (2006.01) |
| *A61K 31/519* | (2006.01) |
| *A61K 31/53* | (2006.01) |
| *A61K 31/541* | (2006.01) |

(52) U.S. Cl.
CPC .......... *A61K 31/506* (2013.01); *A61K 31/197* (2013.01); *A61K 31/198* (2013.01); *A61K 31/4985* (2013.01); *A61K 31/519* (2013.01); *A61K 31/53* (2013.01); *A61K 31/5377* (2013.01); *A61K 31/541* (2013.01); *A61K 31/575* (2013.01); *A61K 33/00* (2013.01); *A61K 35/20* (2013.01); *A61K 39/3955* (2013.01); *A61K 45/06* (2013.01); *A61P 1/16* (2018.01)

(58) Field of Classification Search
CPC ................................ A61K 31/505; A61P 1/16
USPC ....................................................... 514/256
See application file for complete search history.

(56) References Cited

U.S. PATENT DOCUMENTS

| | | | |
|---|---|---|---|
| 2004/0082658 | A1 | 4/2004 | Harter et al. |
| 2011/0028493 | A1 | 2/2011 | Matsunaga et al. |
| 2014/0038956 | A1 | 2/2014 | Hirth-Dietrich et al. |
| 2014/0082658 | A1 | 3/2014 | Wang |

FOREIGN PATENT DOCUMENTS

| | | |
|---|---|---|
| JP | 2014-507478 A | 3/2014 |
| WO | WO-2008/124505 A2 | 10/2008 |
| WO | 2011/056511 A2 | 5/2011 |
| WO | 2012/122340 A1 | 9/2012 |
| WO | WO-2014/144100 A2 | 9/2014 |
| WO | 2016/014463 A1 | 1/2016 |
| WO | 2017/095697 A1 | 6/2017 |
| WO | 2017/136309 A1 | 8/2017 |
| WO | 2017/200857 A1 | 11/2017 |

OTHER PUBLICATIONS

Hoffmann et al., Stimulation of soluble guanylyl cyclase protects against obesity by recruiting brown adipose tissue. Nat Commun. May 26, 2015;6:7235. 9 pages.
Knorr et al., Nitric oxide-independent activation of soluble guanylate cyclase by BAY 60-2770 in experimental liver fibrosis. Arzneimittelforschung. 2008;58(2):71-80.
Ahluwalia et al., Antiinflammatory activity of soluble guanylate cyclase: cGMP-dependent down-regulation of P-selectin expression and leukocyte recruitment. Proc Natl Acad Sci U S A. Feb. 3, 2004;101(5):1386-91.
Boustany-Kari et al., A Soluble Guanylate Cyclase Activator Inhibits the Progression of Diabetic Nephropathy in the ZSF1 Rat. J Pharmacol Exp Ther. Mar. 2016;356(3):712-9.

(Continued)

*Primary Examiner* — Raymond J Henley, III
(74) *Attorney, Agent, or Firm* — McCarter & English, LLP; Steven G. Davis; Xin Zhang

(57) ABSTRACT

The present disclosure relates to methods, uses, pharmaceutical compositions and kits comprising an sGC stimulator or a pharmaceutically acceptable salt thereof, alone or in combination with one or more additional therapeutic agents, for the treatment of Nonalcoholic Steatohepatitis (NASH).

23 Claims, 9 Drawing Sheets

(56) References Cited

OTHER PUBLICATIONS

Costell et al., Comparison of soluble guanylate cyclase stimulators and activators in models of cardiovascular disease associated with oxidative stress. Front Pharmacol. Jul. 5, 2012;3:128.
De Oliveira et al., Steatohepatitis in OB/OB mice by S-nitroso-N-acetylcysteine treatment. J Am Coll Nutr. Apr. 2008,27(2):299-305.
Gur et al., Exploring the potential of NO-independent stimulators and activators of soluble guanylate cyclase for the medical treatment of erectile dysfunction. Curr Pharm Des. May 2010;16(14):1619-33.
Journal of the Japanese Society of Gastroenterology. vol. 108, p. A25, Abstract No. S-4-6.
Nowatzky et al., Antifibrotic Effect of the SGC-Stimulator Bay 41-2272 in the Bile Duct Ligation Liver Fibrosis Model in Rats. Hepatology. Oct. 2011;54(4):755A, Abstract No. 838.
Sandner et al., Anti-fibrotic effects of soluble guanylate cyclase stimulators and activators: A review of the preclinical evidence. Respir Med. Jan. 2017;122 Suppl 1:S1-S9.
Xie et al., Role of differentiation of liver sinusoidal endothelial cells in progression and regression of hepatic fibrosis in rats. Gastroenterology. Apr. 2012;142(4):918-927.e6.
Japanese Office Action for Application No. 2018-559177, dated Feb. 24, 2021, 7 pages.

USE OF SGC STIMULATORS FOR THE TREATMENT OF NONALCOHOLIC STEATOHEPATITIS (NASH)

CROSS REFERENCE TO RELATED APPLICATIONS

This application is a 35 U.S.C. § 371 national stage filing of International Application No. PCT/US2017/015749, filed Jan. 31, 2017, which claims priority of U.S. provisional applications 62/289,463, filed Feb. 1, 2016, and 62/398,872, filed Sep. 23, 2016, the entire disclosures of which are hereby incorporated herein by reference.

TECHNICAL FIELD

The present disclosure relates to methods of using soluble guanylate cyclase (sGC) stimulators and pharmaceutically acceptable salts thereof, alone or in combination with one or more additional therapeutic agents, for the treatment of Non-alcoholic Steatohepatitis (NASH).

BACKGROUND

NASH

Nonalcoholic Steatohepatitis (NASH) is a common, often "silent" liver disease. It resembles alcoholic liver disease, but occurs in people who drink little or no alcohol. Three major features characterize NASH and distinguish it from other liver disease of metabolic origin: abnormal fat accumulation or deposition in the liver (liver steatosis), liver inflammation, and liver injury or hepatic tissue damage (fibrosis).

Most people with NASH feel well and are not aware that they have a liver problem. Nevertheless, NASH can be severe and can lead to cirrhosis, in which the liver is permanently damaged and scarred and no longer able to work properly. Cirrhosis can progress even further to become hepatocellular carcinoma. Approximately 10-15% of patients with histologically proven NASH progress to cirrhosis and its sequelae such as liver failure and hepatocellular carcinoma (HCC).

NASH affects 2 to 5% of Americans. An additional 10 to 20 percent of Americans have fat in their liver, but no inflammation or liver damage, a condition called "fatty liver" (or steatosis). Although having fat in the liver is not normal, by itself it probably causes little harm or permanent damage. If fat is suspected based on blood test results or scans of the liver in a person who consumes little or no alcohol, this problem is called nonalcoholic fatty liver disease (NAFLD). If a liver biopsy is performed in this case, it will show that some people have NASH while others have simple fatty liver (FL).

Both NASH and NAFLD are becoming more common, possibly because of the greater number of Americans with obesity. In the past 10 years, the rate of obesity has doubled in adults and tripled in children. Obesity also contributes to diabetes and high blood cholesterol, which can further complicate the health of someone with NASH.

NASH is usually first suspected in a person who is found to have elevations in liver tests that are included in routine blood test panels, such as alanine aminotransferase (ALT) or aspartate aminotransferase (AST) and triglycerides (TG). When further evaluation shows no apparent reason for liver disease (such as medications, viral hepatitis, or excessive use of alcohol) and when x-rays or imaging studies of the liver show fat, NASH is suspected. The only means of proving a diagnosis of NASH and separating it from simple fatty liver is a liver biopsy. For a liver biopsy, a needle is inserted through the skin to remove a small piece of the liver. NASH is diagnosed when examination of the tissue with a microscope shows fat along with inflammation and damage to liver cells or fibrosis. If the tissue shows fat without inflammation and damage, simple fatty liver or NAFLD is diagnosed. An important piece of information learned from the biopsy is whether scar tissue (fibrotic tissue) has developed in the liver. Currently, no blood tests or scans can reliably provide this information.

NASH is usually a silent disease with few or no symptoms. Patients generally feel well in the early stages and only begin to have symptoms, such as fatigue, weight loss, and weakness, once the disease is more advanced or cirrhosis develops. The progression of NASH can take years, even decades. The process can stop and, in some cases, reverse on its own without specific therapy. Alternatively, NASH can slowly worsen, causing further scarring (fibrosis) to appear and accumulate in the liver. As fibrosis worsens, cirrhosis develops; the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in America, behind hepatitis C and alcoholic liver disease.

Although NASH has become more common, its underlying cause is still not clear. It most often occurs in persons who are middle-aged and overweight or obese. Many patients with NASH have elevated blood lipids, such as cholesterol and triglycerides, and many have diabetes or pre-diabetes, but not every obese person or every patient with diabetes or pre-diabetes has NASH. Furthermore, some patients with NASH are not obese, do not have diabetes or pre-diabetes, and have normal blood cholesterol and lipids. NASH can occur without any apparent risk factor and can even occur in children. Thus, NASH is not simply obesity that affects the liver.

While the underlying mechanisms for the liver injury that causes NASH is not known, several factors are possible candidates. These include insulin resistance, release of toxic inflammatory proteins by fat cells (cytokines) and oxidative stress.

Currently, no specific therapies for NASH exist. The most important recommendations given to persons with this disease are to reduce their weight (if obese or overweight), follow a balanced and healthy diet, increase physical activity, avoid alcohol, avoid unnecessary medications and control their blood sugar, usually by using diabetes medications.

Experimental approaches under evaluation in patients with NASH include antioxidants, such as vitamin E, selenium, and betaine. These medications act by reducing the oxidative stress that appears to increase inside the liver in patients with NASH. Whether these substances actually help treat the disease is not known, but the results of clinical trials should become available in the next few years. Another experimental approach to treating NASH is the use of newer antidiabetic medications-even in persons without diabetes or pre-diabetes. Most patients with NASH have insulin resistance, meaning that the insulin normally present in the bloodstream is less effective for them in controlling blood glucose and fatty acids in the blood than it is for people who do not have NASH. The newer antidiabetic medications make the body more sensitive to insulin and may help reduce liver injury in patients with NASH. Studies of these medications, including metformin, rosiglitazone, and pioglitazone, obeticholic acid or INT-767 (a dual farnesoid X receptor (FXR) and TGR5 agonist) are currently underway.
NASH and the NO/cGMP Pathway In the body, nitric oxide (NO) is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; neuronal NOS (nNOS or NOS I), involved in neurotransmission and long term potentiation; and constitutive endothelial NOS (eNOS or NOS III) which regulates smooth muscle relaxation and blood pressure.

Soluble guanylate cyclase (sGC) is the primary receptor for NO in vivo. In response to NO activation, sGC converts guanosine triphosphate (GTP) into the secondary messenger cyclic guanosine monophosphate (cGMP). The increased level of cGMP, in turn, modulates the activity of downstream effectors including protein kinases, such as protein kinase G (PKG), phosphodiesterases (PDEs) and ion channels.

Experimental evidence in both cell and animal studies suggest the notion that dysregulation of the NO/cGMP/PKG pathway in the liver may play a vital role in the development of the inflammation, steatosis and fibrosis that are characteristic of NASH (see, for example: "Nitric oxide plays a crucial role in the development/progression of nonalcoholic steatohepatitis in the choline-deficient, L-amino acid-defined diet-fed rat model", Fujita K et al., Alcohol Clin Exp Res., 2010; 34 Suppl 1:S18-24 or "Nitric Oxide in liver diseases", Yasuko Iwakiri et al., Trends in Pharmacol. Sci., 36(8), 524 (2015)).

Substances targeting various steps of the NO pathway have been evaluated, mostly in animal models, for the treatment of NASH. For example, Arginine supplementation was evaluated in a rat model of NASH induced by the administration of intralipid (IL) (Marwa M. Abu-Serie et al., Lipids in Health and Disease, 14(128), 1, (2015)). NO-donors, such as S-nitrosothiols (e.g. S-Nitroso-N-acetylcysteine, SNAP) have been suggested to prevent and reverse NASH in OB/OB mice (de Oliverira C P et al., J. Am. Coll. Nutri., 27(2), 299-305 (2008)). SNAP has also been shown to prevent the onset of NASH in a rat animal model (de Oliverira C P et al., World J Gastroenterol, 12(12), 1905-1911 (2006). However, no NO-donors have been approved for human use in NASH. NO-donors sodium nitroprusside, isosorbide dinitrate and nitroglycerin which are used for the treatment of certain cardiovascular disorders are known to possess limitations that preclude their long term use, such as the development of tolerance and other side effects.

The liver-selective NO donor NCX-1000 (a ursodeoxycholic acid derivative possessing NO donor properties) was shown to reverse experimental NASH in rats (Haddad Y et al., Int J Hepatol. 2011; 2011:136816. doi: 10.4061/2011/136816. Epub 2011 Oct. 16.). The same compound, when tested in humans, did not decrease portal pressure in patients with cirrhosis (Berzigotti A et al., Am J Gastroenterol. 2010 May; 105(5):1094-101. doi: 10.1038/ajg.2009.661. Epub 2009 Nov. 17). Another liver-selective NO donor, V-PYRRO/NO was shown to be protective against liver steatosis and to improve postprandial glucose tolerance in mice fed a high fat diet (Edyta Maslak et al., Biochem Pharmacol, 93, 389-400 (2015). There have also been reports of the use of PDE5 inhibitors (e.g. sildenafil) for the treatment of hepatic steatosis in several animal models (see for example, Tateya et al., Diabetes, 62, 1913-1922 (2013)).

NO and its derivatives play important roles both in the physiology and in the pathophysiology of the liver. Certain patterns of the effect of NO on the pathogenesis and progression of liver diseases have been observed. In general, NO derived from endothelial NO synthase (eNOS) in liver sinusoidal endothelial cells (LSECs) appears to be protective against disease development, while inducible NOS (iNOS)-derived NO appears to contribute to pathological processes. It has been suggested that under pathological conditions, iNOS produces large amounts of NO and that this is a major source of reactive nitrogen species and thus oxidative stress. It has also been suggested that the increased iNOS-derived NO observed in liver disease may inhibit eNOS activity (which helps maintain homeostasis in the liver), contributing to decreased eNOS derived NO and to downregulation of the NO-cGMP-PKG pathway.

BRIEF SUMMARY OF THE INVENTION

Thus, it may be advantageous to activate sGC under conditions in which NO signaling is impaired. sGC stimulators are compounds able to stimulate sGC synergistically with NO and also in an NO-independent manner. As a result, they may offer considerable advantages over other current alternative therapies targeted at delivering NO to the liver or at increasing its synthesis. There is a need to develop methods of treating NASH by administering stimulators of sGC, especially when those sGC stimulators are able to distribute preferentially to the liver.

There remains a need for novel treatments for NASH. Targeting the aberrant NO-cGMP-PKG pathway by using an sGC stimulator of the disclosure is a novel and useful therapeutic approach for treating NASH.

In one aspect, the invention provides a method of treating NASH, comprising administering a therapeutically or prophylactically effective amount of an sGC stimulator, or pharmaceutically acceptable salt thereof, alone or in combination with a therapeutically or prophylactically effective amount of one or more additional therapeutic agents to a patient in need thereof.

In another aspect, the invention provides pharmaceutical compositions comprising an sGC stimulator or a pharmaceutically acceptable salt thereof, for use in the treatment of NASH in a patient in need thereof.

In another aspect, the invention provides pharmaceutical compositions comprising an sGC stimulator, or a pharmaceutically acceptable salt thereof, in combination with one or more additional therapeutic agents, for use in the treatment of NASH in a patient in need thereof.

In still a further aspect, the invention provides a kit comprising at least two separate unit dosage forms (A) and (B), wherein (A) is a therapeutic agent, a combination of more than one therapeutic agent, a pharmaceutically acceptable salt thereof, or a pharmaceutical composition thereof, and (B) is an sGC stimulator, a pharmaceutically acceptable salt thereof, or a pharmaceutical composition comprising an sGC stimulator or a pharmaceutically acceptable salt thereof for use in the treatment of NASH in a patient in need thereof.

DETAILED DESCRIPTION

Figure 1:
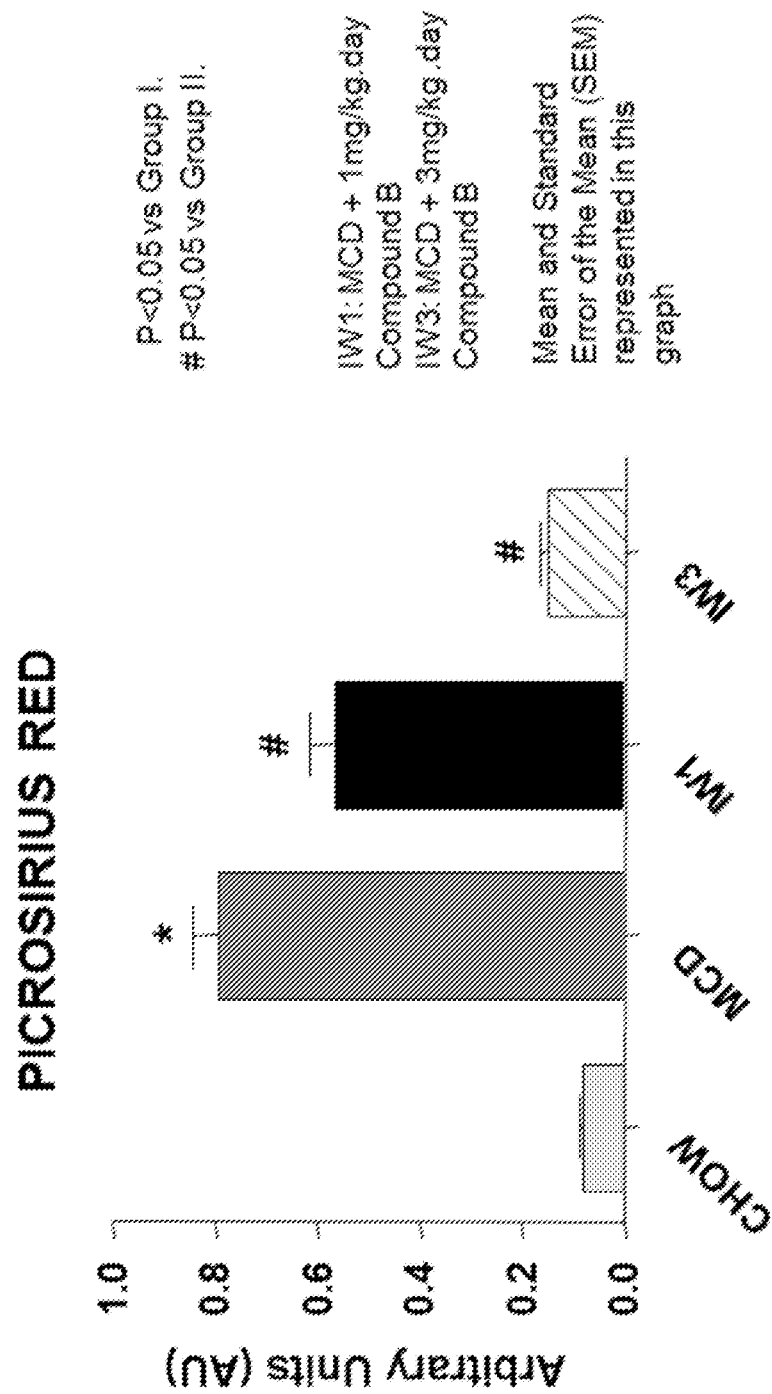
FIG. 1 illustrates fibrosis as detected using Picrosirius Red staining in animals treated with embodiments of the invention.

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls. The compounds described herein may be defined by their chemical structures and/or chemical names. Where a compound is referred to by both a chemical structure and a chemical name, and the chemical structure and chemical name conflict, the chemical structure is determinative of the compound's identity.

Therapeutic Methods

The terms "disease", "disorder" and "condition" may be used interchangeably here to refer to an sGC, cGMP and/or NO mediated medical or pathological condition.

As used herein, the terms "subject" and "patient" are used interchangeably to refer to an animal (e.g., a bird such as a chicken, quail or turkey, or a mammal), preferably a "mammal" including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject or patient is a human.

As used herein, the term a "patient in need thereof" is used to refer to a patient suffering from NASH. In some embodiments, the "patient in need thereof" is a patient with NASH or who has been diagnosed with NASH or who is genetically predisposed to the development of NASH or who may be predisposed to the development of NASH because he or she suffers from metabolic syndrome, obesity, diabetes or pre-diabetes. In still other embodiments a patient in need thereof is a person that has been tested and found to display the clinical findings characteristic of NASH (abnormal accumulation of fat in the liver, liver inflammation and liver fibrosis), even though he or she may not show any physical symptoms of NASH yet. In some instances, a "patient in need thereof" displays symptoms of NASH even though a diagnosis has not been made yet. In some embodiments, the "patient in need thereof" is a patient suffering from metabolic syndrome, obesity, diabetes or pre-diabetes.

As used herein, the term "treat", "treating" or "treatment" with regard to a disorder or disease refers to alleviating or abrogating the cause and/or effects or symptoms or clinical manifestations of the disorder or disease. More specifically, as used herein, the terms "treat", "treatment" and "treating" refer to the reduction or amelioration or slowing down of the progression, severity and/or duration of NASH. In some embodiments, the terms "treat", "treatment" and "treating" refer to the reduction, amelioration or slowing down of the progression, the severity and/or the duration of one or more physical symptoms or clinical manifestations (preferably, one or more measurable physical symptoms or clinical manifestations) of the condition, as a result of the administration of one or more therapies (e.g., an sGC stimulator or a pharmaceutically acceptable salt thereof, either alone or in combination therapy). In some embodiments, "treatment" may result in total or partial reversal of the disease (i.e., as determined by normalization of the clinical parameters, findings or manifestations associated with the disease). In other embodiments, "treatment" may result in slowing down or halting the progression of NASH into cirrhosis.

In some embodiments, the terms "treat," "treatment" and "treating" refer to delaying the onset of NASH in a patient in need thereof. In some embodiments, the terms "treat," "treatment" and "treating" refer to delaying the onset of a physical symptom or set of physical symptoms or clinical manifestations or findings associated with NASH. In other embodiments, the terms "treat," "treatment" and "treating" refer to delaying the onset of a physical symptom or set of physical symptoms or clinical manifestations or findings associated with liver cirrhosis. In some embodiments, clinical manifestation of cirrhosis are determined by histology.

In some embodiments, treatment results in the amelioration of at least one measurable physical symptom of NASH, such as, for example, weight loss, weakness or fatigue. In other embodiments, treatment results in amelioration of at least one clinical parameter or finding of NASH, such as, for example, abnormal liver fat accumulation, liver fibrosis as determined by biopsy, liver inflammation, abnormal levels of liver enzymes, abnormal levels of inflammatory cytokines or NAS score.

In other embodiments, treatment results in the reduction, inhibition or slowing down of the progression of NASH, either physically by, e.g., stabilization of a measurable symptom or set of symptoms (such as fatigue, weight loss or weakness), or clinically/physiologically by, e.g., stabilization of a measurable parameter, such as abnormal fat accumulation in liver, abnormal levels of liver enzymes, abnormal levels of liver inflammatory markers, abnormal findings in a liver biopsy, NAS score or both. In another embodiment, treatment may also result in averting the cause and/or effects or clinical manifestation of NASH, or one of the symptoms developed as a result of NASH, prior to the disease or disorder fully manifesting itself.

In some embodiments, treatment results in an increase in survival rate or survival time in a patient with NASH. In some embodiments, treatment results in the reduction of the potential for a patient with NASH needing a liver transplant. In other embodiments, treatment results in the elimination of the need for a NASH patient to undergo a liver transplant. In other embodiments, it results in the reduction of chances a patient with NASH will develop cirrhosis. In other embodiments, it results in prevention of progression to cirrhosis as determined by histology.

Treatment can involve administering a compound, composition or kit described herein to a patient diagnosed with NASH and may involve administering the compound to a patient who does not have active symptoms. Conversely, treatment may involve administering the compound, composition or kit to a patient at risk of developing NASH, or to a patient reporting one or more of the physiological symptoms of the disease, even though a diagnosis of this disease may not have been made.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically effective amount of the compound to be administered will be governed by such considerations, and is the minimum amount necessary to ameliorate, cure or treat the disease or disorder or one or more of its symptoms.

The term "prophylactically effective amount" refers to an amount effective in substantially lessening the chances of developing a disorder or in reducing the severity of the disorder or one or more of its symptoms before it is diagnosed or before the symptoms fully develop.

In one aspect, the invention provides a method of treating NASH, comprising administering a therapeutically or prophylactically effective amount of an sGC stimulator, or pharmaceutically acceptable salt thereof, alone or in combination with a therapeutically or prophylactically effective amount of one or more additional therapeutic agents to a patient in need thereof.

In another aspect, the invention provides a pharmaceutical composition comprising an sGC stimulator or a pharmaceutically acceptable salt thereof, for use in the treatment of NASH in a patient in need thereof. In another aspect, the invention provides a pharmaceutical composition comprising an sGC stimulator, or a pharmaceutically acceptable salt thereof, in combination with one or more additional therapeutic agents, for use in the treatment of NASH in a patient in need thereof.

In still a further aspect, the invention provides a kit comprising at least two separate unit dosage forms (A) and (B), wherein (A) is a therapeutic agent, a combination of more than one therapeutic agent, a pharmaceutically acceptable salt thereof, or a pharmaceutical composition thereof, and (B) is an sGC stimulator, a pharmaceutically acceptable salt thereof, or a pharmaceutical composition comprising an sGC stimulator or a pharmaceutically acceptable salt thereof for use in the treatment of NASH in a patient in need thereof.

In some embodiments of the above methods, uses, compositions and kits, the patient in need thereof is an adult. In other embodiments, the patient is a child. In some embodiments of the above methods, uses, compositions and kits, the patient is clinically obese. In other embodiments, the patient has been diagnosed with diabetes or pre-diabetes. In other embodiments, the patient has been diagnosed with metabolic syndrome. In other embodiments, the patient is one of normal weight. In still other embodiments, the patient is clinically overweight.

In some embodiments of the above methods, uses, compositions and kits, the administration of an sGC stimulator or pharmaceutically acceptable salt thereof, alone or in combination with another therapeutic agent, results in an observable or measurable decrease in the level of steatosis or abnormal fat accumulation in the liver. In some embodiments, it results in an observable or measurable decrease in the degree of inflammation or hepatitis. In some embodiments, it results in an observable or measurable decrease in the degree of fibrosis, cirrhosis, or sclerosis of the liver. In other embodiments, it results in an observable or measurable simultaneous reduction in the levels of steatosis, inflammation and fibrosis of the liver.

In some embodiments of the above methods, uses, compositions and kits, the administration of an sGC stimulator or pharmaceutically acceptable salt thereof, alone or in combination with another therapeutic agent, results in an observable or measurable reduction in fatigue. In some embodiments, it results in an observable or measurable reduction in weakness. In other embodiments, it results in an observable or measurable reduction in the elevation of liver enzyme levels. In other embodiments, it results in an observable or measurable reduction in the elevation of inflammatory cytokine levels.

In some embodiments of the above methods, uses, compositions and kits, the administration of an sGC stimulator or pharmaceutically acceptable salt thereof, alone or in combination with another therapeutic agent, results in an observable or measurable inhibition of sudden or uncontrolled weight loss. In other embodiments, it results in an observable or measurable weight loss in a person who is clinically overweight or obese.

In some embodiments of the above methods, uses, compositions and kits, the administration of an sGC stimulator or a pharmaceutically acceptable salt thereof, alone or in combination with another therapeutic agent, results in an observable or measurable improvement in one or more of the levels of inflammation, steatosis and fibrosis of the liver.

In some embodiments of the above methods, uses, compositions and kits, the administration of an sGC stimulator or a pharmaceutically acceptable salt thereof, alone or in combination with another therapeutic agent, results in an observable or measurable improvement in the NAS (NAFDL activity score) score value. Total NAS score represents the sum of scores for steatosis, lobular inflammation, and ballooning, and ranges from 0-8. Diagnosis of NASH (or, alternatively, fatty liver not diagnostic of NASH) should be made first, then NAS is used to grade activity. In the reference study, NAS scores of 0-2 are largely considered not diagnostic of NASH, scores of 3-4 are evenly divided among those considered not diagnostic, borderline, or positive for NASH. Scores of 5-8 occur in cases that are largely considered diagnostic of NASH.

In some embodiments of the above methods, uses, compositions and kits, the administration of an sGC stimulator or a pharmaceutically acceptable salt thereof, alone or in combination with another therapeutic agent, results in a measurable reduction in the degree of steatosis or abnormal fat accumulation in the liver as determined by tissue biopsy.

In some embodiments of the above methods, uses, compositions and kits, the administration of an sGC stimulator or a pharmaceutically acceptable salt thereof, alone or in combination with another therapeutic agent, results in a measurable reduction in the degree of inflammation of the liver or hepatitis as determined by tissue biopsy.

In some embodiments of the above methods, uses, compositions and kits, the administration of an sGC stimulator or a pharmaceutically acceptable salt thereof, alone or in combination with another therapeutic agent, results in a measurable reduction in the degree of fibrosis, sclerosis or cirrhosis of the liver as determined by liver tissue biopsy or magnetic resonance elastography or histology.

In some embodiments of the above methods, uses, compositions and kits, the administration of an sGC stimulator or a pharmaceutically acceptable salt thereof, or a pharmaceutical composition comprising an sGC stimulator or a pharmaceutically acceptable salt thereof, alone or in combination with another therapeutic agent, to a patient in need thereof, is aimed or results in reducing the chances that a patient with NAFLD will develop NASH. In other embodiments, it diminishes the chances that a patient with diabetes, pre-diabetes or metabolic syndrome will develop necroinflammatory damage to the liver, fibrosis, liver injury, sclerosis of the liver or cirrhosis. In other embodiments, it diminishes the chances that a patient who is clinically overweight or obese will develop NASH.

In some embodiments of the above methods, uses, compositions and kits, the administration of an sGC stimulator or a pharmaceutically acceptable salt thereof, or a pharmaceutical composition comprising an sGC stimulator or a pharmaceutically acceptable salt thereof, alone or in combination with another therapeutic agent, to a patient in need thereof, is aimed at or results in a total or partial reversal of NASH, as determined by partial or total normalization of one or more clinical findings.

In some embodiments of the above methods, uses, compositions and kits, the administration of an sGC stimulator or a pharmaceutically acceptable salt thereof, or a pharmaceutical composition comprising an sGC stimulator or a pharmaceutically acceptable salt thereof, alone or in combination with another therapeutic agent, to a patient in need thereof, is aimed at or results in slowing down or halting the progression of NASH into cirrhosis as determined by histology.

In some embodiments of the above methods, uses, compositions and kits, the administration of an sGC stimulator or a pharmaceutically acceptable salt thereof, or a pharmaceutical composition comprising an sGC stimulator or a pharmaceutically acceptable salt thereof, alone or in combination with another therapeutic agent, to a patient in need thereof, is aimed at or results in increasing the survival time of a patient diagnosed with NASH.

In some embodiments of the above methods, uses, compositions and kits, the administration of an sGC stimulator or a pharmaceutically acceptable salt thereof, or a pharmaceutical composition comprising an sGC stimulator or a pharmaceutically acceptable salt thereof, alone or in combination with another therapeutic agent, to a patient in need thereof, is aimed at or results in the reduction or total elimination for the need of the patient to undergo a liver transplant.

sGC Stimulators
Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

Compounds herein disclosed may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. As will be apparent to one of ordinary skill in the art, groups such as —H, halogen, —$NO_2$, —CN, —OH, —$NH_2$ or —$OCF_3$ would not be substitutable groups.

The phrase "up to", as used herein, refers to zero or any integer number that is equal to or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, relevant knowledge of the art.

A compound, such as those herein disclosed, may be present in its free form (e.g. an amorphous form, or a crystalline form or a polymorph). Under certain conditions, compounds may also form co-forms. As used herein, the term co-form is synonymous with the term multi-component crystalline form. When one of the components in the co-form has clearly transferred a proton to the other component, the resulting co-form is referred to as a "salt". The formation of a salt is determined by how large the difference is in the pKas between the partners that form the mixture. For purposes of this disclosure, compounds include pharmaceutically acceptable salts, even if the term "pharmaceutically acceptable salts" is not explicitly noted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention. As an example, a substituent drawn as below:

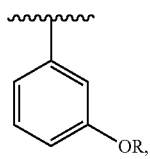

wherein R may be hydrogen, would include both compounds shown below:

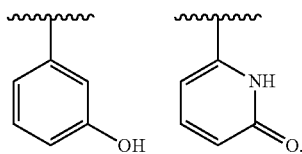 [SMILES: *c1cccc(O)c1 ; *c1cccc(=O)[nH]1]

One embodiment of the invention includes isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^{3}$H and $^{14}$C) are useful in compound and/or substrate tissue distribution assays. Tritiated (i.e., $^{3}$H) and carbon-14 (i.e., $^{14}$C) isotopes are useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as O $^{13}$N, $^{11}$C, and $^{18}$F are useful for positron emission tomography (PET) studies to examine substrate receptor occupancy.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. To be perfectly clear, the term "aliphatic chain" may be used interchangeably with the term "aliphatic" or "aliphatic group".

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, sp$^{2}$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances, the term can be used in the phrase "aromatic carbocycle", and in this case it refers to an "aryl group" as defined below.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_{3}$-$C_{12}$ hydrocarbon or a bicyclic $C_{7}$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Cycloalkyl", as used herein, refers to a ring system in which is completely saturated and which has a single point of attachment to the rest of the molecule. Unless otherwise specified, a cycloalkyl group may be monocyclic, bicyclic, tricyclic, fused, spiro or bridged. In one embodiment, the term "cycloalkyl" refers to a monocyclic $C_3$-$C_{12}$ saturated hydrocarbon or a bicyclic $C_7$-$C_{12}$ saturated hydrocarbon. In some embodiments, any individual ring in a bicyclic or tricyclic ring system has 3-7 members. Suitable cycloalkyl groups include, but are not limited to, cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like.

"Heterocycle" (or "heterocyclyl" or "heterocyclic), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances, the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is on the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "aralkyl" refers to a radical having an aryl ring substituted with an alkylene group, wherein the open end of the alkylene group allows the aralkyl radical to bond to another part of the compound. The alkylene group is a bivalent, straight-chain or branched, saturated hydrocarbon group. As used herein, the term "$C_{7-12}$ aralkyl" means an aralkyl radical wherein the total number of carbon atoms in the aryl ring and the alkylene group combined is 7 to 12. Examples of "aralkyl" include, but not limited to, a phenyl ring substituted by a $C_{1-6}$ alkylene group, e.g., benzyl and phenylethyl, and a naphthyl group substituted by a $C_{1-2}$ alkylene group.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6, 5 heteroaromatic system, as used herein, for example, is a six membered heteroaromatic ring fused to a second five membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tricyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to an atom or a chain of atoms connecting two different parts of a molecule. The two atoms that are connected through the bridge (usually but not always, two tertiary carbon atoms) are referred to as "bridgeheads". In addition to the bridge, the two bridgeheads are connected by at least two individual atoms or chains of atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxatricyclo[3.3.1.0³,⁷]nonyl. "Spiro" bicyclic ring systems share only one ring atom (usually a quaternary carbon atom) between the two rings.

The term "ring atom" refers to an atom such as C, N, O or S that is part of the ring of an aromatic ring, a cycloaliphatic ring, a heterocyclic or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR⁺ (as in N-substituted pyrrolidinyl).

In some embodiments, where specifically indicated, two independent occurrences of a variable may be taken together with the atom(s) to which each variable is bound to form a 5-8-membered, heterocyclyl, aryl, or heteroaryl ring or a 3-8-membered cycloaliphatic ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, cycloaliphatic or aryl ring, wherein the group is attached to the rest of the molecule by a single point of attachment; and b) two independent occurrences of a substituent that are bound to different atoms and are taken together with both of those atoms to form a heterocyclyl, heteroaryl, cycloaliphatic or aryl ring, wherein the ring that is formed has two points of attachment with the rest of the molecule. For example, where a phenyl group is substituted with two occurrences of —OR° as in Formula D1:

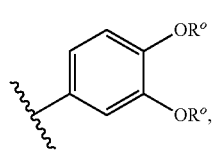

these two occurrences of —OR° are taken together with the carbon atoms to which they are bound to form a fused 6-membered oxygen containing ring as in Formula D2:

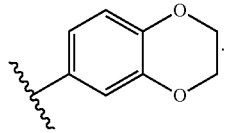

It will be appreciated that a variety of other rings can be formed when two independent occurrences of a substituent are taken together with the atom(s) to which each substituent is bound and that the examples detailed above are not intended to be limiting. These will be specified in each case as necessary.

In some embodiments, an alkyl or aliphatic chain can be optionally interrupted with another atom or group. If this is the case, this will clearly be indicated in the definition of the specific alkyl or aliphatic chain (for instance, a certain variable will be described as being a $C_{1-6}$ alkyl group, wherein said alkyl group is optionally interrupted by a certain group). Unless otherwise indicated, alkyl and aliphatic chains will be considered to be formed by carbon atoms only without interruptions. This means that a methylene unit of the alkyl or aliphatic chain can optionally be replaced with said other atom or group. Unless otherwise specified, the optional replacements form a chemically stable compound. Optional interruptions, where indicated, can occur both within the chain and/or at either end of the chain; i.e. both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to an H on the terminal end. For example, if —CH₂CH₂CH₃ were optionally interrupted with —O—, the resulting compound could be —OCH₂CH₃, —CH₂OCH₃, or —CH₂CH₂OH. In another example, if the divalent linker —CH₂CH₂CH₂— were optionally interrupted with —O—, the resulting compound could be —OCH₂CH₂—, —CH₂OCH₂—, or —CH₂CH₂O—. The optional replacements, wherein specifically indicated, can also completely replace all of the carbon atoms in a chain. For example, a $C_3$ aliphatic can be optionally replaced by —N(R')—, —C(O)—, and —N(R')— to form —N(R')C(O)N(R')— (a urea).

In general, the term "vicinal" refers to the placement of substituents on a group that includes two or more carbon atoms, wherein the substituents are attached to adjacent carbon atoms.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

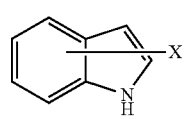

-continued

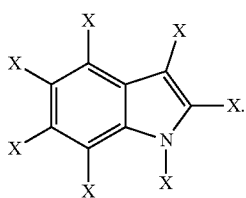

D4

This also applies to multiple ring systems fused to optional ring systems (which would be represented by dotted lines). For example, in Formula D5, X is an optional substituent both for ring A and ring B.

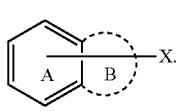

D5

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

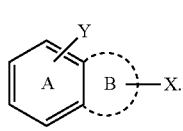

D6

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH$_2$CHF$_2$ and a $C_{1-2}$ haloalkoxy could be —OC(Br)HCHF$_2$. This term includes perfluorinated alkyl groups, such as —CF$_3$ and —CF$_2$CF$_3$.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1-3}$ cyanoalkyl could be —C(CN)$_2$CH$_2$CH$_3$ and a $C_{1-2}$ cyanoalkenyl could be =CHC(CN)H$_2$.

As used herein, an "amino" group refers to —NH$_2$.

The term "hydroxyl" or "hydroxy" refers to —OH.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$.

In all other situations, a "linker", as used herein, refers to a divalent group in which the two free valences are on different atoms (e.g. carbon or heteroatom) or are on the same atom but can be substituted by two different substituents. For example, a methylene group can be $C_1$ alkyl linker (—CH$_2$—) which can be substituted by two different groups, one for each of the free valences (e.g. as in Ph-CH$_2$-Ph, wherein methylene acts as a linker between two phenyl rings). Ethylene can be $C_2$ alkyl linker (—CH$_2$CH$_2$—) wherein the two free valences are on different atoms. The amide group, for example, can act as a linker when placed in an internal position of a chain (e.g. —CONH—). A linker can be the result of interrupting an aliphatic chain by certain functional groups or of replacing methylene units on said chain by said functional groups. E.g. a linker can be a $C_{1-6}$ aliphatic chain in which up to two methylene units are substituted by —C(O)— or —NH— (as in —CH$_2$—NH—CH$_2$—C(O)—CH$_2$— or —CH$_2$—NH—C(O)—CH$_2$—). An alternative way to define the same —CH$_2$—NH—CH$_2$—C(O)—CH$_2$— and —CH$_2$—NH—C(O)—CH$_2$— groups is as a $C_3$ alkyl chain optionally interrupted by up to two —C(O)— or —NH— moieties. Cyclic groups can also form linkers: e.g. a 1,6-cyclohexanediyl can be a linker between two R groups, as in

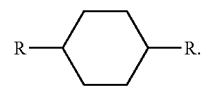

A linker can additionally be optionally substituted in any portion or position.

Divalent groups of the type R—CH= or R$_2$C=, wherein both free valences are in the same atom and are attached to the same substituent, are also possible. In this case, they will be referred to by their IUPAC accepted names. For instance an alkylidene (such as, for example, a methylidene (=CH$_2$) or an ethylidene (=CH—CH$_3$)) would not be encompassed by the definition of a linker in this disclosure.

The compounds of the invention are defined herein by their chemical structures and/or chemical names. Where a compound is referred to by both a chemical structure and a chemical name, and the chemical structure and chemical name conflict, the chemical structure is determinative of the compound's identity.

In some embodiments of the above methods, uses, pharmaceutical compositions and kits, the sGC stimulator is selected from those described in patent application publications WO2013101830 (e.g., any one of compounds 1 to 122), WO2012064559 (e.g., any one of compounds I-1 to 1-68), WO2012003405 (e.g., any one of compounds I-1 to 1-312), WO2011115804 (e.g., any one of compounds I-1 to 1-63), WO2014047111 (e.g., any one of compounds I-1 to 1-5), WO2014047325 (e.g., any one of compounds I-1 to I-10); WO2014144100 (e.g., any one of compounds I-1 to 1-634); WO2015089182 (e.g., any one of compounds I-1 to I-72), WO2016044447 (e.g., any one of compounds 1 to 217), WO2016044446 (e.g., any one of compounds I-1 to 1-94), WO2016044445 (e.g., any one of compound I-1 to 1-39), WO2016044441 (e.g., any one of compound I-1 to I-20), or is a pharmaceutically acceptable salt thereof.

In other embodiments of the above methods, uses, pharmaceutical compositions and kits, the sGC stimulator is a compound described in one or more of the following publications: US20140088080 (WO2012165399), WO2014084312, U.S. Pat. Nos. 6,414,009, 6,462,068, 6,387,940, 6,410,740 (WO 98 16507), U.S. Pat. No. 6,451, 805 (WO 98 23619), U.S. Pat. No. 6,180,656 (WO 98 16223), US20040235863 (WO2003004503), US 20060052397, U.S. Pat. No. 7,173,037 (WO2003095451), US 20060167016, U.S. Pat. No. 7,091,198 (WO2004009589), US 20060014951, U.S. Pat. No. 7,410, 973 (WO2004009590), US 20100004235 (WO2007124854, e.g., Examples 1, 2, 3, 6, 7, 18 or 19), US20100029653 (WO 2008031513, e.g., Examples 1, 2, 3, 4 or 7), US20100113507 (WO2007128454, e.g., Example 1, 4 or 7), US 20110038857, U.S. Pat. No. 8,114,400 (WO2008061657), US20110218202 (WO 2010065275, e.g., Examples 1, 3, 59, 60 or 111), US20110245273 (WO 2010078900, e.g., Examples 1 or 5), US2012029002 (WO 2010079120), US20120022084, US 20130237551, U.S. Pat. No. 8,420,656 (WO 2011147809, WO 2011147810), US20130210824 (WO2013104598), US20130172372 (WO2012004259, e.g., Examples 2, 3 or 4), US20130267548 (WO2012059549, e.g., Examples 1, 2, 7, 8 or 13), WO 2012143510 (e.g., Examples 1, 2, 3, 4, 5, 6, 7, 8, 9 or 10), WO2012004258 (e.g., Examples 1, 18, 19 or 27), WO2012152629 (e.g., Examples 11 or 12), WO2012152630 (e.g., Examples 1, 5, 8, 11, 15 or 19), WO2012010577 (e.g., Examples 3-1, 4, 5 or 6), WO2012028647 (e.g., Examples 1, 2 or 3), WO2013104597 (e.g., Examples 16, 18, 22 or 23), WO2013131923 (e.g., Examples 1, 2, 7, 8 or 9), WO2013104703, WO2013004785 (e.g., Examples 1, 3 or 6), WO2013030288, US20090209556, U.S. Pat. No. 8,455, 638, US20110118282 (WO2009032249), US20100292192, US20110201621, U.S. Pat. Nos. 7,947,664, 8,053,455 (WO2009094242), US20100216764, U.S. Pat. No. 8,507, 512, (WO2010099054), US20110218202 (WO2010065275), US20130012511 (WO2011119518), US20130072492 (WO2011149921, e.g., Example #160, Example #164 and Example #181), US20130210798 (WO2012058132), U.S. Pat. No. 8,796,305 (WO2014068095), US20140128372 and US20140179672 (WO2014068099), U.S. Pat. No. 8,778,964 (US20140128386, US20140128424, WO2014068104), WO2014131741, US20140249168 (WO2014131760), WO2011064156, WO2011073118, WO1998023619, WO2000006567, WO2000006569, WO2000021954, WO2000066582, WO2001083490, WO2002042299, WO2002042300, WO2002042301, WO2002042302, WO2002092596, WO2003097063, WO2004031186, WO2004031187, WO2014195333, WO2015018814, WO2015082411, WO2015124544, U.S. Pat. No. 6,833,364 (DE19834047), WO2001017998 (DE19942809), WO2001047494 (DE19962926), WO2002036120 (DE10054278), WO2011064171, WO2013086935, WO2014128109, WO2012010578, WO2013076168, WO2000006568, WO2015124544, WO2015150366, WO2015150364, WO2015150363, WO2015150362, WO2015140199, WO2015150350, WO2015140254, WO2015088885 and WO2015088886.

In some further embodiments of the above methods, uses, pharmaceutical compositions and kits, the sGC stimulator is a compound described in one or more of the following publications: WO2000006568, WO2001017998, WO2001047494 and WO2002036120.

In some further embodiments of the above methods, uses, pharmaceutical compositions and kits, the sGC stimulator is a compound described in one or more of the following publications: US20110131411, WO2011064156 and WO2011073118.

In some further embodiments of the above methods, uses, pharmaceutical compositions and kits, the sGC stimulator is a compound described in one or more of the following publications: US20140315926, WO2003095451, WO2011064171, WO2013086935 and WO2014128109.

In some further embodiments of the above methods, uses, pharmaceutical compositions and kits, the sGC stimulator is a compound described in one or more of the following publications: WO2011147809, WO2012010578, WO2012059549 and WO2013076168.

In some embodiments of the above methods, uses, pharmaceutical compositions and kits, the sGC stimulator is a compound depicted below:

riociguat (BAY 63-2521, Adempas®, FDA approved drug, described in DE19834044)

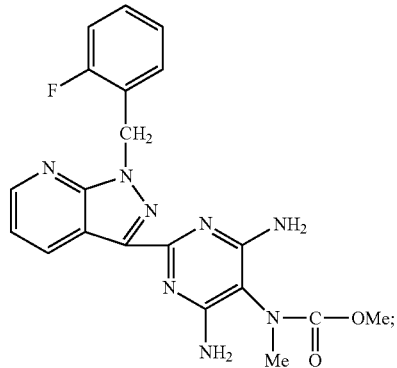 [SMILES: COC(=O)N(C)c1c(N)nc(-c2nn(Cc3ccccc3F)c3ncccc23)nc1N]

neliciguat (BAY 60-4552, described in WO 2003095451)

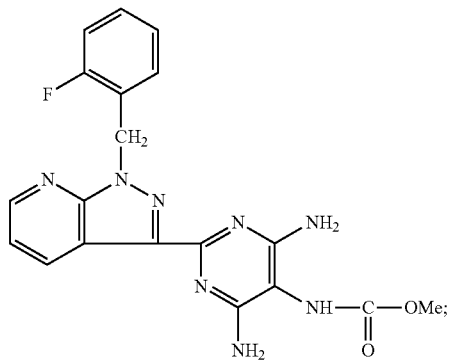 [SMILES: COC(=O)Nc1c(N)nc(-c2nn(Cc3ccccc3F)c3ncccc23)nc1N]

vericiguat (BAY 1021189)
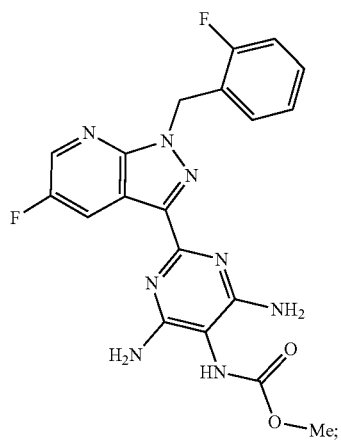
BAY 41-2272 (described in DE19834047 and DE19942809)
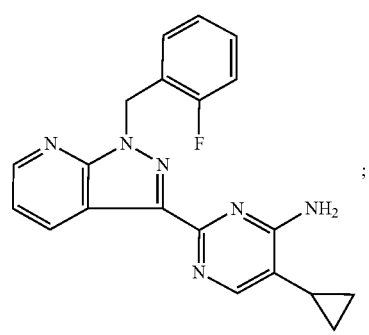 [SMILES: Nc1nc(-c2nn(Cc3ccccc3F)c3ncccc23)ncc1C1CC1]
BAY 41-8543 (described in DE19834044)
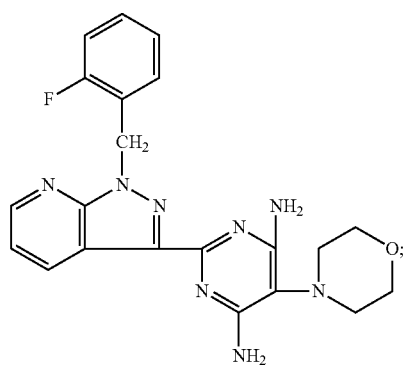 [SMILES: Nc1nc(-c2nn(Cc3ccccc3F)c3ncccc23)nc(N)c1N1CCOCC1]
etriciguat (described in WO 2003086407)
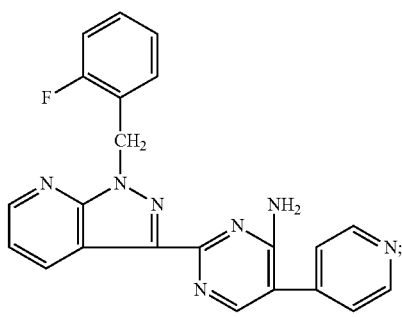 [SMILES: Nc1nc(-c2nn(Cc3ccccc3F)c3ncccc23)ncc1-c1ccncc1]
one of the compounds depicted below and described in US20130072492 (WO 2011149921):
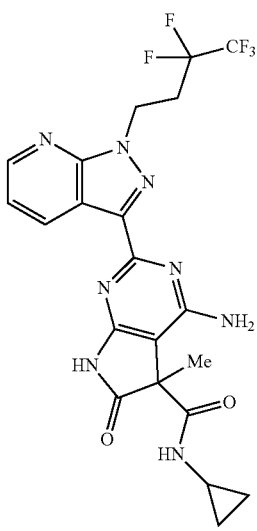
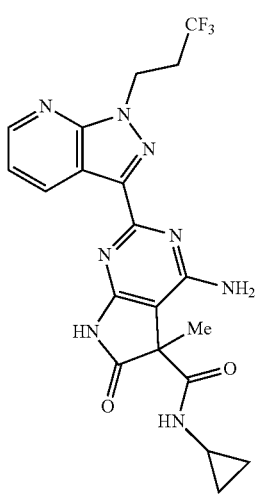

-continued

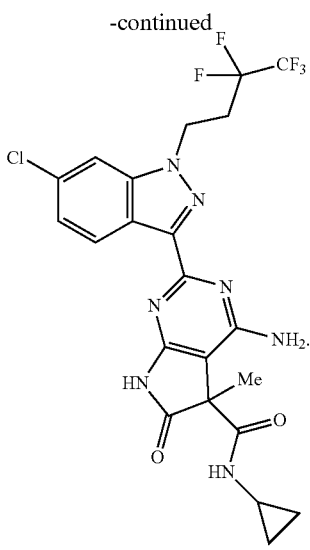

In another aspect, the invention is directed to a compound according to Formula I', or a pharmaceutically acceptable salt thereof.

Formula I'

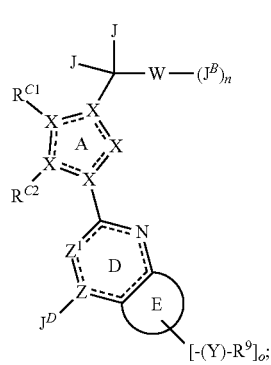

wherein:
ring A is a 5-membered heteroaryl ring; each instance of X is independently selected from C or N and the bond between each two instances of X is either a single or a double bond so as to make ring A an aromatic heterocycle; wherein a minimum of 2 instances of X and a maximum of 3 instances of X in ring A can simultaneously be N;
W is either
i) absent, and $J^B$ is connected directly to the carbon atom bearing two J groups; each J is independently selected from hydrogen or methyl, n is 1 and $J^B$ is a $C_{2-7}$ alkyl chain optionally substituted by between 2 and up to 9 instances of fluorine; wherein, optionally, one —CH$_2$— unit of said $C_{2-7}$ alkyl chain can be replaced by —O— or —S—.
ii) a ring B selected from phenyl, a 5 or 6-membered heteroaryl ring, containing 1 or 2 ring heteroatoms independently selected from N, O or S, a $C_{3-7}$ cycloalkyl ring and a 4 to 7-membered heterocyclic ring, containing up to 3 heteroatoms independently selected from O, N or S;
wherein when W is ring B
each J is hydrogen;
n is 0 or an integer selected from 1, 2 or 3;
each $J^B$ is independently selected from halogen, —CN, a $C_{1-6}$ aliphatic, —OR$^B$ or a $C_{3-8}$ cycloaliphatic group;

wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic;
wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);
$Z^1$ in ring D is selected from CH, CF or N; Z is selected from C or N; wherein if $Z^1$ is CH or CF, then Z must be C; and if $Z^1$ is N, then Z may be C or N;
each $J^D$ is independently selected from $J^A$, —CN, —NO$_2$, —OR$^D$, —SR$^D$, C(O)R$^D$, —C(O)OR$^D$, —OC(O)R$^D$, —C(O)N(R$^D$)$_2$, —N(R$^D$)$_2$, —N(R$^d$)C(O)R$^D$, —N(R$^d$)C(O)OR$^D$, —N(R$^d$)C(O)N(R$^D$)$_2$, —OC(O)N(R$^D$)$_2$, SO$_2$R$^D$, —SO$_2$N(R$^D$)$_2$, —N(R$^d$)SO$_2$R$^D$, —N(R$^d$)SO$_2$NHR$^D$, —N(R$^d$)SO$_2$NHC(O)OR$^D$, N(R$^d$)SO$_2$NHC(O)R$^D$, a $C_{1-6}$ aliphatic, —($C_{1-6}$ aliphatic)-R$^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-R$^D$ moiety, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of $R^{5d}$;
$J^A$ is selected from a lone pair on nitrogen, hydrogen, halogen, oxo, methyl, hydroxyl, methoxy, trifluoromethyl, trifluoromethoxy or —NR$^a$R$^b$; wherein R$^a$ and R$^b$ are each independently selected from hydrogen, $C_{1-6}$ alkyl or a 3-6 cycloalkyl ring; or wherein R$^a$ and R$^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;
each $R^D$ is independently selected from hydrogen, a $C_{1-6}$ aliphatic, —($C_{1-6}$ aliphatic)-R$^f$, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-R$^f$ moiety, each said $C_{3-8}$ cycloaliphatic ring, each said 4 to 10-membered heterocyclic ring, each said phenyl and each said 5 to 6-membered heteroaryl ring is optionally and independently substituted with up to 5 instances of $R^{5a}$; wherein when any $R^D$ is one of a $C_{1-6}$ aliphatic or a —($C_{1-6}$ aliphatic)-R$^f$ group, one or two —CH$_2$— units that form said $C_{1-6}$ aliphatic chains may, optionally, be replaced by a group independently selected from —N(R$^d$)—, —CO— or —O—;

each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$; wherein when any $R^d$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —N($R^{dd}$)—, —CO— or —O—;

each $R^{dd}$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$;

each $R^f$ is independently selected from a $C_{1-3}$ alkyl, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N or S; and wherein each said $C_{3-8}$cycloaliphatic ring, each said 4 to 10-membered heterocyclic ring, each said phenyl and each said 5 to 6-membered heteroaryl ring is optionally and independently substituted by up to 5 instances of $R^{5c}$;

when $J^D$ is —C(O)N($R^D$)$_2$, N($R^D$)$_2$, —N($R^d$)C(O)N($R^D$)$_2$, —OC(O)N($R^D$)$_2$ or —SO$_2$N($R^D$)$_2$, the two $R^D$ groups together with the nitrogen atom attached to the two $R^D$ groups may form 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O or S, in addition to the nitrogen atom to which the two $R^D$ groups are attached; and wherein each said 4 to 8-membered heterocyclic ring and each said 5-membered heteroaryl ring is optionally and independently substituted by up to 5 instances of $R^5$;

when $J^D$ is —N($R^d$)C(O)$R^D$, the $R^D$ group together with the carbon atom attached to the $R^D$ group, with the nitrogen atom attached to the $R^d$ group, and with the $R^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, in addition to the nitrogen atom to which the $R^d$ group is attached; and wherein each said 4 to 8-membered heterocyclic ring and each said 5-membered heteroaryl ring is optionally and independently substituted by up to 5 instances of $R^5$;

when $J^D$ is —N($R^d$)C(O)O$R^D$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, and with said $R^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)C(O)N($R^D$)$_2$, one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is N($R^d$)SO$_2R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

each $R^5$ is independently selected from halogen, —CN, $C_{1-6}$ alkyl, —($C_{1-6}$ alkyl)-$R^6$, —O$R^6$, —S$R^6$, —CO$R^6$, —OC(O)$R^6$, —C(O)O$R^6$, —C(O)N($R^6$)$_2$, —C(O)N($R^6$)SO$_2R^6$, —N($R^6$)C(O)$R^6$, —N($R^6$)C(O)O$R^6$, —N($R^6$)C(O)N($R^6$)$_2$, —N($R^6$)$_2$, —SO$_2R^6$, —SO$_2$OH, —SO$_2$NHOH, —SO$_2$N($R^6$)$_2$, —SO$_2$N($R^6$)COO$R^6$, —SO$_2$N($R^6$)C(O)$R^6$, —N($R^6$)SO$_2R^6$, —(C=O)NHO$R^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of the —($C_{1-6}$ alkyl)-$R^6$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^5$, attached to the same or different atoms of $J^D$, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —CONH$_2$, —OH or halogen; wherein R is hydrogen or a $C_{1-2}$ alkyl;

each $R^{5a}$ is independently selected from halogen, —CN, $C_{1-6}$ alkyl, —($C_{1-6}$ alkyl)$R^{6a}$, —OR$^{6a}$, —SR$^{6a}$, —COR$^{6a}$, OC(O)R$^{6a}$, —C(O)OR$^{6a}$, C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, N(R$^{6a}$)C(O)N(R$^{6a}$)$_2$, N(R$^{6a}$)$_2$, —SO$_2$R$^{6a}$, —SO$_2$OH, —SO$_2$NHOH, —SO$_2$N(R$^{6a}$)$_2$, —SO$_2$N(R$^{6a}$)COOR$^{6a}$, —SO$_2$N(R$^{6a}$)C(O)R$^{6a}$, N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)R$^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

each $R^{5b}$ is independently selected from halogen, —CN, $C_{1-6}$ alkyl, —($C_{1-6}$ alkyl)R$^{6a}$, OR$^{6a}$, SR$^{6a}$, —COR$^{6a}$, OC(O)R$^{6a}$, —C(O)OR$^{6a}$, C(O)N(R$^{6a}$)$_2$, —C(O)N(R$^{6a}$)SO$_2$R$^{6a}$ N(R$^{6a}$)C(O)R$^{6a}$, —N(R$^{6a}$)C(O)OR$^{6a}$, N(R$^{6a}$)C(O)N(R$^{6a}$)$_2$, N(R$^{6a}$)$_2$, —SO$_2$R$^{6a}$, —SO$_2$OH, —SO$_2$NHOH, —SO$_2$N(R$^{6a}$)$_2$, —SO$_2$N(R$^{6a}$)COOR$^{6a}$, —SO$_2$N(R$^{6a}$)C(O)R$^{6a}$, N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)R$^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O($C_{1-4}$ alkyl), —OH or halogen; wherein R is hydrogen or a $C_{1-2}$ alkyl;

each $R^5$ is independently selected from halogen, —CN, $C_{1-6}$ alkyl, —($C_{1-6}$ alkyl)-R$^{6b}$, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^6$)SO$_2$R6b, —N(R$^{6b}$)C(O)R$^{6b}$, —N(R$^{6b}$)C(O)OR$^{6b}$, N(R$^{6b}$)C(O)N(R$^{6b}$)$_2$, N(R$^{6b}$)$_2$, —SO$_2$R$^{6b}$, —SO$_2$OH, —SO$_2$NHOH, —SO$_2$N(R$^{6b}$)$_2$, —SO$_2$N(R$^{6b}$)COOR$^{6b}$, —SO$_2$N(R$^{6b}$)C(O)R$^{6b}$, N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl $C_{1-6}$ alkyl portion of said —($C_{1-6}$ alkyl)-R$^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO ($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^5$ attached to the same or different atoms of $R^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each $R^{5d}$ is independently selected from halogen, —CN, $C_{1-6}$ alkyl, —($C_{1-6}$ alkyl)-$R^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R6, —SO$_2$OH, —SO$_2$NHOH, —SO$_2$N(R$^6$)COR$^6$, —SO$_2$N(R$^6$)$_2$, —N(R$^6$)SO$_2$R6, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-$R^6$ moiety, $C_{7-12}$ aralkyl, $C_{3-8}$cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$haloalkyl) or oxo;

two instances of $R^{5d}$ attached to the same or different atoms of $J^D$, together with said atom or atoms of $J^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each $R^6$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$haloalkyl), C(O)N($C_{1-6}$alkyl)($C_{1-6}$haloalkyl), —COO($C_{1-6}$alkyl), —COO($C_{1-6}$ haloalkyl), —O($C_{1-4}$ alkyl), —O($C_{1-4}$haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

two instances of $R^6$ linked to the same nitrogen atom of $R^5$ or $R^{5d}$, together with said nitrogen atom of $R^5$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6a}$ linked to a nitrogen atom of $R^{5a}$ or $R^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6b}$ linked to a nitrogen atom of $R^5$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

ring E is a 5 to 7-membered heterocycle or a 5-membered heteroaryl ring; said heterocycle or heteroaryl ring containing up to 4 heteroatoms independently selected from N, O and S;

o is 0 or an integer selected from 1, 2, 3 or 4;

Y is either absent or is a $C_{1-6}$ alkyl chain, optionally substituted by up to 6 instances of fluoro; and
wherein in said Y that is a $C_{1-6}$ alkyl chain, up to 3 methylene units of this alkyl chain, can be replaced by a group selected from —O—, —C(O)— or —N((Y')—$R^{90}$)—, wherein $Y^1$ is either absent or is a $C_{1-6}$ alkyl chain, optionally substituted by up to 6 instances of fluoro; and:

when $Y^1$ is absent, each $R^{90}$ is independently selected from hydrogen, —COR$^{10}$, —C(O)OR$^{10}$, —C(O)N(R$^{10}$)$_2$, —C(O)N(R$^{10}$)SO$_2$R$^{10}$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —(C=O)NHOR$^{10}$a $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$; and when $Y^1$ is present, each $R^{90}$ is independently selected from hydrogen, halogen, —CN, —$OR^{10}$, —$COR^{10}$, —OC(O)$R^{10}$, —C(O)$OR^{10}$, —C(O)N($R^{10}$)$_2$, —C(O)N($R^{10}$)SO$_2R^{10}$—N($R^{10}$)C(O)$R^{10}$, —N($R^{10}$)C(O)$OR^{10}$, —N($R^{10}$)C(O)N($R^{10}$)$_2$, —N($R^{10}$)$_2$, —SO$_2R^{10}$, —SO$_2$N($R^{10}$)$_2$, —SO$_2$N($R^{10}$)COO$R^{10}$, —SO$_2$N($R^{10}$)C(O)$R^{10}$, —N($R^{10}$)SO$_2R^{10}$, —(C=O)NHO$R^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^9$ is independently selected from hydrogen, halogen, a $C_{1-6}$ alkyl, —CN, —$OR^{10}$, —$COR^{10}$, —OC(O)$R^1$, —C(O)$OR^{10}$, —C(O)N($R^{10}$)$_2$, —C(O)N($R^{10}$)SO$_2R^{10}$, —N($R^{10}$)C(O)$R^{10}$, —N($R^{10}$)C(O)$OR^{10}$, —N($R^{10}$)C(O)N($R^{10}$)$_2$, —N($R^{10}$)$_2$, —SO$_2R^{10}$, —S$_2$N($R^{10}$)$_2$, —SO$_2$N($R^{10}$)COO$R^{10}$, —SO$_2$N($R^{10}$)C(O)$R^{10}$, —N($R^{10}$)SO$_2R^{10}$, —(C=O)NHO$R^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{1-6}$ alkyl, each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^1$;

each $R^{10}$ is independently selected from hydrogen, a $C_{1-6}$ alkyl, —($C_{1-6}$ alkyl)-$R^{13}$, phenyl, benzyl, a $C_{3-8}$cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of $R^{11a}$;

each $R^{13}$ is independently selected from a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of $R^{11b}$;

each $R^{11}$ is independently selected from halogen, oxo, $C_{1-6}$ alkyl, —CN, —$OR^{12}$, —$COR^{12}$, —C(O)$OR^{12}$, —C(O)N($R^{12}$)$_2$, —N($R^{12}$)C(O)$R^{12}$, —N($R^{12}$)C(O)$OR^{12}$, —N($R^{12}$)C(O)N(R)$_2$, —N($R^{12}$)$_2$, —SO$_2R^{12}$, —SO$_2$N($R^{12}$)$_2$ or —N($R^{12}$)SO$_2R^{12}$; wherein each of said $C_{1-6}$ alkyl is optionally and independently substituted by up to 6 instances of fluoro and/or 3 instances of $R^{121}$;

each $R^{11a}$ is independently selected from halogen, oxo, $C_{1-6}$ alkyl, —CN, —$OR^{12}$, —$COR^{12}$, —C(O)$OR^{12}$, —C(O)N($R^{12}$)$_2$, —N($R^{12}$)C(O)$R^{12}$, —N($R^{12}$)C(O)$OR^{12}$, —N($R^{12}$)C(O)N(R)$_2$, —N($R^{12}$)$_2$, —SO$_2R^{12}$, —SO$_2$N($R^{12}$)$_2$ or —N($R^{12}$)SO$_2R^{12}$; wherein each of said $C_{1-6}$ alkyl is optionally and independently substituted by up to 6 instances of fluoro and/or 3 instances of $R^{121}$; and each $R^{11b}$ is independently selected from halogen, $C_{1-6}$ alkyl, oxo, —CN, —$OR^{12}$, —$COR^{12}$, —C(O)$OR^{12}$, —C(O)N($R^{12}$)$_2$, —N($R^{12}$)C(O)$R^{12}$, —N($R^{12}$)C(O)$OR^{12}$, —N($R^{12}$)C(O)N(R)$_2$, —N($R^{12}$)$_2$, —SO$_2R^{12}$, —SO$_2$N($R^{12}$)$_2$ or —N($R^{12}$)SO$_2R^{12}$; wherein each of said $C_{1-6}$ alkyl is optionally and independently substituted by up to 6 instances of fluoro and/or 3 instances of $R^{121}$;

each $R^{12}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ fluoroalkyl) or oxo;

each $R^{121}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ fluoroalkyl) or oxo;

$R^{C1}$ is either i) a ring C; or ii) is selected from a lone pair on a nitrogen atom, hydrogen, halogen, oxo, —CN, $C_{1-6}$ aliphatic, —($C_{1-6}$ aliphatic)-$R^N$, —$OR^7$, —OC(O)$R^7$, —O($R^7$)C(O)N($R^7$)$_2$, —$COR^7$, —C(O)$OR^7$, —C(O)N($R^7$)$_2$, —N($R^7$)C(O)$R^7$, —N($R^7$)C(O)$OR^7$, —N($R^7$)C(O)N($R^7$)$_2$, —N($R^7$)$_2$, —$SR^7$, —S(O)$R^7$, —SO$_2$R7, —SO$_2$N($R^7$)$_2$, —C(O)N($R^7$)SO$_2$R7, —SO$_2$N($R^7$)COO$R^7$, —SO$_2$N($R^7$)C(O)$R^7$ or —N($R^7$)SO$_2$R7; wherein each said $C_{1-6}$ aliphatic, each $C_{1-6}$ aliphatic portion of said —($C_{1-6}$ aliphatic)-$R^N$, is optionally and independently substituted with up to 6 instances of fluoro and up to 2 instances of —CN, —$OR^7$, oxo, —N(R)$_2$, —N($R^8$)C(O)$R^8$, —N($R^8$)C(O)$OR^8$, —N(R)C(O)N($R^8$)$_2$, —SO$_2$R8, —SO$_2$N($R^8$)$_2$, —NHO$R^8$, —SO$_2$N($R^8$)COOR, —SO$_2$N(R)C(O)$R^8$, —N($R^8$)SO$_2$R;

wherein each $R^7$ is independently selected from hydrogen, $C_{1-6}$ alkyl, $C_{1-6}$ fluoroalkyl, a $C_{3-8}$ cycloalkyl ring, phenyl, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo;

each $R^{11}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^N$ is independently selected from a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$;

each $J^M$ is independently selected from —CN, a $C_{1-6}$ aliphatic, —$OR^M$, —$SR^M$, N($R^M$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7c}$;

each $R^M$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to p instances of $J^C$; wherein p is 0 or an integer selected from 1, 2 or 3.

each $J^C$ is independently selected from halogen, —CN, —$NO_2$, a $C_{1-6}$ aliphatic, —$OR^H$, —$SR^H$, N($R^H$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7d}$; or alternatively, two Je groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; alternatively, two instances of $R^H$ linked to the same nitrogen atom of N($R^H$)$_2$, together with said nitrogen atom of N($R^H$)$_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S;

each $R^{7c}$ is independently selected from halogen, —CN, —$NO_2$, $C_{1-4}$ alkyl, $C_{1-4}$ haloalkyl, $C_{3-8}$ cycloalkyl ring, —$OR^{8b}$, —$SR^{8b}$, —N($R^{8b}$)$_2$, —C(O)O($C_{1-4}$ alkyl), —C(O)OH, —NR(CO)CO($C_{1-4}$ alkyl) or an oxo group; wherein each said cycloalkyl group is optionally and independently substituted with up to 3 instances of halogen;

each $R^{7d}$ is independently selected from halogen, —CN, —$NO_2$, $C_{1-4}$ alkyl, $C_{1-4}$ haloalkyl, $C_{3-8}$ cycloalkyl ring, —C(O)O($C_{1-4}$ alkyl), —C(O)OH, —$OR^{8c}$, —$SR^{8c}$, —N($R^{8c}$)$_2$, or an oxo group; wherein each said cycloalkyl group is optionally and independently substituted with up to 3 instances of halogen;

each $R_{8b}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{8c}$ is independently selected from hydrogen, $C_{1-6}$ alkyl, $C_{1-6}$ fluoroalkyl, a $C_{3-8}$ cycloalkyl ring, a4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo; and $R^{C2}$ is selected from a lone pair on a nitrogen atom, hydrogen, halogen, —OH, —O($C_{1-6}$ alkyl), —O(halo$C_{1-6}$ alkyl), —O($C_{1-6}$haloalkyl), —O(cyclopropyl), cyclopropyl, $C_{1-6}$alkyl, $C_{1-6}$haloalkyl and —CN;

In some of the above embodiments, the compound is one selected from the Table X, below:
TABLE X
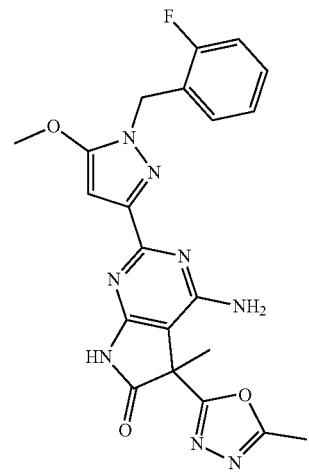
I-1
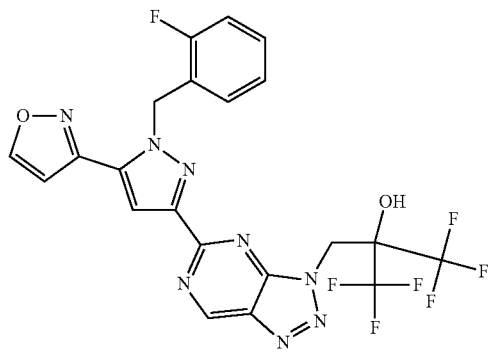 [SMILES: OC(Cn1nnc2cnc(-c3cc(-c4ccon4)n(Cc4ccccc4F)n3)nc21)(C(F)(F)F)C(F)(F)F]
I-2
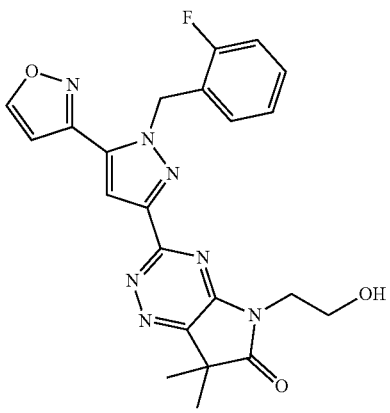 [SMILES: CC1(C)C(=O)N(CCO)c2nc(-c3cc(-c4ccon4)n(Cc4ccccc4F)n3)nnc21]
I-4
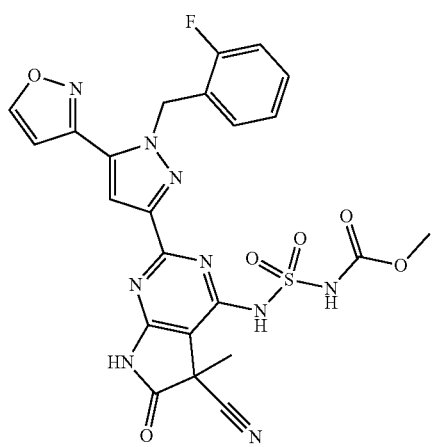 [SMILES: COC(=O)NS(=O)(=O)Nc1nc(-c2cc(-c3ccon3)n(Cc3ccccc3F)n2)nc2c1C(C)(C#N)C(=O)N2]
I-5
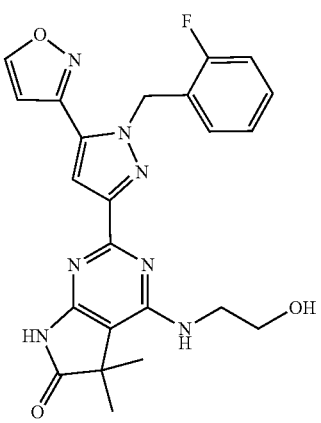 [SMILES: CC1(C)C(=O)Nc2nc(-c3cc(-c4ccon4)n(Cc4ccccc4F)n3)nc(NCCO)c21]
I-6

TABLE X-continued
I-7
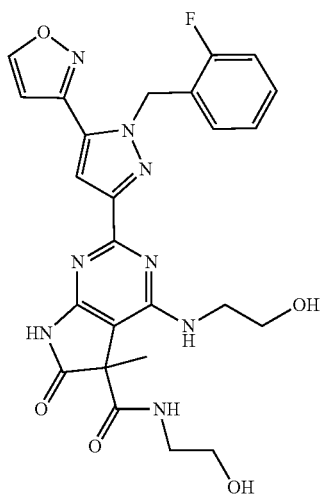 [SMILES: CC1(C(=O)NCCO)C(=O)Nc2nc(-c3cc(-c4ccon4)n(Cc4ccccc4F)n3)nc(NCCO)c21]
I-8
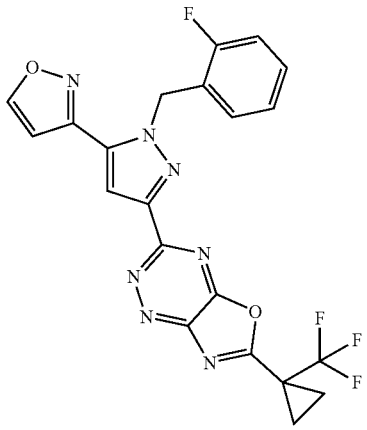 [SMILES: Fc1ccccc1Cn1nc(-c2nnc3nc(C4(C(F)(F)F)CC4)oc3n2)cc1-c1ccon1]
I-9
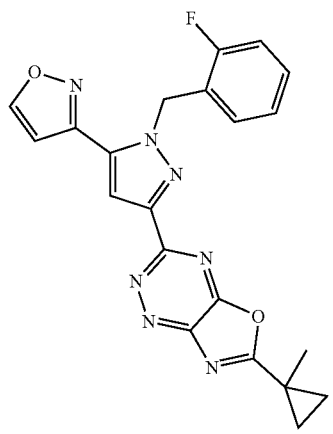 [SMILES: CC1(c2nc3nnc(-c4cc(-c5ccon5)n(Cc5ccccc5F)n4)nc3o2)CC1]
I-10
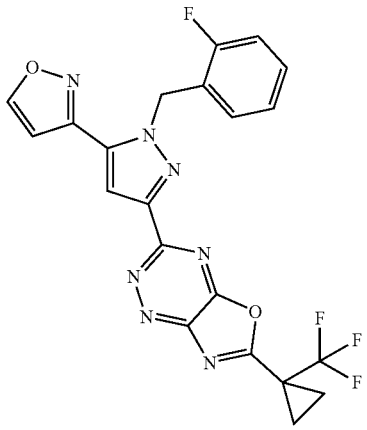 [SMILES: Fc1ccccc1Cn1nc(-c2nnc3nc(C4(C(F)(F)F)CC4)oc3n2)cc1-c1ccon1]
I-11
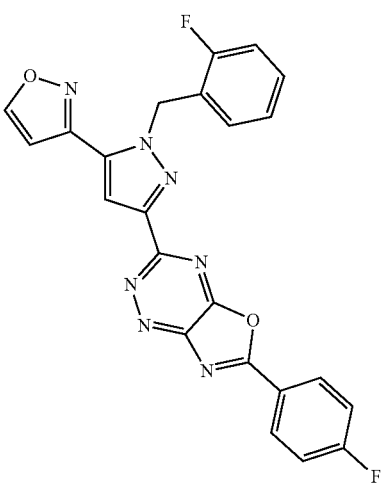 [SMILES: Fc1ccc(-c2nc3nnc(-c4cc(-c5ccon5)n(Cc5ccccc5F)n4)nc3o2)cc1]
I-12
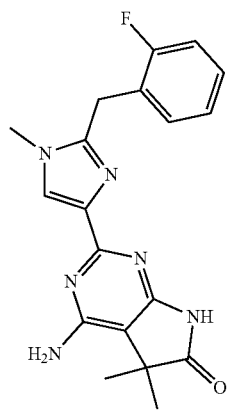 [SMILES: Cn1cc(-c2nc(N)c3c(n2)NC(=O)C3(C)C)nc1Cc1ccccc1F]

TABLE X-continued
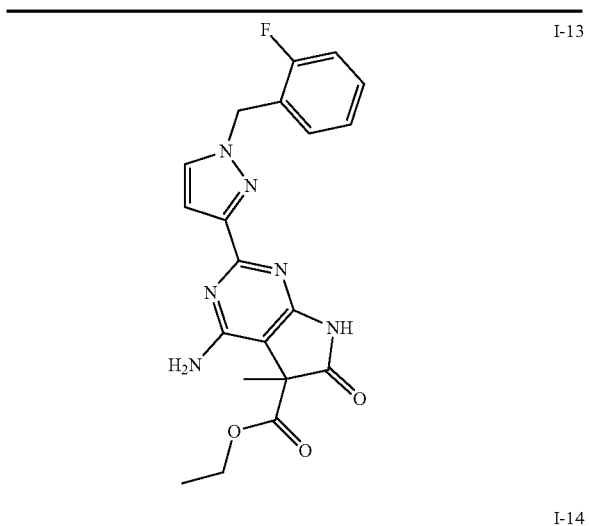
I-13
I-14
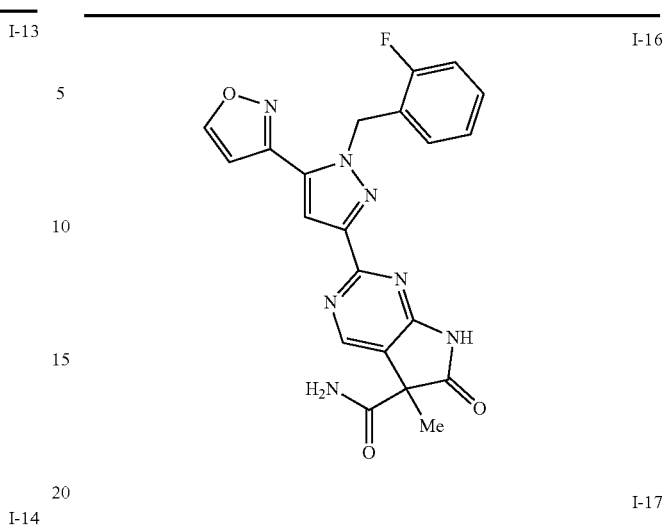
I-16
I-17
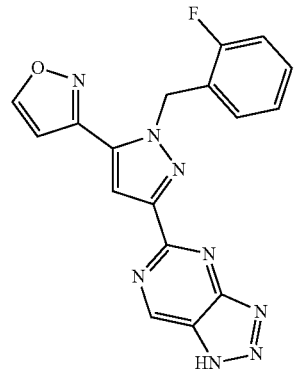 [SMILES: Fc1ccccc1Cn1nc(-c2ncc3[nH]nnc3n2)cc1-c1ccon1]
I-15
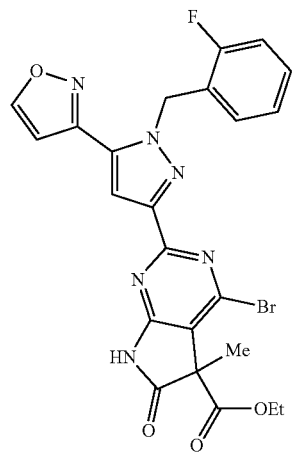 [SMILES: CCOC(=O)C1(C)C(=O)Nc2nc(-c3cc(-c4ccon4)n(Cc4ccccc4F)n3)nc(Br)c21]
I-18

TABLE X-continued
I-19
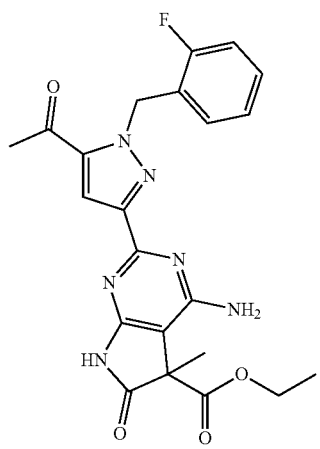 [SMILES: CCOC(=O)C1(C)C(=O)Nc2nc(-c3cc(C(C)=O)n(Cc4ccccc4F)n3)nc(N)c21]
I-20
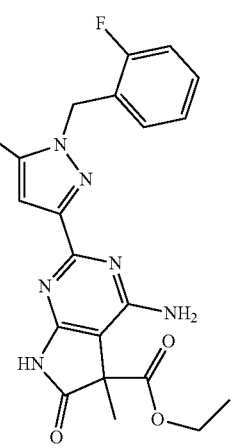
I-21
TABLE X-continued
I-22
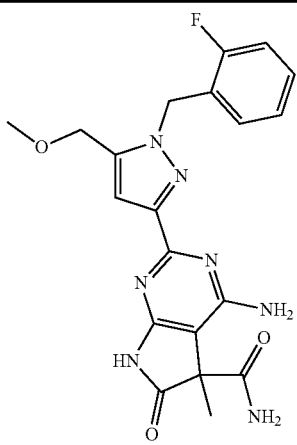
I-23
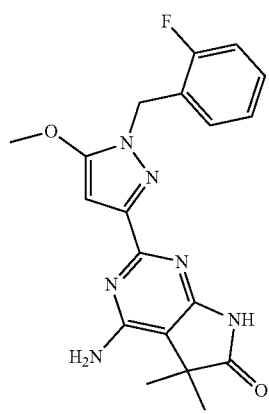 [SMILES: COc1cc(-c2nc(N)c3c(n2)NC(=O)C3(C)C)nn1Cc1ccccc1F]
I-24
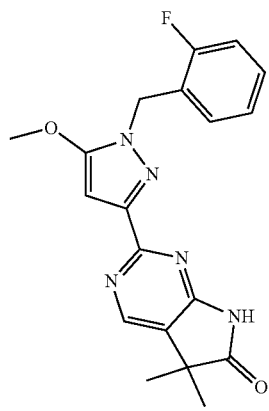 [SMILES: COc1cc(-c2ncc3c(n2)NC(=O)C3(C)C)nn1Cc1ccccc1F]
I-25
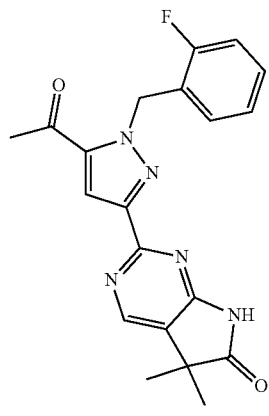 [SMILES: CC(=O)c1cc(-c2ncc3c(n2)NC(=O)C3(C)C)nn1Cc1ccccc1F]

TABLE X-continued
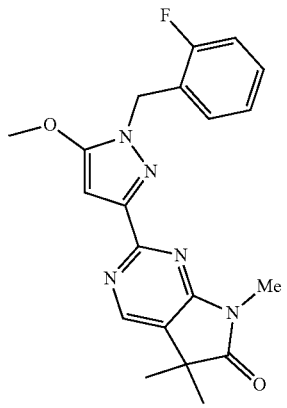 [SMILES: COc1cc(-c2ncc3c(n2)N(C)C(=O)C3(C)C)nn1Cc1ccccc1F] I-26
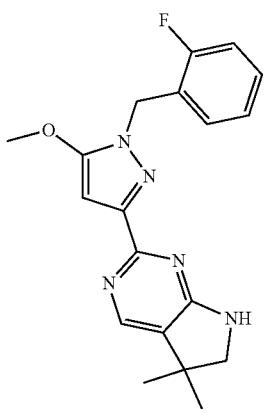 [SMILES: COc1cc(-c2ncc3c(n2)NCC3(C)C)nn1Cc1ccccc1F] I-27
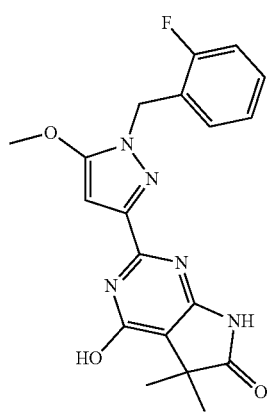 [SMILES: COc1cc(-c2nc(O)c3c(n2)NC(=O)C3(C)C)nn1Cc1ccccc1F] I-28
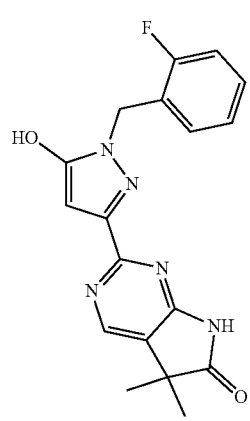 [SMILES: CC1(C)C(=O)Nc2nc(-c3cc(O)n(Cc4ccccc4F)n3)ncc21] I-29
TABLE X-continued
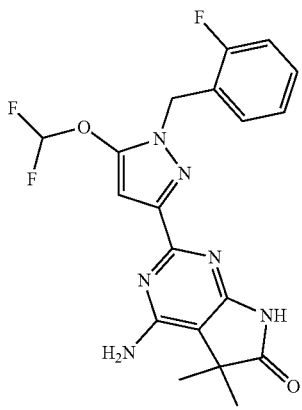 [SMILES: CC1(C)C(=O)Nc2nc(-c3cc(OC(F)F)n(Cc4ccccc4F)n3)nc(N)c21] I-30
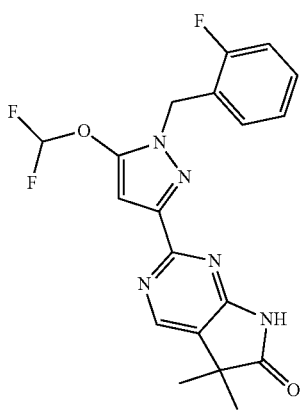 [SMILES: CC1(C)C(=O)Nc2nc(-c3cc(OC(F)F)n(Cc4ccccc4F)n3)ncc21] I-31
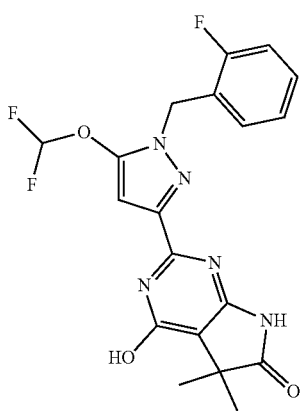 [SMILES: CC1(C)C(=O)Nc2nc(-c3cc(OC(F)F)n(Cc4ccccc4F)n3)nc(O)c21] I-32
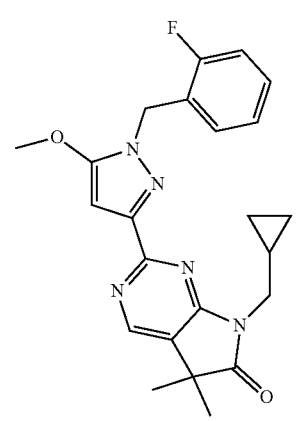 [SMILES: COc1cc(-c2ncc3c(n2)N(CC2CC2)C(=O)C3(C)C)nn1Cc1ccccc1F] I-33

TABLE X-continued
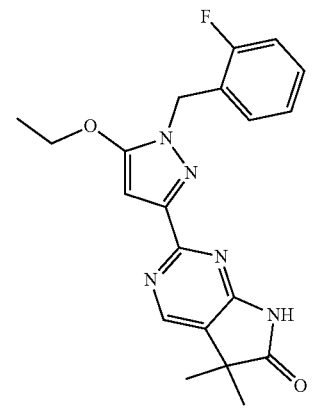 [SMILES: CCOc1cc(-c2ncc3c(n2)NC(=O)C3(C)C)nn1Cc1ccccc1F] I-34
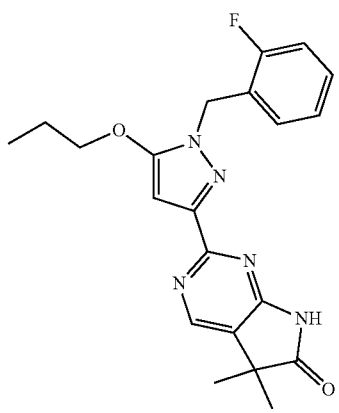 [SMILES: CCCOc1cc(-c2ncc3c(n2)NC(=O)C3(C)C)nn1Cc1ccccc1F] I-35
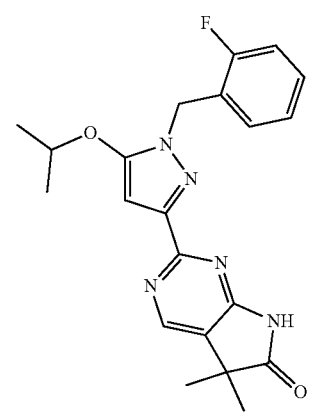 [SMILES: CC(C)Oc1cc(-c2ncc3c(n2)NC(=O)C3(C)C)nn1Cc1ccccc1F] I-36
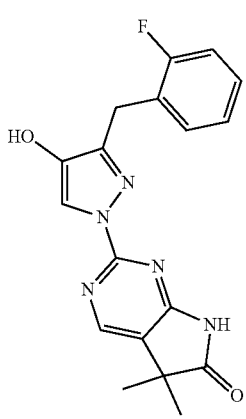 [SMILES: CC1(C)C(=O)Nc2nc(-n3cc(O)c(Cc4ccccc4F)n3)ncc21] I-37
TABLE X-continued
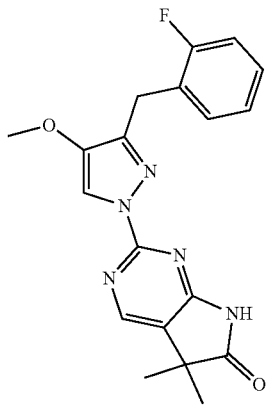 [SMILES: COc1cn(-c2ncc3c(n2)NC(=O)C3(C)C)nc1Cc1ccccc1F] I-38
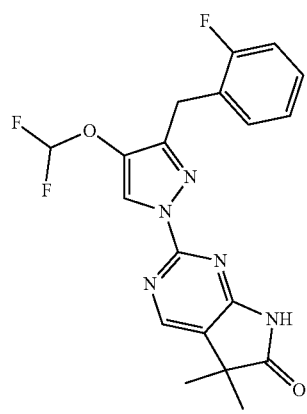 [SMILES: CC1(C)C(=O)Nc2nc(-n3cc(OC(F)F)c(Cc4ccccc4F)n3)ncc21] I-39
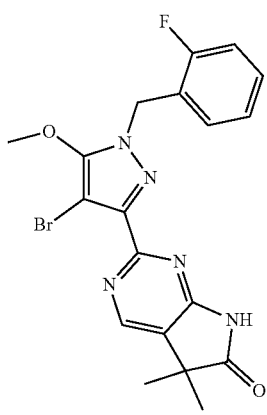 I-40
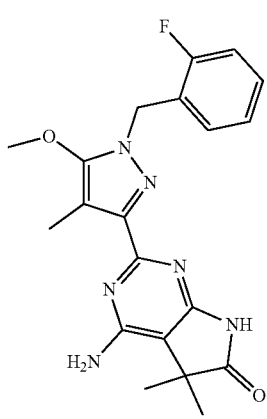 [SMILES: COc1c(C)c(-c2nc(N)c3c(n2)NC(=O)C3(C)C)nn1Cc1ccccc1F] I-41

TABLE X-continued
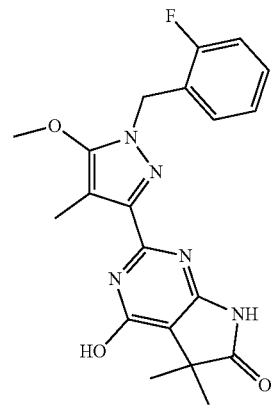 [SMILES: COc1c(C)c(-c2nc(O)c3c(n2)NC(=O)C3(C)C)nn1Cc1ccccc1F]
I-42
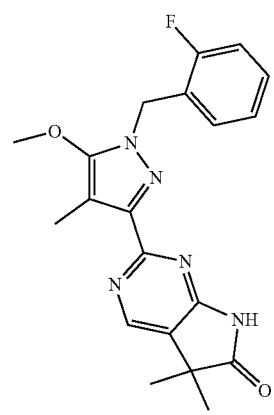 [SMILES: COc1c(C)c(-c2ncc3c(n2)NC(=O)C3(C)C)nn1Cc1ccccc1F]
I-43
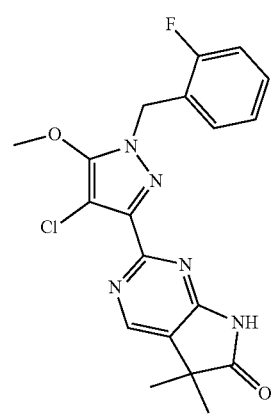 [SMILES: COc1c(Cl)c(-c2ncc3c(n2)NC(=O)C3(C)C)nn1Cc1ccccc1F]
I-44
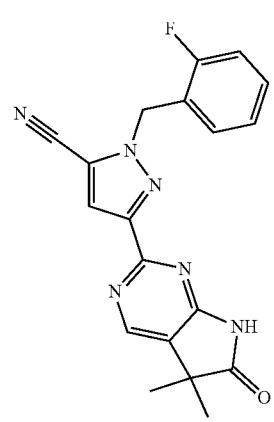 [SMILES: CC1(C)C(=O)Nc2nc(-c3cc(C#N)n(Cc4ccccc4F)n3)ncc21]
I-45
TABLE X-continued
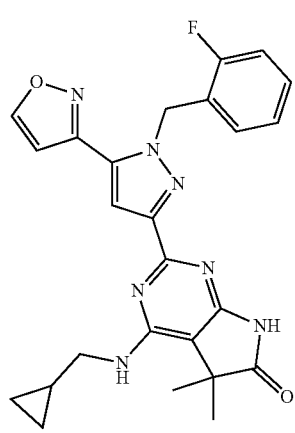 [SMILES: CC1(C)C(=O)Nc2nc(-c3cc(-c4ccon4)n(Cc4ccccc4F)n3)nc(NCC3CC3)c21]
I-46
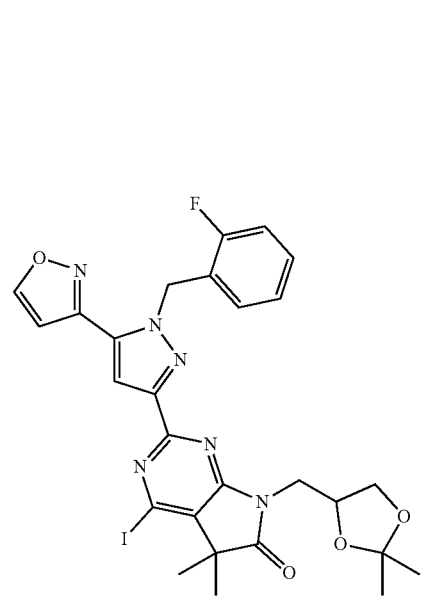 [SMILES: CC1(C)OCC(CN2C(=O)C(C)(C)c3c(I)nc(-c4cc(-c5ccon5)n(Cc5ccccc5F)n4)nc32)O1]
I-47
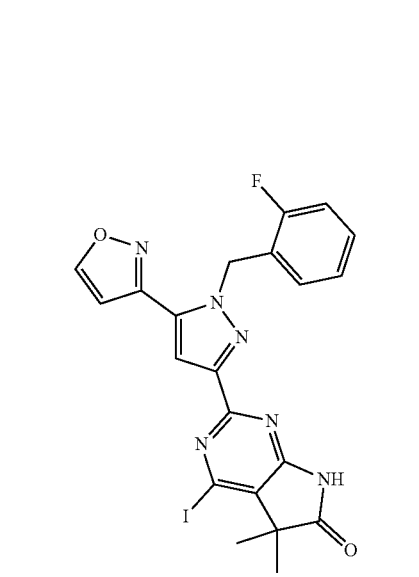 [SMILES: CC1(C)C(=O)Nc2nc(-c3cc(-c4ccon4)n(Cc4ccccc4F)n3)nc(I)c21]
I-48

TABLE X-continued
| | |
|---|---|
| 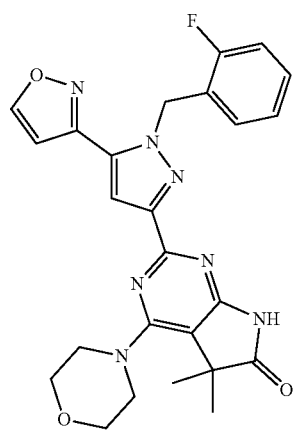 [SMILES: CC1(C)C(=O)Nc2nc(-c3cc(-c4ccon4)n(Cc4ccccc4F)n3)nc(N3CCOCC3)c21] I-49 | 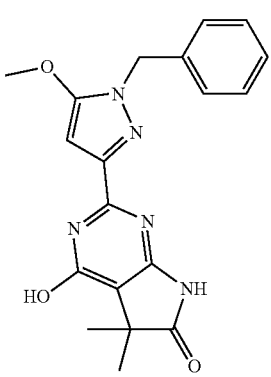 [SMILES: COc1cc(-c2nc(N)c3c(n2)NC(=O)C3(C)C)nn1Cc1ccccc1] I-53 |
| 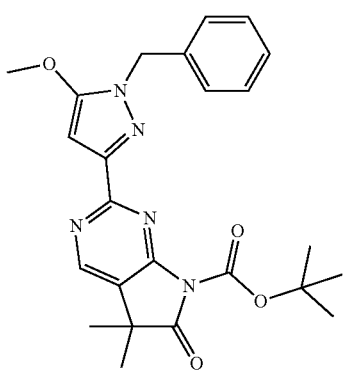 [SMILES: COc1cc(-c2ncc3c(n2)N(C(=O)OC(C)(C)C)C(=O)C3(C)C)nn1Cc1ccccc1] I-50 | 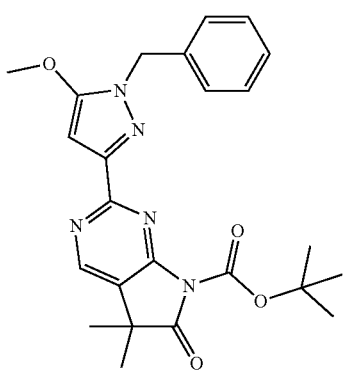 [SMILES: COc1cc(-c2ncc3c(n2)N(C(=O)OC(C)(C)C)C(=O)C3(C)C)nn1Cc1ccccc1] I-54 |
| I-51 | I-55 |
| I-52 | 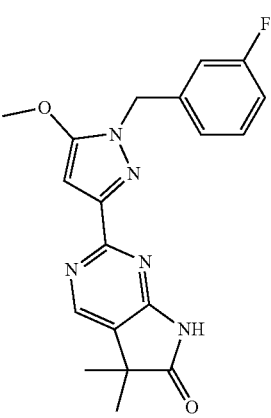 [SMILES: COc1cc(-c2ncc3c(n2)NC(=O)C3(C)C)nn1Cc1cccc(F)c1] I-55 |
| 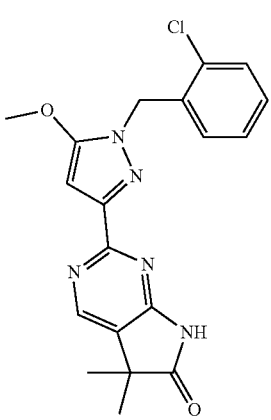 [SMILES: COc1cc(-c2ncc3c(n2)NC(=O)C3(C)C)nn1Cc1ccccc1Cl] | 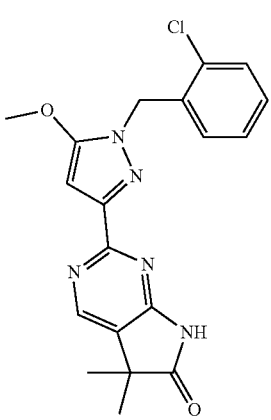 [SMILES: COc1cc(-c2ncc3c(n2)NC(=O)C3(C)C)nn1Cc1ccccc1Cl] I-56 |

TABLE X-continued
I-57
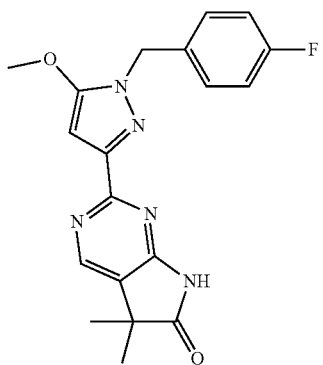 [SMILES: COc1cc(-c2ncc3c(n2)NC(=O)C3(C)C)nn1Cc1ccc(F)cc1]
I-58
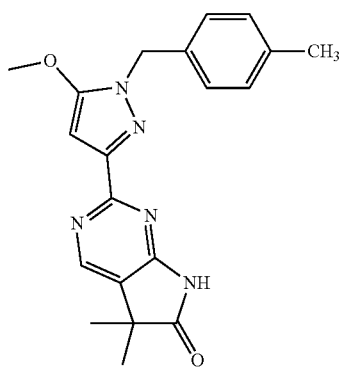
I-59
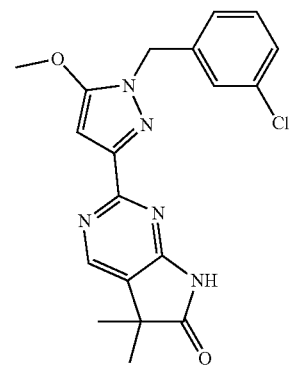 [SMILES: COc1cc(-c2ncc3c(n2)NC(=O)C3(C)C)nn1Cc1cccc(Cl)c1]
I-60
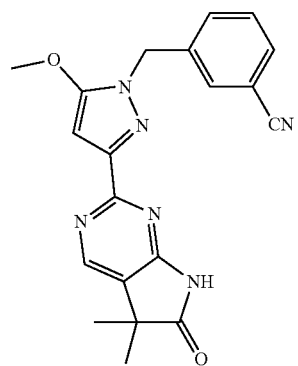 [SMILES: COc1cc(-c2ncc3c(n2)NC(=O)C3(C)C)nn1Cc1cccc(C#N)c1]
TABLE X-continued
I-61
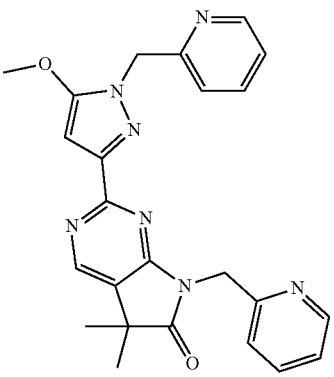 [SMILES: COc1cc(-c2ncc3c(n2)N(Cc2ccccn2)C(=O)C3(C)C)nn1Cc1ccccn1]
I-62
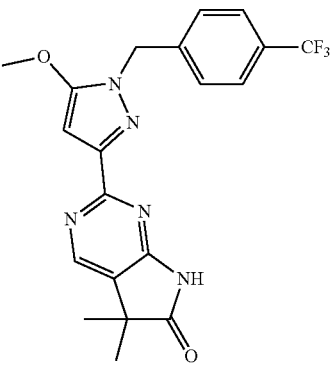 [SMILES: COc1cc(-c2ncc3c(n2)NC(=O)C3(C)C)nn1Cc1ccc(C(F)(F)F)cc1]
I-63
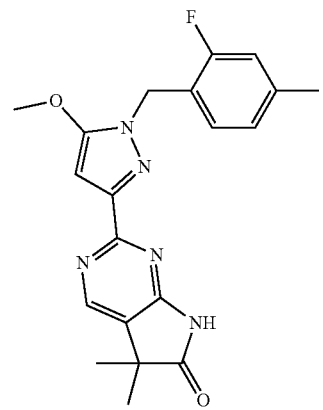
I-64
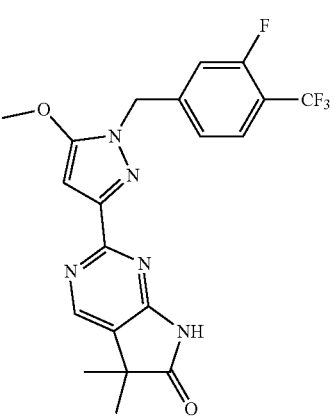 [SMILES: COc1cc(-c2ncc3c(n2)NC(=O)C3(C)C)nn1Cc1ccc(C(F)(F)F)c(F)c1]

TABLE X-continued
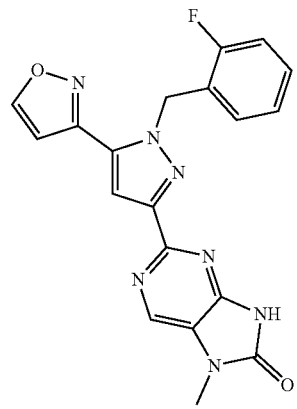 [SMILES: Cn1c(=O)[nH]c2nc(-c3cc(-c4ccon4)n(Cc4ccccc4F)n3)ncc21] I-65
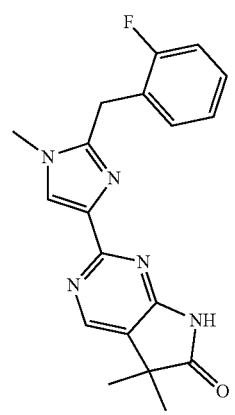 [SMILES: Cn1cc(-c2ncc3c(n2)NC(=O)C3(C)C)nc1Cc1ccccc1F] I-66
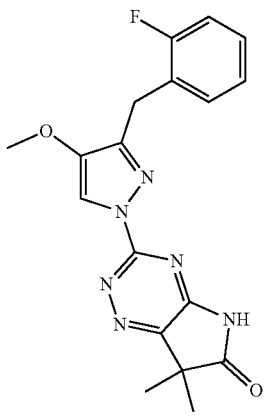 [SMILES: COc1cn(-c2nnc3c(n2)NC(=O)C3(C)C)nc1Cc1ccccc1F] I-67
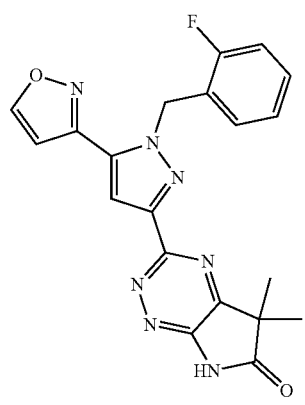 [SMILES: CC1(C)C(=O)Nc2nnc(-c3cc(-c4ccon4)n(Cc4ccccc4F)n3)nc21] I-68
TABLE X-continued
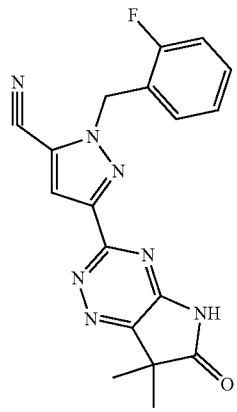 [SMILES: CC1(C)C(=O)Nc2nc(-c3cc(C#N)n(Cc4ccccc4F)n3)nnc21] I-69
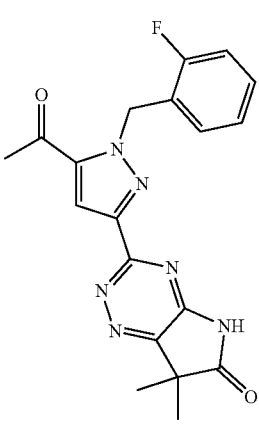 [SMILES: CC(=O)c1cc(-c2nnc3c(n2)NC(=O)C3(C)C)nn1Cc1ccccc1F] I-70
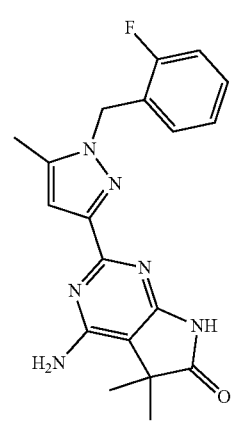 [SMILES: Cc1cc(-c2nc(N)c3c(n2)NC(=O)C3(C)C)nn1Cc1ccccc1F] I-71
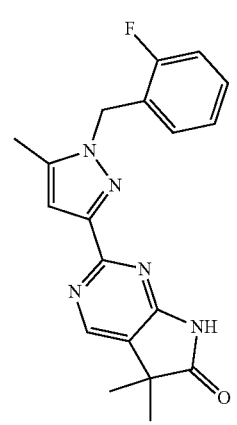 [SMILES: Cc1cc(-c2ncc3c(n2)NC(=O)C3(C)C)nn1Cc1ccccc1F] I-72

TABLE X-continued
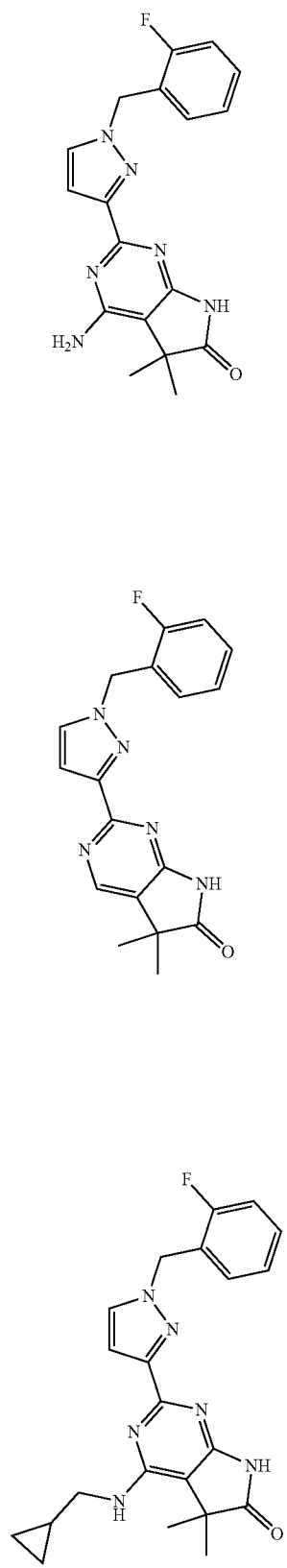
I-73
I-74
I-75
TABLE X-continued
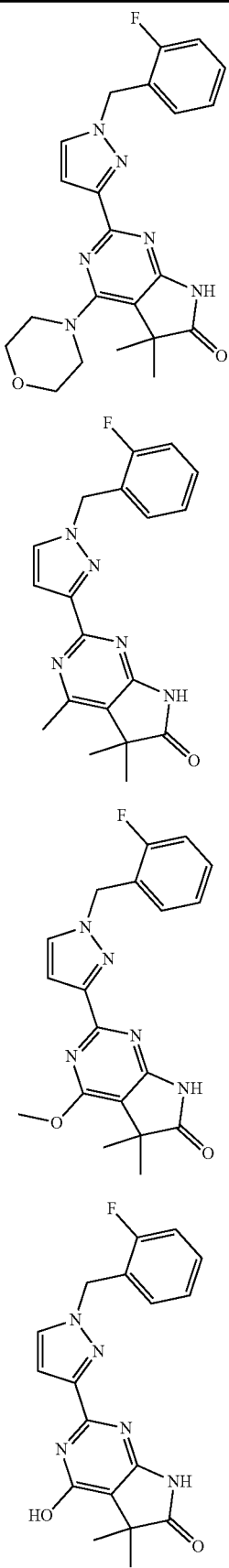
I-76
I-77
I-78
I-79

TABLE X-continued
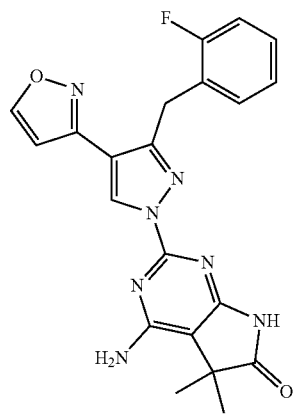 [SMILES: CC1(C)C(=O)Nc2nc(-n3cc(-c4ccon4)c(Cc4ccccc4F)n3)nc(N)c21]
I-80
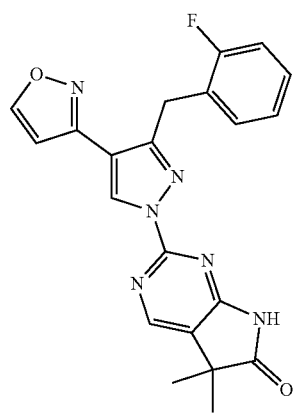 [SMILES: CC1(C)C(=O)Nc2nc(-n3cc(-c4ccon4)c(Cc4ccccc4F)n3)ncc21]
I-81
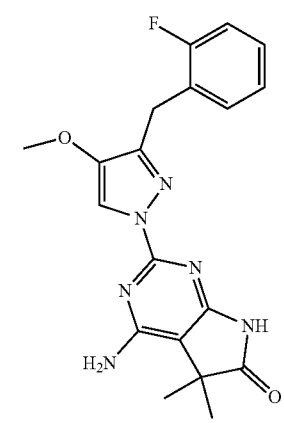 [SMILES: COc1cn(-c2nc(N)c3c(n2)NC(=O)C3(C)C)nc1Cc1ccccc1F]
I-82
TABLE X-continued
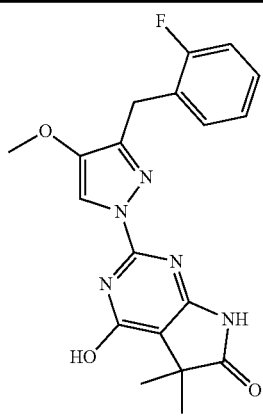
I-83
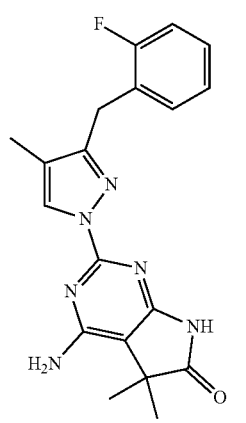 [SMILES: Cc1cn(-c2nc(N)c3c(n2)NC(=O)C3(C)C)nc1Cc1ccccc1F]
I-84
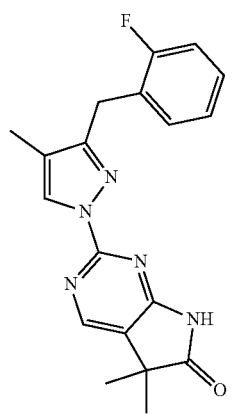 [SMILES: Cc1cn(-c2ncc3c(n2)NC(=O)C3(C)C)nc1Cc1ccccc1F]
I-85
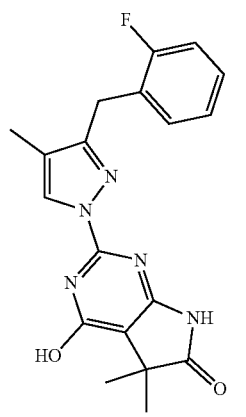 [SMILES: Cc1cn(-c2nc(O)c3c(n2)NC(=O)C3(C)C)nc1Cc1ccccc1F]
I-86

TABLE X-continued
I-87
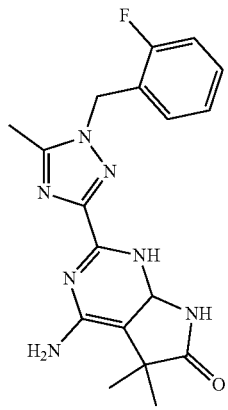 [SMILES: Cc1nc(C2=NC(N)=C3C(NC(=O)C3(C)C)N2)nn1Cc1ccccc1F]
I-88
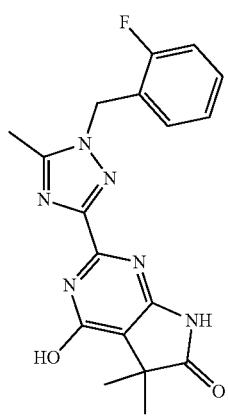 [SMILES: Cc1nc(-c2nc(O)c3c(n2)NC(=O)C3(C)C)nn1Cc1ccccc1F]
I-89
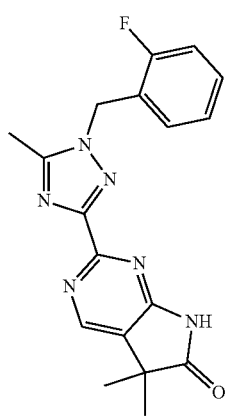
I-90
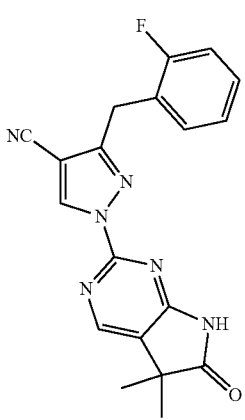 [SMILES: CC1(C)C(=O)Nc2nc(-n3cc(C#N)c(Cc4ccccc4F)n3)ncc21]
TABLE X-continued
I-91
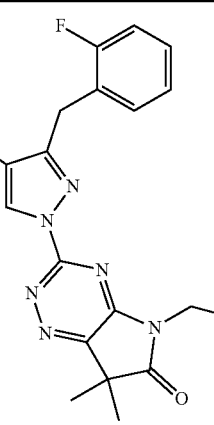
I-92
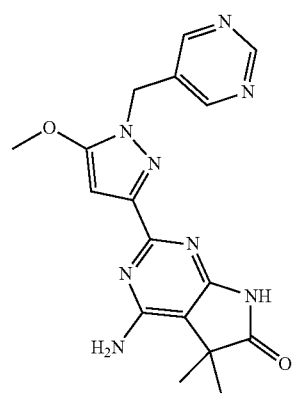 [SMILES: COc1cc(-c2nc(N)c3c(n2)NC(=O)C3(C)C)nn1Cc1cncnc1]
I-93
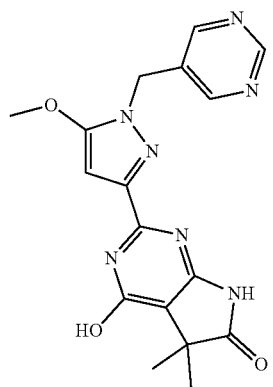 [SMILES: COc1cc(-c2nc(O)c3c(n2)NC(=O)C3(C)C)nn1Cc1cncnc1]
I-94
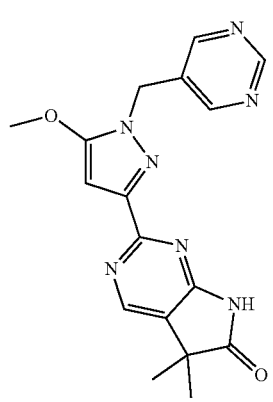 [SMILES: COc1cc(-c2ncc3c(n2)NC(=O)C3(C)C)nn1Cc1cncnc1]

In some of the above embodiments, the compound is one selected from Table XX, below:
TABLE XX
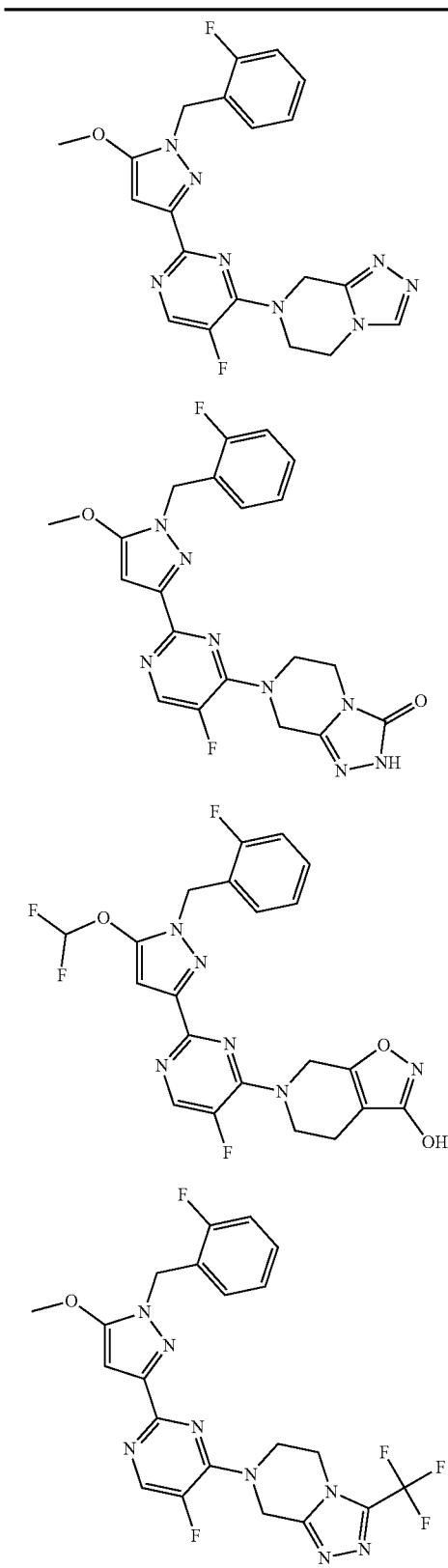
TABLE XX-continued
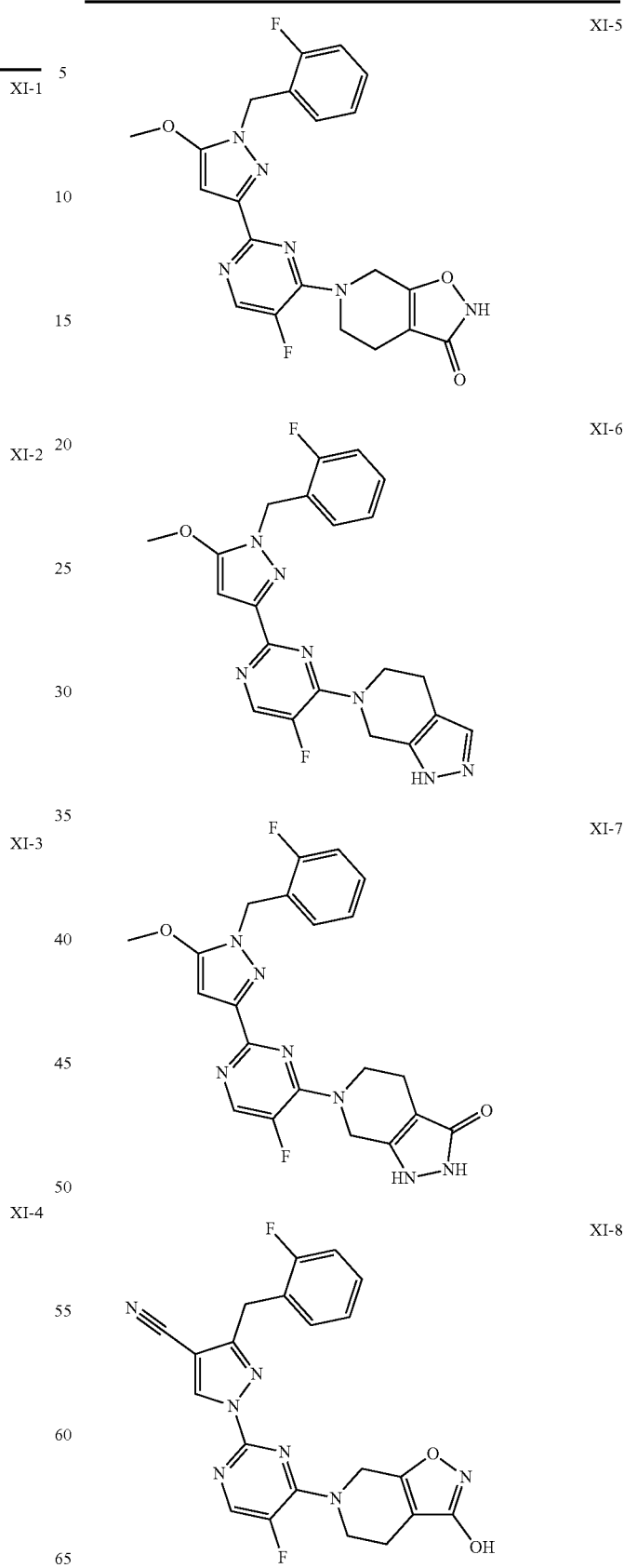

TABLE XX-continued
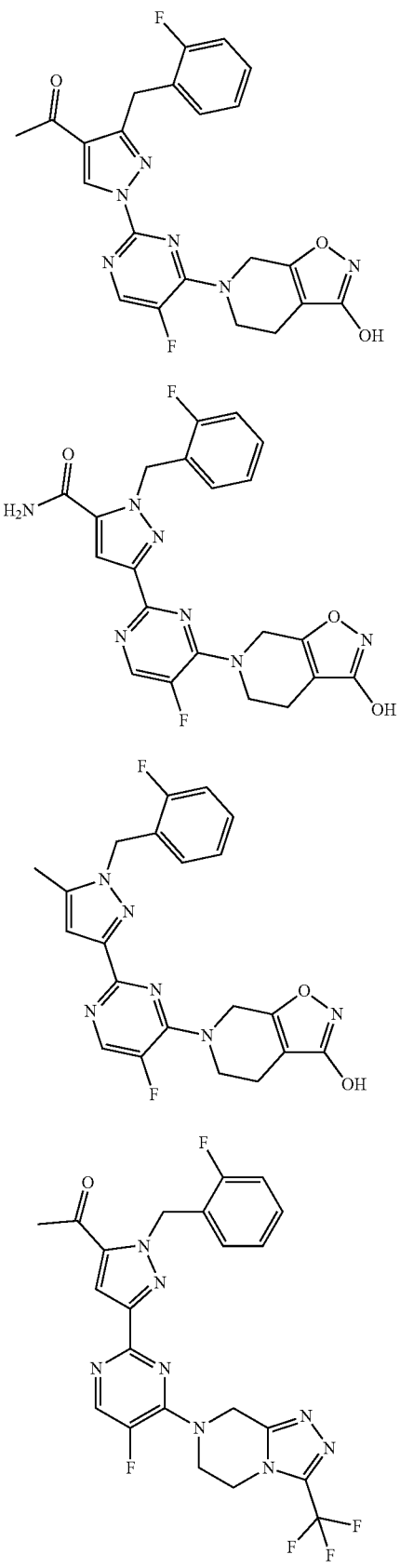
XI-9
XI-10
XI-12
XI-13
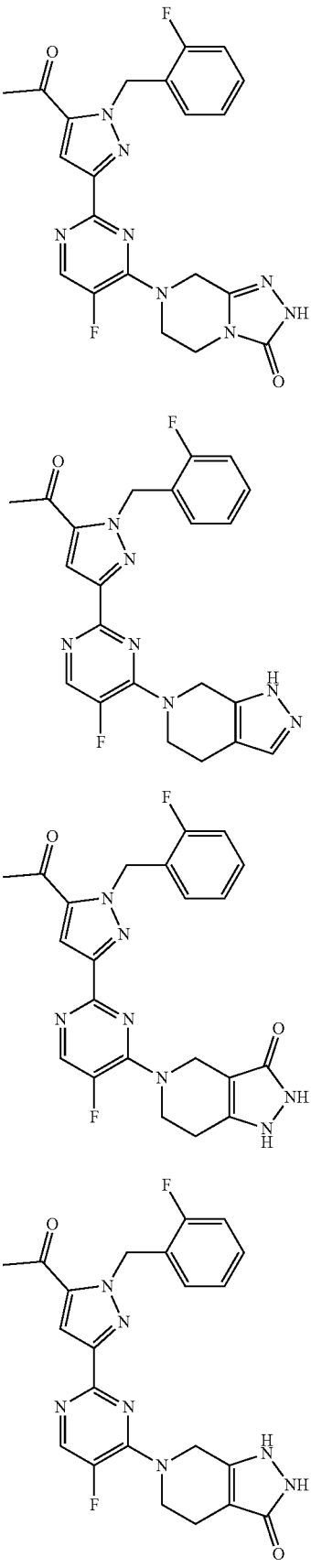
XI-14
XI-15
XI-16
XI-17

TABLE XX-continued
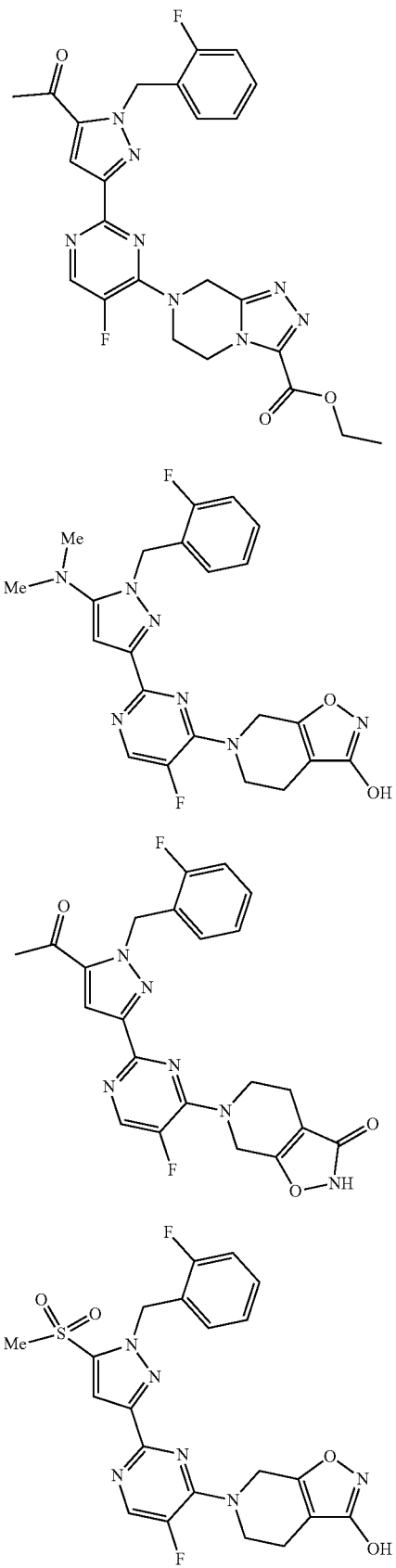
XI-18
XI-19
XI-20
XI-21
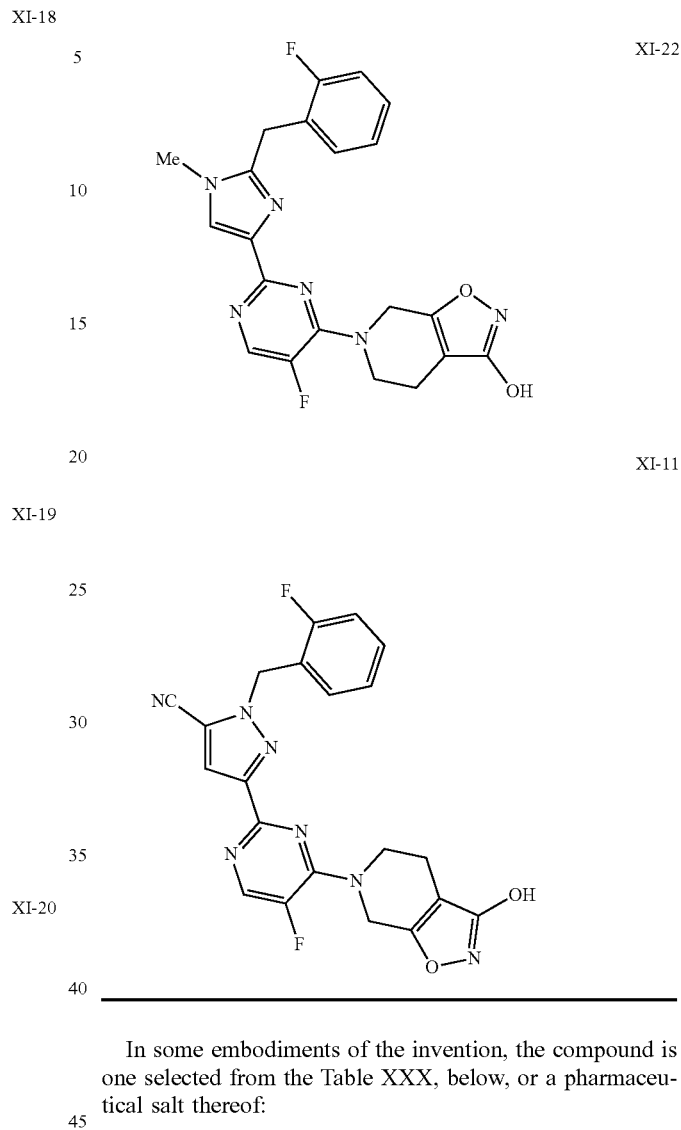
XI-22
XI-11
In some embodiments of the invention, the compound is one selected from the Table XXX, below, or a pharmaceutical salt thereof:
TABLE XXX
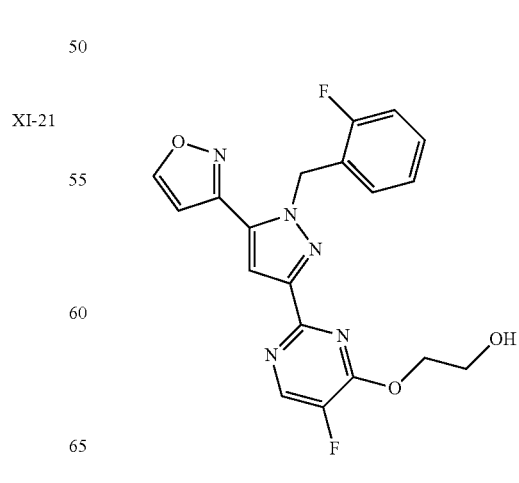
XXI-1

TABLE XXX-continued
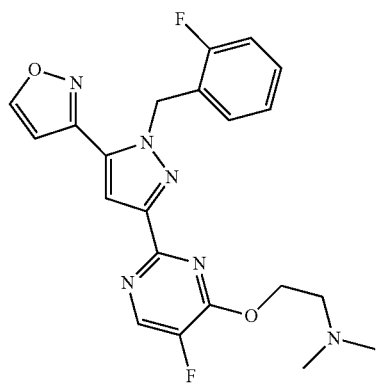 [SMILES: CN(C)CCOc1nc(-c2cc(-c3ccon3)n(Cc3ccccc3F)n2)ncc1F]
XXI-2
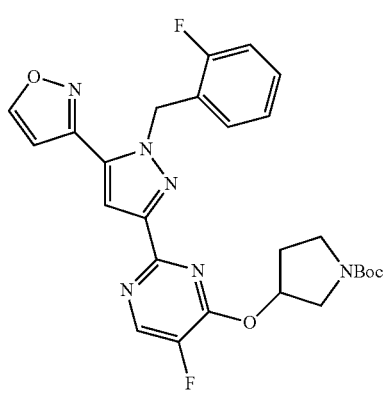 [SMILES: CC(C)(C)OC(=O)N1CCC(Oc2nc(-c3cc(-c4ccon4)n(Cc4ccccc4F)n3)ncc2F)C1]
XXI-3
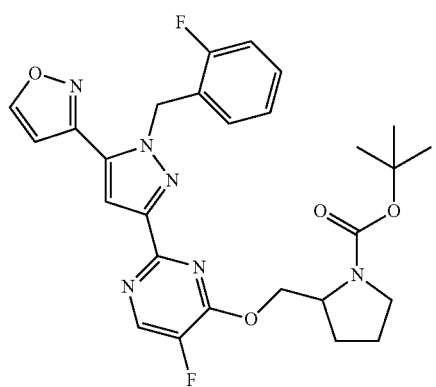 [SMILES: CC(C)(C)OC(=O)N1CCCC1COc1nc(-c2cc(-c3ccon3)n(Cc3ccccc3F)n2)ncc1F]
XXI-4
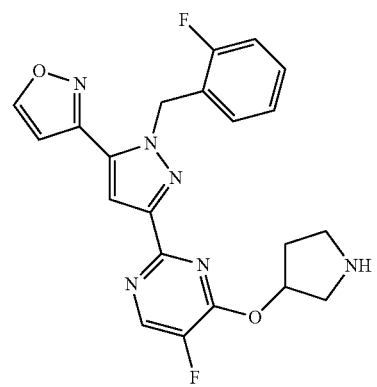 [SMILES: Fc1ccccc1Cn1nc(-c2ncc(F)c(OC3CCNC3)n2)cc1-c1ccon1]
XXI-5
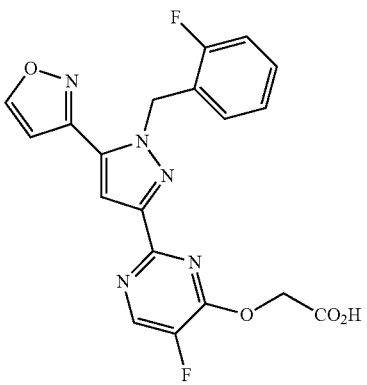 [SMILES: O=C(O)COc1nc(-c2cc(-c3ccon3)n(Cc3ccccc3F)n2)ncc1F]
XXI-6
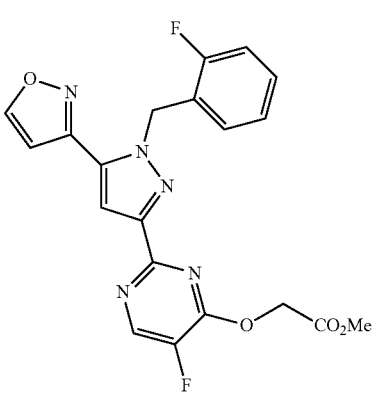 [SMILES: COC(=O)COc1nc(-c2cc(-c3ccon3)n(Cc3ccccc3F)n2)ncc1F]
XXI-7
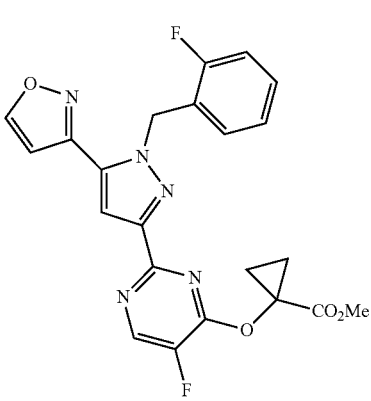 [SMILES: COC(=O)C1(Oc2nc(-c3cc(-c4ccon4)n(Cc4ccccc4F)n3)ncc2F)CC1]
XXI-8
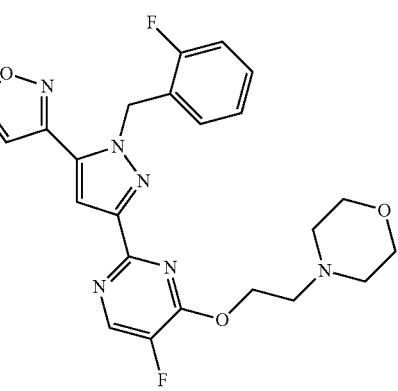
XXI-9

TABLE XXX-continued
XXI-10 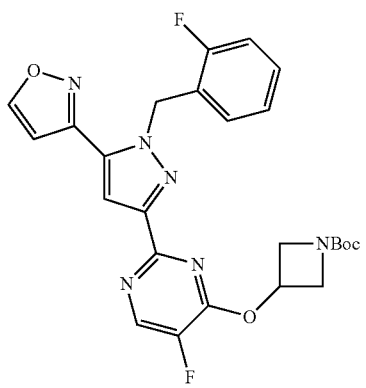 [SMILES: CC(C)(C)OC(=O)N1CC(Oc2nc(-c3cc(-c4ccon4)n(Cc4ccccc4F)n3)ncc2F)C1]
XXI-11 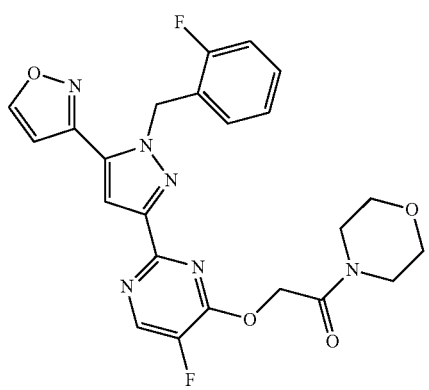 [SMILES: O=C(COc1nc(-c2cc(-c3ccon3)n(Cc3ccccc3F)n2)ncc1F)N1CCOCC1]
XXI-12 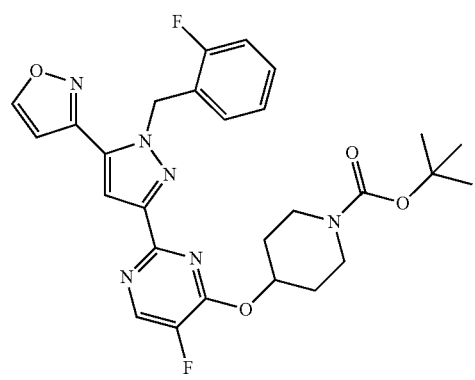 [SMILES: CC(C)(C)OC(=O)N1CCC(Oc2nc(-c3cc(-c4ccon4)n(Cc4ccccc4F)n3)ncc2F)CC1]
XXI-13 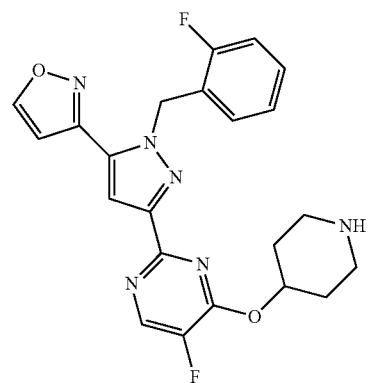 [SMILES: Fc1ccccc1Cn1nc(-c2ncc(F)c(OC3CCNCC3)n2)cc1-c1ccon1]
TABLE XXX-continued
XXI-14 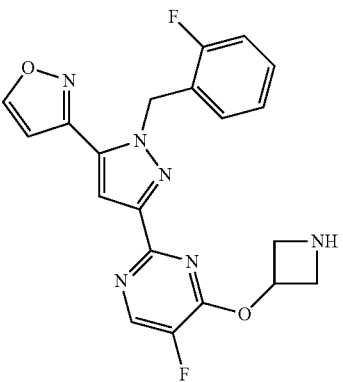 [SMILES: Fc1ccccc1Cn1nc(-c2ncc(F)c(OC3CNC3)n2)cc1-c1ccon1]
XXI-15 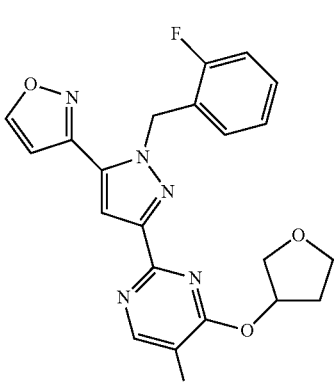
XXI-16 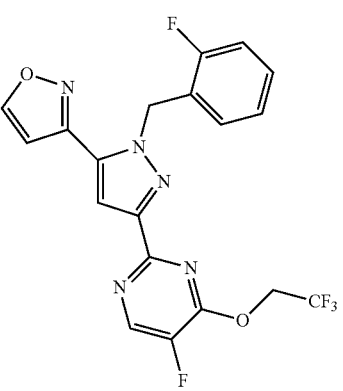 [SMILES: Fc1ccccc1Cn1nc(-c2ncc(F)c(OCC(F)(F)F)n2)cc1-c1ccon1]
XXI-17 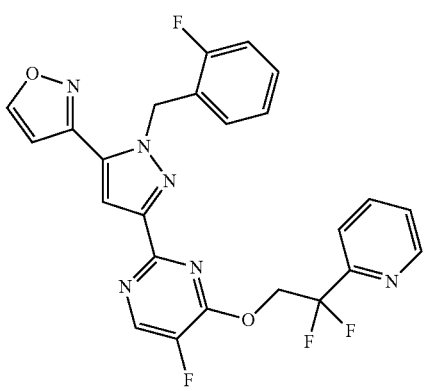 [SMILES: Fc1ccccc1Cn1nc(-c2ncc(F)c(OCC(F)(F)c3ccccn3)n2)cc1-c1ccon1]

TABLE XXX-continued
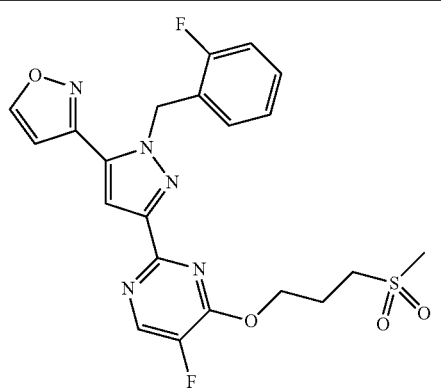
XXI-18
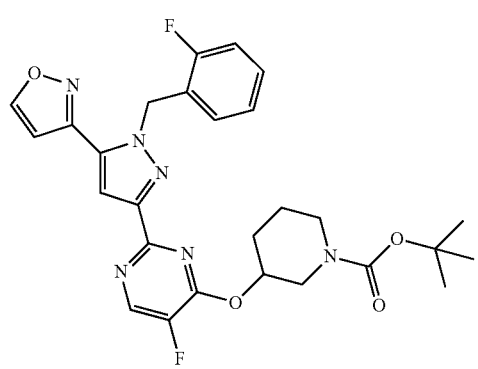 [SMILES: CC(C)(C)OC(=O)N1CCCC(Oc2nc(-c3cc(-c4ccon4)n(Cc4ccccc4F)n3)ncc2F)C1]
XXI-19
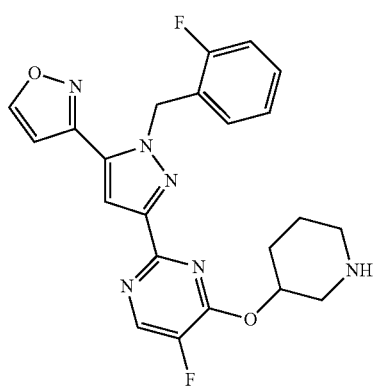 [SMILES: Fc1ccccc1Cn1nc(-c2ncc(F)c(OC3CCCNC3)n2)cc1-c1ccon1]
XXI-20
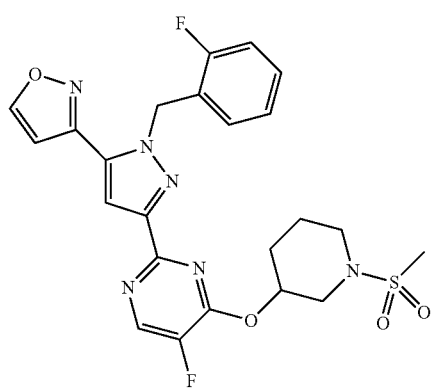 [SMILES: CS(=O)(=O)N1CCCC(Oc2nc(-c3cc(-c4ccon4)n(Cc4ccccc4F)n3)ncc2F)C1]
XXI-21
TABLE XXX-continued
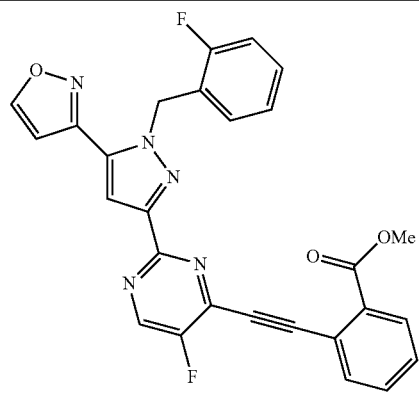
XXI-23
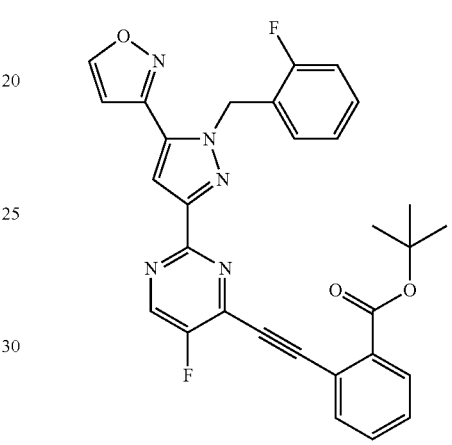
XXI-24
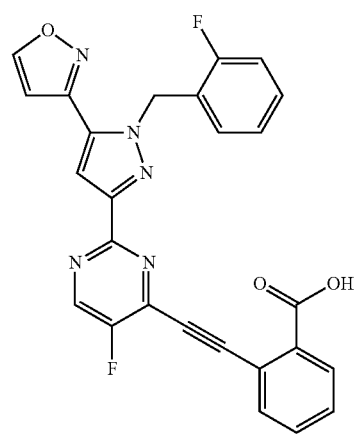 [SMILES: O=C(O)c1ccccc1C#Cc1nc(-c2cc(-c3ccon3)n(Cc3ccccc3F)n2)ncc1F]
XXI-25
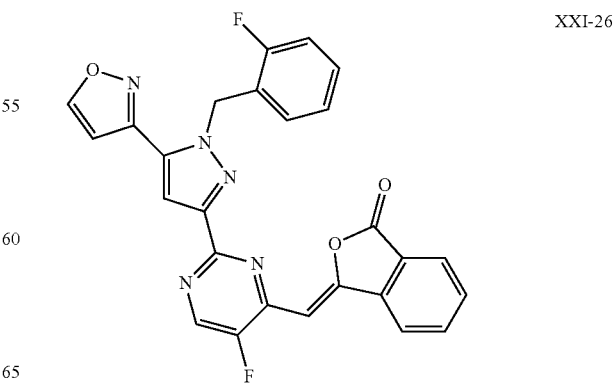
XXI-26

TABLE XXX-continued
XXI-27
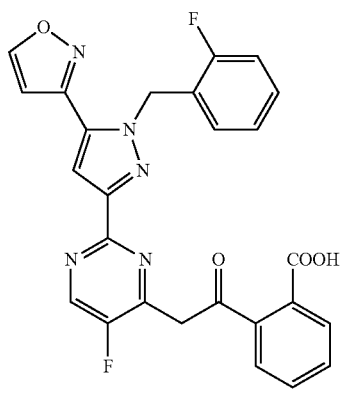 [SMILES: O=C(O)c1ccccc1C(=O)Cc1nc(-c2cc(-c3ccon3)n(Cc3ccccc3F)n2)ncc1F]
XXI-30
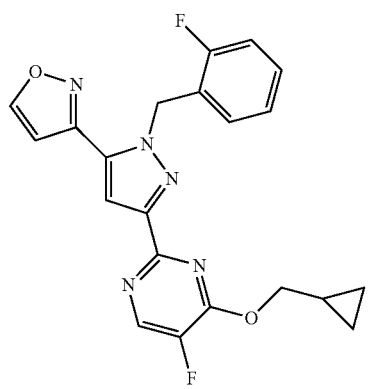 [SMILES: Fc1ccccc1Cn1nc(-c2ncc(F)c(OCC3CC3)n2)cc1-c1ccon1]
XXI-32
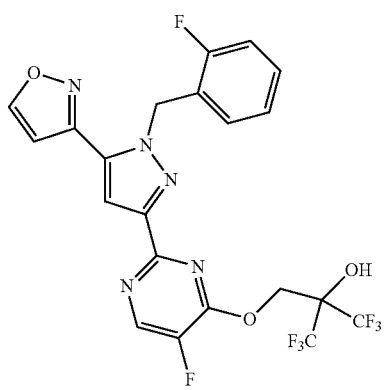 [SMILES: OC(COc1nc(-c2cc(-c3ccon3)n(Cc3ccccc3F)n2)ncc1F)(C(F)(F)F)C(F)(F)F]
XXI-34
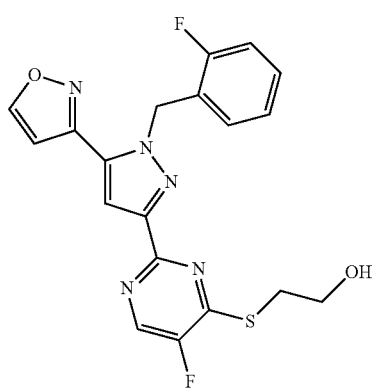 [SMILES: OCCSc1nc(-c2cc(-c3ccon3)n(Cc3ccccc3F)n2)ncc1F]
TABLE XXX-continued
XXI-36
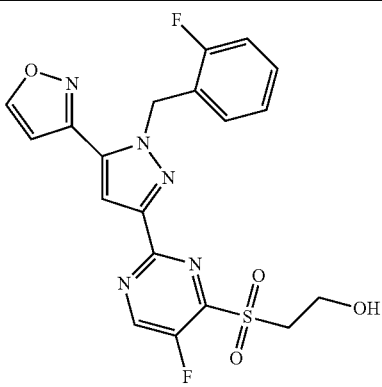
XXI-37
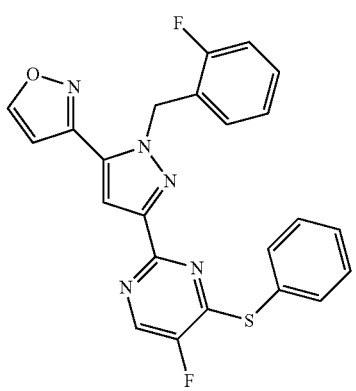 [SMILES: Fc1ccccc1Cn1nc(-c2ncc(F)c(Sc3ccccc3)n2)cc1-c1ccon1]
XXI-29
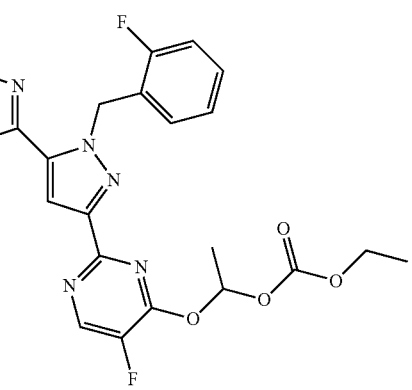
XXI-31
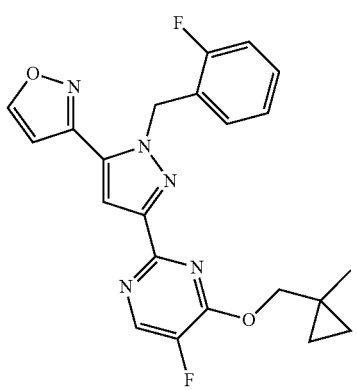 [SMILES: CC1(COc2nc(-c3cc(-c4ccon4)n(Cc4ccccc4F)n3)ncc2F)CC1]

TABLE XXX-continued
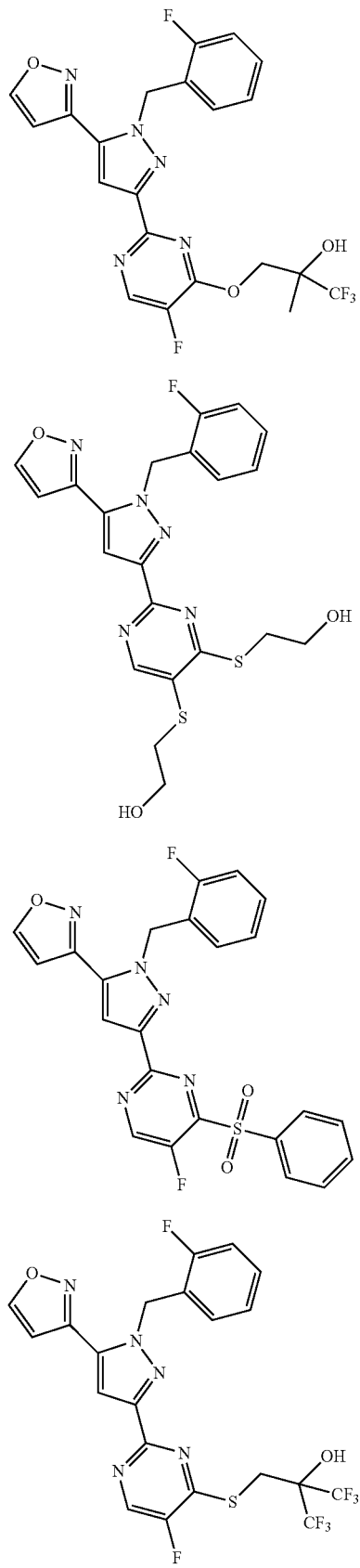
XXI-33
XXI-35
XXI-38
XXI-39
In some embodiments of the above methods, uses, compositions and kits, the sGC stimulator is one depicted in Table IV or Table XIV.
TABLE IV
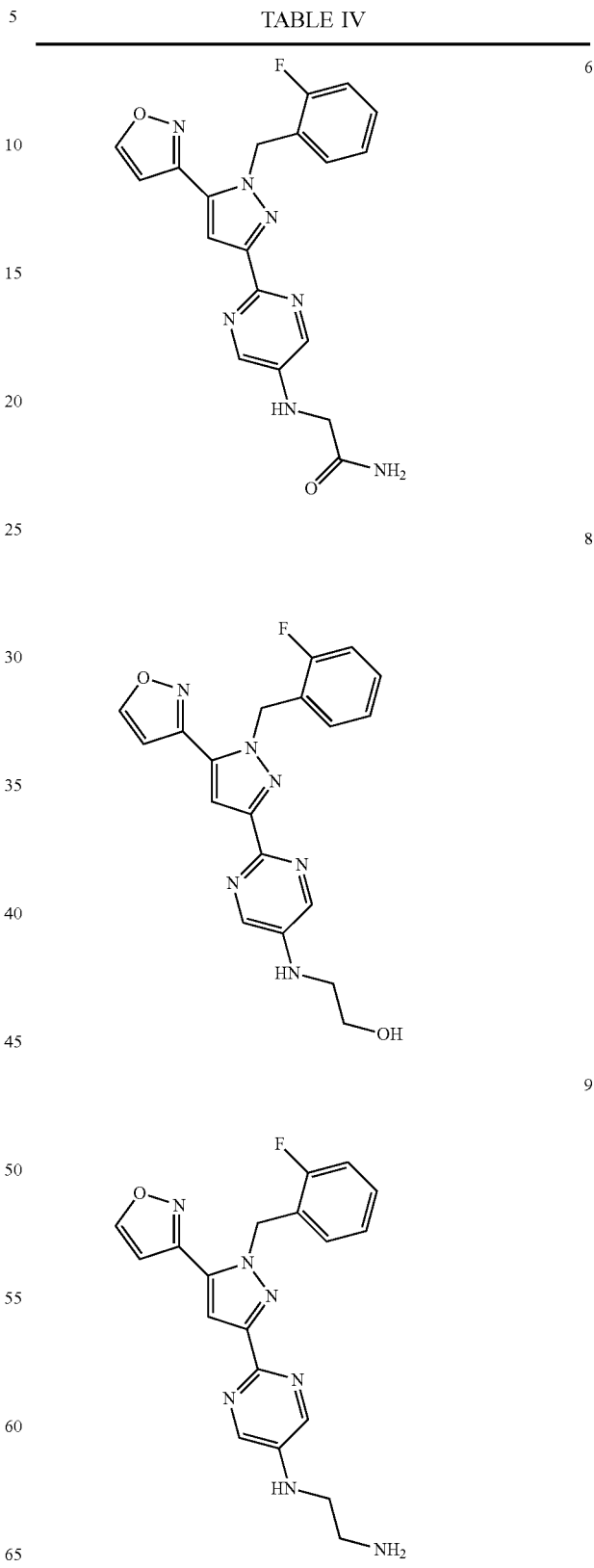
6
8
9

TABLE IV-continued
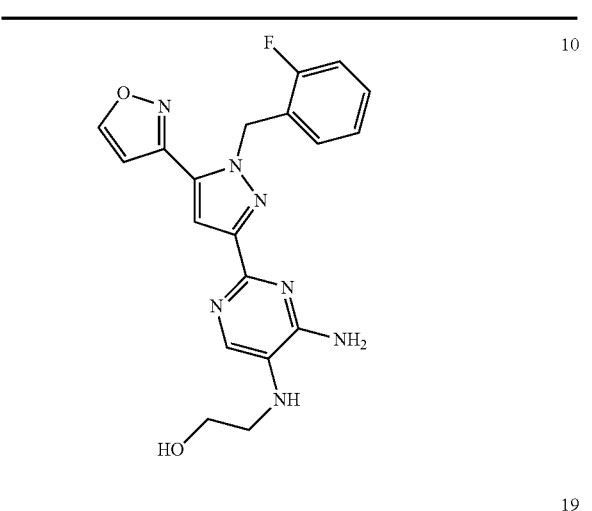
19
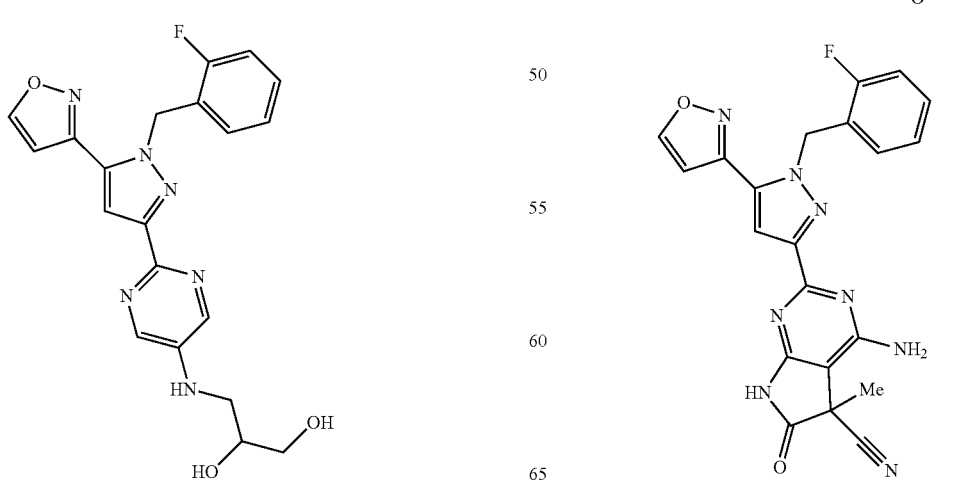
21
TABLE IV-continued
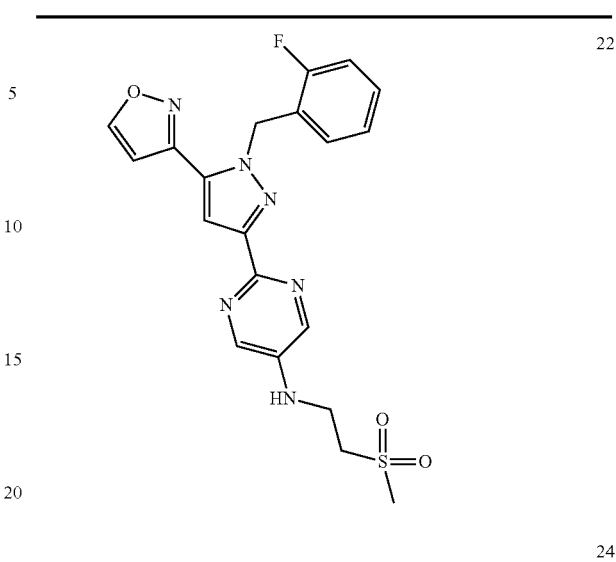
22
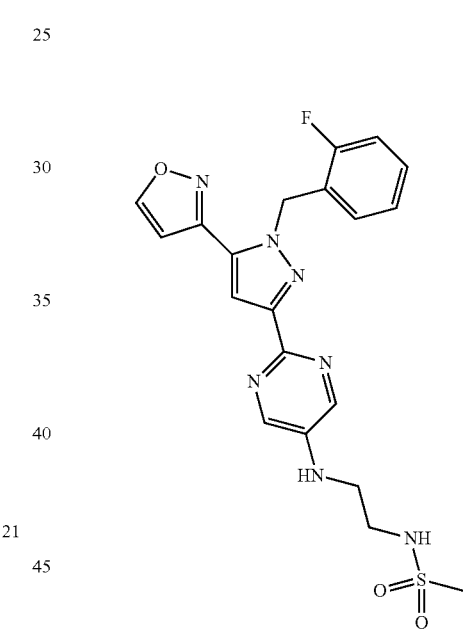
24
29

TABLE IV-continued
37
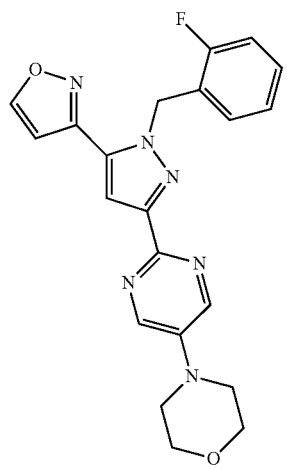 [SMILES: Fc1ccccc1Cn1nc(-c2ncc(N3CCOCC3)cn2)cc1-c1ccon1]
61
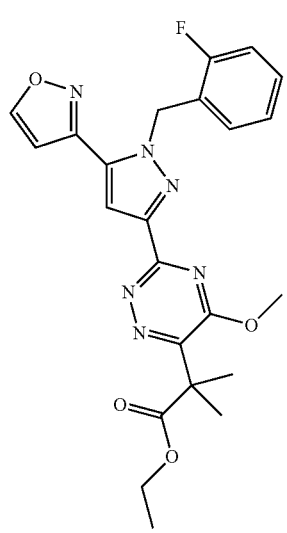 [SMILES: CCOC(=O)C(C)(C)c1nnc(-c2cc(-c3ccon3)n(Cc3ccccc3F)n2)nc1OC]
109
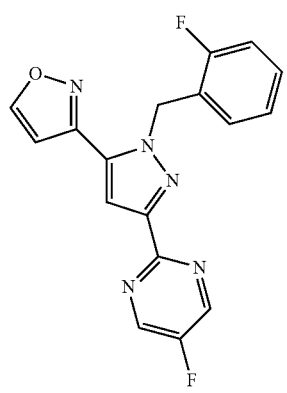 [SMILES: Fc1cnc(-c2cc(-c3ccon3)n(Cc3ccccc3F)n2)nc1]
TABLE IV-continued
110
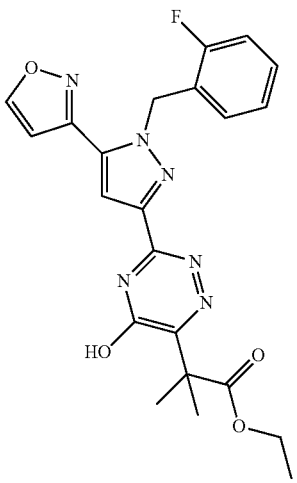 [SMILES: CCOC(=O)C(C)(C)c1nnc(-c2cc(-c3ccon3)n(Cc3ccccc3F)n2)nc1O]
111
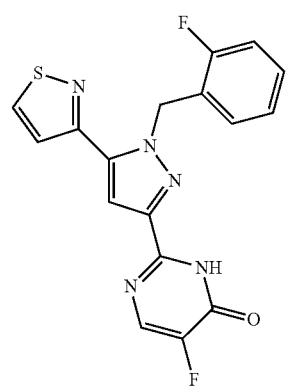 [SMILES: O=c1[nH]c(-c2cc(-c3ccsn3)n(Cc3ccccc3F)n2)ncc1F]
142
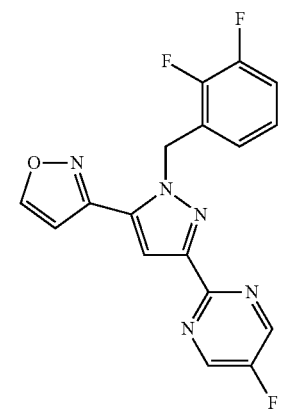 [SMILES: Fc1cnc(-c2cc(-c3ccon3)n(Cc3cccc(F)c3F)n2)nc1]
143
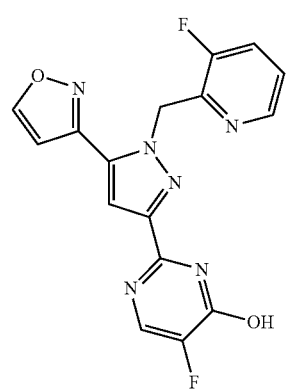 [SMILES: Oc1nc(-c2cc(-c3ccon3)n(Cc3ncccc3F)n2)ncc1F]

TABLE IV-continued
| | |
|---|---|
| 144 | 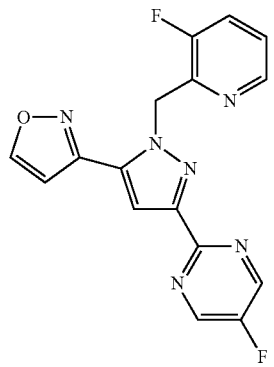 [SMILES: Fc1cnc(-c2cc(-c3ccon3)n(Cc3ncccc3F)n2)nc1] |
| 145 | 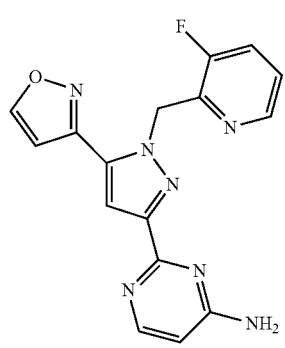 [SMILES: Nc1ccnc(-c2cc(-c3ccon3)n(Cc3ncccc3F)n2)n1] |
| 146 | 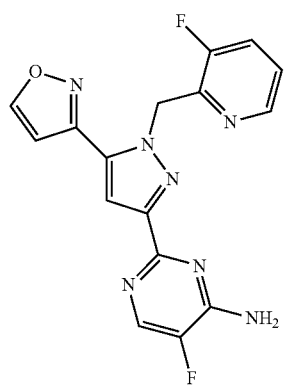 [SMILES: Nc1nc(-c2cc(-c3ccon3)n(Cc3ncccc3F)n2)ncc1F] |
| 182 | 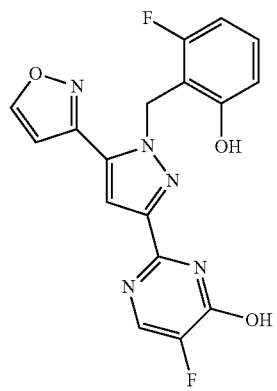 [SMILES: Oc1cccc(F)c1Cn1nc(-c2ncc(F)c(O)n2)cc1-c1ccon1] |
| 185 | 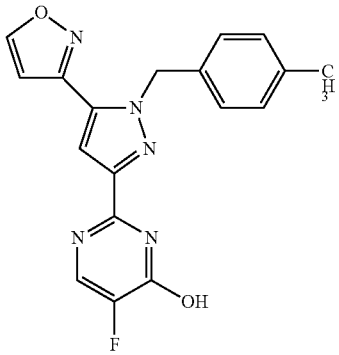 [SMILES: Cc1ccc(Cn2nc(-c3ncc(F)c(O)n3)cc2-c2ccon2)cc1] |
| 186 | 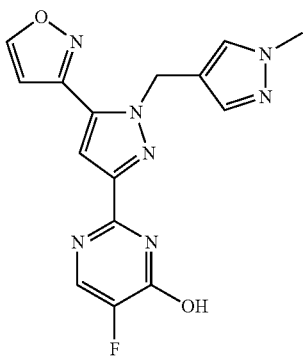 [SMILES: Cn1cc(Cn2nc(-c3ncc(F)c(O)n3)cc2-c2ccon2)cn1] |
| 187 | 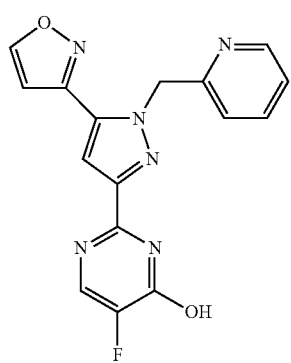 [SMILES: Oc1nc(-c2cc(-c3ccon3)n(Cc3ccccn3)n2)ncc1F] |
| 188 | 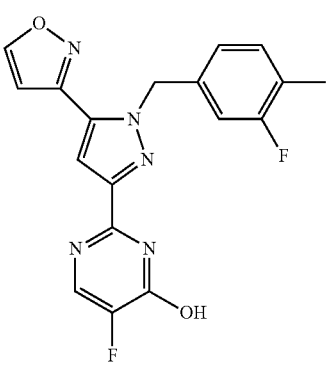 [SMILES: Cc1ccc(Cn2nc(-c3ncc(F)c(O)n3)cc2-c2ccon2)cc1F] |

TABLE IV-continued
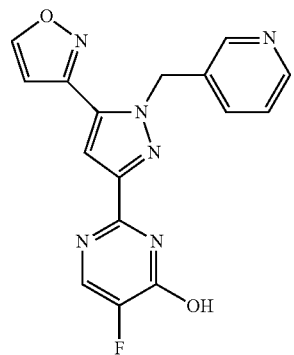 [SMILES: Oc1nc(-c2cc(-c3ccon3)n(Cc3cccnc3)n2)ncc1F]
189
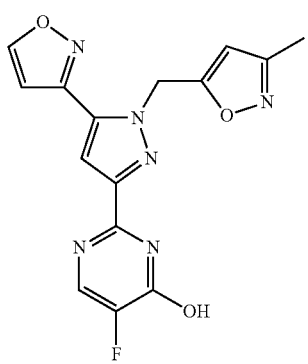 [SMILES: Cc1cc(Cn2nc(-c3ncc(F)c(O)n3)cc2-c2ccon2)on1]
190
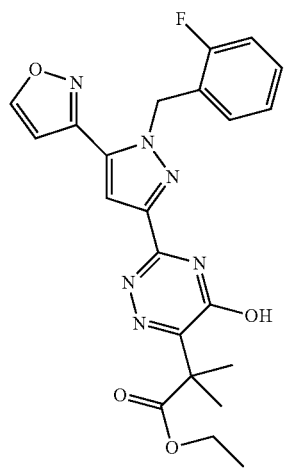 [SMILES: CCOC(=O)C(C)(C)c1nnc(-c2cc(-c3ccon3)n(Cc3ccccc3F)n2)nc1O]
191
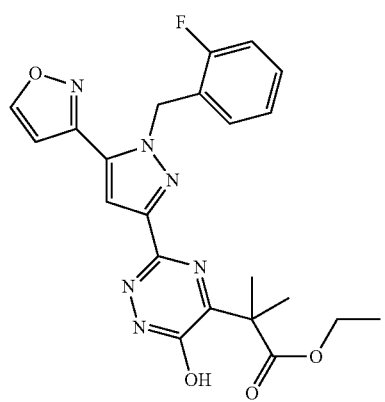 [SMILES: CCOC(=O)C(C)(C)c1nc(-c2cc(-c3ccon3)n(Cc3ccccc3F)n2)nnc1O]
192
TABLE IV-continued
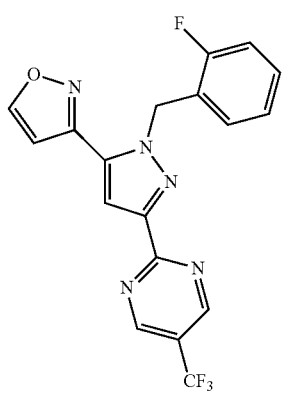 [SMILES: Fc1ccccc1Cn1nc(-c2ncc(C(F)(F)F)cn2)cc1-c1ccon1]
205
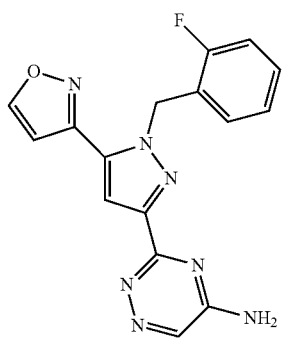 [SMILES: Nc1cnnc(-c2cc(-c3ccon3)n(Cc3ccccc3F)n2)n1]
207
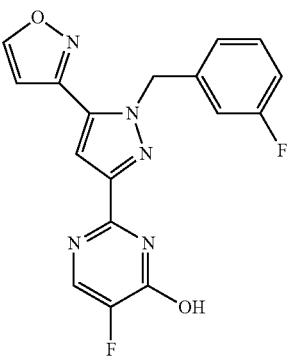 [SMILES: Oc1nc(-c2cc(-c3ccon3)n(Cc3cccc(F)c3)n2)ncc1F]
197
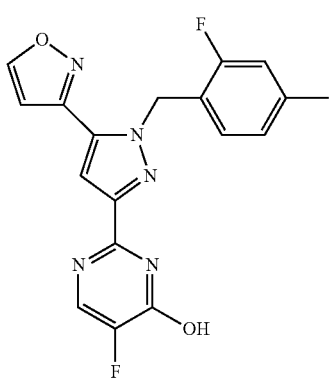 [SMILES: Cc1ccc(Cn2nc(-c3ncc(F)c(O)n3)cc2-c2ccon2)c(F)c1]
208

TABLE IV-continued
| | |
|---|---|
| 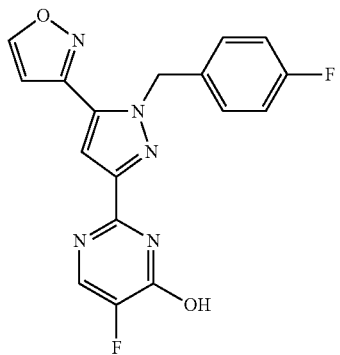 [SMILES: Oc1nc(-c2cc(-c3ccon3)n(Cc3ccc(F)cc3)n2)ncc1F] | 213 |
| 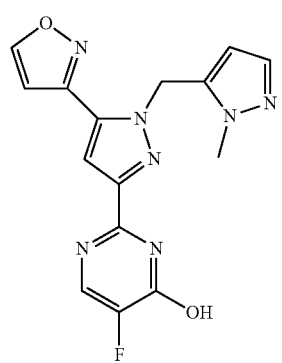 [SMILES: Cn1nccc1Cn1nc(-c2ncc(F)c(O)n2)cc1-c1ccon1] | 212 |
| 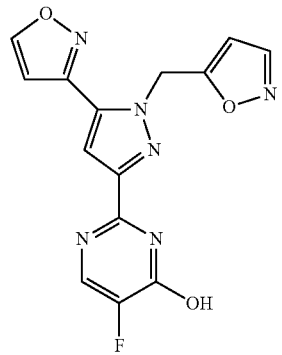 [SMILES: Oc1nc(-c2cc(-c3ccon3)n(Cc3ccno3)n2)ncc1F] | 211 |
| 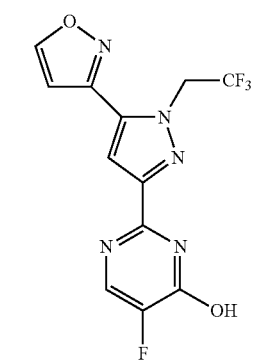 [SMILES: Oc1nc(-c2cc(-c3ccon3)n(CC(F)(F)F)n2)ncc1F] | 214 |
TABLE IV-continued
| | |
|---|---|
| 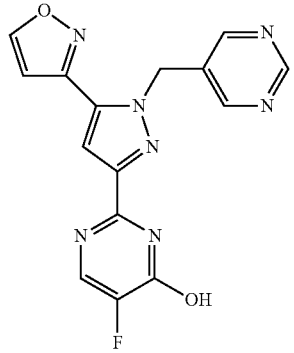 [SMILES: Oc1nc(-c2cc(-c3ccon3)n(Cc3cncnc3)n2)ncc1F] | 216 |
| 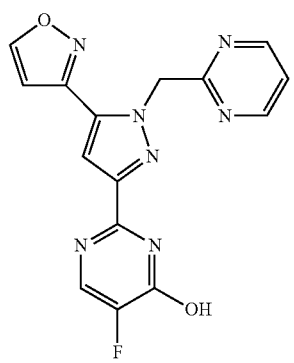 [SMILES: Oc1nc(-c2cc(-c3ccon3)n(Cc3ncccn3)n2)ncc1F] | 215 |
| 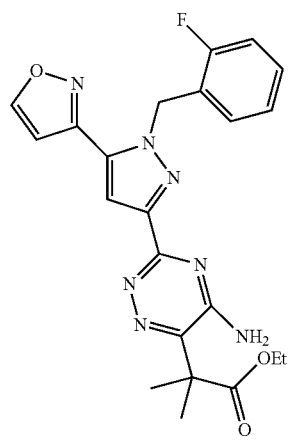 [SMILES: CCOC(=O)C(C)(C)c1nnc(-c2cc(-c3ccon3)n(Cc3ccccc3F)n2)nc1N] | 209 |
TABLE XIV
| | |
|---|---|
| 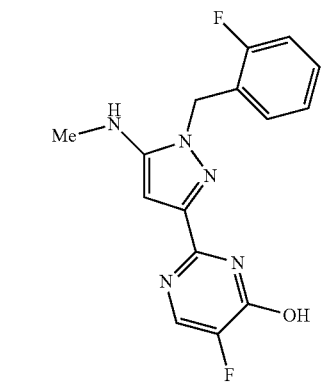 [SMILES: CNc1cc(-c2ncc(F)c(O)n2)nn1Cc1ccccc1F] | 1 |

TABLE XIV-continued
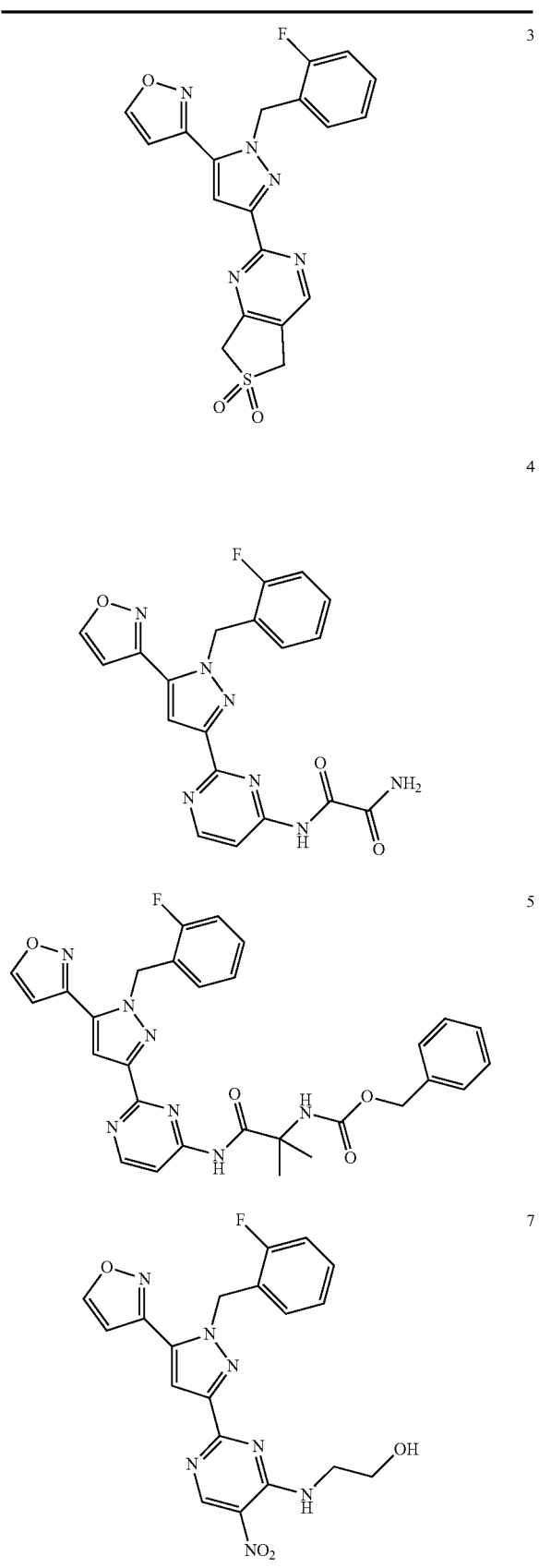
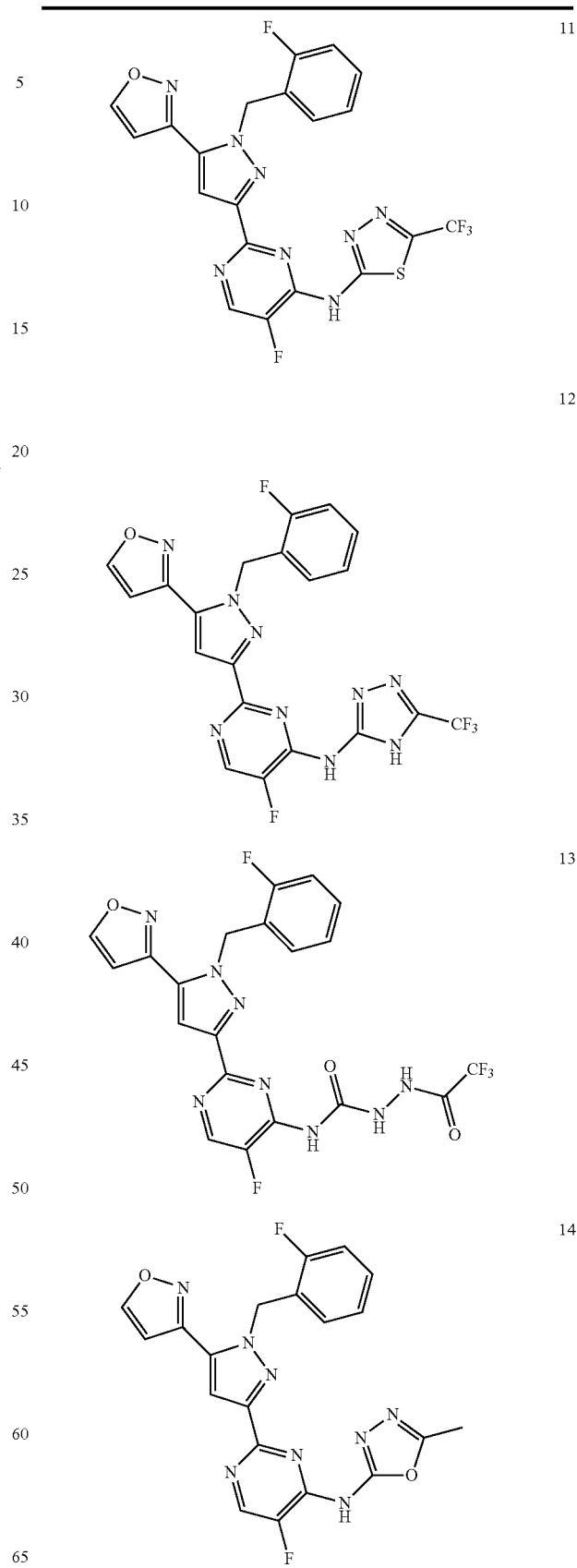

TABLE XIV-continued
| | |
|---|---|
| 15 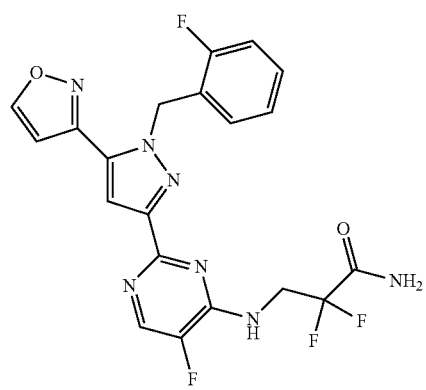 [SMILES: NC(=O)C(F)(F)CNc1nc(-c2cc(-c3ccon3)n(Cc3ccccc3F)n2)ncc1F] | 25 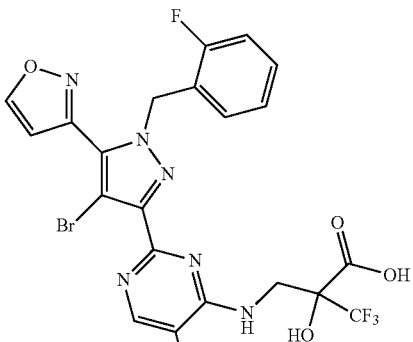 |
| 16 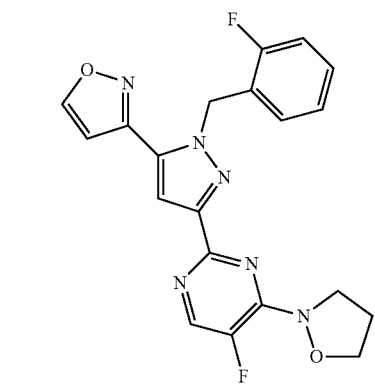 [SMILES: Fc1ccccc1Cn1nc(-c2ncc(F)c(N3CCCO3)n2)cc1-c1ccon1] | 26 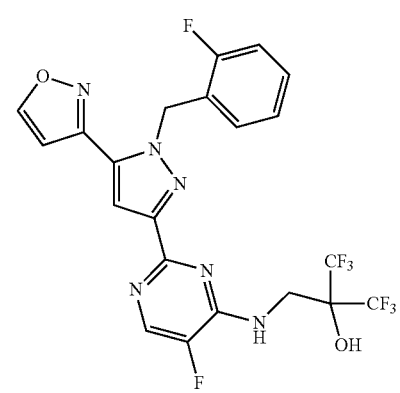 |
| 17 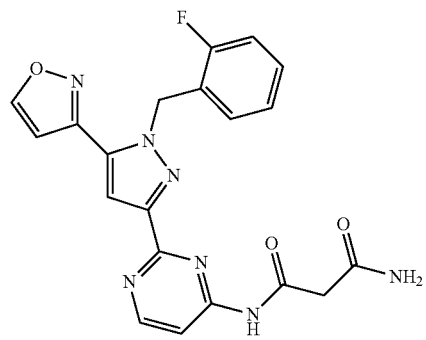 [SMILES: NC(=O)CC(=O)Nc1ccnc(-c2cc(-c3ccon3)n(Cc3ccccc3F)n2)n1] | 27 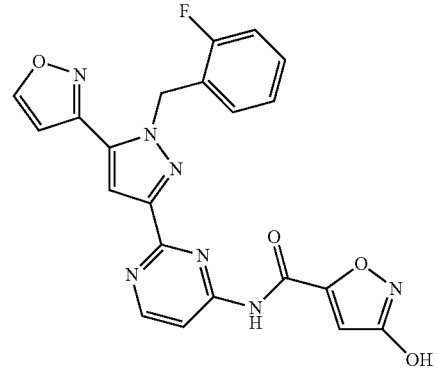 |
| 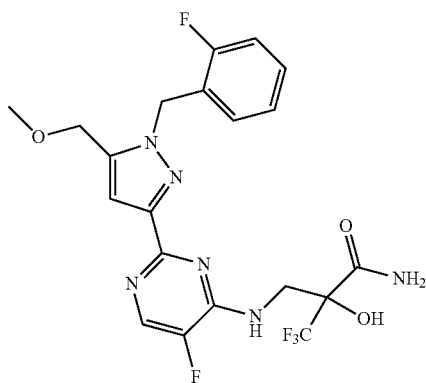 [SMILES: COCc1cc(-c2ncc(F)c(NCC(O)(C(N)=O)C(F)(F)F)n2)nn1Cc1ccccc1F] | 28 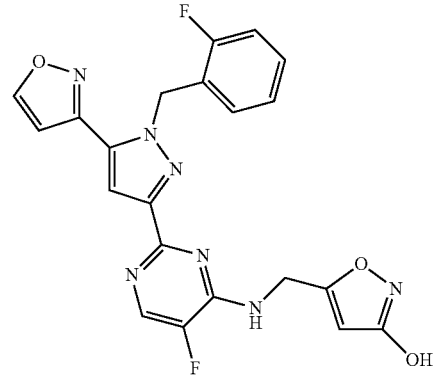 [SMILES: Oc1cc(CNc2nc(-c3cc(-c4ccon4)n(Cc4ccccc4F)n3)ncc2F)on1] |

TABLE XIV-continued
30
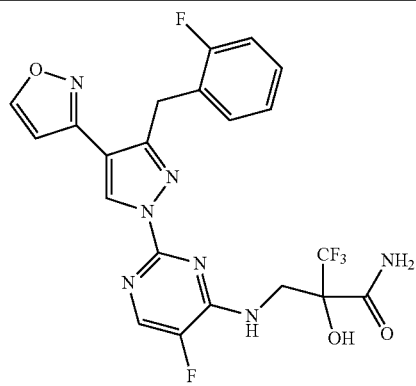
32
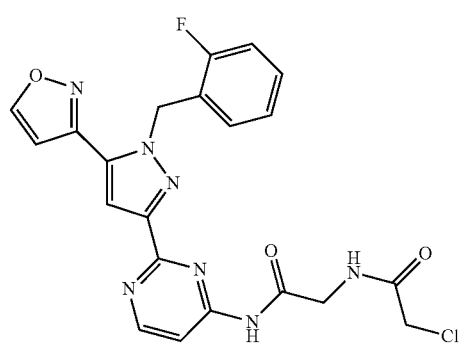 [SMILES: O=C(CCl)NCC(=O)Nc1ccnc(-c2cc(-c3ccon3)n(Cc3ccccc3F)n2)n1]
33
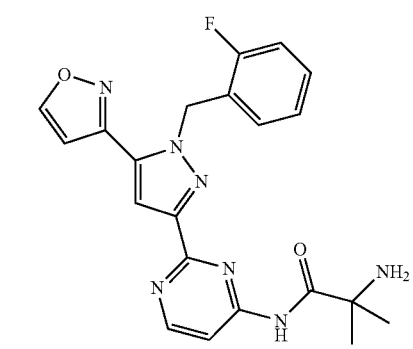 [SMILES: CC(C)(N)C(=O)Nc1ccnc(-c2cc(-c3ccon3)n(Cc3ccccc3F)n2)n1]
34
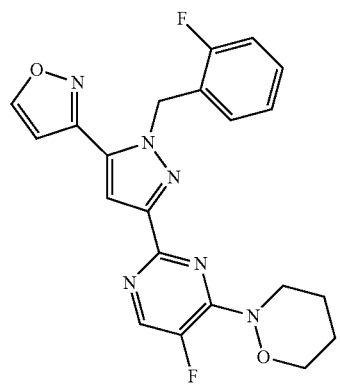 [SMILES: Fc1ccccc1Cn1nc(-c2ncc(F)c(N3CCCCO3)n2)cc1-c1ccon1]
TABLE XIV-continued
35
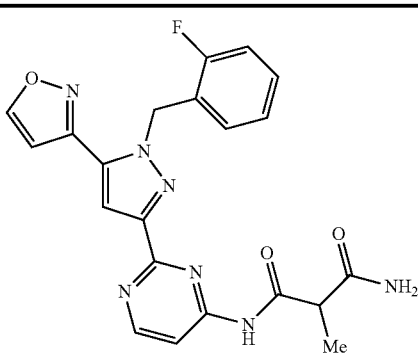
36
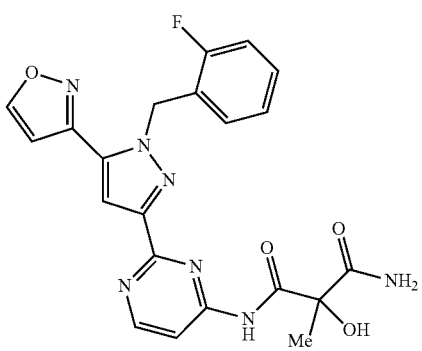 [SMILES: CC(O)(C(N)=O)C(=O)Nc1ccnc(-c2cc(-c3ccon3)n(Cc3ccccc3F)n2)n1]
38
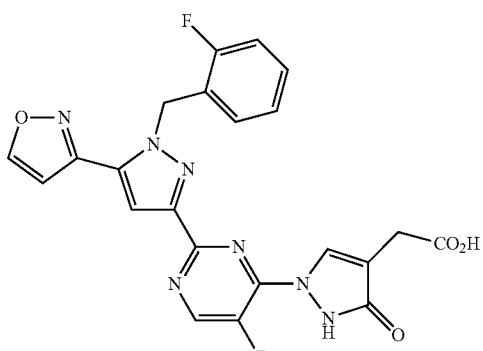
39
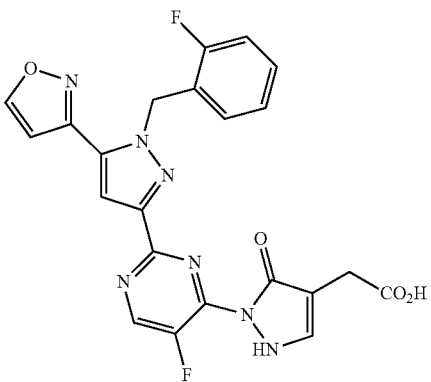 [SMILES: O=C(O)Cc1c[nH]n(-c2nc(-c3cc(-c4ccon4)n(Cc4ccccc4F)n3)ncc2F)c1=O]

TABLE XIV-continued
| | |
|---|---|
| 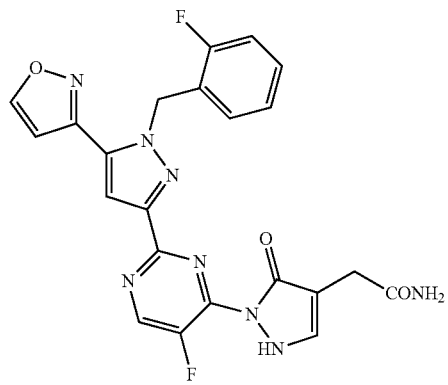 [SMILES: NC(=O)Cc1c[nH]n(-c2nc(-c3cc(-c4ccon4)n(Cc4ccccc4F)n3)ncc2F)c1=O] | 40 |
| 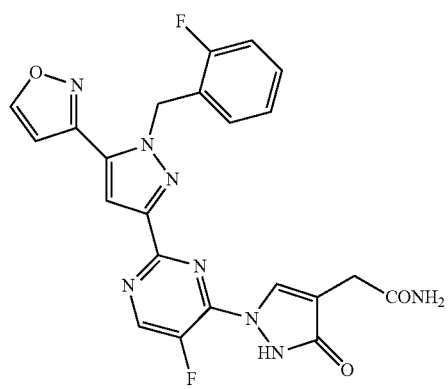 [SMILES: NC(=O)Cc1cn(-c2nc(-c3cc(-c4ccon4)n(Cc4ccccc4F)n3)ncc2F)[nH]c1=O] | 41 |
| 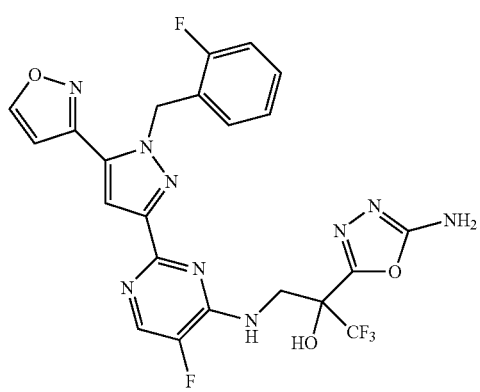 [SMILES: Nc1nnc(C(O)(CNc2nc(-c3cc(-c4ccon4)n(Cc4ccccc4F)n3)ncc2F)C(F)(F)F)o1] | 42 |
| 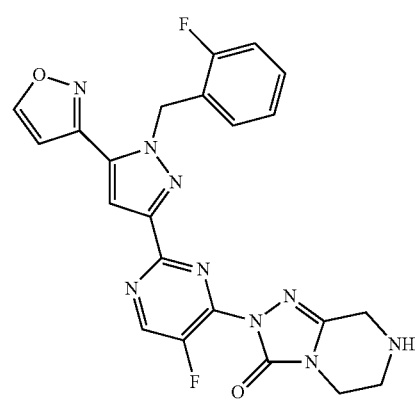 [SMILES: O=c1n(-c2nc(-c3cc(-c4ccon4)n(Cc4ccccc4F)n3)ncc2F)nc2n1CCNC2] | 43 |
| 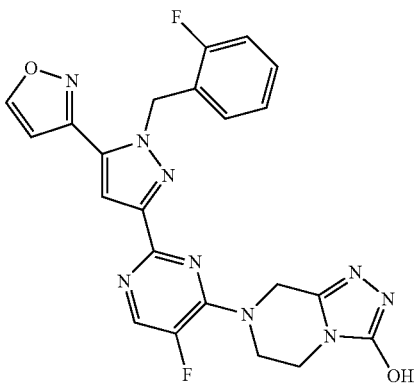 [SMILES: Oc1nnc2n1CCN(c1nc(-c3cc(-c4ccon4)n(Cc4ccccc4F)n3)ncc1F)C2] | 44 |
| 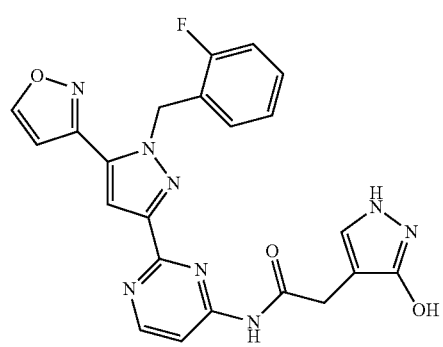 [SMILES: O=C(Cc1c[nH]nc1O)Nc1ccnc(-c2cc(-c3ccon3)n(Cc3ccccc3F)n2)n1] | 45 |
| 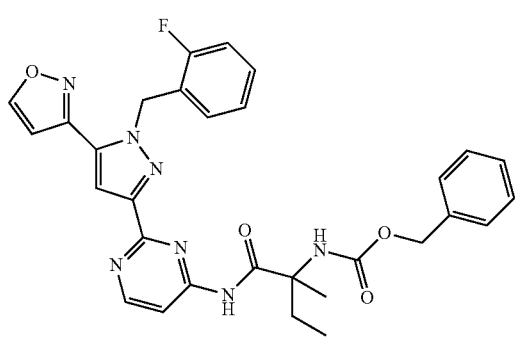 [SMILES: CCC(C)(NC(=O)OCc1ccccc1)C(=O)Nc1ccnc(-c2cc(-c3ccon3)n(Cc3ccccc3F)n2)n1] | 46 |
| 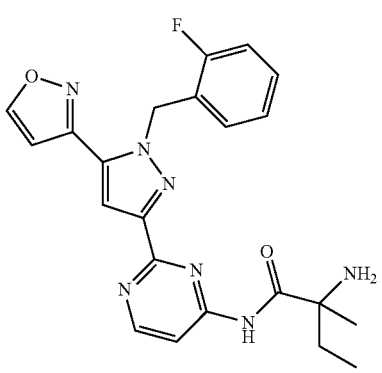 [SMILES: CCC(C)(N)C(=O)Nc1ccnc(-c2cc(-c3ccon3)n(Cc3ccccc3F)n2)n1] | 47 |

TABLE XIV-continued
48
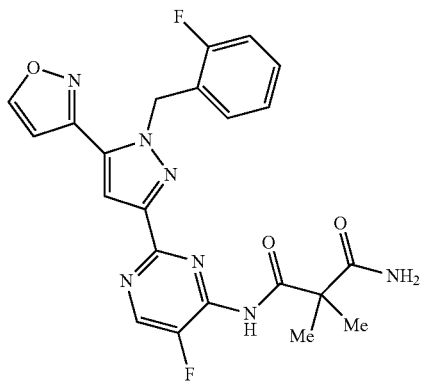 [SMILES: CC(C)(C(N)=O)C(=O)Nc1nc(-c2cc(-c3ccon3)n(Cc3ccccc3F)n2)ncc1F]
49
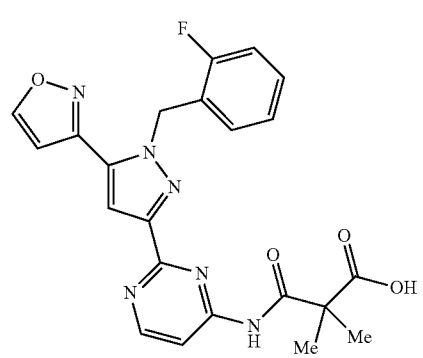 [SMILES: CC(C)(C(=O)O)C(=O)Nc1ccnc(-c2cc(-c3ccon3)n(Cc3ccccc3F)n2)n1]
50
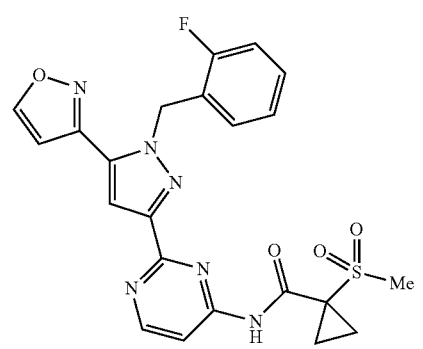 [SMILES: CS(=O)(=O)C1(C(=O)Nc2ccnc(-c3cc(-c4ccon4)n(Cc4ccccc4F)n3)n2)CC1]
51
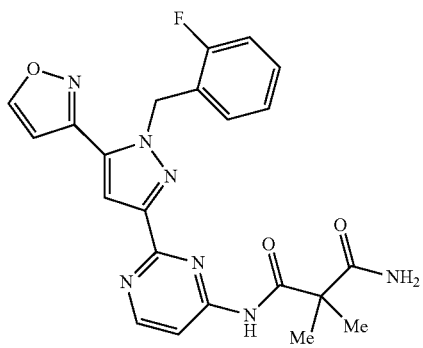 [SMILES: CC(C)(C(N)=O)C(=O)Nc1ccnc(-c2cc(-c3ccon3)n(Cc3ccccc3F)n2)n1]
TABLE XIV-continued
52
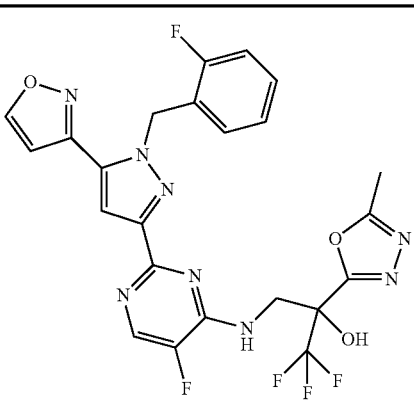
54
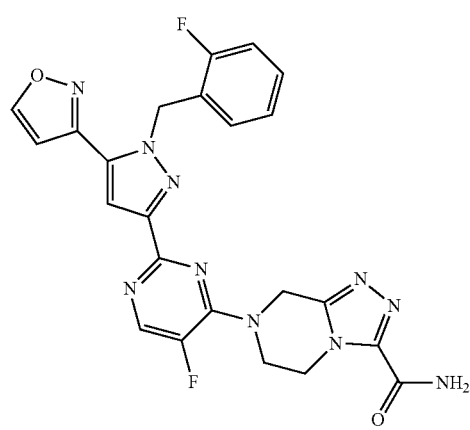 [SMILES: NC(=O)c1nnc2n1CCN(c1nc(-c3cc(-c4ccon4)n(Cc4ccccc4F)n3)ncc1F)C2]
55
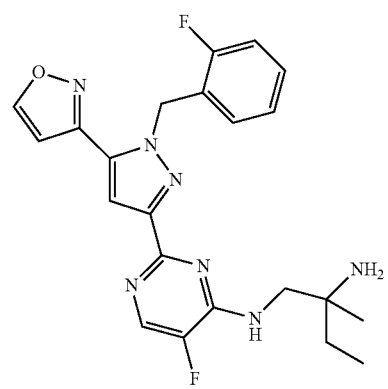 [SMILES: CCC(C)(N)CNc1nc(-c2cc(-c3ccon3)n(Cc3ccccc3F)n2)ncc1F]
56
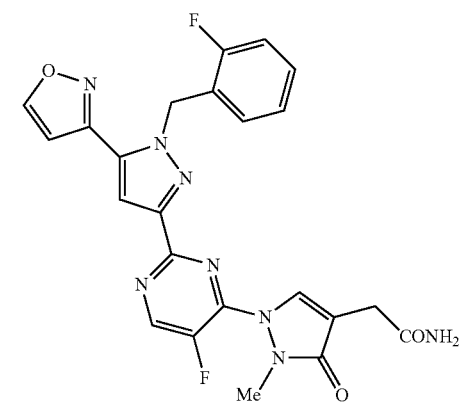 [SMILES: Cn1c(=O)c(CC(N)=O)cn1-c1nc(-c2cc(-c3ccon3)n(Cc3ccccc3F)n2)ncc1F]

TABLE XIV-continued
57
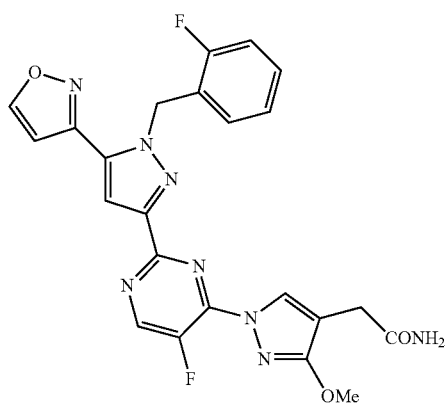 [SMILES: COc1nn(-c2nc(-c3cc(-c4ccon4)n(Cc4ccccc4F)n3)ncc2F)cc1CC(N)=O]
59
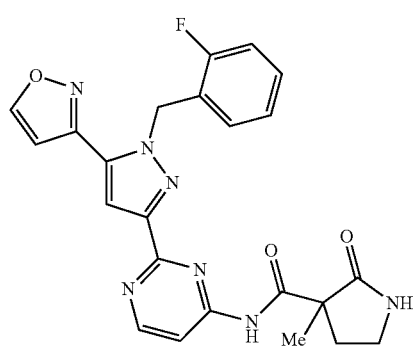 [SMILES: CC1(C(=O)Nc2ccnc(-c3cc(-c4ccon4)n(Cc4ccccc4F)n3)n2)CCNC1=O]
60
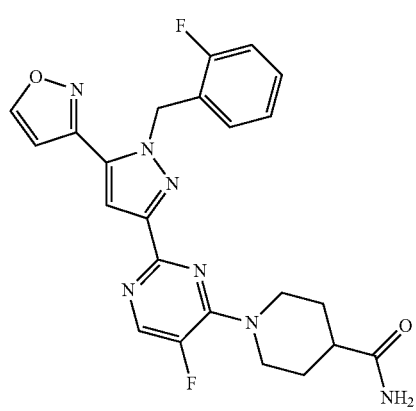 [SMILES: NC(=O)C1CCN(c2nc(-c3cc(-c4ccon4)n(Cc4ccccc4F)n3)ncc2F)CC1]
62
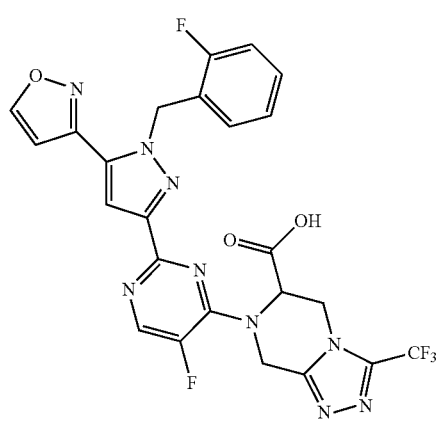 [SMILES: O=C(O)C1Cn2c(nnc2C(F)(F)F)CN1c1nc(-c2cc(-c3ccon3)n(Cc3ccccc3F)n2)ncc1F]
TABLE XIV-continued
64
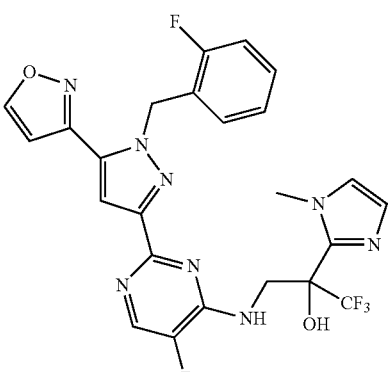
65
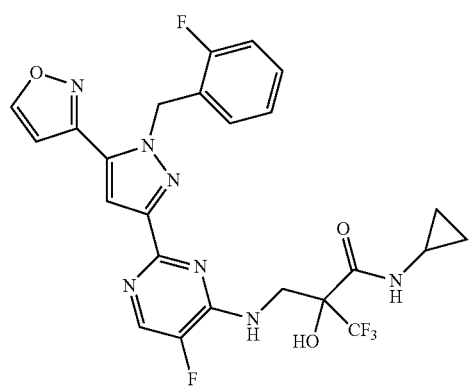 [SMILES: O=C(NC1CC1)C(O)(CNc1nc(-c2cc(-c3ccon3)n(Cc3ccccc3F)n2)ncc1F)C(F)(F)F]
66
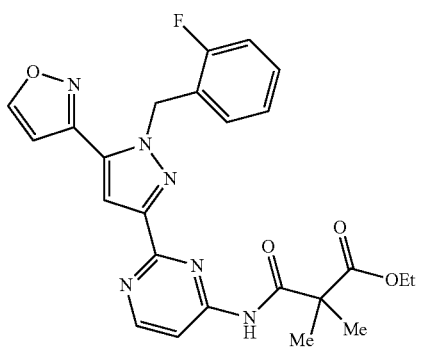 [SMILES: CCOC(=O)C(C)(C)C(=O)Nc1ccnc(-c2cc(-c3ccon3)n(Cc3ccccc3F)n2)n1]
67
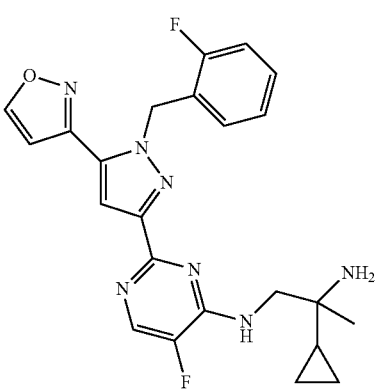 [SMILES: CC(N)(CNc1nc(-c2cc(-c3ccon3)n(Cc3ccccc3F)n2)ncc1F)C1CC1]

TABLE XIV-continued
| | |
|---|---|
| 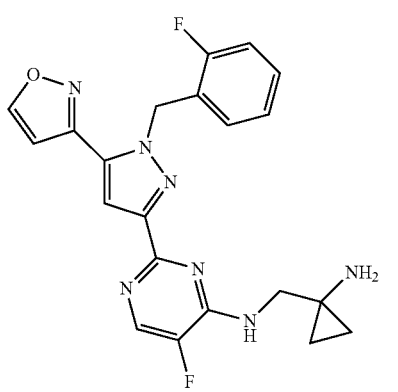 [SMILES: NC1(CNc2nc(-c3cc(-c4ccon4)n(Cc4ccccc4F)n3)ncc2F)CC1] | 68 |
| 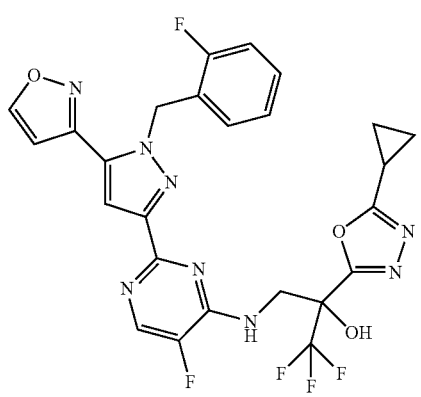 [SMILES: OC(CNc1nc(-c2cc(-c3ccon3)n(Cc3ccccc3F)n2)ncc1F)(c1nnc(C2CC2)o1)C(F)(F)F] | 69 |
| 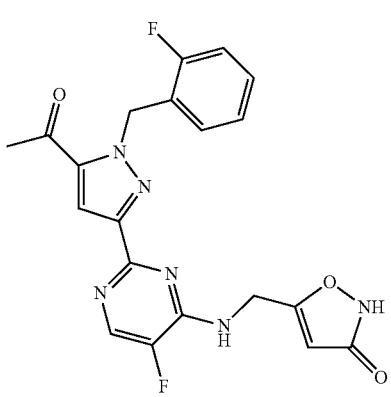 [SMILES: CC(=O)c1cc(-c2ncc(F)c(NCc3cc(=O)[nH]o3)n2)nn1Cc1ccccc1F] | 70 |
| 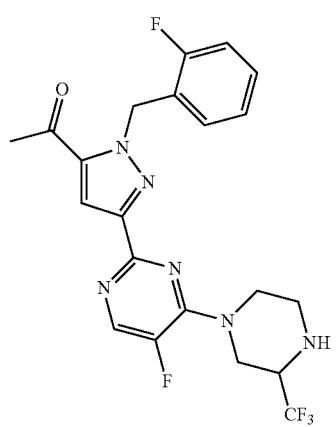 [SMILES: CC(=O)c1cc(-c2ncc(F)c(N3CCNC(C(F)(F)F)C3)n2)nn1Cc1ccccc1F] | 71 |
TABLE XIV-continued
| | |
|---|---|
| 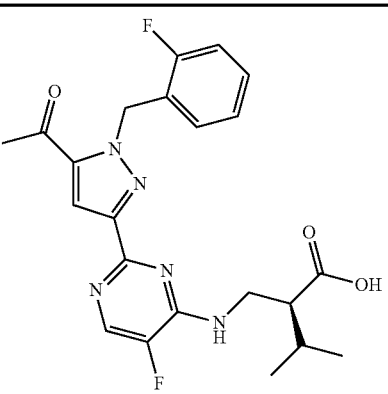 | 72 |
| 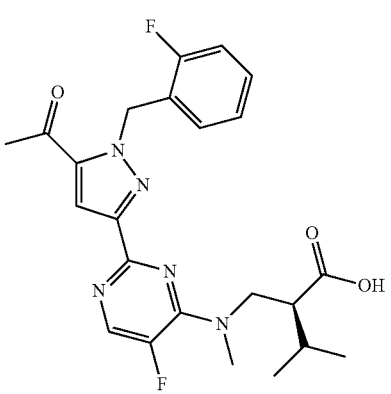 [SMILES: CC(=O)c1cc(-c2ncc(F)c(N(C)C[C@@H](C(=O)O)C(C)C)n2)nn1Cc1ccccc1F] | 73 |
| 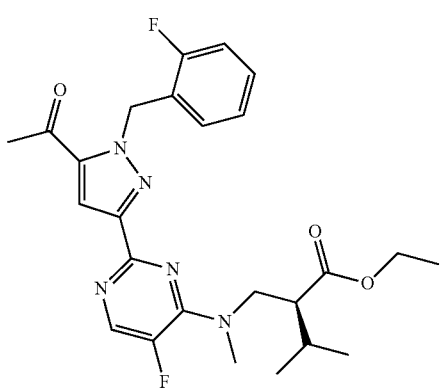 [SMILES: CCOC(=O)[C@H](CN(C)c1nc(-c2cc(C(C)=O)n(Cc3ccccc3F)n2)ncc1F)C(C)C] | 74 |
| 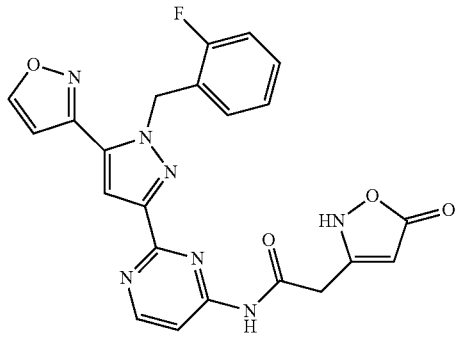 [SMILES: O=C(Cc1cc(=O)o[nH]1)Nc1ccnc(-c2cc(-c3ccon3)n(Cc3ccccc3F)n2)n1] | 75 |

TABLE XIV-continued
76
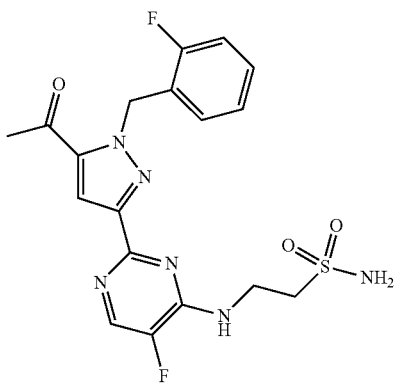 [SMILES: CC(=O)c1cc(-c2ncc(F)c(NCCS(N)(=O)=O)n2)nn1Cc1ccccc1F]
77
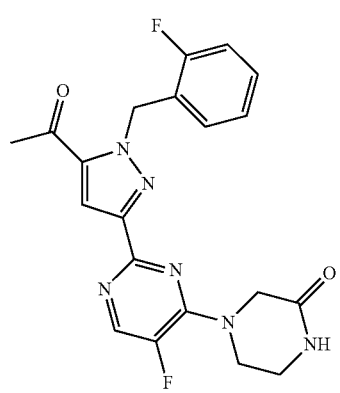 [SMILES: CC(=O)c1cc(-c2ncc(F)c(N3CCNC(=O)C3)n2)nn1Cc1ccccc1F]
78
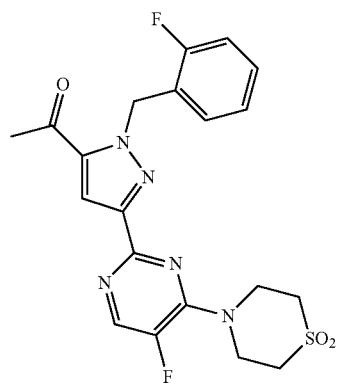 [SMILES: CC(=O)c1cc(-c2ncc(F)c(N3CCS(=O)(=O)CC3)n2)nn1Cc1ccccc1F]
79
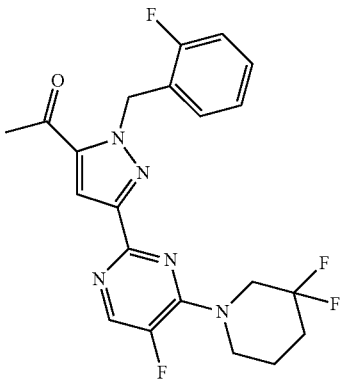 [SMILES: CC(=O)c1cc(-c2ncc(F)c(N3CCCC(F)(F)C3)n2)nn1Cc1ccccc1F]
TABLE XIV-continued
80
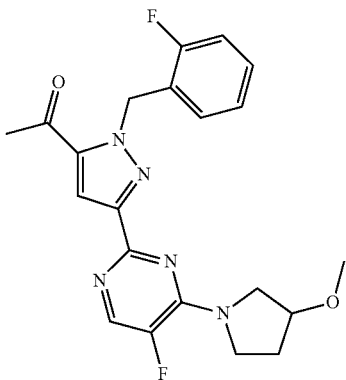 [SMILES: COC1CCN(c2nc(-c3cc(C(C)=O)n(Cc4ccccc4F)n3)ncc2F)C1]
81
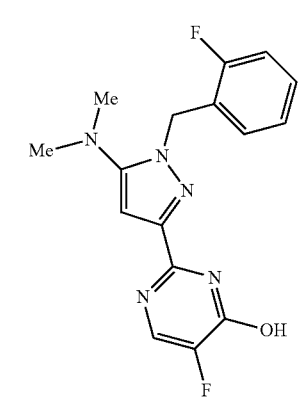 [SMILES: CN(C)c1cc(-c2ncc(F)c(O)n2)nn1Cc1ccccc1F]
82
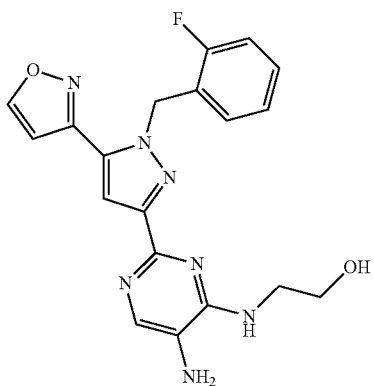 [SMILES: Nc1cnc(-c2cc(-c3ccon3)n(Cc3ccccc3F)n2)nc1NCCO]
83
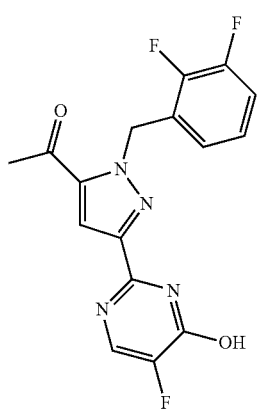 [SMILES: CC(=O)c1cc(-c2ncc(F)c(O)n2)nn1Cc1cccc(F)c1F]

TABLE XIV-continued
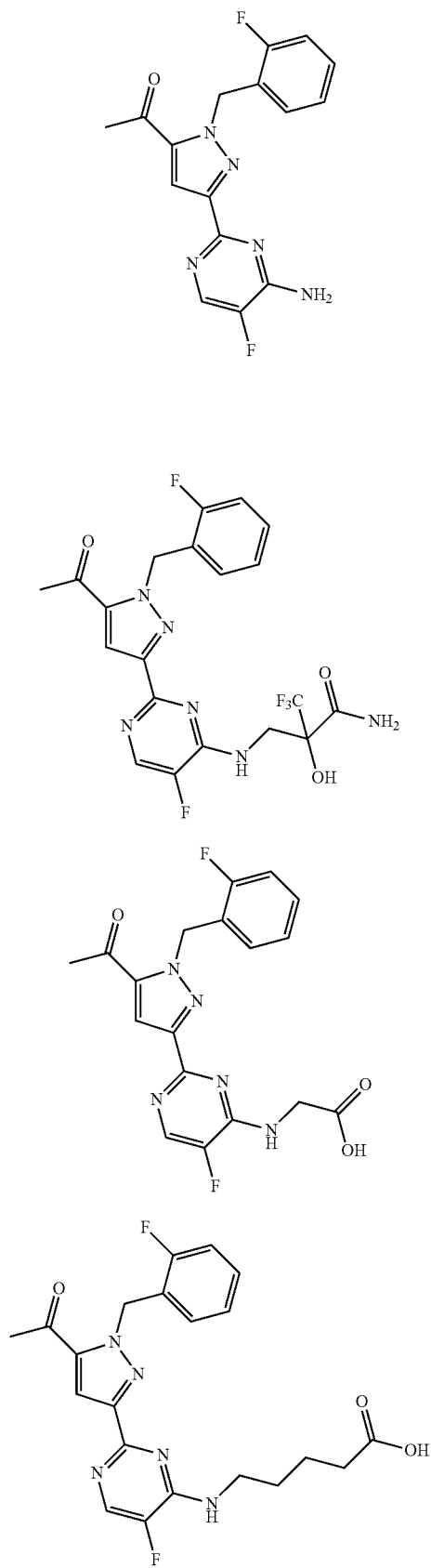
TABLE XIV-continued
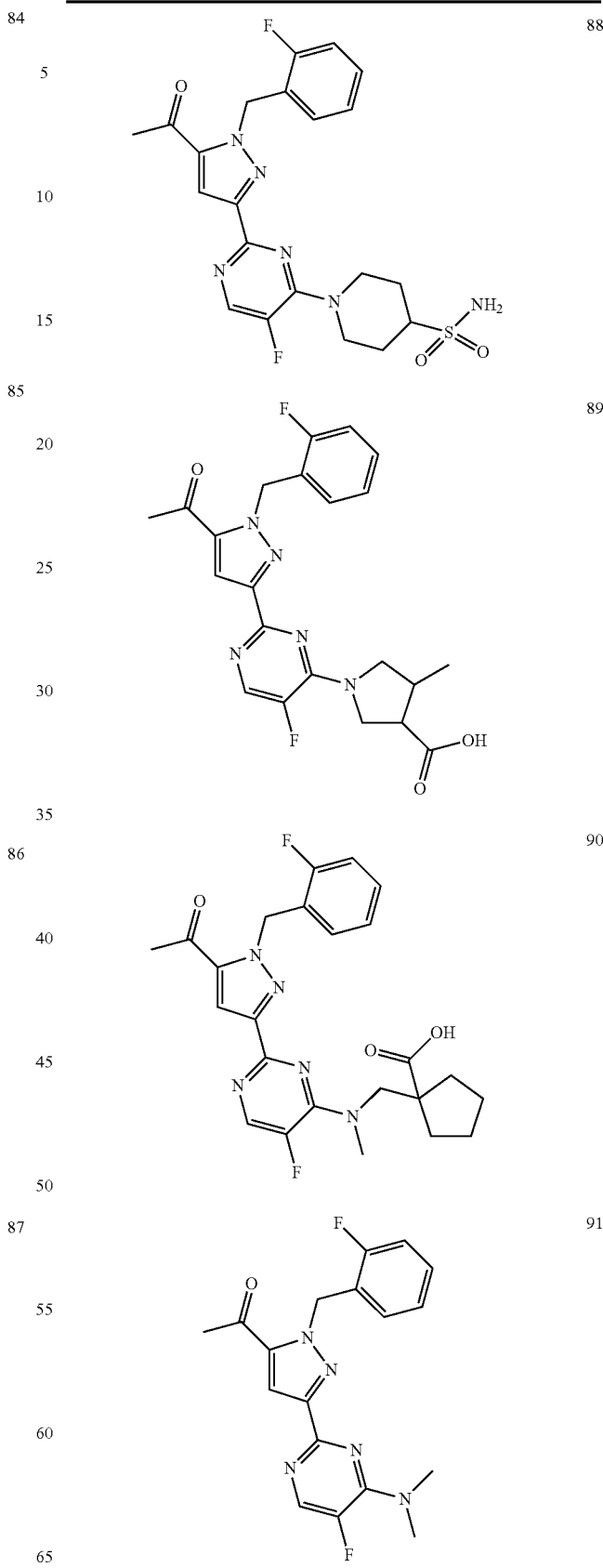

TABLE XIV-continued
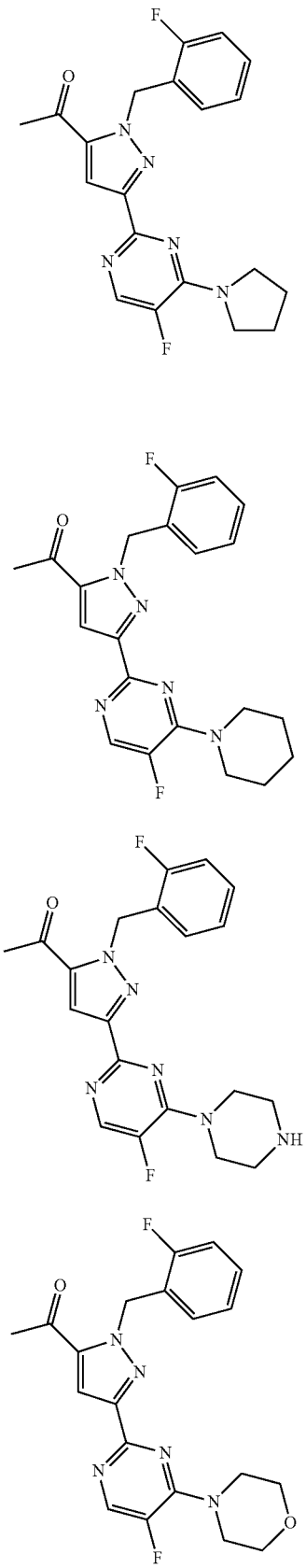
TABLE XIV-continued
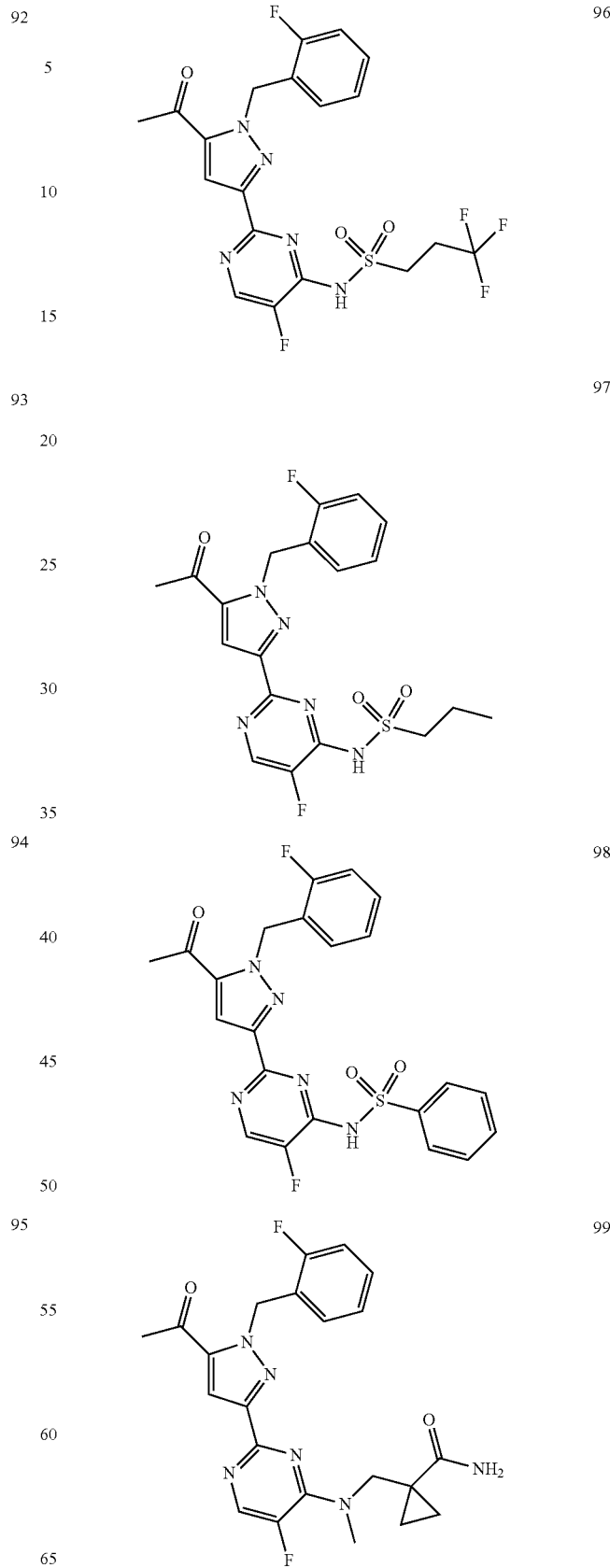

TABLE XIV-continued
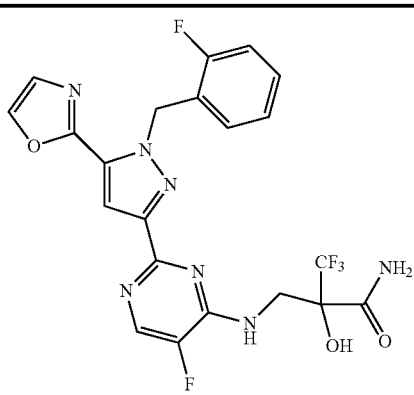
102
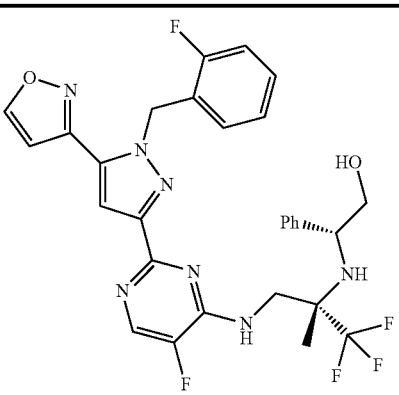
107
103
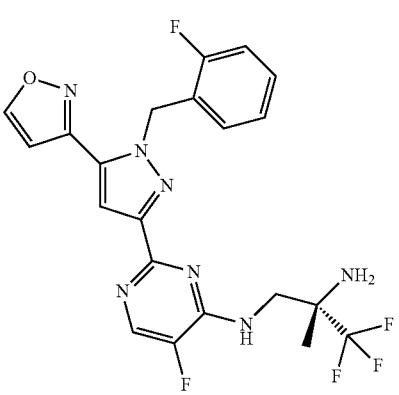 [SMILES: C[C@](N)(CNc1nc(-c2cc(-c3ccon3)n(Cc3ccccc3F)n2)ncc1F)C(F)(F)F]
108
105
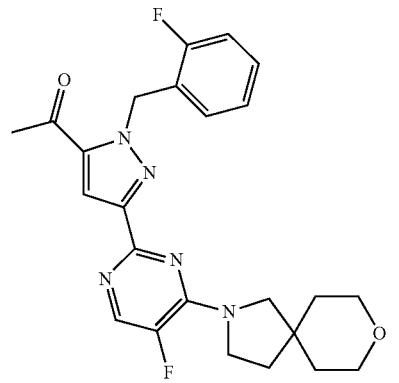 [SMILES: CC(=O)c1cc(-c2ncc(F)c(N3CCC4(CCOCC4)C3)n2)nn1Cc1ccccc1F]
112
106
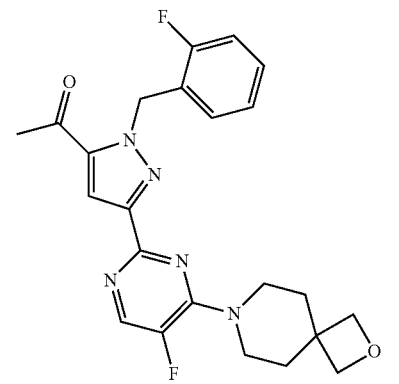 [SMILES: CC(=O)c1cc(-c2ncc(F)c(N3CCC4(CC3)COC4)n2)nn1Cc1ccccc1F]
113

TABLE XIV-continued
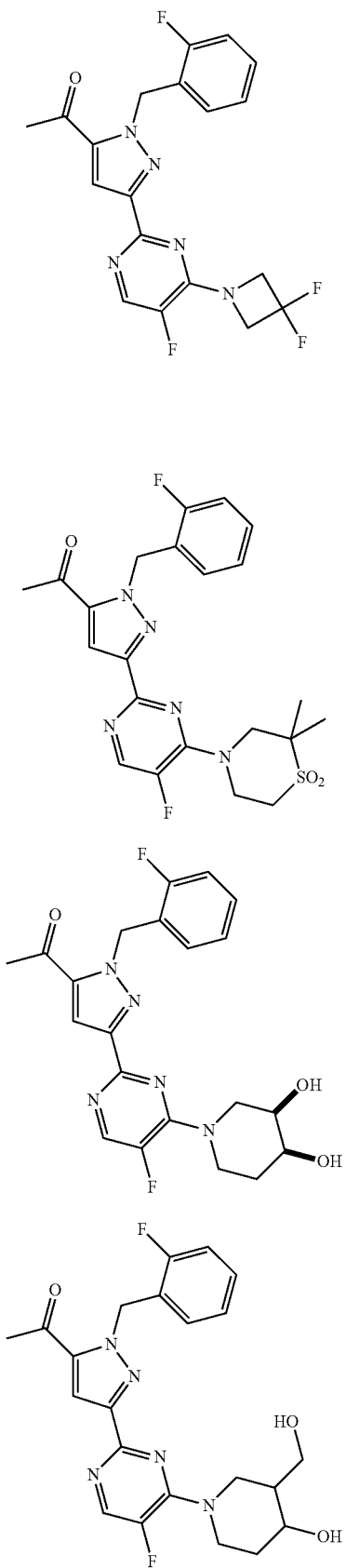
TABLE XIV-continued
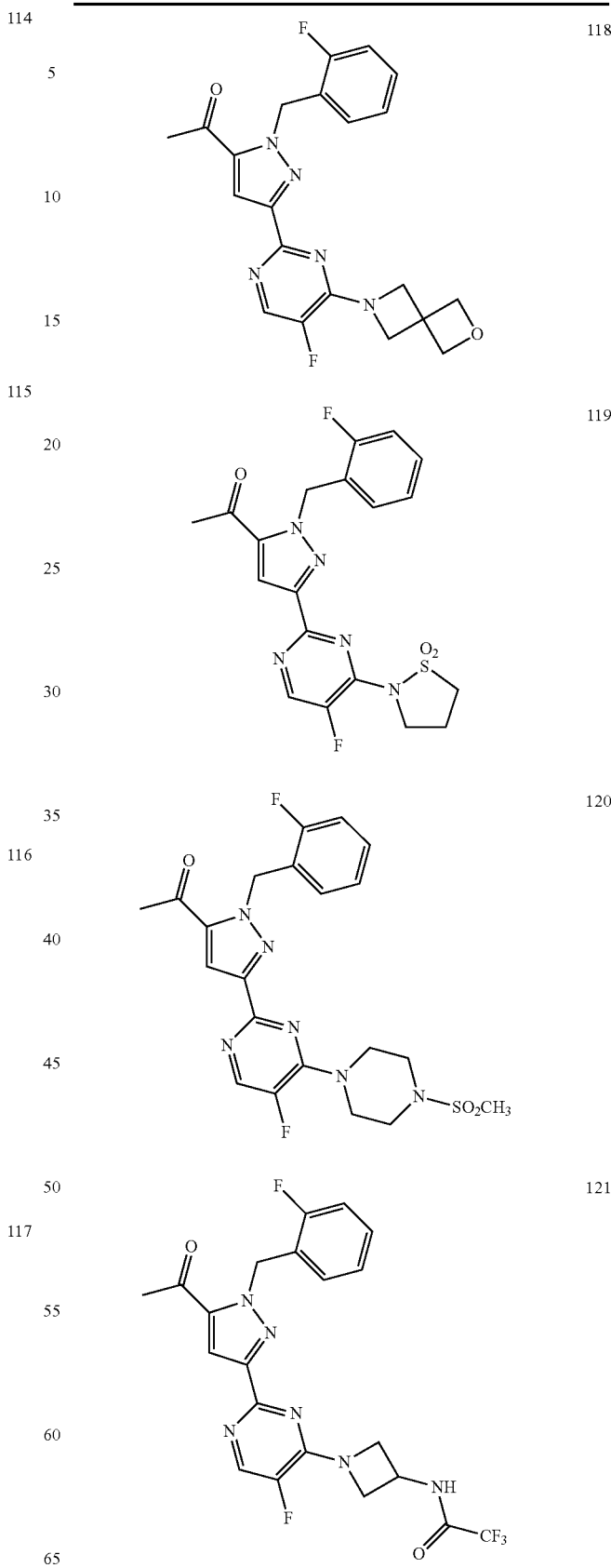

TABLE XIV-continued
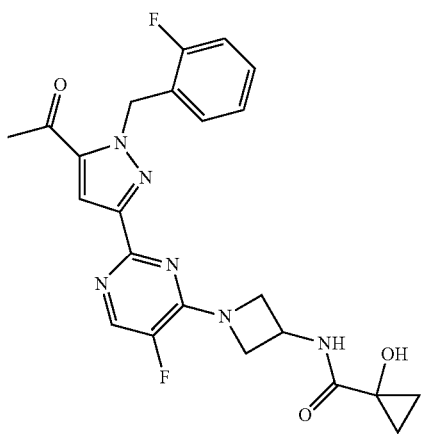 [SMILES: CC(=O)c1cc(-c2ncc(F)c(N3CC(NC(=O)C4(O)CC4)C3)n2)nn1Cc1ccccc1F]
122
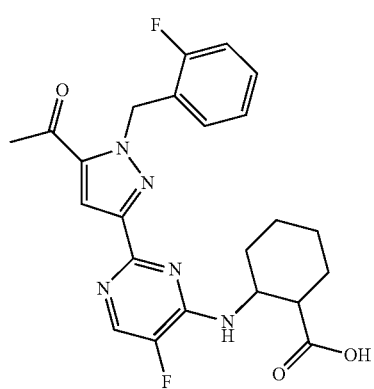 [SMILES: CC(=O)c1cc(-c2ncc(F)c(NC3CCCCC3C(=O)O)n2)nn1Cc1ccccc1F]
123
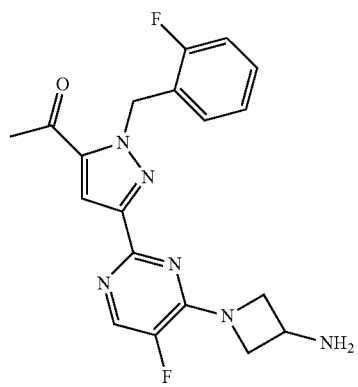 [SMILES: CC(=O)c1cc(-c2ncc(F)c(N3CC(N)C3)n2)nn1Cc1ccccc1F]
124
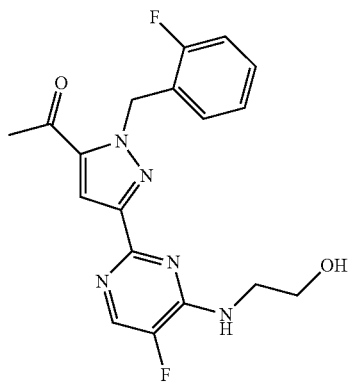 [SMILES: CC(=O)c1cc(-c2ncc(F)c(NCCO)n2)nn1Cc1ccccc1F]
125
TABLE XIV-continued
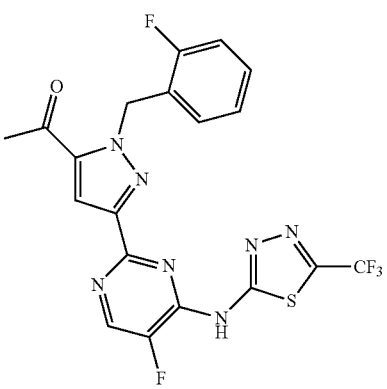 [SMILES: CC(=O)c1cc(-c2ncc(F)c(Nc3nnc(C(F)(F)F)s3)n2)nn1Cc1ccccc1F]
126
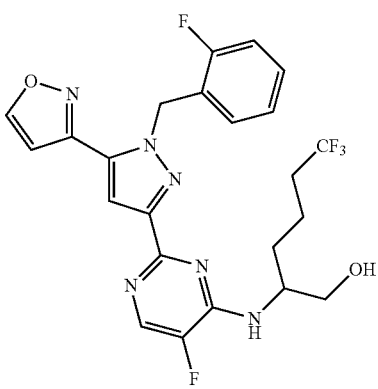 [SMILES: OCC(CCCC(F)(F)F)Nc1nc(-c2cc(-c3ccon3)n(Cc3ccccc3F)n2)ncc1F]
127
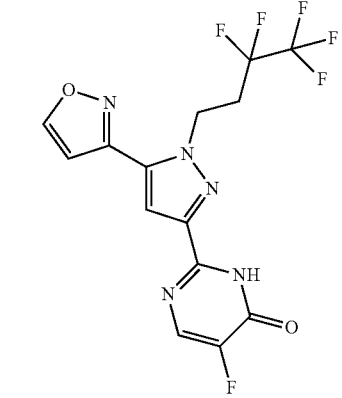 [SMILES: O=c1[nH]c(-c2cc(-c3ccon3)n(CCC(F)(F)C(F)(F)F)n2)ncc1F]
128
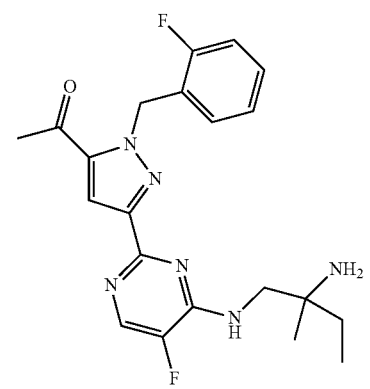 [SMILES: CCC(C)(N)CNc1nc(-c2cc(C(C)=O)n(Cc3ccccc3F)n2)ncc1F]
129

TABLE XIV-continued
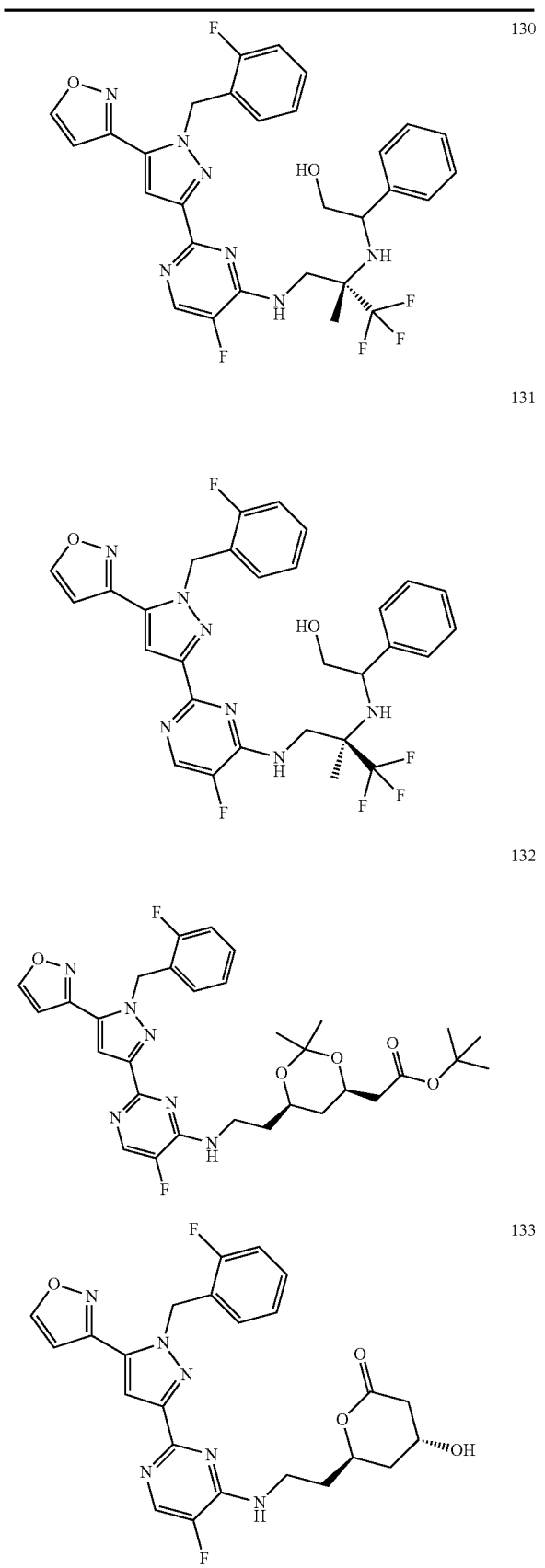
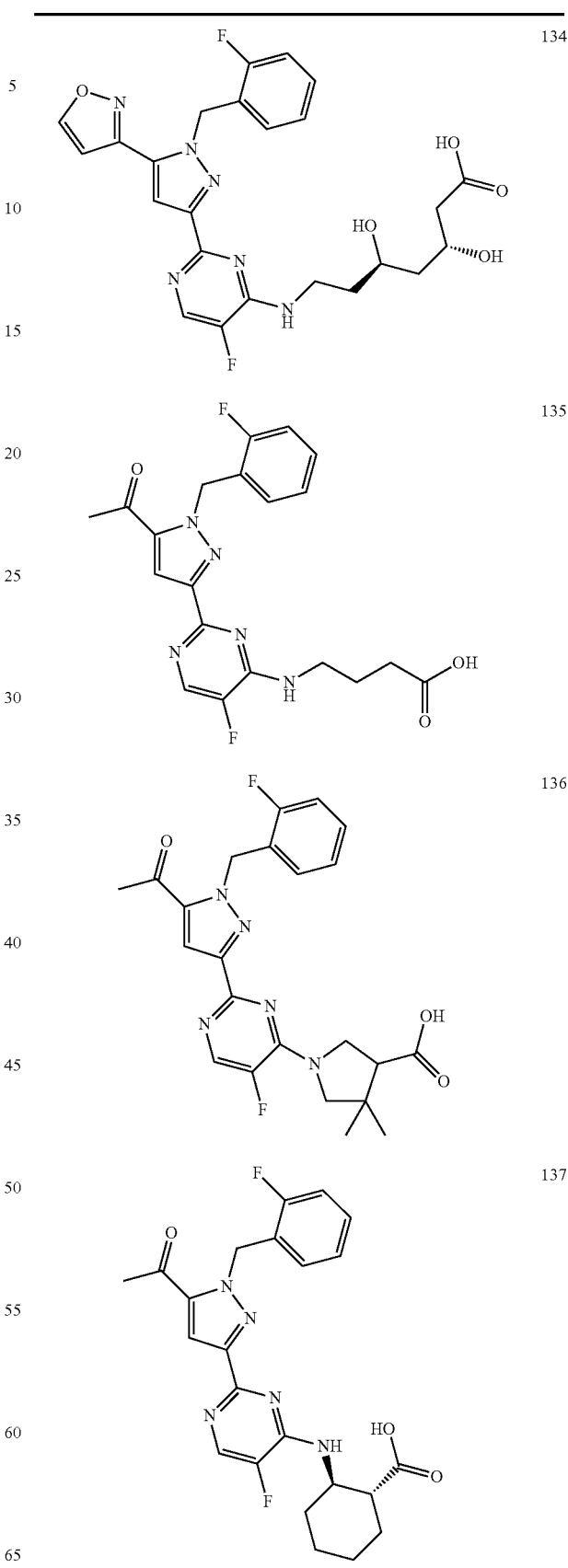

TABLE XIV-continued
138
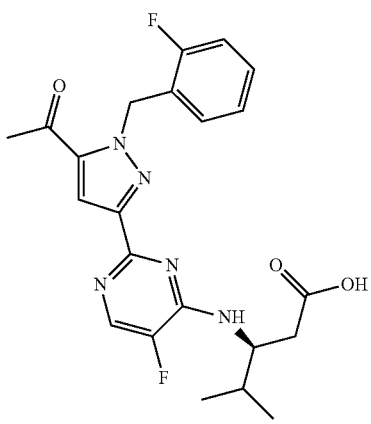 [SMILES: CC(=O)c1cc(-c2ncc(F)c(N[C@@H](CC(=O)O)C(C)C)n2)nn1Cc1ccccc1F]
139
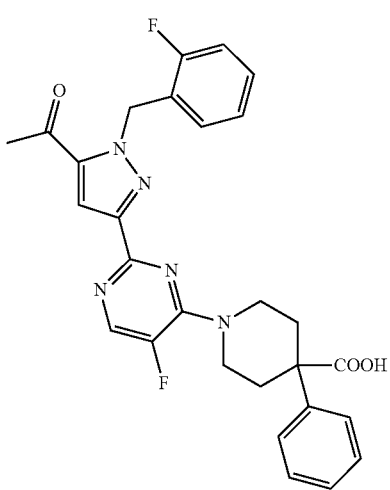 [SMILES: CC(=O)c1cc(-c2ncc(F)c(N3CCC(C(=O)O)(c4ccccc4)CC3)n2)nn1Cc1ccccc1F]
140
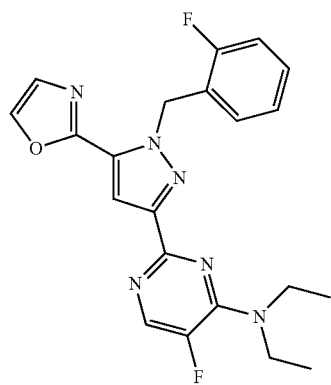 [SMILES: CCN(CC)c1nc(-c2cc(-c3ncco3)n(Cc3ccccc3F)n2)ncc1F]
TABLE XIV-continued
141
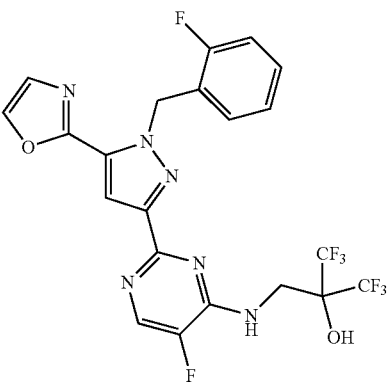 [SMILES: OC(CNc1nc(-c2cc(-c3ncco3)n(Cc3ccccc3F)n2)ncc1F)(C(F)(F)F)C(F)(F)F]
147
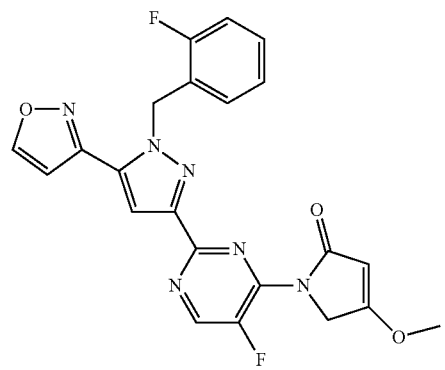 [SMILES: COC1=CC(=O)N(c2nc(-c3cc(-c4ccon4)n(Cc4ccccc4F)n3)ncc2F)C1]
148
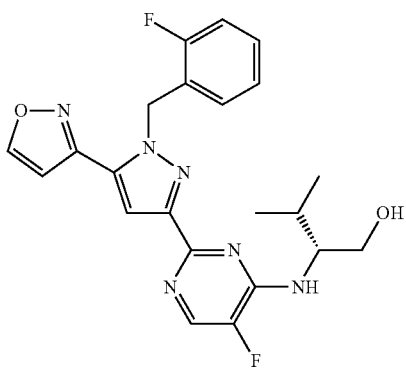 [SMILES: CC(C)[C@H](CO)Nc1nc(-c2cc(-c3ccon3)n(Cc3ccccc3F)n2)ncc1F]
149
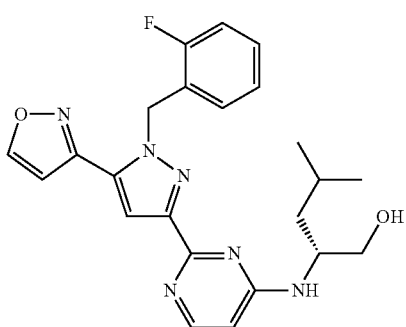

TABLE XIV-continued
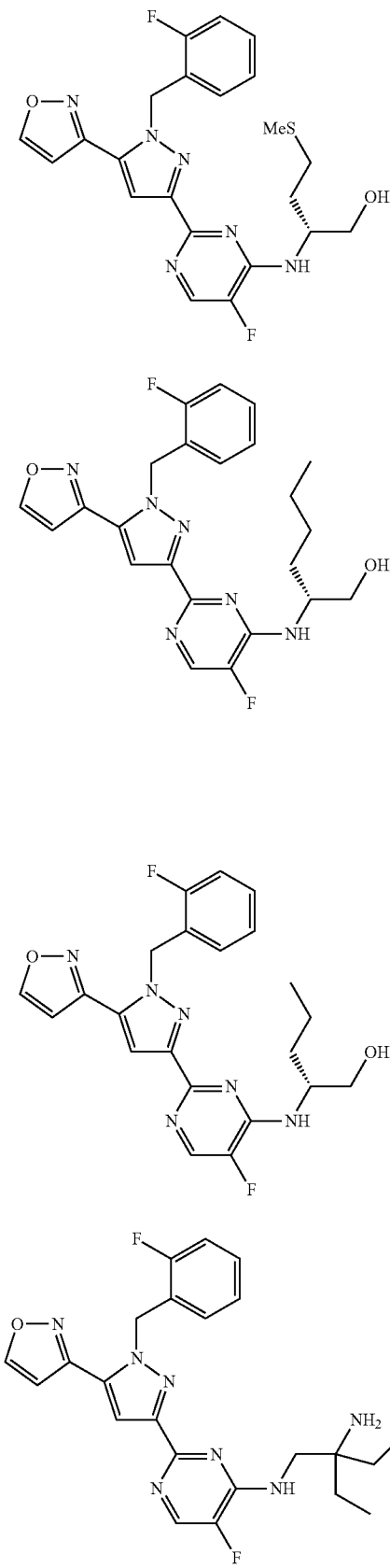
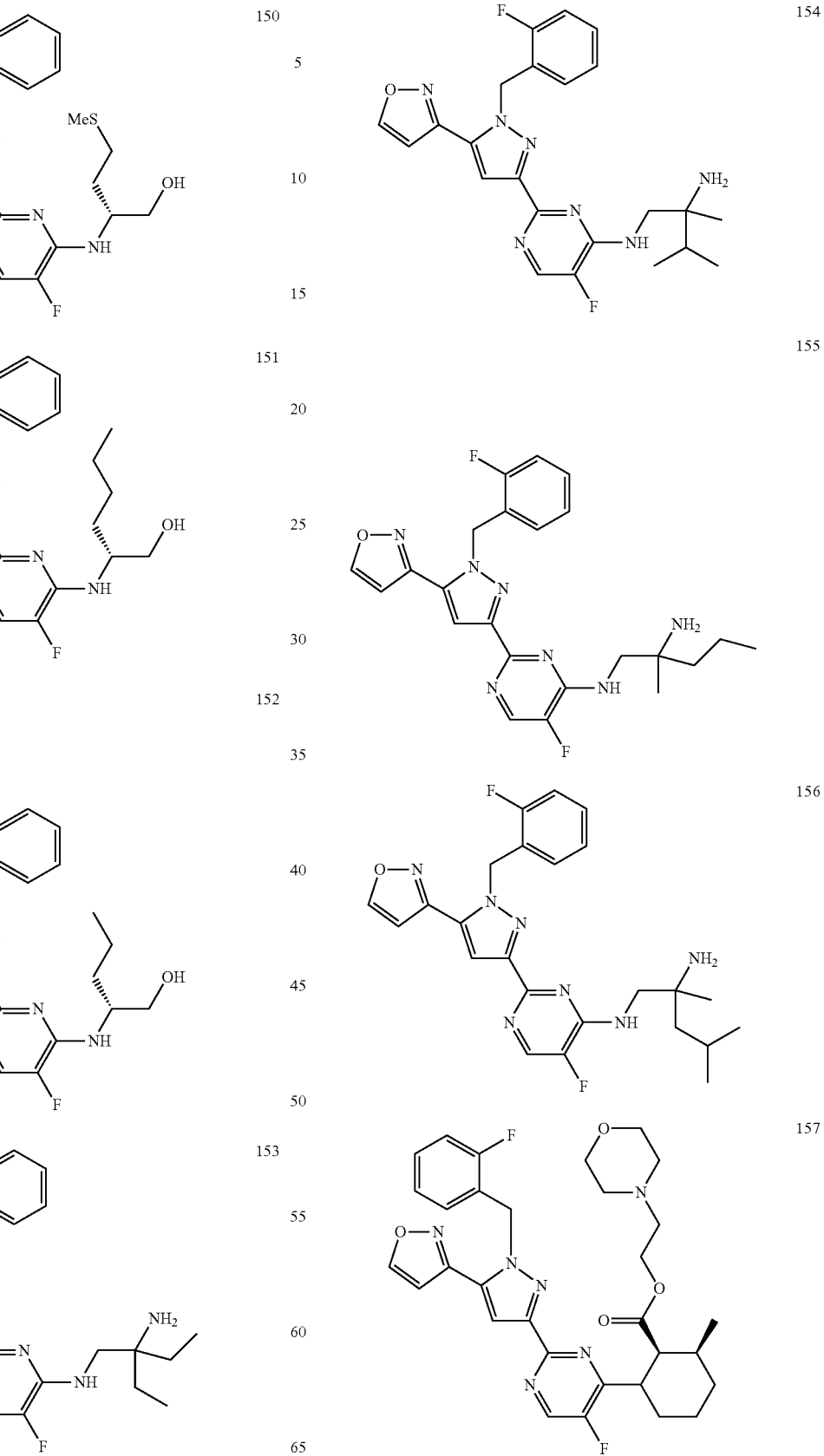

TABLE XIV-continued
158
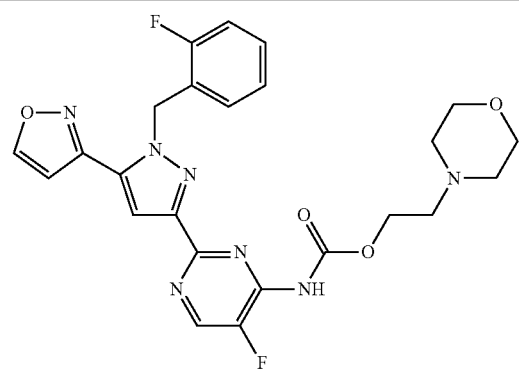 [SMILES: O=C(Nc1nc(-c2cc(-c3ccon3)n(Cc3ccccc3F)n2)ncc1F)OCCN1CCOCC1]
159
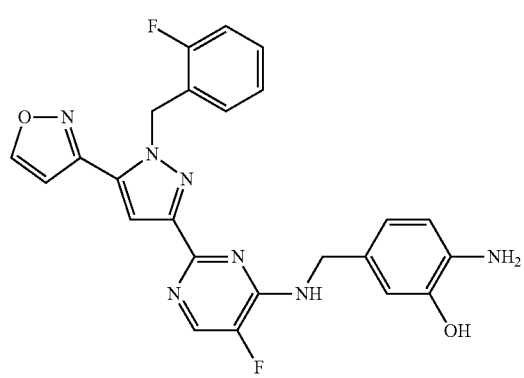 [SMILES: Nc1ccc(CNc2nc(-c3cc(-c4ccon4)n(Cc4ccccc4F)n3)ncc2F)cc1O]
160
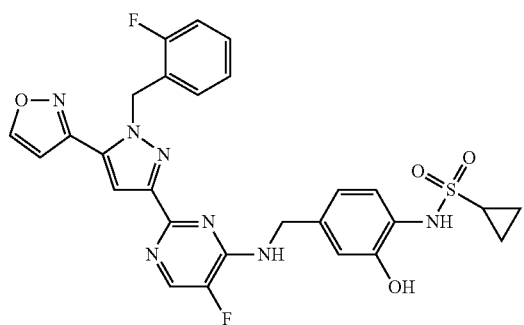 [SMILES: O=S(=O)(Nc1ccc(CNc2nc(-c3cc(-c4ccon4)n(Cc4ccccc4F)n3)ncc2F)cc1O)C1CC1]
161
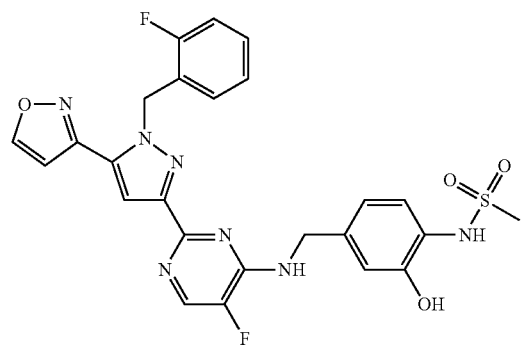 [SMILES: CS(=O)(=O)Nc1ccc(CNc2nc(-c3cc(-c4ccon4)n(Cc4ccccc4F)n3)ncc2F)cc1O]
TABLE XIV-continued
162
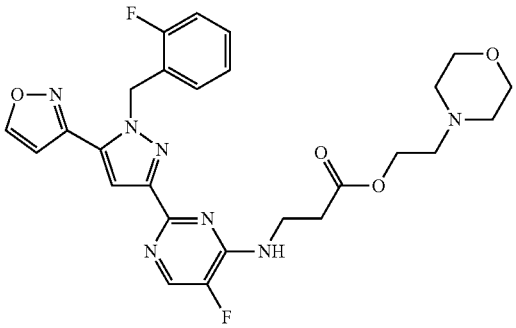 [SMILES: O=C(CCNc1nc(-c2cc(-c3ccon3)n(Cc3ccccc3F)n2)ncc1F)OCCN1CCOCC1]
163
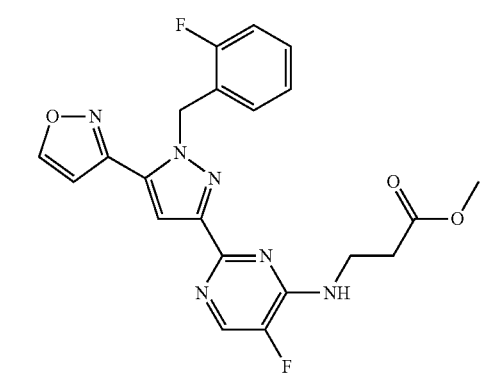 [SMILES: COC(=O)CCNc1nc(-c2cc(-c3ccon3)n(Cc3ccccc3F)n2)ncc1F]
164
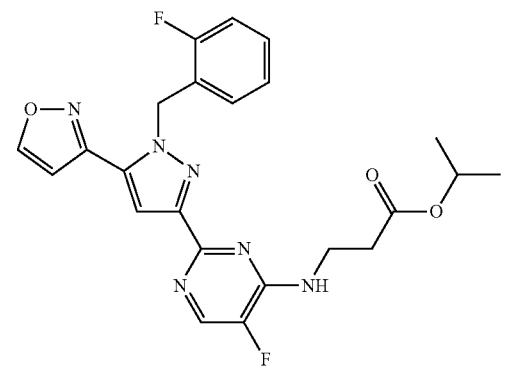 [SMILES: CC(C)OC(=O)CCNc1nc(-c2cc(-c3ccon3)n(Cc3ccccc3F)n2)ncc1F]
165
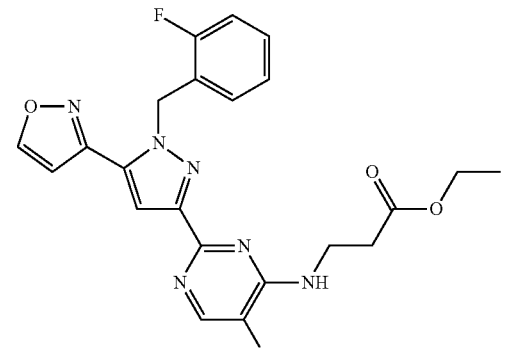

TABLE XIV-continued
166
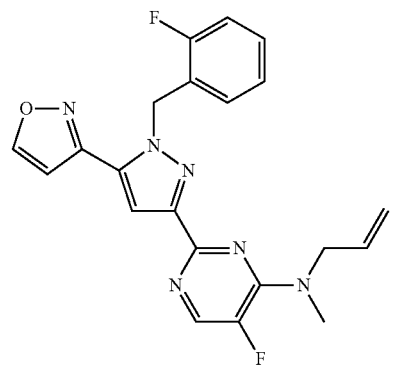 [SMILES: C=CCN(C)c1nc(-c2cc(-c3ccon3)n(Cc3ccccc3F)n2)ncc1F]
167
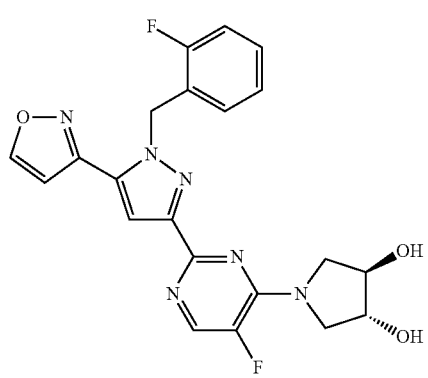 [SMILES: O[C@@H]1CN(c2nc(-c3cc(-c4ccon4)n(Cc4ccccc4F)n3)ncc2F)C[C@H]1O]
168
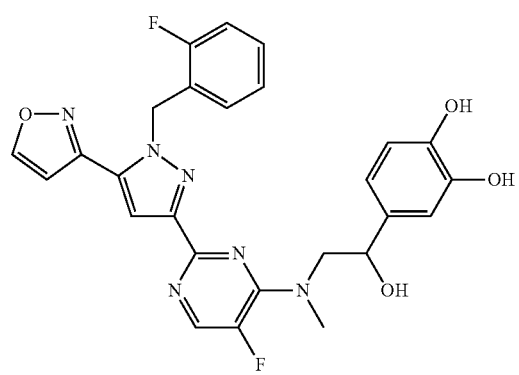 [SMILES: CN(CC(O)c1ccc(O)c(O)c1)c1nc(-c2cc(-c3ccon3)n(Cc3ccccc3F)n2)ncc1F]
169
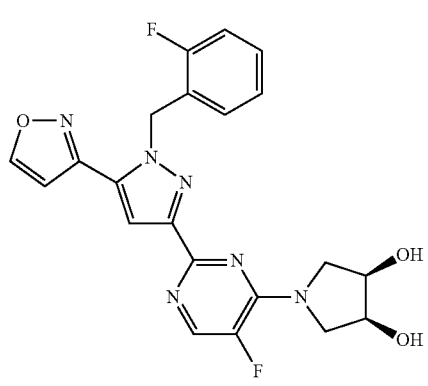 [SMILES: O[C@@H]1CN(c2nc(-c3cc(-c4ccon4)n(Cc4ccccc4F)n3)ncc2F)C[C@@H]1O]
TABLE XIV-continued
170
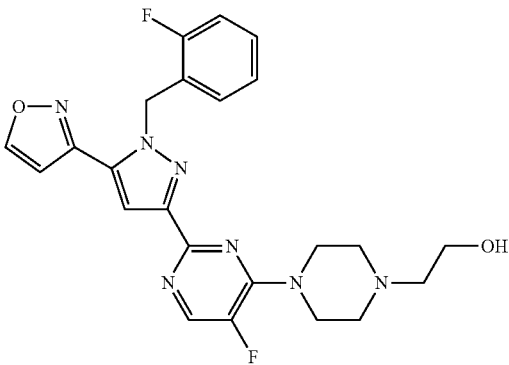 [SMILES: OCCN1CCN(c2nc(-c3cc(-c4ccon4)n(Cc4ccccc4F)n3)ncc2F)CC1]
171
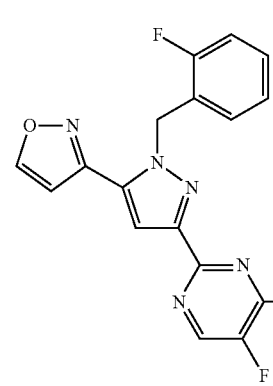
172
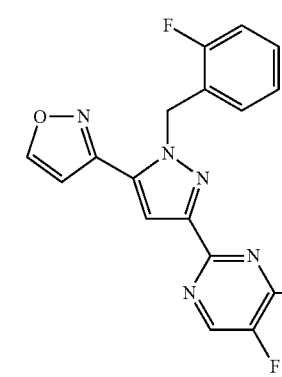
173
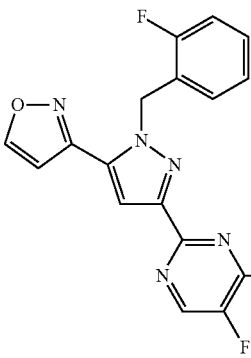

TABLE XIV-continued
174
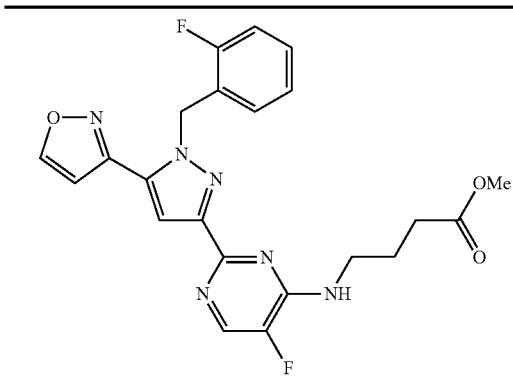
175
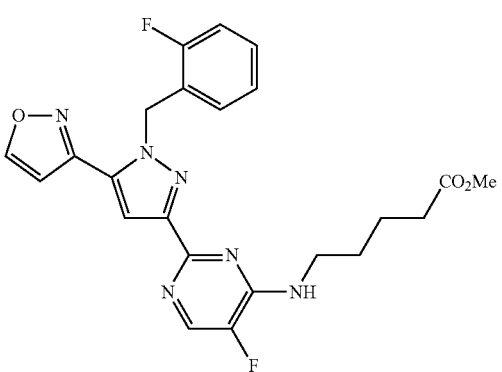 [SMILES: COC(=O)CCCCNc1nc(-c2cc(-c3ccon3)n(Cc3ccccc3F)n2)ncc1F]
176
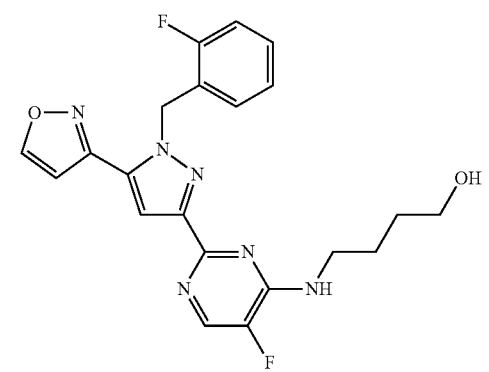 [SMILES: OCCCCNc1nc(-c2cc(-c3ccon3)n(Cc3ccccc3F)n2)ncc1F]
177
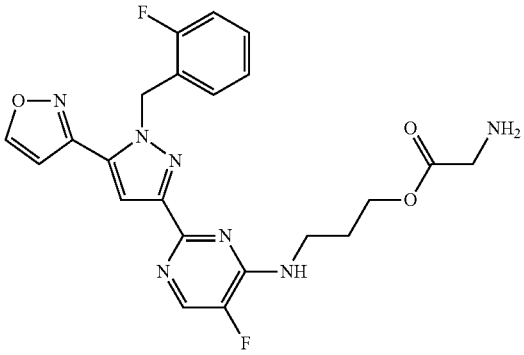 [SMILES: NCC(=O)OCCCNc1nc(-c2cc(-c3ccon3)n(Cc3ccccc3F)n2)ncc1F]
TABLE XIV-continued
178
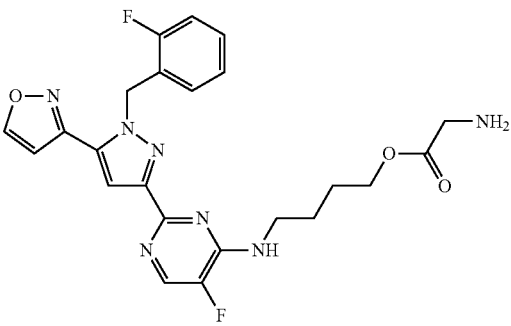 [SMILES: NCC(=O)OCCCCNc1nc(-c2cc(-c3ccon3)n(Cc3ccccc3F)n2)ncc1F]
179
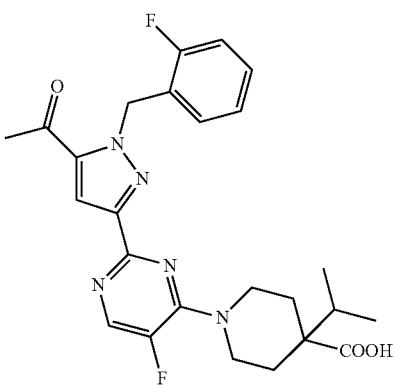 [SMILES: CC(=O)c1cc(-c2ncc(F)c(N3CCC(C(=O)O)(C(C)C)CC3)n2)nn1Cc1ccccc1F]
180
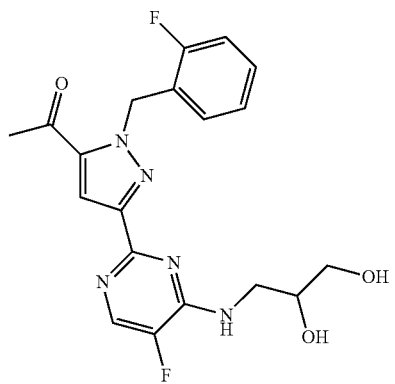 [SMILES: CC(=O)c1cc(-c2ncc(F)c(NCC(O)CO)n2)nn1Cc1ccccc1F]
181
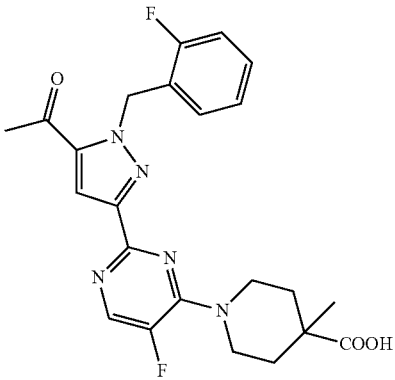 [SMILES: CC(=O)c1cc(-c2ncc(F)c(N3CCC(C)(C(=O)O)CC3)n2)nn1Cc1ccccc1F]

TABLE XIV-continued
183
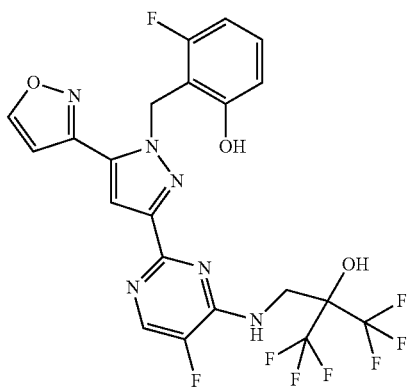 [SMILES: Oc1cccc(F)c1Cn1nc(-c2ncc(F)c(NCC(O)(C(F)(F)F)C(F)(F)F)n2)cc1-c1ccon1]
184
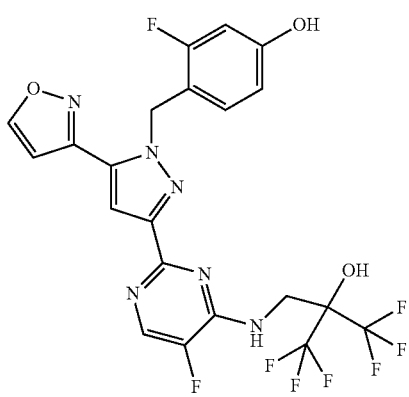 [SMILES: Oc1ccc(Cn2nc(-c3ncc(F)c(NCC(O)(C(F)(F)F)C(F)(F)F)n3)cc2-c2ccon2)c(F)c1]
193
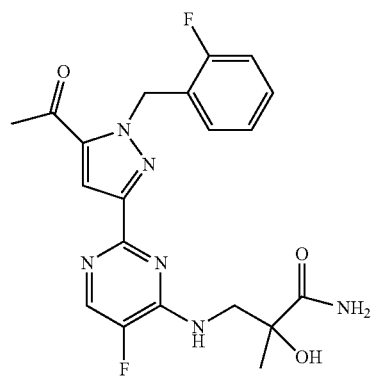 [SMILES: CC(=O)c1cc(-c2ncc(F)c(NCC(C)(O)C(N)=O)n2)nn1Cc1ccccc1F]
194
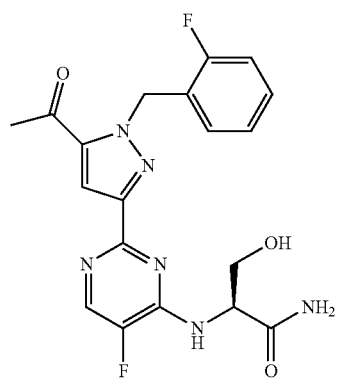 [SMILES: CC(=O)c1cc(-c2ncc(F)c(N[C@@H](CO)C(N)=O)n2)nn1Cc1ccccc1F]
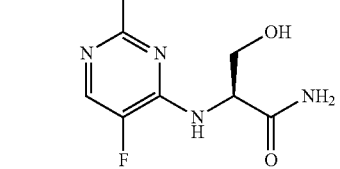
195
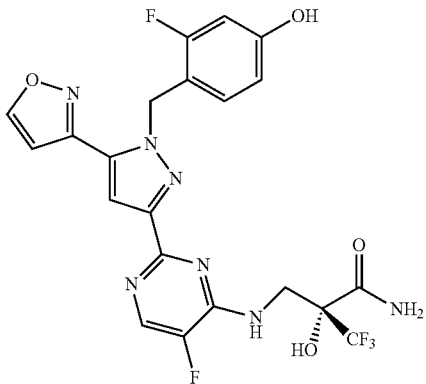 [SMILES: NC(=O)[C@](O)(CNc1nc(-c2cc(-c3ccon3)n(Cc3ccc(O)cc3F)n2)ncc1F)C(F)(F)F]
196
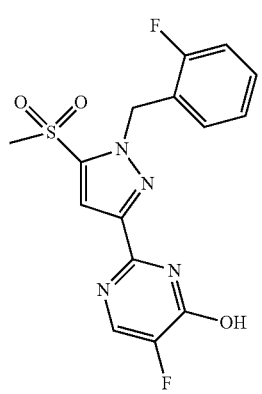 [SMILES: CS(=O)(=O)c1cc(-c2ncc(F)c(O)n2)nn1Cc1ccccc1F]
198
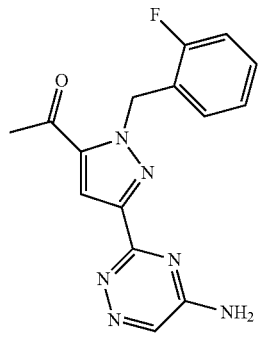 [SMILES: CC(=O)c1cc(-c2nncc(N)n2)nn1Cc1ccccc1F]
199
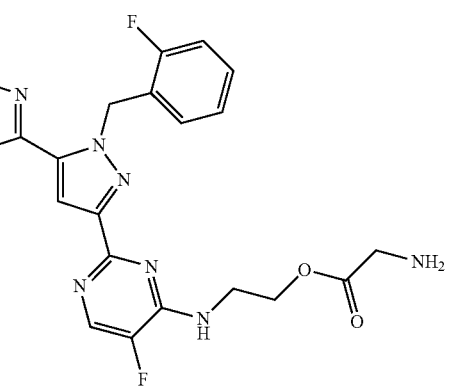

TABLE XIV-continued
200
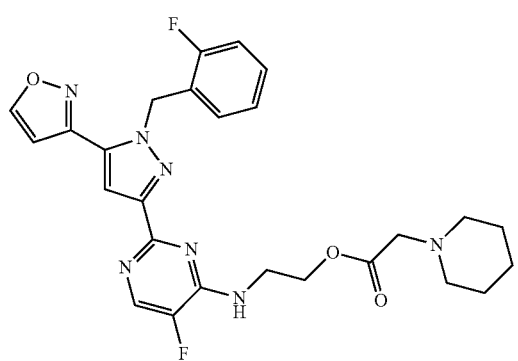 [SMILES: O=C(CN1CCCCC1)OCCNc1nc(-c2cc(-c3ccon3)n(Cc3ccccc3F)n2)ncc1F]
201
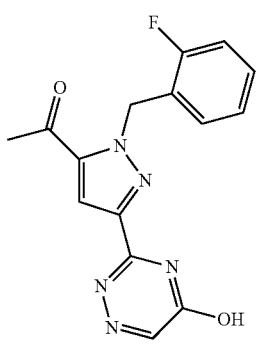 [SMILES: CC(=O)c1cc(-c2nncc(O)n2)nn1Cc1ccccc1F]
202
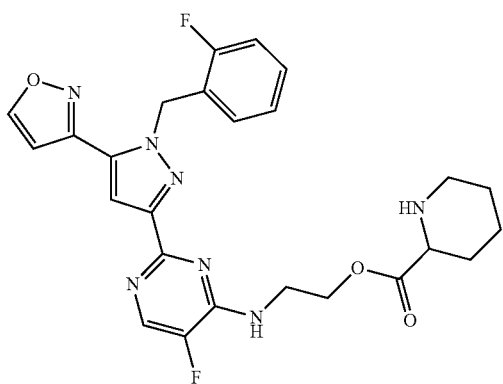 [SMILES: O=C(OCCNc1nc(-c2cc(-c3ccon3)n(Cc3ccccc3F)n2)ncc1F)C1CCCCN1]
203
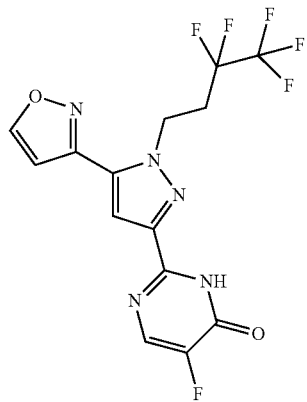 [SMILES: O=c1[nH]c(-c2cc(-c3ccon3)n(CCC(F)(F)C(F)(F)F)n2)ncc1F]
TABLE XIV-continued
204
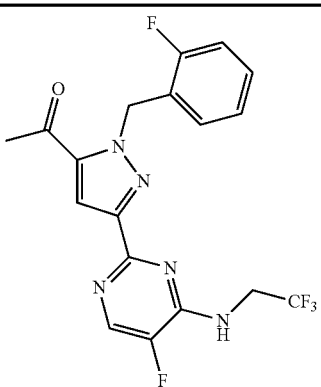
206
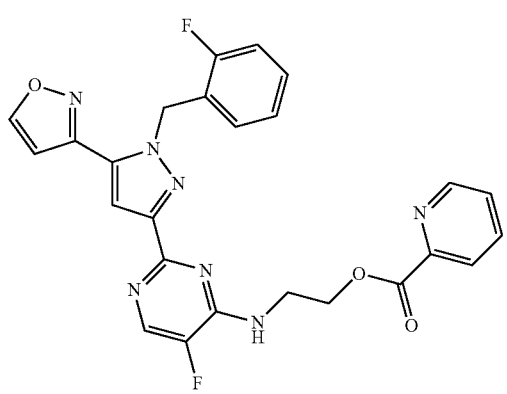 [SMILES: O=C(OCCNc1nc(-c2cc(-c3ccon3)n(Cc3ccccc3F)n2)ncc1F)c1ccccn1]
217
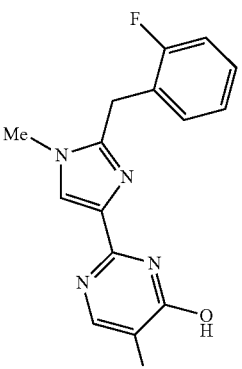
In some embodiments of the above methods, uses, pharmaceutical compositions and kits, the sGC stimulator is a compound according to Formula IA, or pharmaceutically acceptable salts thereof,
Formula IA
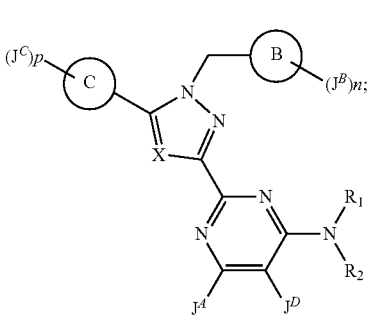

wherein:

X is selected from N, CH, C($C_{1-4}$ alkyl), C($C_{1-4}$ haloalkyl), CCl and CF;

ring B is a phenyl or a 6-membered heteroaryl ring containing 1 or 2 ring nitrogen atoms, or ring B is a thiophene;

n is 0 or an integer selected from 1 to 3;

each $J^B$ is independently selected from halogen, —CN, a $C_{1-6}$ aliphatic, —$OR^B$ or a $C_{3-8}$ cycloaliphatic ring; wherein each of said $C_{1-6}$ aliphatic and each of said $C_{3-8}$ cycloaliphatic group is optionally substituted with up to 3 instances of halogen;

each $R^B$ is independently selected from hydrogen, a $C_{1-6}$ aliphatic or a $C_{3-8}$ cycloaliphatic ring; wherein each of said $R^B$ that is a $C_{1-6}$ aliphatic and each of said $R^B$ that is a $C_{3-8}$ cycloaliphatic ring is optionally substituted with up to 3 instances of halogen;

$J^A$ is selected from hydrogen, halogen, methyl, methoxy, trifluoromethyl, trifluoromethoxy or —$NR^aR^b$, wherein $R^a$ and $R^b$ are each independently selected from hydrogen, $C_{1-6}$ alkyl or a 3-6 cycloalkyl ring;

$J^D$ is hydrogen or selected from halogen, —CN, —$CF_3$, methoxy, trifluoromethoxy, nitro, amino or methyl;

$R^1$ and $R^2$, together with the nitrogen atom to which they are attached, form a 4 to 8-membered heterocyclic ring or 5 or 6-membered heteroaryl ring; wherein said 4 to 8-membered heterocyclic ring or said 5 or 6-membered heteroaryl ring optionally contains in addition to the nitrogen atom to which $R^1$ and $R^2$ are attached, up to 3 ring heteroatoms independently selected from N, O or S, and is optionally substituted by up to 5 instances of $R^5$; or alternatively, $R^1$ and $R^2$ are each independently selected from hydrogen, $C_{1-6}$ alkyl, a $C_{3-8}$ cycloalkyl ring, a 4 to 8-membered heterocyclic ring, a 5 or 6-membered heteroaryl or a $C_{1-6}$ alkyl-$R^Y$; wherein each of said 4 to 8-membered heterocyclic ring and each of said 5 or 6-membered heteroaryl ring contains up to 3 ring heteroatoms independently selected from N, O and S; and wherein each of said $C_{1-6}$ alkyl, each of said $C_{3-8}$ cycloalkyl ring, each of said 4 to 8-membered heterocyclic ring group, each of said 5 or 6-membered heteroaryl and each of said $C_{1-6}$ alkyl portion of each said $C_{1-6}$ alkyl-R is optionally and independently substituted with up to 5 instances of $R^{5a}$; provided that $R^1$ and $R^2$ are not simultaneously hydrogen; and provided than when X is one of CH, C($C_{1-4}$ alkyl), C($C_{1-4}$haloalkyl), CCl or CF, neither of $R^1$ and $R^2$ is a pyridine or a pyrimidine; or alternatively, $J^D$ and one of $R^1$ or $R^2$ can form a 5-6 membered heterocyclic ring containing up to two heteroatoms selected from O, N and S and optionally substituted with up to 3 instances of oxo or —(Y)—$R^9$.

wherein Y is either absent or is a linkage in the form of a $C_{1-6}$ alkyl chain optionally substituted by up to 6 instances of fluoro;

each $R^9$ is independently selected from hydrogen, fluoro, —CN, —$OR^{10}$, —$SR^{10}$, —$COR^{10}$, —$OC(O)R^{10}$, —$C(O)OR^{10}$, —$C(O)N(R^{10})_2$, —$C(O)N(R^1)SO_2R^{10}$—$N(R^1)C(O)R^{10}$, —$N(R^{10})C(O)OR^{10}$, —$N(R^{10})C(O)N(R^{10})_2$, —$N(R^{10})_2$, —$SO_2R^{10}$, —$SO_2N(R^{10})_2$, —$SO_2N(R^{10})COOR^{10}$, —$SO_2N(R^{10})C(O)R^{10}$, —$N(R^{10})SO_2R^{10}$, —(C=O)$NHOR^{10}$, a $C_{3-6}$ cycloalkyl ring, a 4-8-membered heterocyclic ring or a 5-6 membered heteroaryl ring; wherein each said 4 to 8-membered heterocyclic ring and each said 5 to 6-membered heteroaromatic ring contains up to 4 ring heteroatoms independently selected from N, O or S; and wherein each said $C_{3-6}$ cycloalkyl ring, each said 4 to 8-membered heterocyclic ring and each said 5 to 6-membered heteroaromatic ring is optionally substituted with up to 3 instances of $R^{11}$;

each $R^{11}$ is independently selected from halogen, $C_{1-6}$ alkyl, —CN, —$OR^{12}$, —$SR^{12}$, —$COR^{12}$, —$OC(O)R^{12}$, —C(O)$OR^{12}$, —$C(O)N(R^{12})_2$, —$C(O)N(R^{12})SO_2R^2$—$N(R^2)C(O)R^{12}$, —$N(R^{12})C(O)OR^{12}$, —$N(R^{12})C(O)N(R^1)_2$, —$N(R^{12})_2$, —$SO_2R^{12}$, —$SO_2N(R^{12})_2$, —$SO_2N(R^{12})COOR^{12}$, —$SO_2N(R^{12})C(O)R^{12}$, —$N(R^{12})SO_2R^{12}$ and —N=$OR^{12}$; wherein each of said $C_{1-6}$ alkyl is optionally and independently substituted by up to 3 instances of fluoro, —OH, —O($C_{1-4}$ alkyl), phenyl or —O($C_{1-4}$ fluoroalkyl)

wherein each $R^{10}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and each said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo; and wherein each $R^{12}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and each said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo;

$R^Y$ is selected from a $C_{3-8}$ cycloalkyl ring, a 4 to 8-membered heterocyclic ring, phenyl, or a 5 to 6-membered heteroaromatic ring; wherein each of said 4 to 8-membered heterocyclic ring and each of said 5 to 6-membered heteroaromatic ring contains up to 4 ring heteroatoms independently selected from N, O or S; and wherein each of said $C_{3-8}$ cycloalkyl ring, each of said 4 to 8-membered heterocyclic ring, each of said phenyl, and each of said 5 to 6-membered heteroaromatic ring is optionally substituted with up to 5 instances of $R^{5c}$;

each $R^{5c}$ is independently selected from halogen, —CN, $C_{1-6}$ alkyl, —$OR^6$, —$SR^{6b}$, —$COR^{6b}$, —$OC(O)R^{6b}$, —$C(O)OR^6$, —$C(O)N(R^{6b})_2$, —$C(O)N(R^{6b})SO_2R^{6b}$, —$N(R^{6b})C(O)R^{6b}$, —$N(R^{6b})C(O)OR^{6b}$, $N(R^{6b})C(O)N(R^{6b})_2$, $N(R^{6b})_2$, —$SO_2R^{6b}$, —$SO_2N(R^{6b})_2$, —$SO_2N(R^{6b})COOR^6$, $SO_2N(R^{6b})C(O)R^{6b}$, $N(R^{6b})SO_2R^{6b}$, —(C=O)$NHOR^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and each of said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo; or two instances of $R^{5c}$ attached to the same or different ring atoms of $R^Y$, together with said ring atom or atoms, may form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said $C_{3-8}$ cycloalkyl ring, 4 to 6-membered heterocyclic ring, phenyl or a 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR"(CO)CO($C_{1-4}$ alkyl), —OH or halogen; wherein $R^{11}$ is hydrogen or a $C_{1-2}$ alkyl;

each $R^{5a}$ is independently selected from halogen, —CN, $C_{1-6}$ alkyl, —OR$^6$, —SR$^6$, —COR$^6$, —OC(O)R$^{6a}$, —C(O)OR$^{6a}$, —C(O)N(R$^{6a}$)$_2$, —C(O)N(R$^{6a}$)SO$_2$R$^{6a}$, N(R$^{6a}$)C(O)R$^{6a}$, —N(R$^{6a}$)C(O)OR$^{6a}$, N(R$^{6a}$)C(O)N(R$^{6a}$)$_2$, N(R$^{6a}$)$_2$, —SO$_2$R$^{6a}$, —SO$_2$N(R$^{6a}$)$_2$, —SO$_2$N(R$^{6a}$)COOR$^{6a}$, —SO$_2$N(R$^{6a}$)C(O)R$^{6a}$, N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring and each of said 4 to 7-membered heterocyclic ring contains up to 4 ring heteroatoms independently selected from N and S, wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$haloalkyl), C(O)N($C_{1-6}$alkyl)($C_{1-6}$haloalkyl), —COO($C_{1-6}$alkyl), —COO($C_{1-6}$ haloalkyl), —O($C_{1-4}$ alkyl), —O($C_{1-4}$haloalkyl) or oxo, wherein each of said 5 or 6-membered heteroaryl ring or 4 to 7-membered heterocyclic ring contains up to 4 ring heteroatoms independently selected from N, O and S; or when one of $R^1$ or $R^2$ is the $C_{3-8}$ cycloalkyl ring, 4 to 8-membered heterocyclic ring or 5 or 6-membered heteroaryl substituted with up to 5 instances of $R^{5a}$, two of the instances of $R^{5a}$ attached to the same or different ring atoms of said $R^1$ or $R^2$, together with said atom or atoms, may optionally form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$haloalkyl, oxo, —(CO)CO($C_{1-4}$ alkyl), —NR'(CO)CO($C_{1-4}$ alkyl) or halogen; wherein R' is hydrogen or a $C_{1-2}$ alkyl;

each $R^5$ is independently selected from halogen, —CN, $C_{1-6}$ alkyl, —OR$^6$, —SR$^6$, —COR$^6$, —OC(O)R$^6$, —C(O)OR$^6$, —C(O)N(R$^6$)$_2$, —C(O)N(R$^6$)SO$_2$R$^6$—N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$N(R$^6$)$_2$, —SO$_2$N(R$^6$)COOR$^6$, —SO$_2$N(R$^6$)C(O)R$^6$, —N(R$^6$)SO$_2$R$^6$, —(C=O)NHOR$^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said $C_{3-8}$ cycloalkyl ring, each of said 4 to 7-membered heterocyclic ring, each of said 5 or 6-membered heteroaryl ring, each said benzyl or each said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$haloalkyl) or oxo;

each $R^6$ is independently selected from hydrogen, a $C_{1-6}$ alkyl, phenyl, benzyl, a $C_{3-8}$ cycloalkyl ring or a 4 to 7-membered heterocyclic ring, a 5 or 6-membered heteroaryl ring; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; or when $R^1$ and $R^2$ attached to the nitrogen atom form the 4 to 8-membered heterocyclic ring or 5 or 6-membered heteroaryl ring substituted with up to 5 instances of $R^5$, two of the instances of $R^5$ attached to the same or different atoms of said ring, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, said 4 to 6-membered heterocyclic ring, said phenyl or said 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$haloalkoxy, oxo, —C(O)O ($C_{1-4}$ alkyl), —C(O)OH, —NR(CO)CO($C_{1-4}$ alkyl), —OH or halogen; wherein R is hydrogen or a $C_{1-2}$ alkyl;

p is an integer selected from 0, 1 or 2;

ring C is a monocyclic 5-membered heteroaryl ring containing up to 4 ring heteroatoms selected from N, O or S; wherein said monocyclic 5-membered heteroaryl ring is not a 1,3,5-triazinyl ring;

each $J^C$ is independently selected from halogen or a $C_{1-4}$ aliphatic optionally and independently substituted by up to 3 instances of $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen.

In other embodiments of the above methods, uses, compositions and kits, the sGC stimulator is a compound having Formula IB Formula IB

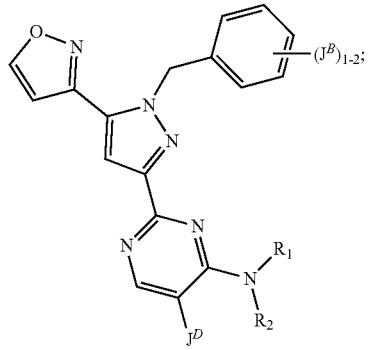

wherein:
$J^D$ is selected from hydrogen or halogen; $J^B$ is halogen and
$R^1$ and $R^2$, together with the nitrogen atom to which they are attached, form a 4 to 8-membered heterocyclic ring or 5-membered heteroaryl ring; wherein said 4 to 8-membered heterocyclic ring or said 5-membered heteroaryl ring optionally contains, in addition to the nitrogen atom to which $R^1$ and $R^2$ are attached, up to 3 ring heteroatoms independently selected from N, O or S, and is optionally substituted by up to 5 instances of $R^{5e}$;

each $R^{5e}$ is independently selected from halogen, —CN, $C_{1-6}$ alkyl, —($C_{1-4}$ alkyl)-$R^6$, a $C_{3-8}$ cycloalkyl ring, $C_{1-4}$ cyanoalkyl, —$OR^6$, —$SR^6$, —$OCOR^6$, —$COR^6$, —C(O) $OR^6$, —C(O)N($R^6$)$_2$, —N($R^6$)C(O)$R^6$, —N($R^6$)$_2$, —$SO_2R^6$, —$SO_2OH$, —$SO_2NHOH$, —$SO_2N(R^6)COR^6$, —$SO_2N(R^6)_2$, —N($R^6$)$SO_2R^6$, benzyl, phenyl or an oxo group; wherein each said phenyl ring and each said benzyl group, is optionally and independently substituted with up to 3 instances of halogen, —OH, —$NH_2$, —NH($C_{1-4}$ alkyl), —N($C_{1-4}$ alkyl)$_2$, —CN, $C_{1-4}$ alkyl, $C_{1-4}$ haloalkyl, —O($C_{1-4}$ alkyl) or —O($C_{1-4}$ haloalkyl); and wherein each said $C_{1-6}$ alkyl, each $C_{1-4}$ alkyl portion of said —($C_{1-4}$ alkyl)-$R^6$ moiety, and each said $C_{3-8}$ cycloalkyl ring is optionally and independently substituted with up to 3 instances of halogen; wherein each $R^6$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

two of the instances of R attached to the same or different atoms of said ring formed by $R^1$, $R^2$ and the nitrogen to which $R^1$ and $R^2$ are attached, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$haloalkyl, $C_{1-4}$ alkoxy, $C_{1-4}$ haloalkoxy, oxo, —C(O) O($C_{1-4}$ alkyl), —C(O)OH, —C(O)$NH_2$, —NR(CO)O ($C_{1-4}$ alkyl), —OH or halogen; wherein R is hydrogen or a $C_{1-2}$ alkyl;

alternatively, R and $R^2$ are each independently selected from hydrogen, $C_{1-6}$ alkyl, a $C_{3-8}$ cycloalkyl ring, a 4 to 10-membered heterocyclic ring, a 5 or 6-membered heteroaryl, phenyl or a $C_{1-6}$ alkyl-$R^Y$; wherein each of said 4 to 10-membered heterocyclic ring and each of said 5 or 6-membered heteroaryl ring contains up to 3 ring heteroatoms independently selected from N, O and S; and wherein each of said $C_{1-6}$ alkyl, each of said $C_{1-6}$ alkyl portion of each said $C_{1-6}$ alkyl-R moiety, each of said $C_{3-8}$ cycloalkyl ring, each of said 4 to 10-membered heterocyclic ring group, each of said 5 or 6-membered heteroaryl, each of said phenyl is optionally and independently substituted with up to 5 instances of $R^5$; provided that neither of $R^1$ or $R^2$ are pyridine or pyrimidine;

$R^Y$ is selected from a $C_{3-8}$ cycloalkyl ring, a 4 to 8-membered heterocyclic ring, phenyl, or a 5 to 6-membered heteroaryl ring; wherein each of said 4 to 8-membered heterocyclic ring and each of said 5 to 6-membered heteroaromatic ring contains between 1 and 4 ring heteroatoms independently selected from N, O or S; and wherein each of said $C_{3-8}$ cycloalkyl ring, each of said 4 to 8-membered heterocyclic ring, each of said phenyl, and each of said 5 to 6-membered heteroaryl ring is optionally substituted with up to 5 instances of $R^5$;

each $R^{5f}$ is independently selected from halogen, —CN, $C_{1-6}$ alkyl, —($C_{1-4}$ alkyl)-$R^a$, a $C_{7-12}$ aralkyl, $C_{3-8}$cycloalkyl ring, $C_{1-4}$ cyanoalkyl, —$OR^{6a}$, —$SR^{6a}$, —$OCOR^{6a}$, —$COR^{6a}$, —$C(O)OR^{6a}$, —$C(O)N(R^{6a})_2$, $N(R^{6a})C(O)R^{6a}$ $N(R^{6a})_2$, —$SO_2R^{6a}$, —$SO_2N(R^{6a})_2$, $N(R^{6a})SO_2R^{6a}$, —$SO_2OH$, —$SO_2NHOH$, —$SO_2N(R^{6a})COR^{6a}$, phenyl or an oxo group; wherein each said phenyl group is optionally and independently substituted with up to 3 instances of halogen, —OH, —$NH_2$, —$NH(C_{1-4}$ alkyl), —$N(C_{1-4}$ alkyl$)_2$, —$NO_2$, —CN, $C_{1-4}$ alkyl, $C_{1-4}$ haloalkyl, —$O(C_{1-4}$ alkyl) or —$O(C_{1-4}$ haloalkyl); and wherein each said $C_{7-12}$ aralkyl, each said $C_{1-6}$ alkyl, each said $C_{1-4}$ alkyl portion of each said —($C_{1-4}$ alkyl)-$R^{6a}$ and each said $C_{3-8}$ cycloalkyl group is optionally and independently substituted with up to three instances of halogen;

each $R^{6a}$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

when one of $R^1$ or $R^2$ is the $C_{3-8}$ cycloalkyl ring, 4 to 8-membered heterocyclic ring or 5 or 6-membered heteroaryl substituted with up to 5 instances of $R^{11}$; two of the instances of $R^5$ attached to the same or different ring atoms of said $R^1$ or $R^2$, together with said atom or atoms, form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)O($C_{1-4}$ alkyl), —NR'(CO)O($C_{1-4}$ alkyl) or halogen; wherein R' is hydrogen or a $C_{1-2}$ alkyl;

each $R^{5g}$ is independently selected from halogen, —CN, $C_{1-6}$ alkyl, —($C_{1-4}$ alkyl)-$R^{6b}$, a benzyl, $C_{3-8}$ cycloalkyl ring, $C_{1-4}$ cyanoalkyl, —$OR^{6b}$, —$SR^{6b}$, —$OCOR^{6b}$, —$COR^{6b}$, —$C(O)OR^{6b}$, —$C(O)N(R^{6b})_2$, $N(R^{6b})C(O)R^6$, —$N(R^{6b})_2$, —$SO_2R^{6b}$, —$SO_2N(R^{6b})_2$, $N(R^{6b})SO_2R^{6b}$, —$SO_2OH$, —$SO_2NHOH$, —$SO_2N(R^{6b})COR^{6b}$, phenyl or an oxo group; wherein each said phenyl and each said benzyl group is optionally and independently substituted with up to 3 instances of halogen, —OH, —$NH_2$, —NH ($C_{1-4}$ alkyl), —N($C_{1-4}$ alkyl)$_2$, —$NO_2$, —CN, $C_{1-4}$ alkyl, $C_{1-4}$ haloalkyl, —$O(C_{1-4}$ alkyl) or —$O(C_{1-4}$ haloalkyl); and wherein each said $C_{1-6}$ alkyl, $C_{1-4}$ alkyl portion of each said ($C_{1-4}$ alkyl)-$R^{6b}$ moiety and each said $C_{3-8}$ cycloalkyl group is optionally and independently substituted with up to 3 instances of halogen;

each $R^{6b}$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

alternatively, two instances of $R^1$ attached to the same or different ring atoms of $R^Y$, together with said ring atom or atoms, form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$haloalkyl, $C_{1-4}$ alkoxy, $C_{1-4}$ haloalkoxy, oxo, —$C(O)O(C_{1-4}$ alkyl), —$C(O)OH$, —$C(O)NH_2$, —NR"(CO)O($C_{1-4}$ alkyl), —OH or halogen; and R" is hydrogen or a $C_{1-2}$ alkyl.

In some embodiments of the above methods, uses, compositions and kits, the sGC stimulator is a compound of Formula IC:

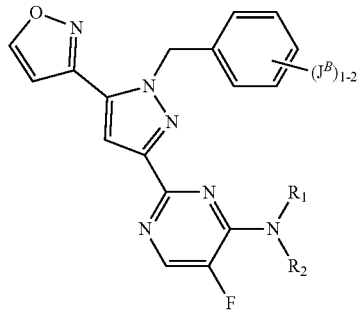

Formula IC wherein $J^B$ is halogen;

$R^1$ is hydrogen or $C_{1-6}$ alkyl;

$R^2$ is a $C_{1-6}$ alkyl group optionally and independently substituted by up to three instances of $R^{5a}$, wherein $R^{5a}$ has been defined in previous paragraphs as part of the description of Formula IA.

In some embodiments of the above methods, uses, compositions and kits, the sGC stimulator is a compound selected from those depicted below:
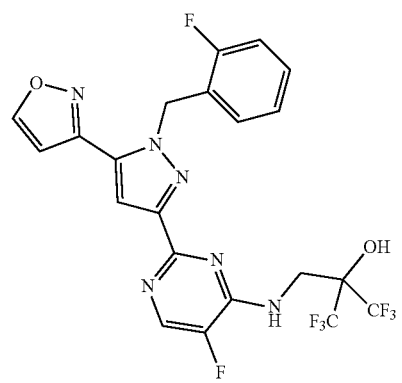
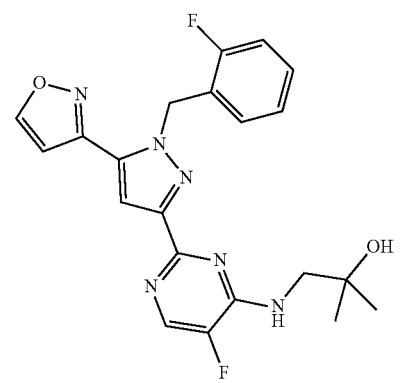
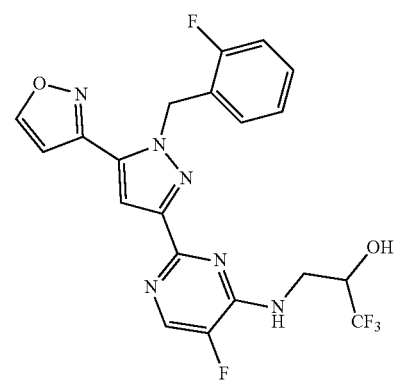
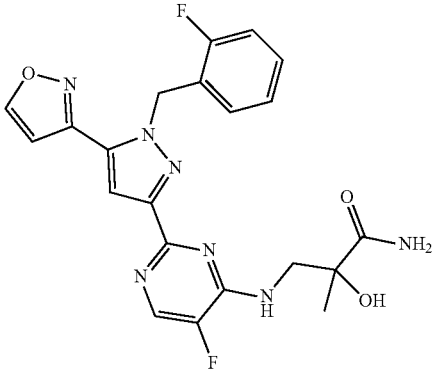
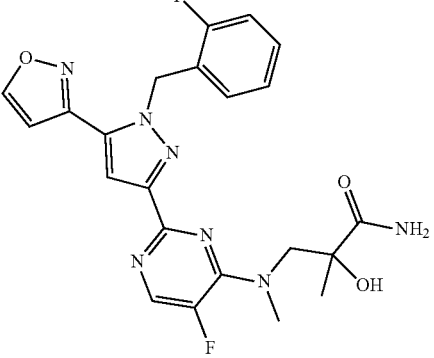
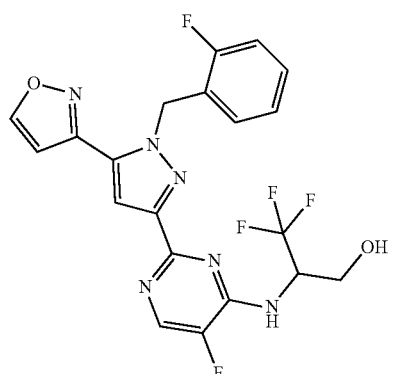
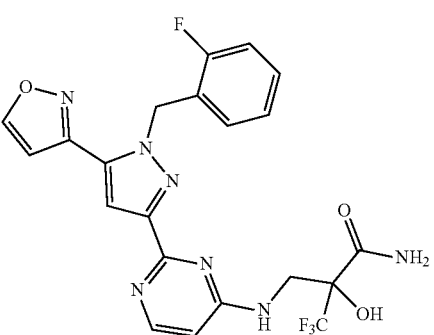
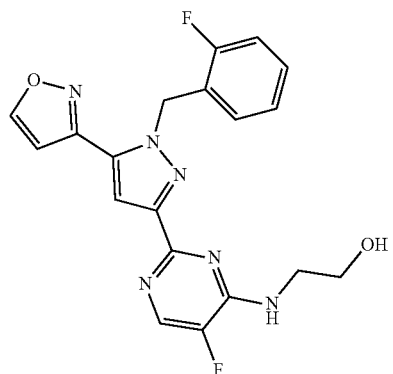

139
-continued
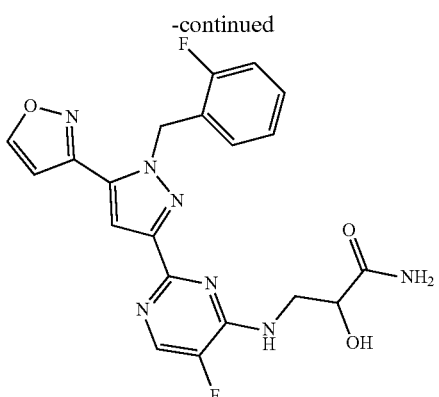
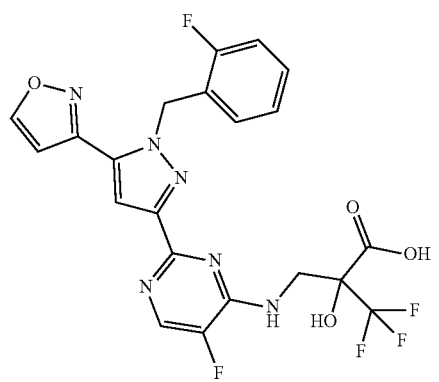
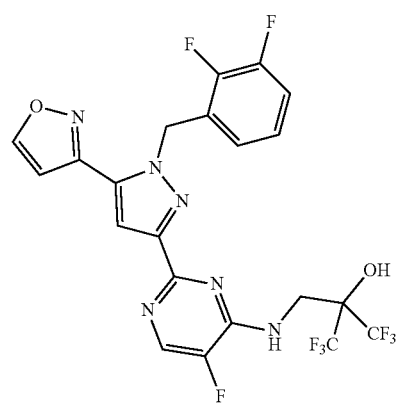
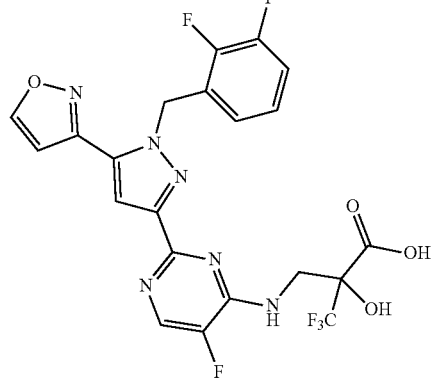
140
-continued
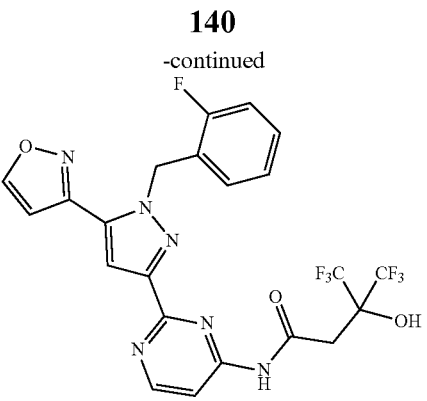
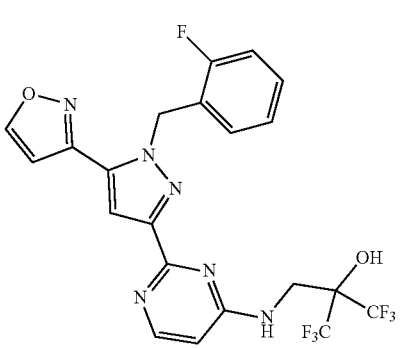
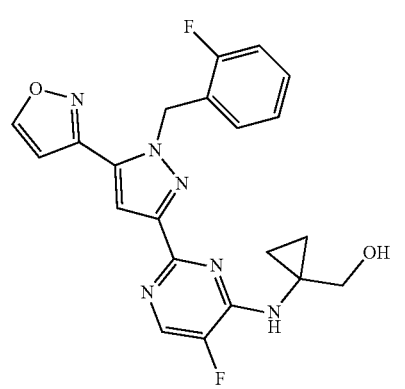
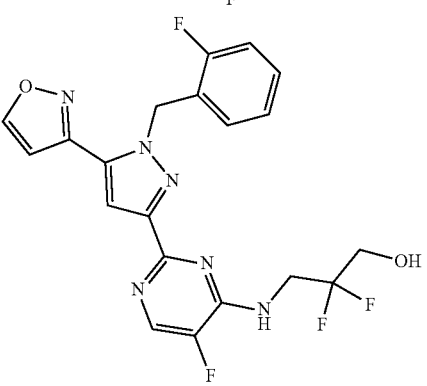

141
-continued

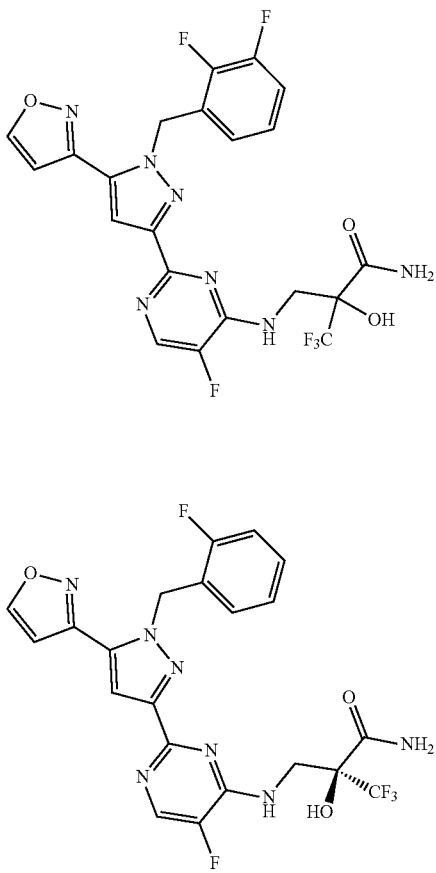

142
-continued

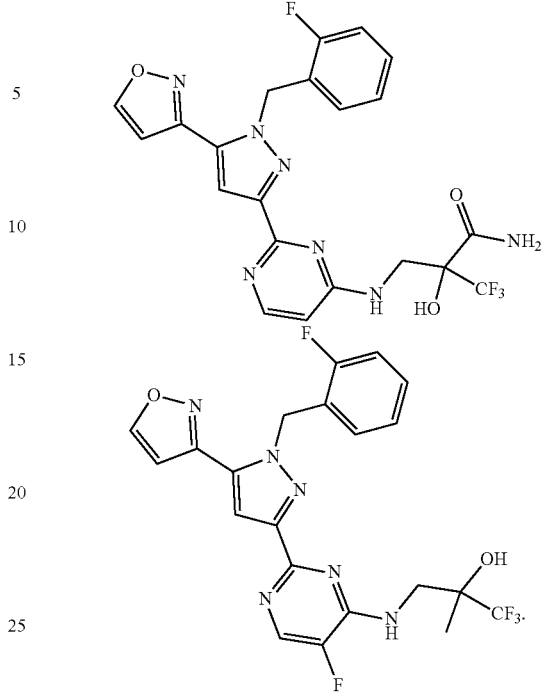

In some embodiments of the above methods, uses, compositions and kits, the sGC stimulator is a compound of Formula XZ:

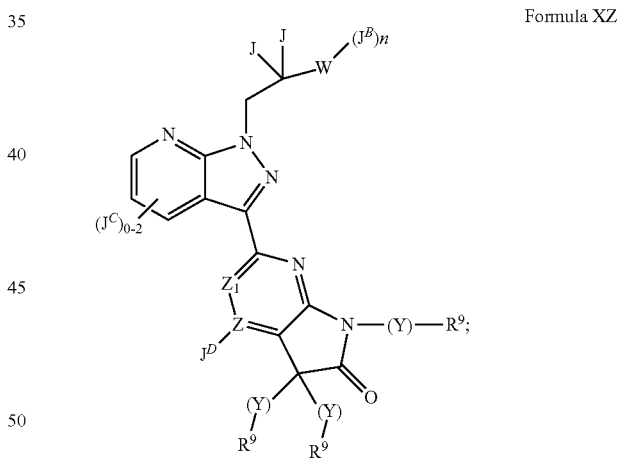

Formula XZ wherein:
W is either
i) absent, and $J^B$ is connected directly to the carbon atom bearing two J groups; each J is independently selected from hydrogen or methyl, n is 1 and $J^B$ is a $C_{2-7}$ alkyl chain optionally substituted by between 2 and 9 instances of fluorine; wherein, optionally, one —$CH_2$— unit of said $C_{2-7}$ alkyl chain can be replaced by —O— or —S—.
ii) a ring B selected from phenyl, a 5 or 6-membered heteroaryl ring, containing 1 or 2 ring heteroatoms independently selected from N, O or S, a $C_{3-7}$ cycloalkyl ring and a 4 to 7-membered heterocyclic compound, containing up to 3 heteroatoms independently selected from O, N or S;

wherein when W is ring B
each J is hydrogen;
n is 0 or an integer selected from 1, 2 or 3;
each $J^B$ is independently selected from halogen, —CN, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);
$Z^1$ in ring D is selected from CH or N; Z is selected from C or N; wherein if $Z^1$ is CH, then Z must be C; and if $Z^1$ is N, then Z may be C or N;
each $J^D$ is independently selected from J, —CN, —$NO_2$, —$OR^D$, —$SR^D$, $C(O)R^D$, —$C(O)OR^D$, —$OC(O)R^D$, —$C(O)N(R^D)_2$, —$N(R^D)_2$, —$N(R^d)C(O)R^D$, —$N(R^d)C(O)OR^D$, —$N(R^d)C(O)N(R^D)_2$, —$OC(O)N(R^D)_2$, $SO_2R^D$, —$S_2N(R^D)_2$, $N(R^d)SO_2R^D$, —$N(R^d)SO_2NHR^D$, —$N(R^d)SO_2NHC(O)OR^D$, $N(R^d)SO_2NHC(O)R^D$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^D$ moiety, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of $R^{5d}$;
$J^A$ is selected from a lone pair on nitrogen, hydrogen, halogen, oxo, methyl, hydroxyl, methoxy, trifluoromethyl, trifluoromethoxy or —$NR^aR^b$; wherein $R^a$ and $R^b$ are each independently selected from hydrogen, $C_{1-6}$ alkyl or a 3-6 cycloalkyl ring; or wherein $R^a$ and $R^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;
each $R^D$ is independently selected from hydrogen, a $C_{1-6}$ aliphatic, —($C_{1-6}$ aliphatic)-$R^f$, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 3 heteroatoms independently selected from 0, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 10-membered heterocyclic ring, each said phenyl and each said 5 to 6-membered heteroaryl ring is optionally and independently substituted with up to 5 instances of $R^{5a}$; wherein when any $R^D$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —$N(R^d)$—, —CO— or —O—;
each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$; wherein when any $R^d$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —$N(R^{dd})$—, —CO— or —O—;
each $R^{dd}$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$;
each $R^f$ is independently selected from a $C_{1-3}$ alkyl, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N or S; and wherein each said $C_{3-8}$ cycloaliphatic ring, each said 4 to 10-membered heterocyclic ring, each said phenyl and each said 5 to 6-membered heteroaryl ring is optionally and independently substituted by up to 5 instances of $R^{5c}$;
when $J^D$ is —$C(O)N(R^D)_2$, $N(R^D)_2$, —$N(R^d)C(O)N(R^D)_2$, —$OC(O)N(R^D)_2$ or —$SO_2N(R^D)_2$, the two $R^D$ groups together with the nitrogen atom attached to the two $R^D$ groups may form 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O or S, in addition to the nitrogen atom to which the two $R^D$ groups are attached; and wherein each said 4 to 8-membered heterocyclic ring and each said 5-membered heteroaryl ring is optionally and independently substituted by up to 5 instances of $R^5$;
when $J^D$ is-$N(R^d)C(O)R^D$, the $R^D$ group together with the carbon atom attached to the $R^D$ group, with the nitrogen atom attached to the $R^d$ group, and with the $R^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, in addition to the nitrogen atom to which the $R^d$ group is attached; and wherein each said 4 to 8-membered heterocyclic ring and each said 5-membered heteroaryl ring is optionally and independently substituted by up to 5 instances of $R^5$;

when $J^D$ is —N($R^d$)C(O)O$R^D$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, and with said $R^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)C(O)N($R^D$)$_2$, one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is N($R^d$)SO$_2$$R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

each $R^5$ is independently selected from halogen, —CN, $C_{1-6}$ alkyl, —($C_{1-6}$ alkyl)-$R^6$, —O$R^6$, —S$R^6$, —CO$R^6$, —OC(O)$R^6$, —C(O)O$R^6$, —C(O)N($R^6$)$_2$, —C(O)N($R^6$)SO$_2$$R^6$, —N($R^6$)C(O)$R^6$, —N($R^6$)C(O)O$R^6$, —N($R^6$)C(O)N($R^6$)$_2$, —N($R^6$)$_2$, —SO$_2$$R^6$, —SO$_2$OH, —SO$_2$NHOH, —SO$_2$N($R^6$)$_2$, —SO$_2$N($R^6$)COO$R^6$, —SO$_2$N($R^6$)C(O)$R^6$, —N($R^6$)SO$_2$$R^6$, —(C=O)NHO$R^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of the —($C_{1-6}$ alkyl)-$R^6$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^5$, attached to the same or different atoms of $J^D$, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —CONH$_2$, —OH or halogen; wherein R is hydrogen or a $C_{1-2}$ alkyl;

each $R^{5a}$ is independently selected from halogen, —CN, $C_{1-6}$ alkyl, —($C_{1-6}$ alkyl)$R^{6a}$, —O$R^6$, —S$R^{6a}$, —CO$R^{6a}$, —OC(O)$R^6$, —C(O)O$R^{6a}$, C(O)N($R^{6a}$)$_2$, —C(O)N($R^{6a}$)SO$_2$$R^{6a}$, N($R^{6a}$)C(O)$R^{6a}$, —N($R^{6a}$)C(O)O$R^{6a}$, N($R^{6a}$)C(O)N($R^{6a}$)$_2$, N($R^{6a}$)$_2$, —SO$_2$$R^{6a}$, —SO$_2$OH, —SO$_2$NHOH, —SO$_2$N($R^{6a}$)$_2$, —SO$_2$N($R^{6a}$)COO$R^{6a}$, —SO$_2$N($R^{6a}$)C(O)$R^{6a}$, N($R^{6a}$)SO$_2$$R^{6a}$, —(C=O)NHO$R^{6a}$ a $C_{3-8}$cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$alkyl, $C_{1-4}$haloalkyl, —OH, —NH$_2$, —NH($C_{1-4}$alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$haloalkyl) or oxo;

each $R^{5b}$ is independently selected from halogen, —CN, $C_{1-6}$ alkyl, —($C_{1-6}$ alkyl)$R^{6a}$, —O$R^6$, —S$R^{6a}$, —CO$R^{6a}$, OC(O)$R^a$, —C(O)O$R^{6a}$, C(O)N($R^a$)$_2$, —C(O)N($R^{6a}$)SO$_2$$R^a$, —N($R^a$)C(O)$R^{6a}$, —N($R^{6a}$)C(O)O$R^{6a}$, N($R^{6a}$)C(O)N($R^{6a}$)$_2$, N($R^{6a}$)$_2$, —SO$_2$$R^a$, —SO$_2$OH, —SO$_2$NHOH, —SO$_2$N($R^{6a}$)$_2$, —SO$_2$N($R^{6a}$)COO$R^{6a}$, —SO$_2$N($R^{6a}$)C(O)$R^{6a}$, N($R^{6a}$)SO$_2$$R^{6a}$, —(C=O)NHO$R^{6a}$ a $C_{3-8}$cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O($C_{1-4}$ alkyl), —OH or halogen; wherein R is hydrogen or a $C_{1-2}$ alkyl;

each $R^{5c}$ is independently selected from halogen, —CN, $C_{1-6}$ alkyl, —($C_{1-6}$ alkyl)-$R^{6b}$, OR$^{6b}$, SR$^{6b}$, —COR$^{6b}$, —OC(O)R$^{6b}$, —C(O)OR$^{6b}$, —C(O)N($R^{6b}$)$_2$, —C(O)N($R^6$)SO$_2$R$^{6b}$, —N($R^{6b}$)C(O)R$^{6b}$, —N($R^{6b}$)C(O)OR$^{6b}$, N($R^{6b}$)C(O)N($R^{6b}$), —N($R^{6b}$)$_2$, —SO$_2$R$^{6b}$, —SO$_2$OH, —SO$_2$NHOH, —SO$_2$N($R^{6b}$)$_2$, —SO$_2$N($R^{6b}$)COOR$^{6b}$, —SO$_2$N($R^{6b}$)C(O)R$^{6b}$, N($R^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^5$ attached to the same or different atoms of $R^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each $R^{5d}$ is independently selected from halogen, —CN, $C_{1-6}$ alkyl, —($C_{1-6}$ alkyl)-$R^6$, —OR$^6$, —SR$^6$, —COR$^6$, —OC(O)R$^6$, —C(O)OR$^6$, —C(O)N($R^6$)$_2$, —N($R^6$)C(O)R$^6$, —N($R^6$)C(O)OR$^6$, —N($R^6$)C(O)N($R^6$)$_2$, —N($R^6$)$_2$, —SO$_2$R$^6$, —SO$_2$OH, —SO$_2$NHOH, —SO$_2$N($R^6$)COR$^6$, —SO$_2$N($R^6$)$_2$, —N($R^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-$R^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$haloalkyl) or oxo;

two instances of $R^{5d}$ attached to the same or different atoms of $J^D$, together with said atom or atoms of $J^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each $R^6$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$haloalkyl), C(O)N($C_{1-6}$alkyl)($C_{1-6}$haloalkyl), —COO($C_{1-6}$alkyl), —COO($C_{1-6}$ haloalkyl), —O($C_{1-4}$ alkyl), —O($C_{1-4}$haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$haloalkyl) or oxo, wherein each of said 5 or 6-membered heteroaryl ring or 4 to 7-membered heterocyclic ring contains up to 4 ring heteroatoms independently selected from N, O and S;

two instances of $R^6$ linked to the same nitrogen atom of $R^5$ or $R^{5d}$, together with said nitrogen atom of R or $R^d$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6a}$ linked to a nitrogen atom of $R^{5a}$ or $R^b$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6b}$ linked to a nitrogen atom of $R^5$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

Y is either absent or is a $C_{1-6}$ alkyl chain, optionally substituted by up to 6 instances of fluoro; and wherein in said Y that is a $C_{1-6}$ alkyl chain, up to 3 methylene units of this alkyl chain, can be replaced by a group selected from —O—, —C(O)— or —N((Y')—R$^{90}$)—, wherein $Y^1$ is either absent or is a $C_{1-6}$ alkyl chain, optionally substituted by up to 6 instances of fluoro; and:

when $Y^1$ is absent, each $R^{90}$ is independently selected from hydrogen, —COR$^{10}$, —C(O)OR$^{10}$, —C(O)N(R$^{10}$)$_2$, —C(O)N(R$^{10}$)SO$_2$R$^{10}$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^1$, —(C=O)NHOR$^{10}$a $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$; and when $Y^1$ is present, each $R^{90}$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^1$)SO$_2$R$^{10}$—N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^9$ is independently selected from hydrogen, halogen, a $C_{1-6}$ alkyl, —CN, —OR$^{10}$, —COR$^{10}$, —OC(O)R$^1$, —C(O)OR$^{10}$, —C(O)N(R$^{10}$)$_2$, —C(O)N(R$^{10}$)SO$_2$, —R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —S$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{1-6}$ alkyl, each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^{10}$ is independently selected from hydrogen, a $C_{1-6}$ alkyl, —($C_{1-6}$ alkyl)-R$^{13}$, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-R$^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of $R^{1a}$;

each $R^{13}$ is independently selected from a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of $R^{11b}$;

each $R^{11}$ is independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^1$)$_2$, —N(R$^1$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of $R^{121}$;

each $R^{11a}$ is independently selected from halogen, oxo, $C_{1-6}$ alkyl, —CN, —$OR^{12}$, —$COR^{12}$, —$C(O)OR^{12}$, —$C(O)N(R^{12})_2$, —$N(R^{12})C(O)R^{12}$, —$N(R^{12})C(O)OR^{12}$, —$N(R^{12})C(O)N(R^1)_2$, —$N(R^{12})_2$, —$SO_2R^{12}$, —$SO_2N(R^{12})_2$ or —$N(R^{12})SO_2R^{12}$; wherein each of said $C_{1-6}$ alkyl is optionally and independently substituted by up to 6 instances of fluoro and/or 3 instances of $R^{121}$; and each $R^{11b}$ is independently selected from halogen, $C_{1-6}$ alkyl, oxo, —CN, —$OR^{12}$, —$COR^{12}$, —$C(O)OR^{12}$, —$C(O)N(R^{12})_2$, —$N(R^{12})C(O)R^{12}$, —$N(R^{12})C(O)OR^{12}$, —$N(R^{12})C(O)N(R^1)_2$, —$N(R^{12})_2$, —$SO_2R^{12}$, —$SO_2N(R^{12})_2$ or —$N(R^{12})SO_2R^{12}$; wherein each of said $C_{1-6}$ alkyl is optionally and independently substituted by up to 6 instances of fluoro and/or 3 instances of $R^{121}$;

each $R^{12}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_1$-4 (fluoroalkyl), —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ fluoroalkyl) or oxo;

each $R^{121}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_1$-4 (fluoroalkyl), —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ fluoroalkyl) or oxo; and each $J^C$ is independently selected from hydrogen or a $C_{1-6}$ alkyl.

In some embodiments of the above methods, uses, compositions and kits, the sGC stimulator is a compound of Formula XY:

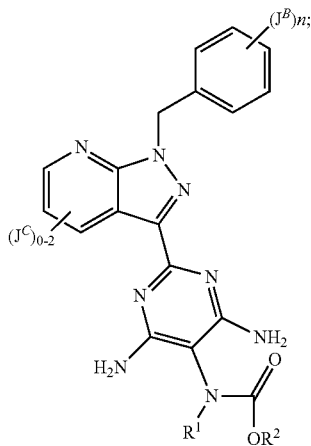

Formula XY wherein n is 0 or an integer selected from 1 to 3;

each $J^B$ is independently selected from halogen, —CN, a $C_{1-6}$ aliphatic, —$OR^B$ or a $C_{3-8}$ cycloaliphatic ring; wherein each of said $C_{1-6}$ aliphatic and each of said $C_{3-8}$ cycloaliphatic group is optionally substituted with up to 3 instances of halogen;

each $R^B$ is independently selected from hydrogen, a $C_{1-6}$ aliphatic or a $C_{3-8}$ cycloaliphatic ring; wherein each of said $R^B$ that is a $C_{1-6}$ aliphatic and each of said $R^B$ that is a $C_{3-8}$ cycloaliphatic ring is optionally substituted with up to 3 instances of halogen;

each $J^C$, if present, is independently selected from halogen;

$R^1$ is hydrogen or $C_{1-6}$ alkyl; and $R^2$ is a $C_{1-6}$ alkyl.

In some embodiments of Formula XY, n is 1 or 2. In some embodiments, n is 1.

In some embodiments of Formula XY, each $J^B$ is a halogen. In some of these embodiments, each $J^B$ is fluoro. In some embodiments of Formula XY, n is 1 and $J^B$ is fluoro.

In some embodiments of Formula XY, one or two instances of $J^C$ are present. In other embodiments, only one instance of $J^C$ is present. In some of these embodiments, $J^C$ is fluoro.

In some embodiments of Formula XY, $R^1$ is selected from hydrogen, methyl or ethyl. In other embodiments, $R^1$ is hydrogen. In still other embodiments, R is methyl.

In some embodiments of Formula XY, $R^2$ is methyl or ethyl. In still other embodiments, $R^2$ is methyl.

In some embodiments of Formula XY, the compound is vericiguat or riociguat, depicted supra.

In some embodiments of the above methods, compositions and kits, the sGC stimulator is one that achieves higher concentration multiples in the liver than in the plasma in an animal model. In some of these embodiments, the sGC stimulator is one that concentrates in the liver of a rat animal model such as that described for the rat in Example 5 below. In some embodiments, concentration is defined as a ratio of compound concentration in liver versus compound concentration in plasma higher than 50 to 1. In some embodiments, liver concentration is defined as a ratio of compound concentration in liver versus compound concentration in plasma higher than 40 to 1. In some embodiments, concentration in the liver is defined as a ratio of compound concentration in liver versus compound concentration in plasma higher than 30 to 1. In some embodiments, liver concentration is defined as a ratio of compound concentration in liver versus compound concentration in plasma higher than 20 to 1. In other embodiments, the ratio is higher than 15 to 1. In still other embodiments, the ratio is higher than 10 to 1. In yet other embodiments, the ratio is higher than 5 to 1. In yet other embodiments, the ratio is at least higher than 4 to 1.

In some embodiments of the above methods, compositions and kits, the sGC stimulator is one that when administered to a subject or patient, results in a compound concentration in liver versus compound concentration in plasma ratio higher than 40 to 1. In other embodiments, the ratio is higher than 30 to 1. In other embodiments, the ratio is higher than 20 to 1. In other embodiments, the ratio is higher than 15 to 1. In still other embodiments, the ratio is higher than 10 to 1. In yet other embodiments, the ratio is higher than 5 to 1. In yet other embodiments, the ratio is at least higher than 4 to 1. In some embodiments, concentration in liver is determined by liver biopsy.

In some embodiments of the above methods, compositions and kits, the sGC stimulator is one that when orally administered to a healthy subject does not result in hypotension. In some embodiments, hypotension is defined by a blood pressure measurement of less than 90/60.

In some embodiments of the above methods, compositions and kits, the sGC stimulator is one that when orally administered to a subject, it does not result in a reduction of at least 10 mmHg in either the systolic or the diastolic blood pressure measurements or both simultaneously.

In some embodiments of the above methods, compositions and kits, the sGC stimulator is one that when orally administered to a subject displaying normal blood pressure, it does not result in a reduction of at least 10 mm Hg in either the systolic or the diastolic blood pressure measurements or both simultaneously. In some embodiments, normal blood pressure is defined as less than 120/80 (systolic/diastolic) or less.

Pharmaceutically Acceptable Salts

In some embodiments of the methods, uses, pharmaceutical compositions and kits, the sGC stimulator may be provided as (i) the compound itself (e.g., as the free base); (ii) a pharmaceutically acceptable salt of the compound; or (iii) part of a pharmaceutical composition. In some embodiments of the above methods, uses, pharmaceutical compositions and kits, the additional therapeutic agent may be provided as (i) the compound itself (e.g., as the free base); (ii) a pharmaceutically acceptable salt of the compound; (iii) or part of a pharmaceutical composition.

The phrase "pharmaceutically acceptable salt," as used herein, refers to pharmaceutically acceptable organic or inorganic salts of a compound described herein. For use in medicine, the salts of the compounds described herein will be pharmaceutically acceptable salts. Other salts may, however, be useful in the preparation of the compounds described herein or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When the compound described herein is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound described herein is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated herein by reference in its entirety. Compounds, compositions and kits of the invention are also useful for veterinary treatment of companion animals, exotic animals and farm animals, including, without limitation, dogs, cats, mice, rats, hamsters, gerbils, guinea pigs, rabbits, horses, pigs and cattle.

Methods of Administration and Co-Administration

In some embodiments of the above methods and uses, the sGC stimulator is administered before a symptom or clinical manifestation of NASH fully develops or is detected in said patient. In other embodiments of the above methods and uses, the sGC stimulator is administered after one or more symptoms or clinical manifestations of NASH develops or is detected in said patient.

As used herein, the terms "in combination" or "co-administration" can be used interchangeably to refer to the use of more than one therapy (e.g., an sGC stimulator and one or more additional therapeutic agents). The use of the terms does not restrict the order in which therapies (e.g., the sGC stimulator and the additional therapeutic agents) are administered to a subject.

In some embodiments, the sGC stimulator is administered prior to, at the same time or after the initiation of treatment with another therapeutic agent.

In some embodiments of the above methods and uses, the additional therapeutic agent and the sGC stimulator are administered simultaneously. In other embodiments of the above methods and uses, the additional therapeutic agent and the sGC stimulator are administered sequentially or separately.

In some embodiments, the above pharmaceutical compositions or kits comprise (a) an sGC stimulator as discussed above or a pharmaceutically acceptable salt thereof, and (b) a pharmaceutically acceptable carrier, vehicle or adjuvant. In some embodiments, the pharmaceutical composition or kit comprises (a) one or more additional therapeutic agents as discussed above, or a pharmaceutically acceptable salt thereof, and (b) a pharmaceutically acceptable carrier, vehicle or adjuvant. In some embodiments, the pharmaceutical composition comprises (i) an sGC stimulator as discussed above, or a pharmaceutically acceptable salt thereof, (ii) one or more additional therapeutic agents as discussed above, or a pharmaceutically acceptable salt thereof, and (iii) a pharmaceutically acceptable carrier, vehicle or adjuvant.

The sGC stimulators and pharmaceutical compositions described herein can be used in combination therapy with one or more additional therapeutic agents. For combination treatment with more than one active agent, the additional active agents may be in the same dosage form or in separate dosage forms. Wherein the additional active agents are present in separate dosage forms, the active agents may be administered separately or in conjunction with the sGC stimulator. In addition, the administration of one agent may be prior to, concurrent to, or subsequent to the administration of the other agent.

When co-administered with other agents, e.g., when co-administered with another sGC stimulator, arginine, etc., an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.001 to about 100 mg/kg body weight/day, from about 0.001 to about 50 mg/kg body weight/day, from about 0.001 to about 30 mg/kg body weight/day, from about 0.001 to about 10 mg/kg body weight/day.

When "combination therapy" is employed, an effective amount can be achieved using a first amount of an sGC stimulator or a pharmaceutically acceptable salt thereof and a second amount of an additional suitable therapeutic agent (e.g. another sGC stimulator, arginine, a NO modulator, a cGMP modulator, a therapeutic that increases the function of nitric oxide synthase, etc.).

In one embodiment of this invention, the sGC stimulator and the additional therapeutic agent are each administered in an effective amount (i.e., each in an amount which would be therapeutically effective if administered alone). In another embodiment, the sGC stimulator and the additional therapeutic agent are each administered in an amount which alone does not provide a therapeutic effect ("a sub-therapeutic dose"). In yet another embodiment, the sGC stimulator can be administered in an effective amount, while the additional therapeutic agent is administered in a sub-therapeutic dose. In still another embodiment, the sGC stimulator can be administered in a sub-therapeutic dose, while the additional therapeutic agent, for example, a suitable anti-inflammatory agent is administered in an effective amount.

"Co-administration" encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, co-administration also encompasses use of each compound in a sequential manner in either order. When co-administration involves the separate administration of the first amount of an sGC stimulator and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, an sGC stimulator and the second therapeutic agent can be administered in any order within about 24 hours of each other, within about 16 hours of each other, within about 8 hours of each other, within about 4 hours of each other, within about 1 hour of each other or within about 30 minutes of each other, within about 5 minutes of each other, etc.

More, specifically, a first therapy (e.g., a prophylactic or therapeutically used sGC stimulator) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks prior to), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks subsequent to) the administration of a second therapy (e.g., an additional therapeutic agent or prophylactic agent described herein) to a subject.

Combination Therapies

In some embodiments of the above methods, uses, compositions and kits, the additional therapeutic agent or agents may be selected from one or more of the following:

(1) Endothelium-derived releasing factor (EDRF) or NO gas.

(2) NO donors such as a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide (Dilatrate®-SR, Imdur®, Ismo®, Isordil®, Isordil®, Titradose®, Monoket®), 3-morpholinosydnonimine; linsidomine chlorohydrate ("SIN-1"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.

(3) Other substances that enhance cGMP concentrations such as protoporphyrin IX, arachidonic acid and phenyl hydrazine derivatives.

(4) Nitric Oxide Synthase substrates: for example, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxylagmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.

(5) Compounds which enhance eNOS transcription.

(6) NO independent heme-independent sGC activators, including, but not limited to:

BAY 58-2667 (described in patent publication DE19943635)

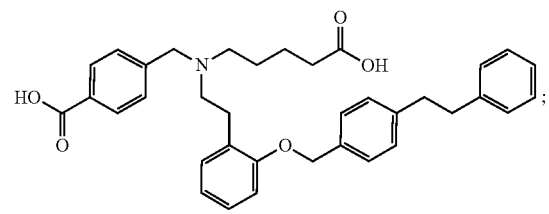 [SMILES: O=C(O)CCCCN(CCc1ccccc1OCc1ccc(CCc2ccccc2)cc1)Cc1ccc(C(=O)O)cc1]

HMR-1766 (ataciguat sodium, described in patent publication WO2000002851)

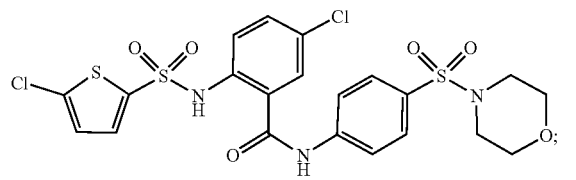 [SMILES: O=C(Nc1ccc(S(=O)(=O)N2CCOCC2)cc1)c1cc(Cl)ccc1NS(=O)(=O)c1ccc(Cl)s1]

S 3448 (2-(4-chloro-phenylsulfonylamino)-4,5-dimethoxy-N-(4-(thiomorpholine-4-sulfonyl)-phenyl)-benzamide (described in patent publications DE19830430 and WO2000002851)

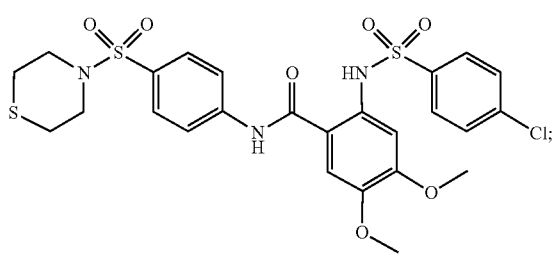 [SMILES: COc1cc(NS(=O)(=O)c2ccc(Cl)cc2)c(C(=O)Nc2ccc(S(=O)(=O)N3CCSCC3)cc2)cc1OC]

and
HMR-1069 (Sanofi-Aventis).

(7) Heme-dependent, NO-independent sGC stimulators including, but not limited to:

YC-1 (see patent publications FEP667345 and D19744026)

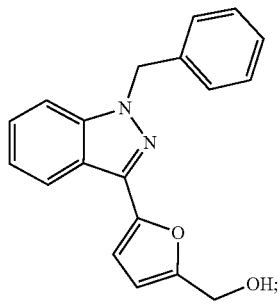 [SMILES: OCc1ccc(-c2nn(Cc3ccccc3)c3ccccc23)o1]

riociguat (BAY 63-2521, Adempas®, described in DE19834044)

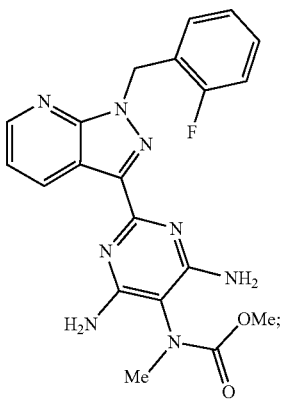 [SMILES: COC(=O)N(C)c1c(N)nc(-c2nn(Cc3ccccc3F)c3ncccc23)nc1N]

neliciguat (BAY 60-4552, described in WO 2003095451)

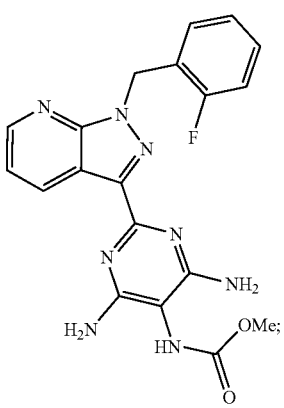 [SMILES: COC(=O)Nc1c(N)nc(-c2nn(Cc3ccccc3F)c3ncccc23)nc1N]

vericiguat (BAY 1021189)
etriciguat (described in WO 2003086407)
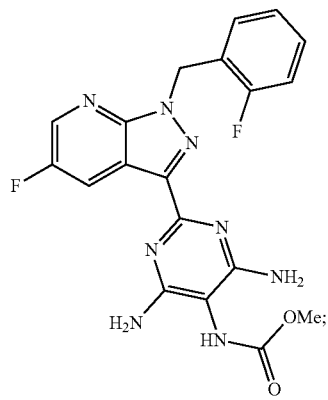 [SMILES: COC(=O)Nc1c(N)nc(-c2nn(Cc3ccccc3F)c3ncc(F)cc23)nc1N]
BAY 41-2272 (described in DE19834047 and DE19942809)
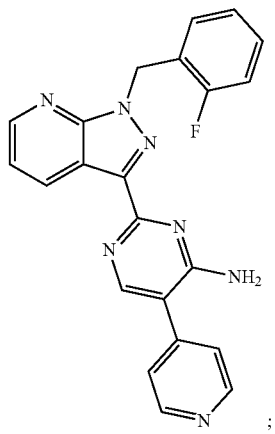
CFM-1571 (described in patent publication WO2000027394)
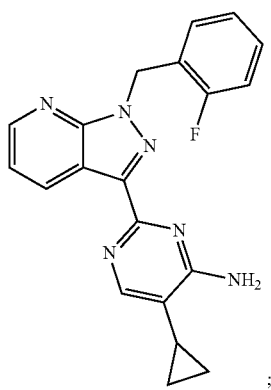 [SMILES: Nc1nc(-c2nn(Cc3ccccc3F)c3ncccc23)ncc1C1CC1]
BAY 41-8543 (described in DE19834044)
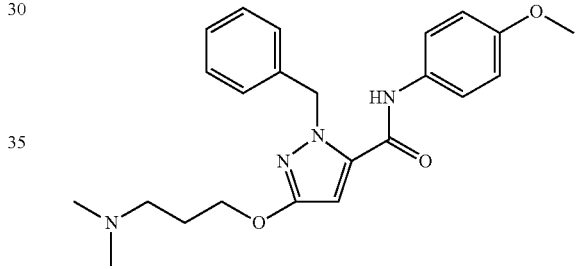
A-344905, its acrylamide analogue A-350619 and the aminopyrimidine analogue A-778935
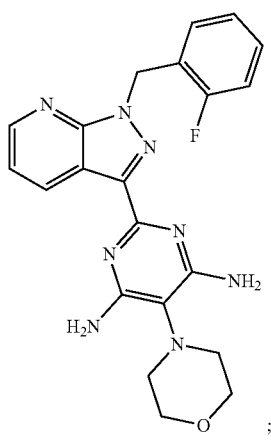 [SMILES: Nc1nc(-c2nn(Cc3ccccc3F)c3ncccc23)nc(N)c1N1CCOCC1]
A350-619
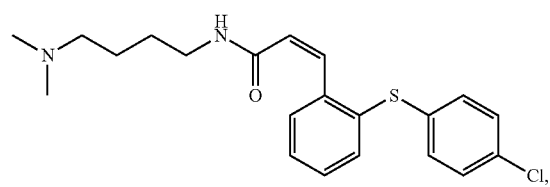
A-344905
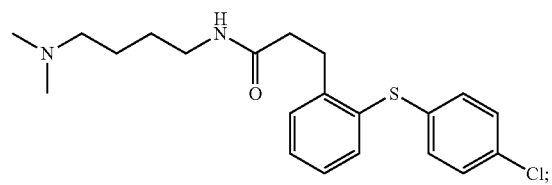

-continued

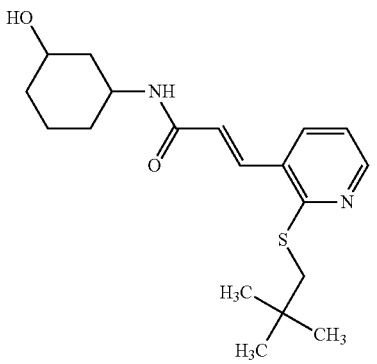
A-778935 and other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds described in Tetrahedron Letters (2003), 44(48): 8661-8663.

(8) Compounds that inhibit the degradation of cGMP, such as:

PDE5 inhibitors, such as, for example, sildenafil (Viagra®) and related agents such as avanafil, lodenafil, mirodenafil, sildenafil citrate (Revatio®), tadalafil (Cialis® or Adcirca®), vardenafil (Levitra®) and udenafil; alprostadil; dipyridamole and PF-00489791; and PDE9 inhibitors, such as, for example, PF-04447943.

(9) Calcium channel blockers of the following types: dihydropyridine calcium channel blockers such asamlodipine (Norvasc®), aranidipine (Sapresta®), azelnidipine (Calblock®), barnidipine (HypoCa®), benidipine (Coniel®), cilnidipine (Atelec®, Cinalong®, Siscard®), clevidipine (Cleviprex®), diltiazem, efonidipine (Landel®), felodipine (Plendil®), lacidipine (Motens®, Lacipil®), lercanidipine (Zanidip®), manidipine (Calslot®, Madipine®), nicardipine (Cardene®, Carden SR®), nifedipine (Procardia®, Adalat®), nilvadipine (Nivadil®), nimodipine (Nimotop®), nisoldipine (Baymycard®, Sular®, Syscor®), nitrendipine (Cardif®, Nitrepin®, Baylotensin®), pranidipine (Acalas®), isradipine (Lomir®); phenylalkylamine calcium channel blockers such as verapamil (Calan®, Isoptin®)

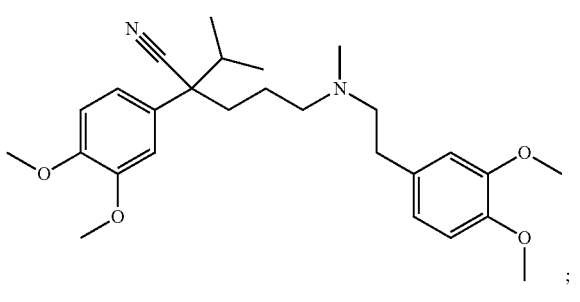

and gallopamil (Procorum®, D600); benzothiazepines such asdiltiazem (Cardizem®)

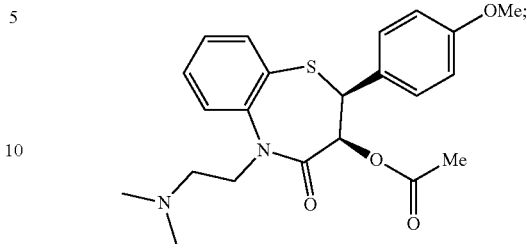

and nonselective calcium channel inhibitors such as mibefradil, bepridil, fluspirilene, and fendiline.

(10) Endothelin receptor antagonists (ERAs) such as the dual ($ET_A$ and $ET_B$) endothelin receptor antagonist bosentan (Tracleer®), sitaxentan (Thelin®) or ambrisentan (Letairis®).

(11) Prostacyclin derivatives or analogues, such as prostacyclin (prostaglandin $I_2$), epoprostenol (synthetic prostacyclin, Flolan®), treprostinil (Remodulin®), iloprost (Ilomedin®), iloprost (Ventavis®); and oral and inhaled forms of Remodulin® under development.

(12) Antihyperlipidemics such as the following types:
bile acid sequestrants like cholestyramine, colestipol, colestilan, colesevelam or sevelamer;
statins like atorvastatin, simvastatin, lovastatin, fluvastatin, pitavastatin, rosuvastatin and pravastatin;
cholesterol absorption inhibitors such as ezetimibe;
other lipid lowering agents such as icosapent ethyl ester, omega-3-acid ethyl esters, reducol;
fibric acid derivatives such as clofibrate, bezafibrate, clinofibrate, gemfibrozil, ronifibrate, binifibrate, fenofibrate, ciprofibrate, choline fenofibrate;
nicotinic acid derivatives such as acipimox and niacin;
combinations of statins, niacin and intestinal cholesterol absorption-inhibiting supplements (ezetimibe and others) and fibrates; and
antiplatelet therapies such as clopidogrel bisulfate.

(13) Anticoagulants, such as the following types:
coumarines (Vitamin K antagonists) such as warfarin (Coumadin®), cenocoumarol, phenprocoumon and phenindione;
heparin and derivatives such as low molecular weight heparin, fondaparinux and idraparinux;
direct thrombin inhibitors such as argatroban, lepirudin, bivalirudin, dabigatran and ximelagatran (Exanta®); and
tissue-plasminogen activators, used to dissolve clots and unblock arteries, such as alteplase.

(14) Antiplatelet drugs such as, for instance, topidogrel, ticlopidine, dipyridamoleand aspirin.

(15) ACE inhibitors, for example the following types:
sulfhydryl-containing agents such as captopril (Capoten®) and zofenopril;
dicarboxylate-containing agents such as enalapril (Vasotec/Renitec®), ramipril (Altace®/Tritace®/Ramace®/Ramiwin®), quinapril (Accupril®), perindopril (Coversyl®/Aceon®), lisinopril (Lisodur®/Lopril®/Novatec®/Prinivil®/Zestril®) and benazepril (Lotensin®);
phosphonate-containing agents such as fosinopril;
naturally occurring ACE inhibitors such as casokinins and lactokinins, which are breakdown products of casein and whey that occur naturally after ingestion of milk products, especially cultured milk;
the lactotripeptides Val-Pro-Pro and Ile-Pro-Pro produced by the probiotic *Lactobacillus helveticus* or derived from casein also having ACE-inhibiting and antihypertensive functions;

other ACE inhibitors such as alacepril, delapril, cilazapril, imidapril, trandolapril, temocapril, moexipril and pirapril.

(16) Supplemental oxygen therapy.

(17) Beta blockers, such as the following types:
non-selective agents such as alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol and timolol;
$\beta_1$—Selective agents such as cebutolol, atenolol, betaxolol, bisoprolol, celiprolol, dobutamine hydrochloride, irsogladine maleate, carvedilol, talinolol, esmolol, metoprolol and nebivolol; and
$\beta_2$—Selective agents such as butaxamine.

(18) Antiarrhythmic agents such as the following types:
Type I (sodium channel blockers) such as quinidine, lidocaine, phenytoin, propafenone;
Type III (potassium channel blockers) such as amiodarone, dofetilide and sotalol; and
Type V such as adenosine and digoxin.

(19) Diuretics such as thiazide diuretics, for example chlorothiazide, chlorthalidone and hydrochlorothiazide, bendroflumethiazide, cyclopenthiazide, methyclothiazide, polythiazide, quinethazone, xipamide, metolazone, indapamide, cicletanine; loop diuretics, such as furosemide and toresamide; potassium-sparing diuretics such as amiloride, spironolactone, canrenoate potassium, eplerenone and triamterene; combinations of these agents; other diuretics such as acetazolamid and carperitide.

(20) Direct-acting vasodilators such as hydralazine hydrochloride, diazoxide, sodium nitroprusside, cadralazine; other vasodilators such as isosorbide dinitrate and isosorbide 5-mononitrate.

(21) Exogenous vasodilators such as Adenocard® and alpha blockers.

(22) Alpha-1-adrenoceptor antagonists such as prazosin, indoramin, urapidil, bunazosin, terazosin and doxazosin; atrial natriuretic peptide (ANP), ethanol, histamine-inducers, tetrahydrocannabinol (THC) and papaverine.

(23) Bronchodilators of the following types:
short acting $\beta_2$ agonists, such as albutamol or albuterol (Ventolin®) and terbutaline;
long acting $\beta_2$ agonists (LABAs) such as salmeterol and formoterol;
anticholinergics such as ipratropium and tiotropium; and theophylline, a bronchodilator and phosphodiesterase inhibitor.

(24) Corticosteroids such as beclomethasone, methylprednisolone, betamethasone, prednisone, prednisolone, triamcinolone, dexamethasone, fluticasone, flunisolide, hydrocortisone, and corticosteroid analogs such as budesonide.

(25) Dietary supplements such as, for example omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.

(26) PGD2 receptor antagonists.

(27) Immunosuppressants such as cyclosporine (cyclosporine A, Sandimmune®, Neoral®), tacrolimus (FK-506, Prograf®), rapamycin (Sirolimus®, Rapamune®) and other FK-506 type immunosuppressants, mycophenolate, e.g., mycophenolate mofetil (CellCept®).

(28) Non-steroidal anti-asthmatics such as 02-agonists like terbutaline, metaproterenol, fenoterol, isoetharine, albuterol, salmeterol, bitolterol and pirbuterol; 02-agonist-corticosteroid combinations such as salmeterol-fluticasone (Advair®), formoterol-budesonide (Symbicort®), theophylline, cromolyn, cromolyn sodium, nedocromil, atropine, ipratropium, ipratropium bromide and leukotriene biosynthesis inhibitors (zileuton, BAY1005).

(29) Non-steroidal anti-inflammatory agents (NSAIDs) such as propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac; fenamic acid derivatives such as flufenamic acid, meclofenamic acid, mefenamic acid, niflumic acid and tolfenamic acid; biphenylcarboxylic acid derivatives such as diflunisal and flufenisal; oxicams such as isoxicam, piroxicam, sudoxicam and tenoxican; salicylates such as acetyl salicylic acid and sulfasalazine; and the pyrazolones such as apazone, bezpiperylon, feprazone, mofebutazone, oxyphenbutazone and phenylbutazone.

(30) Cyclooxygenase-2 (COX-2) inhibitors such as celecoxib (Celebrex®), rofecoxib (Vioxx®), valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine;

(31) Anti-diabetic agents such as insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®), α-glucosidase inhibitors such as acarbose, epalrestat, voglibose, miglitol; thiazolidinone compounds such as rosiglitazone (Avandia®), troglitazone (Rezulin®), ciglitazone, pioglitazone (Actos®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; DPP-IV inhibitors such as sitagliptin (Januvia®), vildagliptin (Galvus®), saxagliptin (Onglyza®), linagliptin (Tradjenta®), anagliptin (Sanwak), teneligliptin, alogliptin, trelagliptin, gemigliptin, dutogliptin and omarigliptin (MK-3102); GLP-1 agonists such as: exenatide (Byetta® Bydureonr, liraglutide (Victoza®, Saxenda®), lIxsenatide (Lyxumia®), albiglutde (TanzeiTrn), dulaglutide (Trulicitv®);

(32) HDL cholesterol-increasing agents such as anacetrapib and dalcetrapib.

(33) Antiobesity drugs such as methamphetamine hydrochloride (Desoxyn®), amfepramone hydrochloride (Tenuate®), phentermine (Ionamin®), benzfetamine hydrochloride (Didrex®), phendimetrazine tartrate (Bontril®, Prelu-2 ®, Plegine®), mazindol (Sanorex®), orlistat (Xenical®), sibutramine hydrochloride monohydrate (Meridia®, Reductil®), rimonabant (Acomplia®), amfepramone, chromium picolinate; combination such as phentermine/topiramate, bupropion/naltrexone, sibutramine/metformin, bupropion SR/zonisamide SR, salmeterol, xinafoate/fluticasone propionate; lorcaserin hydrochloride, phentermine/topiramate, cetilistat, exenatide, liraglutide, metformin hydrochloride, sibutramine/metformin, bupropion SR/zonisamide SR, CORT-108297, canagliflozin, chromium picolinate, GSK- 1521498, LY-377604, metreleptin, obinepitide, P-57AS3, PSN-821, salmeterolxinafoate/fluticasone propionate, sodium tungstate, somatropin (recombinant), tesamorelin, tesofensine, velneperit, zonisamide, beloranib hemioxalate, insulinotropin, resveratrol, sobetirome, tetrahydrocannabivarin and beta-lapachone.

(34) Angiotensin receptor blockers such as losartan, valsartan, candesartan, cilexetil, eprosaran, irbesartan, telmisartan, olmesartran, medoxomil, azilsartan and medoxomil.

(35) Renin inhibitors such as aliskiren hemifumirate.

(36) Centrally acting alpha-2-adrenoceptor agonists such as methyldopa, clonidine and guanfacine.

(37) Adrenergic neuron blockers such as guanethidine and guanadrel.

(38) Imidazoline I-1 receptor agonists such as rimenidine dihydrogen phosphate and moxonidine hydrochloride hydrate.

(39) Aldosterone antagonists such as spironolactone and eplerenone.

(40) Potassium channel activators such as pinacidil.

(41) Dopamine D1 agonists such as fenoldopam mesilate; other dopamine agonists such as ibopamine, dopexamine and docarpamine.

(42) 5-HT2 antagonists such as ketanserin.

(43) Vasopressin antagonists such as tolvaptan.

(44) Calcium channel sensitizers such as levosimendan or activators such as nicorandil.

(45) PDE-3 inhibitors such as amrinone, milrinone, enoximone, vesnarinone, pimobendan, and olprinone.

(46) Adenylate cyclase activators such as colforsin dapropate hydrochloride.

(47) Positive inotropic agents such as digoxin and metildigoxin; metabolic cardiotonic agents such as ubidecarenone; brain natriuretic peptides such as nesiritide.

(48) Drugs used for the treatment of erectile dysfunction such as alprostadil, aviptadil, and phentolamine mesilate.

(49) PPAR agonist such as: fibrates (clofibrate, gemfibrozil, ciprofibrate, bezafibrate, and fenofibrate); thiazolidinediones; saroglitazar;

(50) FXR agonists such as cafestol, chenodeoxycholic acid, obeticholic acid and fexaramine.

(51) Caspase inhibitors

(52) LOXL2 monoclonal antibodies

(53) Acetyl Co-A Carboxylase (ACC) inhibitors

(54) CCR2/CCR5 antagonists

(55) Fatty acid/bile acid conjugates

(56) Galectin-3 inhibitors ($5^7$) ursodeoxycholic acid (UDCA)

(58) DGAT1 inhibitors

(59) Neprisylin (NEP) inhibitors such as sacubitril

(60) combinations of NEP inhibitors with Angiotensin receptor antagonists, such as entresto (LCZ696), a combination of valsartan and sacubitril, and

(61) IMM-124E (Bovine colostrum powder from cow's immunized with LPS).

Pharmaceutical Compositions and their Routes of Administration

The compounds herein disclosed, and their pharmaceutically acceptable salts, thereof may be formulated as pharmaceutical compositions or "formulations".

A typical formulation is prepared by mixing a compound described herein, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound described herein is being formulated. Solvents are generally selected based on solvents recognized by persons skilled in the art as safe (e.g., one described in the GRAS (Generally Recognized as Safe) database) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g., enteric or slow release) preservatives, antioxidants, opaquing agents, glidants, processing aids, colorants, sweeteners, perfuming agents, flavoring agents and other known additives to provide an elegant presentation of the drug (i.e., a compound described herein or pharmaceutical composition thereof) or aid in the manufacturing of the pharmaceutical product (i.e., medicament).

The formulations may be prepared using conventional dissolution and mixing procedures. For example, the bulk drug substance (i.e., one or more of the compounds described herein, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8.

A compound described herein or a pharmaceutically acceptable salt thereof is typically formulated into pharmaceutical dosage forms to provide an easily controllable dosage of the drug and to enable patient compliance with the prescribed regimen. Pharmaceutical formulations of compounds described herein, or a pharmaceutically acceptable salt thereof, may be prepared for various routes and types of administration. Various dosage forms may exist for the same compound. The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total composition (weight:weight). The pharmaceutical composition can be prepared to provide easily measurable amounts for administration. For example, an aqueous solution intended for intravenous infusion may contain from about 3 to 500 g of the active ingredient per milliliter of solution in order that infusion of a suitable volume at a rate of about 30 mL/hr can occur.

The pharmaceutical compositions described herein will be formulated, dosed, and administered in a fashion, i.e., amounts, concentrations, schedules, course, vehicles, and route of administration, consistent with good medical practice. Factors for consideration in this context include the particular disorder being treated, the particular human or other mammal being treated, the clinical condition of the individual patient, the cause of the disorder, the site of delivery of the agent, the method of administration, the scheduling of administration, and other factors known to medical practitioners, such as the age, weight, and response of the individual patient.

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release".

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Gastroretentive formulations" are preparations designed to have increased retention in the stomach cavity. In some cases, they are used where a drug is preferentially or primarily absorbed via the stomach, is designed to treat the stomach directly, or where drug dissolution or absorption is aided drug absorption is aided by prolonged exposure to gastric acids. Examples of gastroretentive formulations include but are not limited to, high-density formulations, where the density of the formulation is higher than gastric fluid; floating formulations, which can float on top of gastric fluids due to increased buoyancy or lower density of the formulation; temporarily expandable formulations that are temporarily larger than the gastric opening; muco- and bio-adhesive formulations; swellable gel formulations; and in situ gel forming formulations. (See, e.g., Bhardwaj, L. et al. African J. of Basic & Appl. Sci. 4(6): 300-312 (2011)).

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent disaggregation to fine particles. This provides a larger surface area exposed to the dissolution medium, resulting in a faster dissolution rate.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. In particular embodiments, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution-retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound described herein that are suitable for oral administration may be prepared as discrete units such as tablets, pills, troches, lozenges, aqueous or oil suspensions, dispersible powders or granules, emulsions, hard or soft capsules, e.g., gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with a water-soluble carrier such as polyethyleneglycol or an oil medium, for example, peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g., for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound described herein in a vegetable oil, for example arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of compounds described herein contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable drug-depot forms are made by forming microencapsuled matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly (anhydrides). Drug-depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl ester wax, cetearyl alcohol, 2 octyldodecanol, benzyl alcohol and water.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using compounds described herein may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of compounds described herein include Tween™-60, Span-80, cetostearyl alcohol, benzyl alcohol, myristyl alcohol, glyceryl mono-stearate and sodium lauryl sulfate.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient. In another aspect, a compound described herein or a pharmaceutically acceptable salt, co-crystal, solvate or pro-drug thereof may be formulated in a veterinary composition comprising a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Kits

The pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) another therapeutic agent and a pharmaceutically acceptable carrier, vehicle or diluent in one or more containers or separate packaging. The kits may optionally comprise instructions describing a method of using the pharmaceutical compositions in one or more of the methods described herein (e.g. preventing or treating one or more of the diseases and disorders described herein). The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another one or other compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

Example 1: Animals Models of NASH

Several animal models of NASH have been described in the literature (for a review, see "Animal Models of Nonalcoholic Steatohepatitis: Eat, Delete, and Inflame", Ibrahim S H et al., Dig Dis Sci. published on line 1 Dec. 2015; DOI 10.1007/s10620-015-3977-1).

In one model, NASH is induced in male mice according to the method used by Fujii et al. (Fujii M, Shibazaki Y, Wakamatsu K, et al. "A murine model for non-alcoholic steatohepatitis showing evidence of association between diabetes and hepatocellular carcinoma", *Med Mol Morphol.*, 2013, 46, 141-52), consisting of a single subcutaneous injection of 200 g streptozotocin 2 days after birth ($1^{st}$ hit) and feeding with high-fat diet (HFD; 57 kcal % fat, cat #: HFD32, CLEA Japan, Japan) starting at 4 weeks of age ($2^{nd}$ hit). In this experimental model, fatty liver and the main histological features of NASH are evident by 5 and 7 weeks after birth, respectively. In this model, animals are kept on HFD for 2-16 weeks.

In another model, NASH is induced in Sprague-Dawley rats by intravenous administration of 20% intralipid (IL) for three weeks (Abu-Serie et al., Lipids in Health and Disease, 14:128 (2015)).

These or similar animal models of NASH could be used to determine the effect of the sGC stimulator compounds here disclosed on the clinical manifestations of NASH.

For example, NASH would be induced in C57BL/6J male mice (using N=4-12 animals per group) by a single subcutaneous injection of ~200 microgram streptozotocin at 2 days after birth, and feeding with a high fat diet ad libitum after 4 weeks of age. Male mice without any treatment, and male mice treated with STZ alone would be used as control animals. The animals would then be treated with an sGC stimulator beginning as early as day 2. The sGC stimulator may be dosed daily or more frequently throughout the study by oral gavage, in chow or water, or by a parenteral route. A series of analyses would be carried out as further described below:

Biochemical Analysis

Fasting blood sugar, Serum alanine aminotransferase (ALT), aspartate aminotransferase (AST) and triglyceride (TG) would be determined. In addition, levels of albumin, urea and creatinine would also be used to determine status of the liver, and degree of function.

Histological Analysis

Liver sections from one lobe (e.g., left lobe) would be embedded, snap frozen in liquid nitrogen, and stored for analysis. The sections would then be cut, air dried and fixed in acetone. For hematoxylin and eosin staining, liver sections would be prefixed by Bouin's solution and then stained with Lillie-Mayer's Hematoxylin and eosin solution. The degree of (zone-3) liver fibrosis could be assessed with Sirius red staining or silver impregnation staining. To visualize macro- and micro-vesicular fat, the sections fixed with 4% PFA-PBS would be stained with oil red O.

Immunohistochemistry

Endogenous peroxidase activity can be blocked using 0.03% $H_2O_2$—PBS, followed by incubation with Block Ace (Dainippon Sumitomo Pharm. Osaka, Japan). The sections are incubated with the optimal dilutions of anti-F4/80 ER-TR7, anti-CD68, anti-BrdU, anti-CD31, anti-glial fibrillary acidic protein (GFAP), anti-type 4 collagen and anti-glutamine synthetase antibodies overnight at 4 degrees C. After incubation with appropriate secondary antibodies, substrate reaction is performed using 3', 3'-diaminobenzidine (DAB) solution. For double staining, Alkaline Phosphatase Substrate Kit 1 (Vector Labs, Burlingame, Calif., USA) can be used. For negative controls, samples are processed, substituting antibody-dilution buffer for the primary antibody.

For quantitative analysis of ER-TR7-, F4/80-, and Sirius red-positive areas, bright field images of stained sections are captured using a digital camera around central veins at 200-fold magnification, and the positive areas in multiple fields (~5) are measured using ImageJ software (National Institute of Health, Bethesda, Md., USA). The results are determined as the means of multiple (~five) different fields of each section.

Non-alcoholic fatty liver disease (NAFLD) activity scores (NAS score) can be calculated according to Kleiner, et al. (Hepatology 41:1313-1321 (2005)). Liver histological analysis is used to determine the NAFLD score. Components of the score include steatosis grade, steatosis location, and presence of microvesicular steatosis, fibrosis stage, inflammation endpoints including lobular inflammation, presence of microgranulomas, and large lipogranulomas, as well as portal inflammation. Liver cell injury endpoints including hepatocyte ballooning, presence of acidophil bodies, pigmented macrophages, and megamitochondria are also components of the score. Other histological findings including degree of Mallory, hyaline and glycogenated nuclei are also used in the score.

Lobular inflammation can be detected in a number of ways, including lobular accumulation of F4/80+ macrophages, Histological Oil-red O staining can be used to measure steatosis/fat deposition.

Fibrosis can be determined in a number of ways. Histologically, for instance, by determining the number of ER-TR7+ fibroblasts, using Sirius Red staining to detect collagen deposition, and pericellular fibrosis detectable around the central vein, or using sliver impregnation staining.

An effect of an sGC stimulator on the NAFLD score or one or more components of the NAFLD score including steatosis, fibrosis, inflammation, or liver cell injury would suggest utility for treatment of NASH. Further, evidence of an effect on these endpoints at a dose associated with small to no effects on blood pressure would suggest utility across a broad group of NASH patients.

Example 2: Carbon Tetrachloride ($CCl_4$)-Induced Changes in Liver Fibrosis Markers in C57BL/6 Mice in the Presence and Absence of an sGC Stimulator Experimental animal models of liver fibrosis using $CCl_4$ in mice have been previously described in the literature (see for example: "Curcumin protects the rat liver from CCL-caused injury and fibrogenesis by attenuating oxidative stress and suppressing inflammation", Fu Y et al., Mol. Pharmacol., 73(2):399-409 (2008)).

A pilot study using male C57BL/6 mice was carried out to explore the changes in liver fibrosis biomarker after one single injection of carbon tetrachloride ($CCl_4$) given by intraperitoneal (IP) administration and the effect of several substances, including an sGC stimulator, in this model. Injection of $CCl_4$ in mice results in elevation of alpha-SMA (alpha-smooth muscle actin) mRNA expression and this can be used as a biomarker of fibrosis in the liver. A reduction in the expression levels of this biomarker and reversal towards the normal levels, upon administration of an sGC stimulator, can be used to assess the potential utility of the compound in the treatment of liver fibrosis.

Mice used were 8 weeks old at receipt, healthy, and unused in other experimental procedures. Housing and care were as specified in the USDA Animal Welfare Act (9 CFR, Parts 1, and 3) and as described in the *Guide for the Care and Use of Laboratory Animals* from the National Research Council. Environmental conditions in housing rooms were set at the following ranges for acclimation and naive groups: temperature: 68±5° F. (22±4° C.), humidity: 50±20%; light cycle: 12 hour light/12-hour dark; air changes: ten or more changes per hour with 100% HEPA filtered fresh air. Mice were given regular chow and water ad libitum and were not fasted overnight prior to compound administration.

The sGC stimulator used in this experiment was Compound A depicted below:

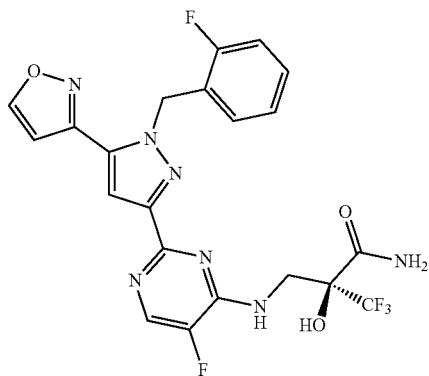

Compound A

The preparation and characterization of this compound was described in patent application publication WO2014144100, published 18 Sep. 2014.

CCl$_4$ was dosed once to all animals, via intraperitoneal administration (IP) at a concentration of 15 µl (dissolved in 85 µl of corn or olive oil) and a dose volume of 100 µl per 30 g of mouse. Compound A was dosed to mice via oral administration (PO, by oral gavage), BID for 3 days at a concentration of 3 mg/mL (0.5% Methylcellulose) and a dose volume of 300 l/30 g mouse. The single dose of CCl$_4$ was administered two hours after the first dose of Compound A. The second dose of Compound A was administered 7 hours after the first dose. After three days of dosing, the animals were sacrificed and plasma and liver samples obtained for analysis.

Tissue Homogenization

Total RNA was extracted from isolated tissues by adding 1 ml Trizol and a stainless steel bead to each sample, and homogenized using a TissueLyser II at the highest speed (30 Hz) for 2 minutes at room temperature. After homogenization, 200 µl chloroform was added to each homogenized sample. The homogenate was vortexed briefly and left in an upright position at room temperature for 2-5 minutes until phase separation became visible by eye. Samples were centrifuged for 15 minutes at the highest speed (13,200 rpm) at 4° C. in an Eppendorf centrifuge.

Total RNA Purification

The Qiagen RNeasy mini kit (Qiagen, Cat #74106) was used for RNA purification.

After 15 minutes at the highest speed (13,200 rpm) centrifugation at 4° C., the supernatant of each sample (~500 µl) was transferred into a new RNase-free tube. An equal volume of 70% ethanol (made with nuclease-free water) was added to each sample and mixed immediately by up-and-down pipetting. The labeled RNeasy spin column was placed onto a tube rack. 700 µl of the 70% ethanol/sample mixture, including any precipitate, was transferred onto the RNeasy spin column placed in a 2-ml collection tube (supplied by Qiagen). The lid was closed and the RNeasy spin column centrifuged for 30 seconds at 10,000 rpm at room temperature, and the flow-through in the 2 ml collection tube discarded. The remainder of ethanol/sample mixture (~300 µl) was added to the same spin column and the previous procedure (steps 3 and 4) repeated. After completion of the above two steps, total RNA was bound to the spin column membrane and the flow-through was discarded. 350 µl of wash buffer (RW1) was applied to RNeasy spin column, the lid closed and the RNeasy spin column centrifuged for 30 seconds at 10,000 rpm at room temperature. The flow-through was discarded. A DNase I stock solution (Qiagen) was prepared by injecting 550 µl RNase-free water into the DNase I vial using an RNase-free needle and syringe. The mixture was mixed gently by inverting the vial and not by vortexing. 10 µl DNase I stock solution was added to 70 µl buffer RDD (Qiagen) and the mixture, mixed gently. 80 µl of RNase-free DNase was added to each spin column for an on-column DNase digestion (15-minute incubation at room temperature). Following the 15-minute incubation step, the RNeasy spin column was washed with an additional 350 µl of buffer RW1, the lid was closed and the RNeasy spin column was centrifuged for 30 seconds at 10,000 rpm at room temperature and the flow-through discarded. The spin column was then washed twice with 500 µl of RPE buffer, centrifuged for 30 seconds between wash steps at 10,000 rpm at room temperature, and the flow-through discarded. The RNeasy spin column was placed onto a new 2 ml collection tube, centrifuged at maximum speed for 1 minute at room temperature to dry the membrane, and the RNeasy spin column then placed onto a new 1.5 ml collection tube (Qiagen). Following the above step, 15 µl nuclease-free water was added twice to the spin column, and the column spun after each of the two 15 µl nuclease-free water addition steps at the highest speed (14,800 rpm) in a Sorvall Legand Micro 21 centrifuge (ThermoFisher) at room temperature to elute the RNA. The eluted total RNA was placed on ice prior to RNA quantitation. Total RNA was measured using a NanoDrop 2000c (ThermoFisher) and the RNA concentration and quality were recorded.

cDNA Synthesis

1 µg of total RNA was used for cDNA synthesis. Single-stranded complementary DNA (cDNA) was synthesized in a 20 µl volume using a high-capacity cDNA reverse transcription kit (Life Technologies) described in Table 1 to obtain 50 ng/µl concentration.

After completion of the cDNA synthesis, an additional 20 µl of nuclease-free water was added to the cDNA to obtain a final cDNA concentration of 25 ng/µl.

RT-qPCR Relative Expression:

25 ng of cDNA was used for TaqMan® real time-quantitative polymerase chain reaction (RT-qPC®) gene expression analysis. Mouse alpha-smooth muscle actin (Life Technologies) and Glyceraldehyde 3-Phosphate Dehydrogenase (GAPDH) (Life Technologies) taqman probes were obtained from Life Technologies. MicroAmp fast optical reaction 96-well plate (Life Technologies) RT-qPCR reaction mix set up is described in Table 2. A total of 20 µl of the PCR reaction were added per well. The plate was sealed with a sealing cover and the reaction mix spun down at 2,000 rpm at 4° C. for 2 minutes prior to placing the plate into the reaimne PCR machine (Applied Biosystems StepOnePlus™ System). All samples were run in duplicate with 'no cDNA template' serving as negative control (NTC) on each plate, and the reactions were performed at the thermal cycler condition indicated in Table 3. After completion of the PCR run, data was exported into an Excel file for relative mRNA expression analysis. The $2^{-\Delta Ct}$ method was used to calculate relative mRNA expression (Livak & Schmittgen, Methods (2001) 25: 402-408).

TABLE 1

| cDNA synthesis Re agents preparation | |
|---|---|
| Reagents | 1 Reaction |
| 10x RT buffer (µl) | 2 |
| 10x RT Random Primers (µl) | 2 |
| 25x dNTP Mix (100 mM) (µl) | 0.8 |
| MultiScribe Reverse Transcriptase (µl) | 1 |
| Rnase Inhibitor (µl) | 1 |
| total of RT Mix per well (µl) | 6.8 |
| Total RNA at 1 µg (µl) | |
| H$_2$O (µl) | |
| total volume (µl) | 20 |
| cDNA Generation PCR program: | |
| 25° C. | 10 min |
| 37° C. | 120 min |
| 85° C. | 5 min |
| 4° C. | for ever |

TABLE 2

| RT-qPCR reaction mix: | | |
|---|---|---|
| Human Intestinal Tissue cDNA | | Single reaction (µl) |
| 20x Taqman Gene Expression Assay (µl) | Acta2 (Life Technologies) | 1 |
| | GAPDH (Life Technologies) | 1 |
| 2x Taqman Gene Expression Master Mix (Life Technologies, PN 4369016) (µl) | | 10 |
| cDNA Template (µl) | | 1 |
| H$_2$O (µl) | | 7 |

TABLE 3

| RT-qPCR Thermal Cycler Condition: Thermal Cycler Condition | | |
|---|---|---|
| Stage | Temperature (° C.) | Time (min:sec) |
| Hold | 50 | 2:00 |
| Hold | 95 | 10:00 |
| Cycle (40 Cycles) | 95 | 0:15 |
| | 60 | 1:00 |

Administration of Compound A in this pilot study resulted in a statistically significant reduction of elevated levels of alpha-SMA expression when compared to samples treated with vehicle (0.5% methyl cellulose). The reduction observed in the Compound A treated samples was significantly more pronounced than the reduction observed in samples treated with pirfenidone, a marketed anti-fibrotic compound approved for the treatment of idiopathic pulmonary fibrosis.

More specifically, a 30 mg/kg dose of Compound A induced a relative reduction of the increased alpha-SMA mRNA expression levels of about 66%, whereas a 400 mg/kg dose of pirfenidone only produced a reduction of about 20%.

These data support the hypothesis that an sGC stimulator (e.g., Compound A) displays liver anti-fibrotic activity in vivo, and also demonstrate the utility of this model for investigating the mechanism of sGC stimulators action on fibrosis, one of the hallmark characteristics of NASH.

Example 3: LPS Model of Acute Inflammation in Mice

Acute murine models of inflammation have previously been described (see for example, Engelberts I et. al., *Lymphokine Cytokine Res.* 10(1-2):127-31 (1991) and Durez P et al., *J Exp Med.* 177:551-5 (1993)). In these models, mice or rats are administered the compound of interest followed by an injection of LPS (LPS stands for lipopolysaccharide, 100 ng IV administration) one hour later. LP S is a component of bacterial cell walls and elicits a rapid and strong systemic inflammatory response. Two hours after LPS injection, blood is collected, plasma and serum are isolated and cytokine levels are measured. The concentrations of TNFα and IL-6 in blood increase after stimulation with bacterial lipopolysaccharide (LP S). Measurement of cytokine production is carried out with either ELISA or cytokine bead assay (CBA).

The sGC stimulator Compound B was assessed in such an animal model using C57BL/6 mice. The structure of Compound B is depicted below:

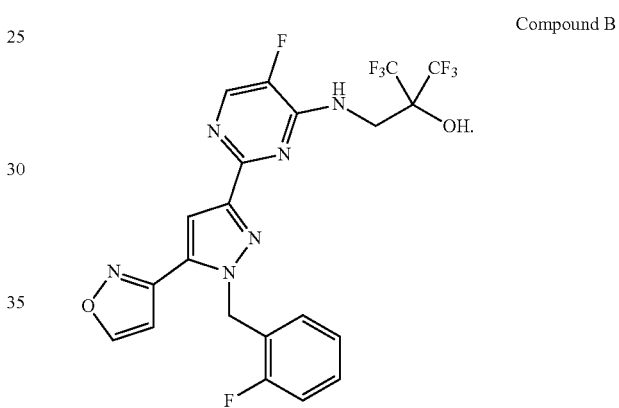

The preparation and characterization of this compound was described in patent application publication WO2014144100, published 18 Sep. 2014.

The ability of Compound B to modulate cytokine release in vivo was assessed. Compound B was administered by oral gavage (formulated in methylcellulose as the carrier) at 1 and 10 mg/kg doses and the levels of the pro-inflammatory cytokines TNFα and IL-6 were measured, as well as the anti-inflammatory cytokine IL-10. Vehicle (V) and dexamethasone (dex, 5 mg/kg) were used as negative and positive controls, respectively, and 10 mice were used per group.

In this study, Compound B at 10 mg/kg significantly reduced levels of IL-6 and TNFα, while increasing the levels of IL-10. These data support the hypothesis that an sGC stimulator (e.g., Compound B) has anti-inflammatory activity in vivo, and also demonstrate the utility of this model for investigating the mechanism of sGC stimulators action on the inflammatory response that is one of the hallmark characteristics of NASH.

Example 4: Effects of sGC Stimulator Treatment in a Mouse Model of Diet-Induced Obesity (DIO) with Hepatic Steatosis NASH frequently occurs in persons who are overweight or obese. Obesity is characterized by excessive fat/energy and expansion of white adipose tissue (WAT). In contrast, brown adipose tissue (BAT) combusts energy to produce heat. Hoffman et al. ("Stimulation of soluble guanylyl cyclase protects against obesity by recruiting brown adipose tissue", Linda S. Hoffmann et al., Nature Communications 6:7235 (2015)) have shown that BAY 41-8543, a small molecule stimulator of soluble guanylate cyclase (sGC), protects against diet-induced weight gain and liver steatosis, induces weight loss in established obesity, and improves the diabetic phenotype. BAY 41-8543 enhances lipid uptake into BAT and increases whole-body energy expenditure, whereas ablation of the heme-containing $\beta_1$-subunit of sGC severely impairs BAT function. BAY 41-8543 enhances differentiation of human brown adipocytes and induces 'browning' of primary white adipocytes. These results suggest that sGC is a potential pharmacological target for the treatment of obesity and its comorbidities, including NASH.

In the above study, transgenic mice are generated by deleting the $\beta_1$ subunit of sGC (sGC$\beta_1^{-/-}$), the subunit which contains the heme/NO-binding domain. Addition of NO increases cGMP in brown adipocytes (BA) isolated from wild-type (WT) mice, but not in sGC$\beta_1^{-/-}$ BA isolated from the transgenic mice. This demonstrates that sGC$\beta_1$ is required for NO-dependent cGMP formation in BA.

When WT mice are fed a high fat diet (HFD), they become obese and display all the metabolic characteristics of the obese phenotype, including reduced insulin sensitivity, increased plasma insulin levels, and increased overall fat accumulation. They also display abnormal levels of fat accumulation in the liver (i.e., steatosis).

BAY 41-8543 (dosed for 8 weeks at 300 mg/kg/24 hours in food and intraperitoneally at 1 mg/kg to guarantee high plasma levels) enhances lipid uptake into BAT and increases whole-body energy expenditure. BAY 41-8543 enhances differentiation of human brown adipocytes and induces "browning" of primary white adipocytes (WA). In the liver of WT mice fed a HFD, displaying the obese phenotype, BAY 41-8543 administration results in a significant reduction of triglyceride content when compared to mice fed regular chow.

These data support the hypothesis that an sGC stimulator has the ability to reduce liver steatosis in vivo, and also demonstrate the utility of this model for investigating the mechanism of sGC stimulators action on steatosis, one of the hallmark characteristics of NASH.

Example 5: Distribution of sGC Stimulators in Tissues, Studies in Rats

The purpose of this experiment was to determine compound concentrations in the plasma and tissues of animals dosed with sGC stimulators for 5 days Q.D.

In a first experiment, the sGC stimulator Compound B (described previously in Example 2) was dosed for 5 Days Q.D. to male Wister rats. Rats were divided into four study groups and dosed according to the below table:

| Experimental Group | Group A | Group B | Group D |
|---|---|---|---|
| Compound and dose | Vehicle | Compound B 1 mg/kg (in vehicle) | Compound B 10 mg/kg (in vehicle) |
| #Rats/Group | 12 Male | 6 Male | 6 Male |
| Dose Volume | 5 mL/kg PO | 5 mL/kg PO | 5 mL/kg PO |

Vehicle was 1% HPMC, 0.2% Tween 80 in 0.5% Methyl Cellulose.

The animals were dosed daily for five consecutive days according to the table above. On each day of dosing, frozen aliquots of each dosing solution were thawed and the animals were weighed and dosed accordingly. On day 5, two hours post the fifth dose, blood was collected by orbital bleed. Blood samples were collected in EDTA tubes pre-loaded with 5 μL of 100 mM IBMX Plasma was be separated by centrifugation for 10 minutes at 4° C. and then stored at −80° C.

A Ketamine/Xylazine/pbs solution as a 5:1:4 ratio was administered I.P. at 1 ul per gram. Once the rat was fully anesthetized (as determined by checking its reflexes) and while the heart was still beating, a needle was inserted into the left ventricle. Approximately 20 mls of PBS/IBMX/heparin solution were then perfused. The right atrium was snipped, and perfusion continued for approximately 10 additional mls (30 mls total). At this point, the femoral artery was snipped and perfusion was continued until there was no longer blood (only clear fluid) collecting in the abdominal cavity. Several tissues, including liver, were isolated and weighed followed by snap freezing.

A second separate and similar experiment was carried out with Compound C. The structure of Compound C is depicted below. The preparation and characterization of this compound was described in patent application publication WO2014144100, published 18 Sep. 2014.

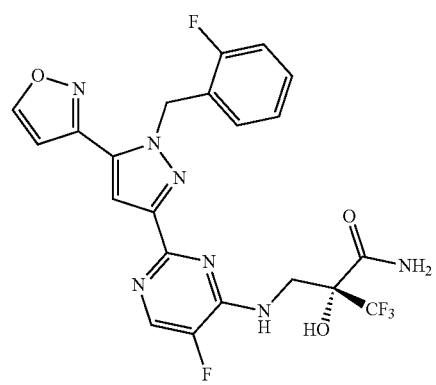

Compound C

For this second experiment, rats were divided into four study groups and dosed according to the below table:

| | Experimental Group | | |
|---|---|---|---|
| | Group A | Group B Compound | Group D |
| Batch | Vehicle | Compound C 1 mg/kg (in vehicle) | Compound C 10 mg/kg (in vehicle) |
| #Rats/Group | 6 Male | 6 Male | 6 Male |
| Dose Volume | 5 mL/kg PO | 5 mL/kg PO | 5 mL/kg PO |

Vehicle was 1% HPMC, 0.2% Tween 80 in 0.5% Methyl Cellulose

Quantitation of Compound B and Compound C in Rat Liver by LC-MS/MS

Samples were analyzed using liquid chromatography (LC) with tandem mass spectrometric detection (MS/MS) using positive electrospray ionization. The standard curve range was from 0.1 to 400 ng/mL. The following Reference Materials were used: Compound B, Compound C, $^{13}$C-labeled Compound B and $^{13}$C-labeled Compound C.

In order to prepare the tissues for measurement, the naïve livers and the livers isolated after treatment were removed from the −80° C. freezer and placed on liquid nitrogen. The liver weight was recorded and then the tissue placed in a Geno grinding vial containing two 7/16" steel beads. The liver was homogenized using a Geno/Grinder 2010 for 3 minutes at 1500 rpm. Approximately 200 mg of tissue from each sample was weighed and recorded. A 4× volume of 100 uM IBMX in 20% acetic acid was added to each pre-weighed sample and vortexed (ex. 200 mg of liver powder/800 μL of 100 μM IBMX in 20% acetic acid). A standard curve was created in naïve liver matrix by diluting 100× DMSO stocks (5 μL of each 100× standard into 495 μL of liver matrix). 300 μL of acetonitrile containing the internal standard (20 ng/mL $^{13}$C-labeled Compound B or $^{13}$C-labeled Compound C) were added to a Phenomenex Phree phospholipid removal 96-well plate. 100 μL of 1× standards and treatment group samples were added to the acetonitrile, then pipetted up and down a few times to ensure mixing and precipitation. The Phree phospholipid removal plate was placed on top of a collection plate and a pressure of 5 psi applied using a positive pressure manifold. Samples were dried under nitrogen in a TurboVap at 55° C. Each sample was resuspended in 50 μL of 0.1% Formic Acid, covered and vortexed. The samples were analyzed by LC-MS/MS.

The following conditions were used for LC/MS/MS analysis.

| LC/MS/MS Conditions | |
|---|---|
| Chromatography Conditions | |
| Column | Hypersil Gold, 2.1 × 50 mm, 3 um |
| Guard | Column Hypersil Gold javelin guard (2.1 × 10) |
| Column Temperature | 25° C. |
| Injection Volume | 10 uL |
| Autosampler Temperature | 4° C. |
| Flow Rate | 1 mL/min |
| Mobile Phases | Mobile Phase A: 0.1% Formic Acid in H$_2$O |
|  | Mobile Phase B: 0.1% Formic Acid in ACN |
|  | Detection Method |
| Ion Mode | TurboIon Spray, positive |
| Compound | MRM |
|  | Transition |
| Compound B | 535.0 > 109.0 |
| $^{13}$C-labeled Compound B | 541.0 > 115.0 |
| Compound C | 510 > 109 |
| $^{13}$C-labeled Compound C | 516 > 115 |

Total liver and plasma concentrations were measured and liver concentrations were corrected for total liver weight. Liver:Plasma ratios were determined by dividing liver compound concentration by the plasma compound concentration. The liver:plasma ratios observed were similar for both dose groups (1 mg/kg and 10 mg/kg). The total Liver:Plasma ratio for Compound B was 19 at 1 mg/kg and 20 at 10 mg/kg. The total Liver:Plasma ratio for Compound C was 6 at 1 mg/kg and 8 at 10 mg/kg. All compounds showed dose proportional increases in total tissue and plasma concentrations.

These data support the notion that some sGC stimulators, such as those of structures resembling Compound B and Compound C or others disclosed herein are able to distribute to the liver, where they will be able to have an effect on aspects of NASH, while at the same time having the potential to minimize systemic effects such as blood pressure lowering.

Using liver microdialysis, it has also been shown that these compounds engage the target sGC in the liver specifically by increasing cGMP and pVASP, both of which are markers of sGC target engagement.

Example 6: Distribution of sGC Stimulators in Tissues, Clinical Studies

In a randomized, double-blind, placebo-controlled, single ascending dose Phase I study enrolling 46 healthy volunteers, participants were randomized 3:1 to receive a single dose of Compound B or placebo administered via an oral capsule. Top-line clinical data were consistent with preclinical findings described above in Example 5 and included evidence of extensive distribution to tissues.

Example 7: Mouse on a Methionine/Choline Deficient High-Fat Diet

Design of the Study:

The study was performed in mice fed a high-fat diet deficient in choline and methionine (MCD-HFD or MCD diet), a model that reproduces the clinical manifestations of human steatohepatitis and fibrosis in mice. These mice received the sGC stimulator Compound B prophylactically (at two doses, 1 and 3 mg/kg/day in the food), starting at the same time as the start of the administration of the high-fat diet deficient in choline/methionine, and before animals started manifesting clinical signs of steatohepatitis.

The prophylactic treatment with Compound B proceeded for a total of 9 weeks simultaneously with the high-fat diet deficient in choline/methionine administration. At the end of the treatment, the degree of inflammation was assessed in the liver by determining levels of gene expression for IL-6, TNFα, IL-10, MCP-1β, IL-1 and IL-Ira, by real-time PCR. Inflammation levels were also determined by assessing inflammatory infiltrate by F4/80 immunohistochemistry, and necroinflammation was assessed by hematoxylin-eosin staining. Liver fibrosis was determined by measuring levels of gene expression for collagen type I and II, MMP-2, TIMP-1 and TGFβ1 at the mRNA level. Histological analysis was carried out of tissue sections stained with Masson's trichrome and Sirius Red.

The study comprised the following experimental groups:

Group I (n=5): Chow Control group received a matching sucrose diet equivalent to the high-fat diet (HFD) for 9 weeks.

Group II (n=15): Choline/methionine deficient HFD Control group (MCD control group) received a Choline/methionine deficient HFD diet for 9 weeks.

Group III (n=10): Choline/methionine deficient HFD for 9 weeks supplemented with Compound B dosed in food (1 mg/kg body weight/day). (IW1 group)

Group IV (n=10): Choline/methionine deficient HFD for 9 weeks supplemented with Compound B dosed in food (3 mg/kg body weight/day). (IW3 group)

Analysis:

After treatment, animals were sacrificed and liver and blood samples were collected. The effects of the sGC stimulator on liver weight, steatosis, inflammation and fibrosis were evaluated as follows:

Analysis of mRNA Expression by Real-Time PCR:

Total RNA was obtained with the RNAqueous kit. RNA concentrations were assessed in a UV-spectrophotometer and the RNA's integrity tested on a 6000 LabChip in a 2100 Bioanalyzer (Agilent Technologies, Palo Alto, Calif.). First strand cDNA synthesis was performed by incubating 1 μg of total RNA with 2.5 µl of 10×RT buffer, 1 µl of 25×dNTPs, 2.5 µl of 10× Primers and 1.25 µl of reverse transcriptase (25 µl final volume) for 10 minutes at 25° C. following 2 hours at 37° C. in a ABI thermal cycler. Ready-to-use primer and probe sets pre-developed by Applied Biosystems (TaqMan Gene Expression Assays) were used to quantify gene expression using R-actin as an endogenous control. Briefly, PCR reactions were performed in duplicate using the Universal TaqMan 2×PCR mastermix in a volume of 20 µl containing 1.25 µl cDNA. Real-time quantitative PCR was performed with an ABI Prism 7900 Sequence Detection System (Applied Biosystems) using the fluorescent TaqMan methodology. Real time PCR results were analyzed with the Sequence Detector Software version 2.1 (Applied Biosystems) and relative quantitation of gene expression was performed using the 2-ΔΔ Ct method. (User Bulletin #2; http://docs.appliedbiosystems.com/pebiodocs/04303859.pdf).

Masson's Trichrome and Sirius Red Staining:

Tissue samples fixed in 10% formalin were embedded in paraffin, cut into 5 µm sections, stained with H&E and analyzed by a registered pathologist unaware of the treatments. Tissue sections were incubated for 10 minutes in 0.5% thiosemicarbazide and stained in 0.1% Sirius Red F3B in saturated picric acid for 1 hour, and subsequently washed with an acetic acid solution (0.5%). Masson's trichrome staining was performed at the Pathology Department of the Hospital Clinic, Barcelona, Spain. Sections were visualized under a Nikon Eclipse E600 microscope (Kawasaki, Kanagawa, Japan) and the relative areas of steatosis and fibrosis were quantitated by histomorphometry using Olympus Cell (Olympus Soft Imaging Solution GmbH, Munster, Germany) and Image J software (Macbiophotonics, McMaster University, Hamilton, ON, Canada), respectively. A minimum of 6-20 independent fields were evaluated.

Masson's trichrome sections were scored by examining randomly chosen fields of view per tissue section as follows:

Stage 0. Absent. Normal lobular architecture

Stage I. Peri central fibrosis (increased thickness of the central vein)

Stage II. Central anastomoses (some fibrous septa connecting central veins)

Stage III. Pre-cirrhotic stage (fibrous septa with marked distortion of the liver lobules)

Stage IV. Cirrhosis (nodule regeneration surrounded by broad connective tissue septa).

Assessment of Inflammatory Infiltrate by F4180 Immunohistochemistry:

Tissue sections were deparaffinized, rehydrated and pretreated with trypsin 0.05%-CaCl$_2$ 0.1% for 20 minutes at 37° C. to unmask the antigen, followed by incubation with H$_2$O$_2$ 3% for 25 minutes at room temperature and dark conditions to block endogenous peroxidase activity, and BSA 2% for 20 minutes at room temperature to avoid unspecific binding of the primary antibody. The sections were then incubated overnight at 4° C. with a primary rat anti-mouse F4/80 antibody (1/100) followed by incubation for 90 minutes at room temperature with a biotinylated rabbit anti-rat IgG secondary antibody (1/200) and incubation with ABC for 45 minutes at room temperature. Color was developed using the DAB substrate and sections will be counterstained with hematoxylin.

Assessment of Necroinflammation:

Tissue samples fixed in 10% formalin were embedded in paraffin and cut in 2 µm sections for hematoxylin-eosin staining. Necroinflammation was analyzed by a registered pathologist unaware of the treatments according to the histological scoring system used on a routine basis in the Pathology Laboratory of the Hospital Clinic: Grade 0 (absent), Grade 1 (spotty necrosis; one or few necrotic hepatocytes), Grade 2 (confluent necrosis) and Grade 3 (bridging necrosis).

Results

Control Groups:

After 9 weeks, animals in Group II (control group on the MCD diet) displayed a large increase of the liver tissue weight versus total body weight ratio when compared to animals in the chow control group (Group I). The liver tissue weight versus total body weight ratio in the MCD animals almost doubled as compared to the chow fed animals. Using Hematoxylin/Eosin stain, fat accumulation was clearly visible in the livers of animals in Group II as compared to animals in Group I.

Figure 4:
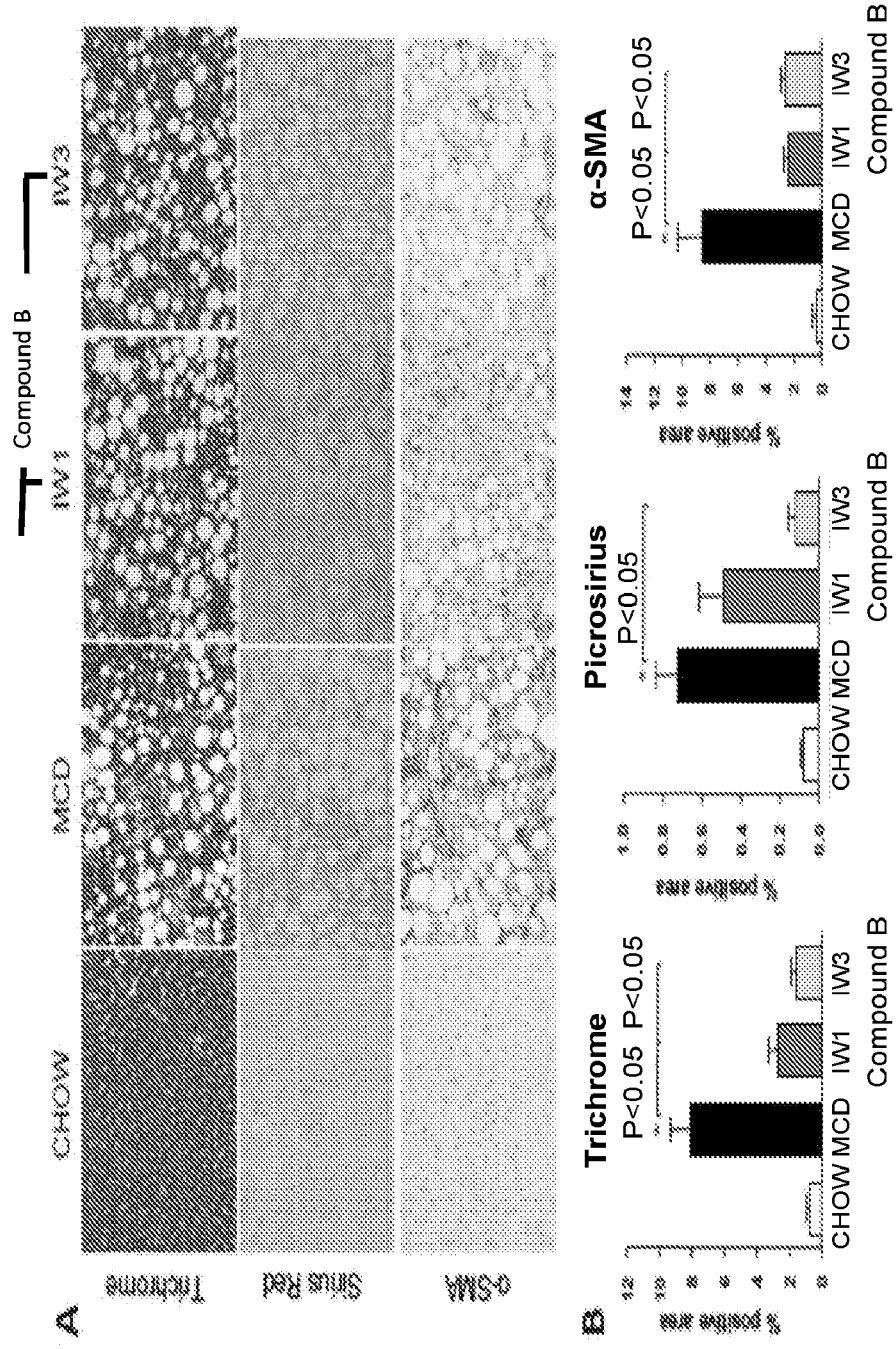
FIG. 4 demonstrates trichrome stain and α-SMA deposition results in livers of MCD/HFD Mice treated with embodiments of the invention.

Using Picrosirius Red staining, fibrosis (in the form of collagen accumulation) was clearly increased by approximately 8-fold in Group II, when compared with livers from animals in Group I. This observation was corroborated when fibrosis was determined by analysis of trichrome stain and also by α-SMA deposition (FIG. 4; comparing chow versus MCD columns).

The levels of mRNA expression were highly elevated for animals in Group II when compared to animals in Group I for the following genes associated with liver fibrosis: COL1A1, COL1A2, TIMP-1, MMP2 and TGFβ1.

The levels of mRNA expression were highly elevated for animals in Group II when compared to animals in Group I for the following genes associated with liver inflammation: TNF-α, IL-6, IL-10, MCP-1, and IL-Ira.

Figure 5:
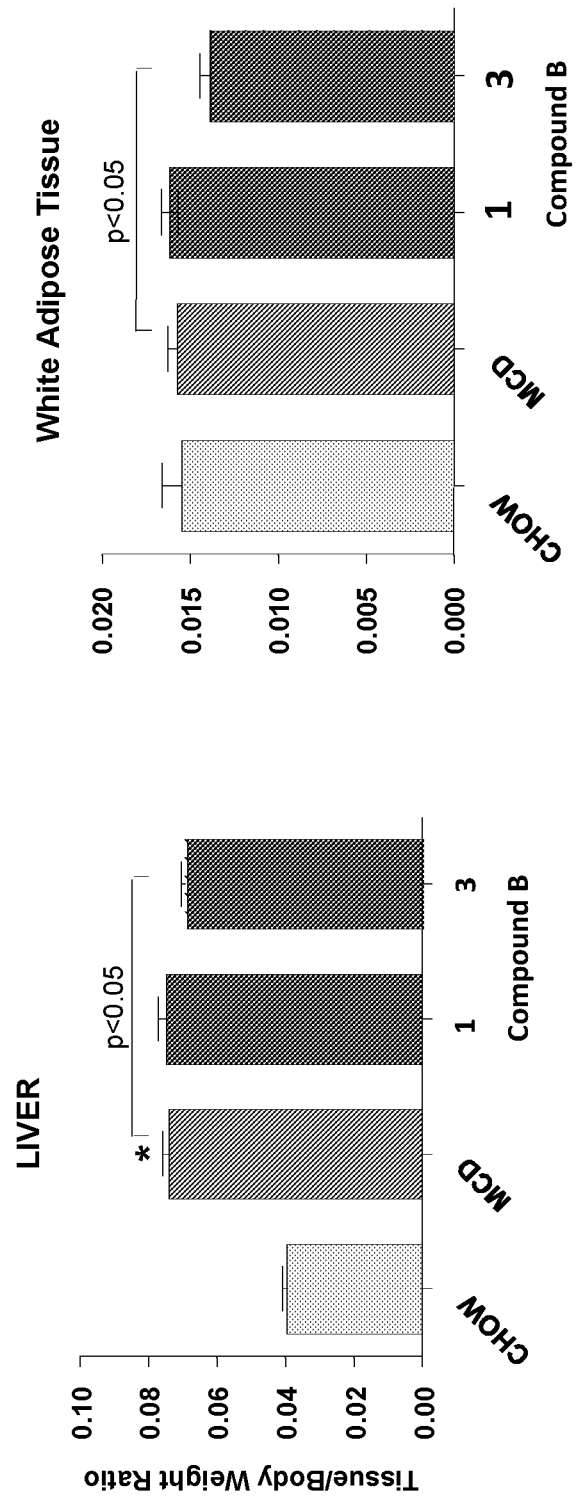
FIG. 5 compares the liver tissue weight versus total body weight ratio (graph on left) and the reduction in the percentage of white adipose tissue in the liver (graph on right) of animals in a control group vs. animals treated with an embodiment of the invention.

Treatment Groups:

After 9 weeks, animals treated with 3 mg/kg of Compound B (Group IV) displayed a statistically significant reduction in the liver tissue weight versus total body weight ratio as compared to the animals in control Group II. After 9 weeks, animals treated with 3 mg/kg of Compound B (Group IV) displayed statistically significant reduction in the percentage of white adipose tissue in the liver as compared with animals in control Group II. These results are summarized in FIG. 5. This supports the notion that sGC stimulators such as Compound B are able to reduce steatosis of the liver.

After 9 weeks, fibrosis as detected using Picrosirius Red staining was significantly reduced in animals treated with 1 mg/kg of Compound B (Group III) and in animals treated with 3 mg/kg of Compound B (Group IV). The reduction was proportional to the dose of Compound B administered as can be seen in FIG. 1. This was confirmed as seen in FIG. 4, by analysis of trichrome stain and also by α-SMA deposition.

Figure 2:
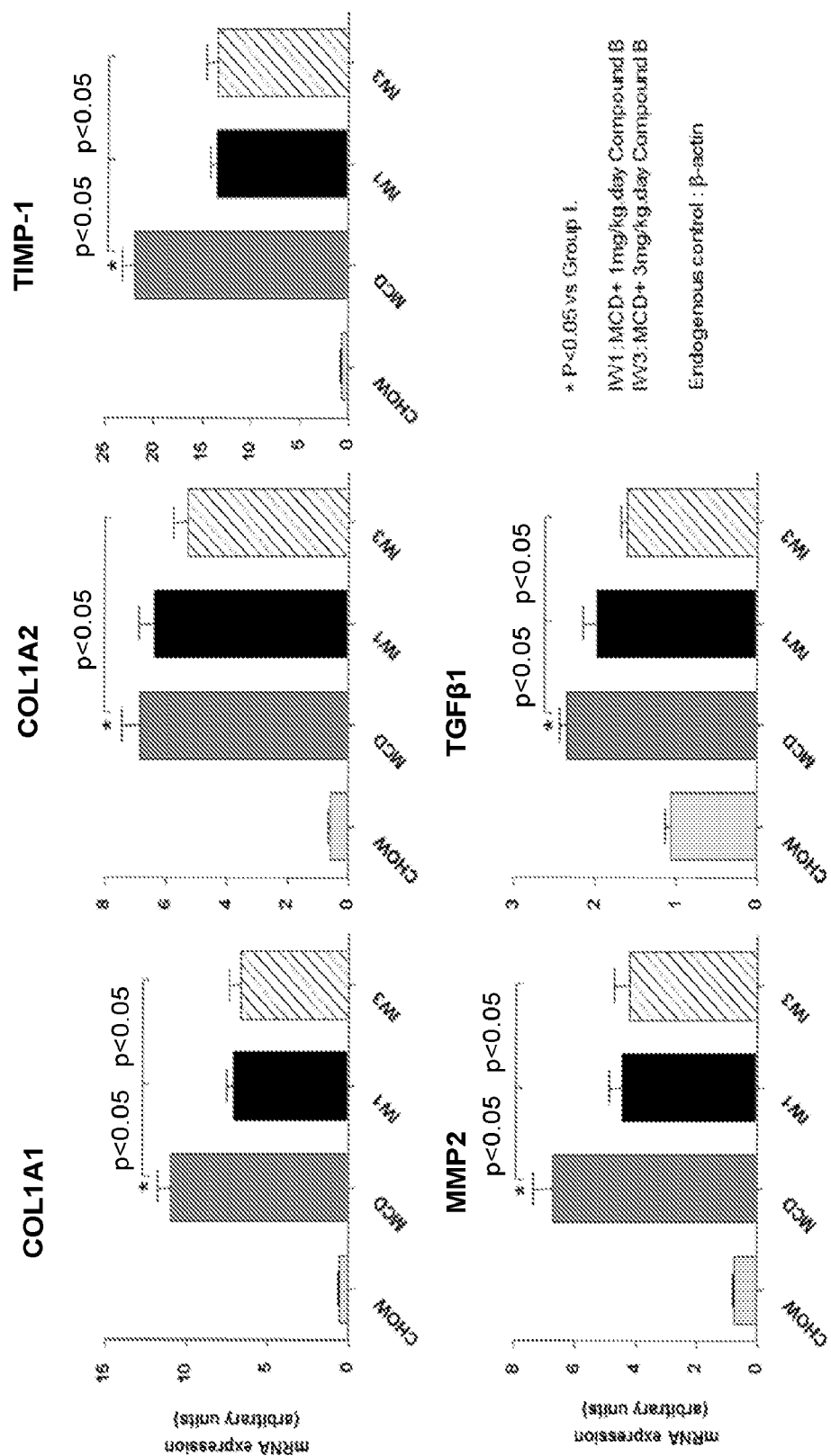
FIG. 2 shows levels of mRNA expression for markers of liver fibrosis evaluated in this study using embodiments of the invention.

After 9 weeks of treatment, the levels of mRNA expression for all markers of liver fibrosis evaluated in this study were reduced in a statistically significant manner in both Group III and Group IV as compared to their levels in the control Group II. These results are summarized in FIG. 2. These results support the notion that sGC stimulators such as Compound B are able to reduce fibrosis of the liver.

Figure 3:
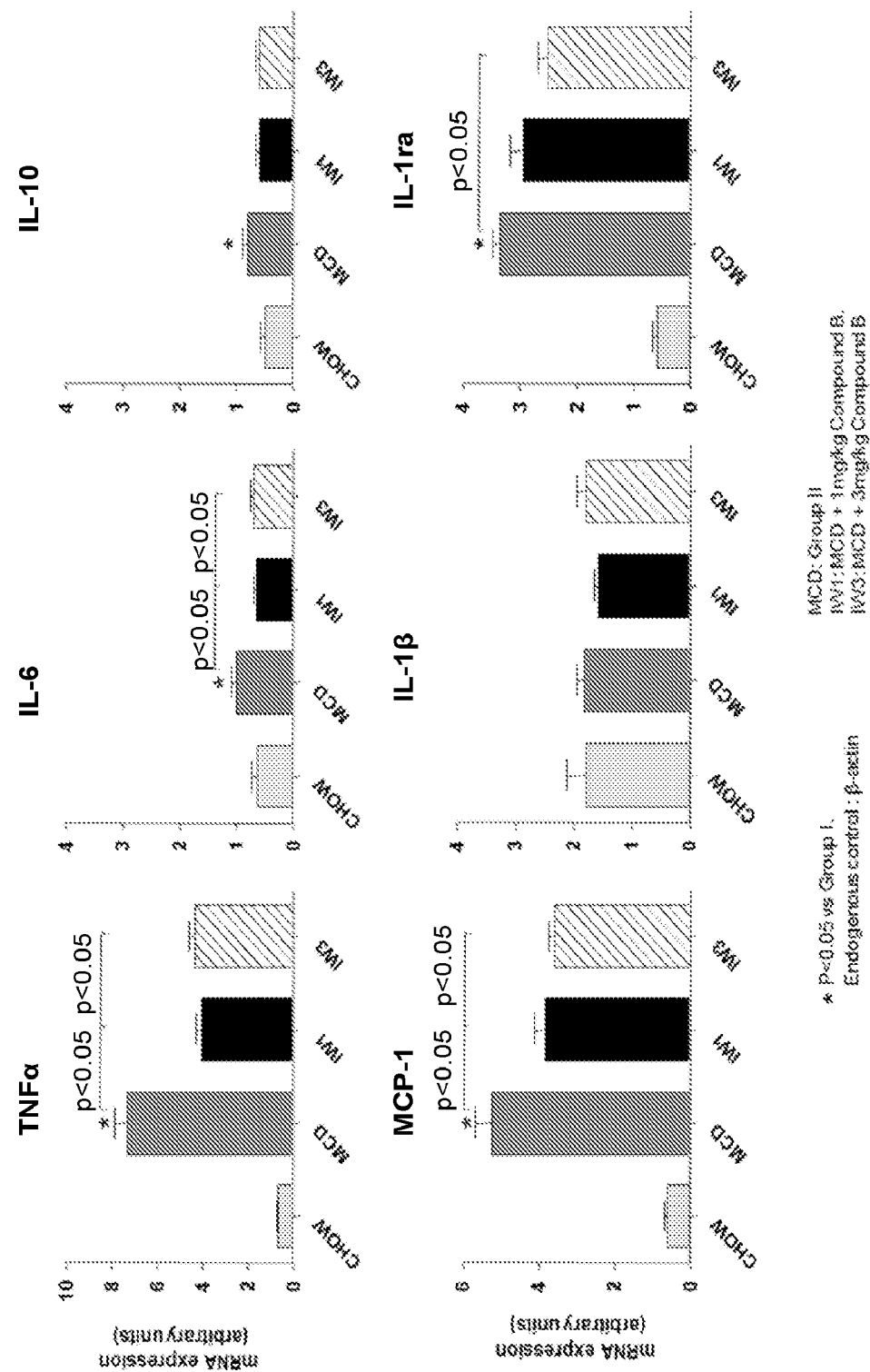
FIG. 3 illustrates levels of mRNA expression for markers of liver inflammation evaluated in this study using embodiments of the invention.

After 9 weeks of treatment, the levels of mRNA expression for all markers of liver inflammation evaluated in this study were reduced in a statistically significant manner in both Group III and Group IV as compared to their levels in the control Group II. These results are summarized in FIG. 3.

Figure 6:
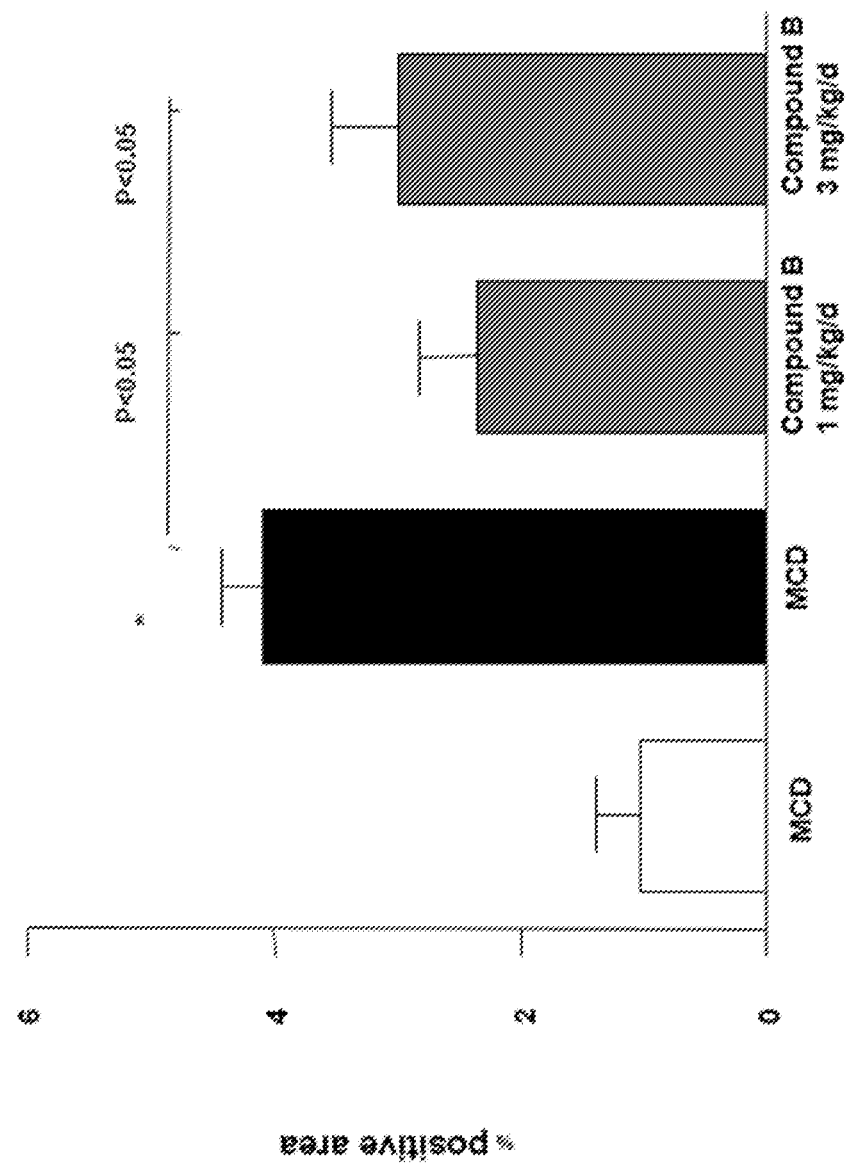
FIG. 6 shows a comparison of inflammatory infiltrate by F4/80 immunohistochemistry in the livers of animals in a control group vs. animals treated with embodiments of the invention.

Assessment of inflammatory infiltrate by F4/80 immunohistochemistry (FIG. 6) showed a decrease in the macrophage numbers for livers in treatment groups III and IV when compared to livers in control group II. The effect was statistically significant for both doses of Compound B used (1 and 3 mg/kg). These results support the notion that sGC stimulators such as Compound B are able to reduce inflammation in the liver of an animal model of NASH.

Figure 7:
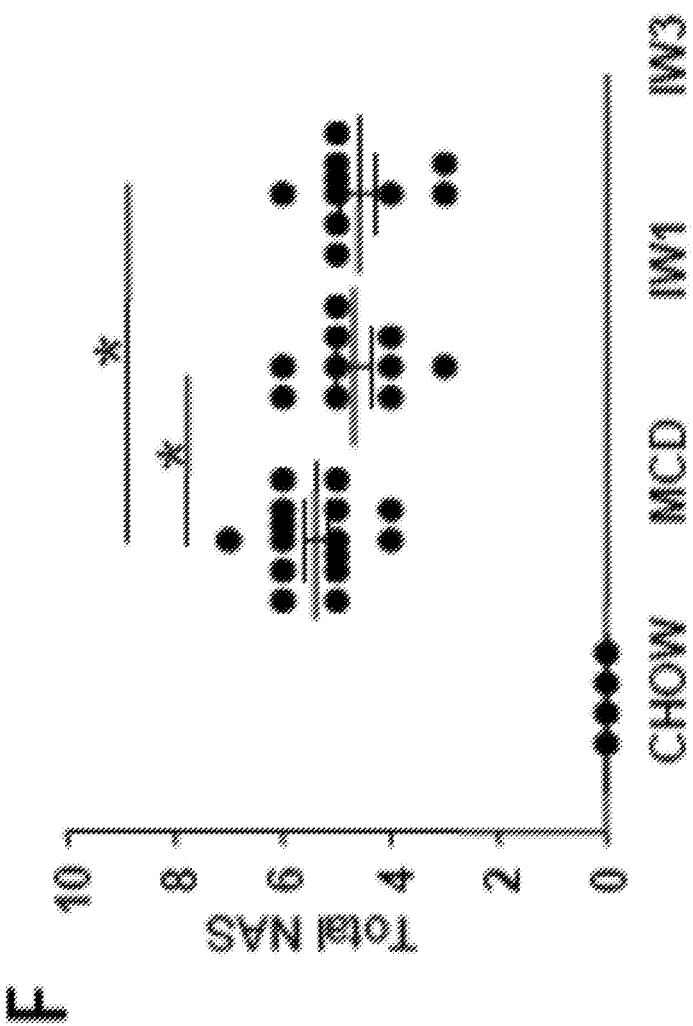
FIG. 7 illustrates a comparison of total NAS score (Steatosis+Inflammation+Ballooning) in the livers of animals in a control group vs. animals treated with embodiments of the invention.

Total NAS (defined above) was reduced after administration of Compound B at 1 mg/kg (Group III) or 3 mg/kg (Group IV) as compared to the NAS score of control group II (FIG. 7).

Example 8: Thioacetamide (TAA) Induced Model of Liver Fibrosis in Rats

Male Sprague-Dawley rats (280-300 g, Envigo) were administered 150 mg/kg TAA or phosphate buffered saline (PBS) 3 times per week via intraperitoneal (i.p.) injection for the duration of the study (8 weeks) at a volume of 5 mL/kg. TAA was prepared fresh on the day of each injection. Four weeks after the initial TAA injection, animals were administered Compound B by chow admixture prepared by Research Diets at a dose equivalent of 1, 3, or 10 mg/kg/day. Animals were weighed weekly and monitored closely for overall changes in health for the duration of the experiment.

At the termination of the in-life study, the medial lobe of the liver was collected in 10% neutral buffered formalin (Sigma, HT501128) and fixed at 4° C. overnight with gentle agitation. Tissues were then washed with phosphate buffered saline (×2) and transferred to 70% ethanol. Samples were then cut into three parts and embedded in a single block and sectioned at 5 microns so that slides with a single section (three parts of the liver) were generated. Slides were stained for collagen using a 0.1% solution of Sirius red in picric acid (Rowley Biochemical, SO-674).

Images were captured using a Nikon DS-QiMc camera mounted to a Nikon Eclipse E400 equipped with an automated stage (Prior Optiscan III). For each liver portion, a random 2×2 image was scanned at 100× magnification (3 per animal). A binary threshold was set to capture positively stained (red) pixels in the image and the percent area of positive pixels was calculated (NIS Elements, v4.40).

Data was analyzed using GraphPad Prism (v6.07). Differences between groups were assessed using a one-way ANOVA followed by a student's t test. Data were considered to be statistically significant with $p<0.05$. Data are presented as Mean±SEM.

Livers from TAA-treated rats showed significantly greater area of collagen deposition compared to vehicle control (1.27±0.14 vs 13.25I.53; p<0.0001). Compared to TAA control, treatment with Compound B significantly reduced collagen staining at 1 mg/kg/d (7.08I.13; p<0.0001), 3 mg/kg/d (9.360.89; p<0.05), and 10 mg/kg/d (9.00±1.28; p<0.05).

Figure 8:
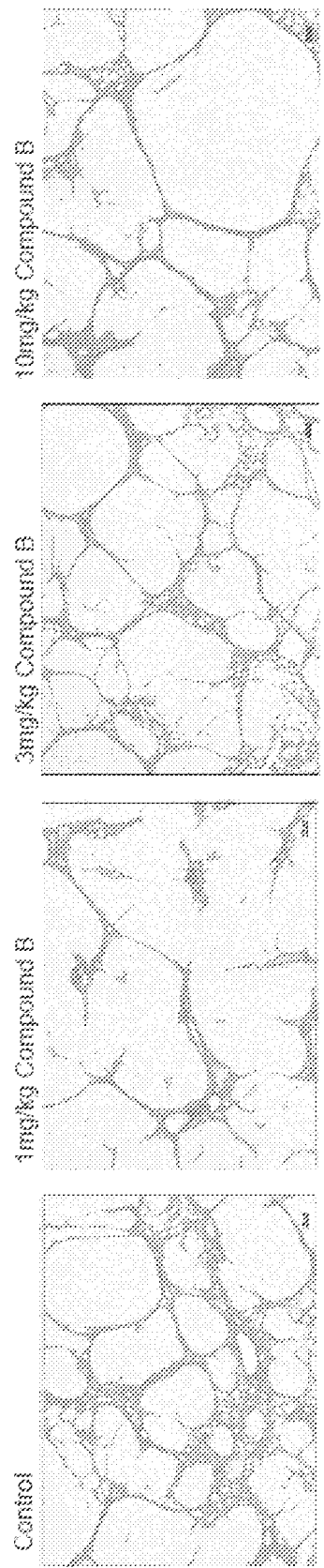
FIG. 8 shows Sirius red stained liver slides displaying collagen accumulation in the livers of animals in a control group vs. animals treated with embodiments of the invention.

FIG. 8 shows images of Sirius red stained liver slides displaying collagen accumulation. Staining, a measurement of tissue fibrosis, was reduced in the TAA groups that were treated with 1, 3 or 10 mg/Kg Compound B when compared to TAA control animals (FIG. 8).

Figure 9:
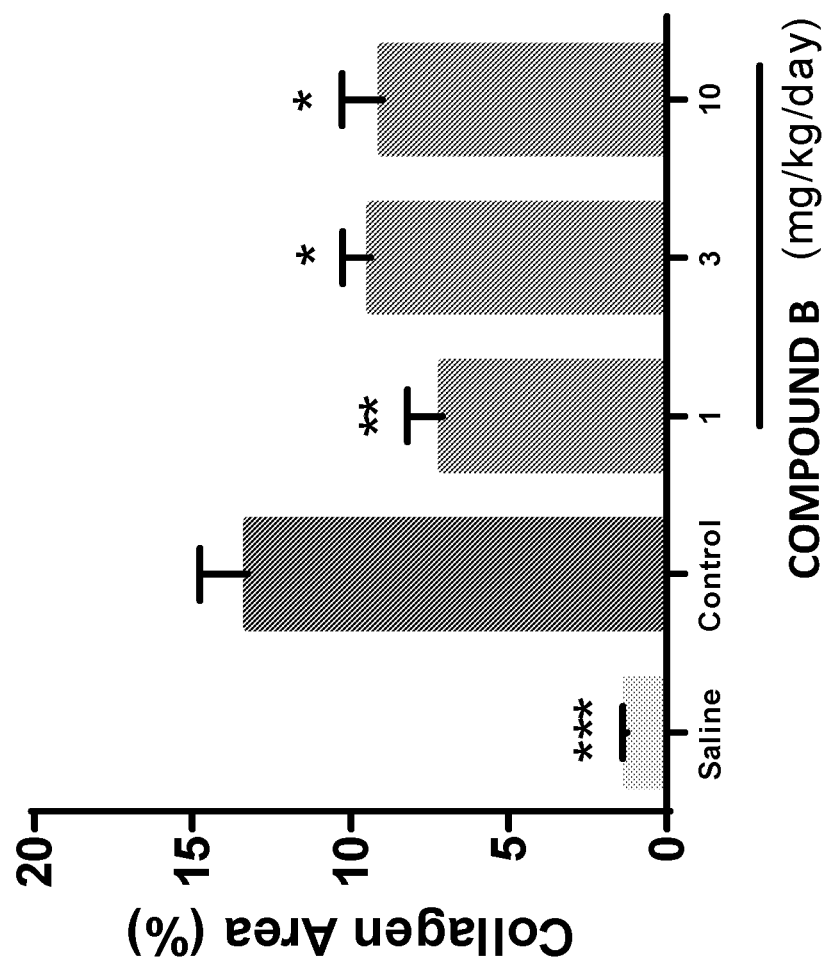
FIG. 9 shows percent collagen accumulation in control animals vs. animals treated with embodiments of the invention.

FIG. 9 shows reduction of % collagen accumulation in TAA treated control animals also treated with 1, 3 or 10 mg/Kg Compound B.

The method described in: "Antifibrotic Activity of Sorafenib in Experimental Hepatic Fibrosis—Refinement of Inhibitory Targets, Dosing and Window of Efficacy In Vivo"; Feng Hong*, Hsin Chou*, Isabel Fiel, and Scott L. Friedman; *Dig Dis Sci*. 2013 January; 58(1): 257-264. doi:10.1007/s10620-012-2325-y.; was used with minor modifications.

Various embodiments of the invention can be described in the text below. As explained supra, it is to be understood that pharmaceutically acceptable salts are included in these embodiments, even though the phrase "pharmaceutically acceptable salt" is not written.

[1.] A method of treating NASH in a patient in need thereof, comprising administering to said patient a therapeutically effective amount of an sGC stimulator or a pharmaceutically acceptable salt thereof.

[2.] A method of [1] above, or according to other embodiments of the invention, wherein said sGC stimulator or pharmaceutically acceptable salt thereof is administered as a monotherapy.

[3.] A method of [1] above, or according to other embodiments of the invention, wherein said sGC stimulator or pharmaceutically acceptable salt thereof is administered in combination with a therapeutically or prophylactically effective amount of one or more additional therapeutic agents.

[4.] A method of [3] above, or according to other embodiments of the invention, wherein the additional therapeutic agent is a compound known to up-regulate the NO-pathway.

[5.] A method of [4] above, or according to other embodiments of the invention, wherein said additional therapeutic agent known to up-regulate the NO-pathway is selected from arginine, nitric oxide, a NO-donor, an sGC stimulator, an sGC activator or a PDE5 inhibitor.

[6.] A method of [5] above, or according to other embodiments of the invention, wherein said additional therapeutic agent is an NO-donor.

[7.] A method of [6] above, or according to other embodiments of the invention, wherein the NO-donor is selected from a nitrate, a nitrite, a NONOate or a nitrosothiol.

[8.] A method of [5] above, or according to other embodiments of the invention, wherein the additional therapeutic agent is an sGC stimulator and is selected from riociguat, neliciguat, vericiguat, BAY-41-2272, BAY 41-8543 or etriciguat.

[9.] A method of [8] above, or according to other embodiments of the invention, wherein the additional therapeutic agent is an sGC stimulator and is selected from riociguat or vericiguat.

[10.] A method of [5] above, or according to other embodiments of the invention, wherein the additional therapeutic agent is an sGC activator selected from ataciguat or cinaciguat.

[11.] A method of [3] above, or according to other embodiments of the invention, wherein the additional therapeutic agent is selected from: a statin, a PPAR agonist, a FXR agonist, a DPP-IV inhibitor, a Caspase inhibitor, a GLP-1 agonist, a LOXL2 monoclonal antibody, an Acetyl Co-A Carboxylase (ACC) inhibitor, a CCR2/CCR5 antagonist, a Fatty acid/bile acid conjugate, a Galectin-3 inhibitors, ursodeoxycholic acid (UDCA), a DGAT1 inhibitor or IMM-124E.

[12.] A method of any one of [1] to [11] above, or according to other embodiments of the invention, wherein the patient in need thereof is an adult.

[13.] A method of any one of [1] to [11] above, or according to other embodiments of the invention, wherein the patient in need thereof is a child

[14.] A method of any one of [1] to [13] above, or according to other embodiments of the invention, wherein the patient in need thereof is a person that has been diagnosed with NASH.

[15.] A method of any one of [1] to [13] above, or according to other embodiments of the invention, wherein the patient in need thereof is a person who displays the characteristic clinical findings associated with NASH.

[16.] A method of any one of [1] or [3] to [13] above, or according to other embodiments of the invention, wherein the sGC stimulator is administered prior to, at the same time as, or after the initiation of treatment with another therapeutic agent.

[17.] A method of any one of [1] to [16] above, or according to other embodiments of the invention, wherein the patient in need thereof is clinically obese.

[18.] A method of any one of [1] to [16] above, or according to other embodiments of the invention, wherein the patient in need thereof has been diagnosed with diabetes or pre-diabetes.

[19.] A method of any one of [1] to [16] above, or according to other embodiments of the invention, wherein the patient in need thereof has been diagnosed with metabolic syndrome.

[20.] A method of any one of [1] to [16] above, or according to other embodiments of the invention, wherein the patient in need thereof is one of normal weight.

[21.] A method of any one of [1] to [16] above, or according to other embodiments of the invention, wherein the patient in need thereof is clinically overweight.

[22.] A method of any one of [1] to [21] above, or according to other embodiments of the invention, wherein the administration of an sGC stimulator or pharmaceutically acceptable salt thereof, alone or in combination with another therapeutic agent, results in an observable or measurable decrease in the level of steatosis or abnormal fat accumulation in the liver.

[23.] A method of any one of [1] to [22] above, or according to other embodiments of the invention, wherein a measurable reduction in the degree of steatosis or abnormal fat accumulation in the liver is determined by tissue biopsy.

[24.] A method of any one of [1] to [21] above, or according to other embodiments of the invention, wherein the administration of an sGC stimulator or pharmaceutically acceptable salt thereof, alone or in combination with another therapeutic agent, results in an observable or measurable decrease in the degree of inflammation of the liver or hepatitis.

[25.] A method of any one of [1] to [21] or [24] above, or according to other embodiments of the invention, wherein a measurable reduction in the degree of inflammation of the liver or hepatitis is determined by tissue biopsy or magnetic resonance elastography.

[26.] A method of any one of [1] to [21] above, or according to other embodiments of the invention, wherein the administration of an sGC stimulator or pharmaceutically acceptable salt thereof, alone or in combination with another therapeutic agent, results in an observable or measurable decrease in the degree of fibrosis, cirrhosis, or sclerosis of the liver.

[27.] A method of any one of [1] to [21] above, or according to other embodiments of the invention, wherein the administration of an sGC stimulator or pharmaceutically acceptable salt thereof, alone or in combination with another therapeutic agent results in an observable or measurable simultaneous reduction in the levels of steatosis, inflammation and fibrosis of the liver.

[28.] A method of any one of [1] to [21] above, or according to other embodiments of the invention, wherein the administration of an sGC stimulator or pharmaceutically acceptable salt thereof, alone or in combination with another therapeutic agent, results in an observable or measurable reduction in fatigue.

[29.] A method of any one of [1] to [21] above, or according to other embodiments of the invention, wherein the administration of an sGC stimulator or pharmaceutically acceptable salt thereof, alone or in combination with another therapeutic agent, results in an observable or measurable reduction in weakness.

[30.] A method of any one of [1] to [21] above, or according to other embodiments of the invention, wherein the administration of an sGC stimulator or pharmaceutically acceptable salt thereof, alone or in combination with another therapeutic agent, results in an observable or measurable reduction in the elevation of liver enzyme levels.

[31.] A method of any one of [1] to [21] above, or according to other embodiments of the invention, wherein the administration of an sGC stimulator or pharmaceutically acceptable salt thereof, alone or in combination with another therapeutic agent, results in an observable or measurable reduction in the elevation of inflammatory cytokine levels.

[32.] A method of any one of [1] to [21] above, or according to other embodiments of the invention, wherein the administration of an sGC stimulator or pharmaceutically acceptable salt thereof, alone or in combination with another therapeutic agent, results in an observable or measurable inhibition of weight loss.

[33.] A method of any one of [1] to [21] above, or according to other embodiments of the invention, wherein the administration of an sGC stimulator or a pharmaceutically acceptable salt thereof, or a pharmaceutical composition comprising an sGC stimulator or a pharmaceutically acceptable salt thereof, alone or in combination with another therapeutic agent, to a patient in need thereof, is aimed at or results in a total or partial reversal of NASH, as determined by partial or total normalization of one or more clinical findings.

[34.] A method of any one of [1] to [21] above, or according to other embodiments of the invention, wherein the administration of an sGC stimulator or a pharmaceutically acceptable salt thereof, alone or in combination with another therapeutic agent, to a patient in need thereof, is aimed at or results in slowing down or halting the progression of NASH into cirrhosis.

[35.] A method of any one of [1] to [21] above, or according to other embodiments of the invention, wherein the administration of an sGC stimulator or a pharmaceutically acceptable salt thereof, alone or in combination with another therapeutic agent, to a patient in need thereof, is aimed at or results in increasing the survival time of a patient diagnosed with NASH.

[36.] A method of any one of [1] to [21] above, or according to other embodiments of the invention, wherein the administration of an sGC stimulator or a pharmaceutically acceptable salt thereof, alone or in combination with another therapeutic agent, to a patient in need thereof, is aimed at or results in the reduction or total elimination for the need of the patient to undergo a liver transplant.

[37.] A method of any one of [1] to [36] above, or according to other embodiments of the invention, wherein the sGC stimulator is one of Formula IA, or a pharmaceutically acceptable salt thereof.

[38.] A method of any one of [1] to [37] above, or according to other embodiments of the invention, wherein the sGC stimulator is one of Formula IB, or a pharmaceutically acceptable salt thereof.

[39.] A method of any one of [1] to [38] above, or according to other embodiments of the invention, wherein the sGC stimulator is one of Formula IC, or a pharmaceutically acceptable salt thereof.

[40.] A method of any one of [1] to [39] above, or according to other embodiments of the invention, wherein the sGC stimulator is selected from one depicted below, or a pharmaceutically acceptable salt thereof:
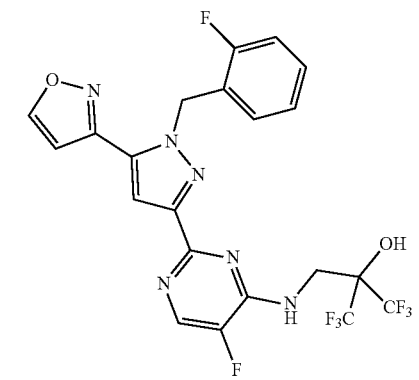
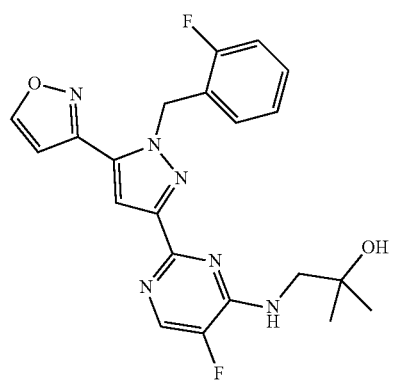
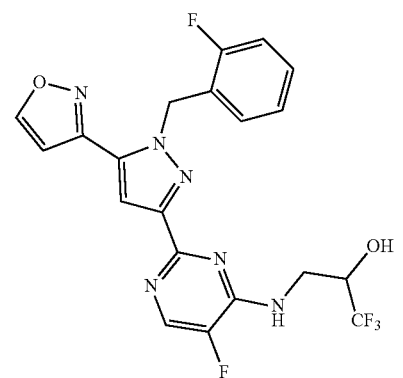
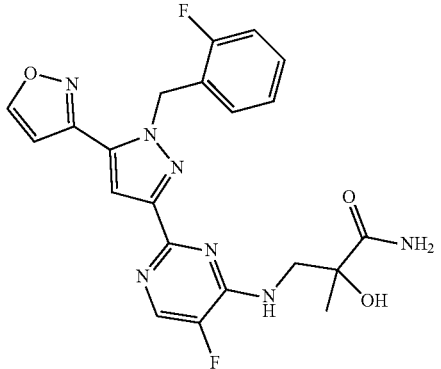
-continued
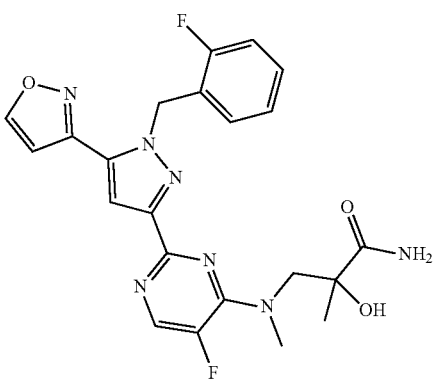
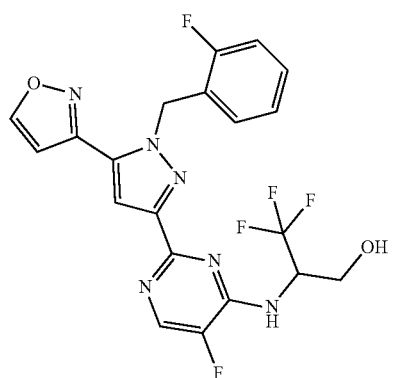
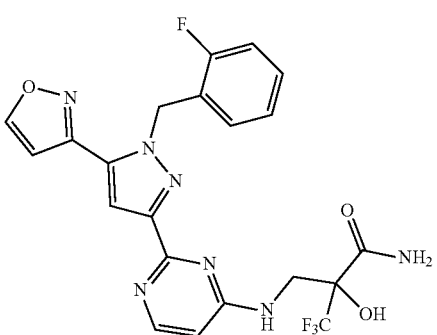
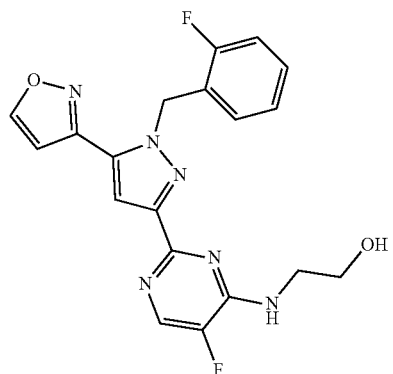

193
-continued
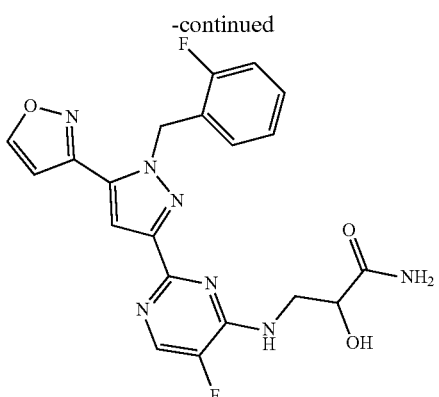
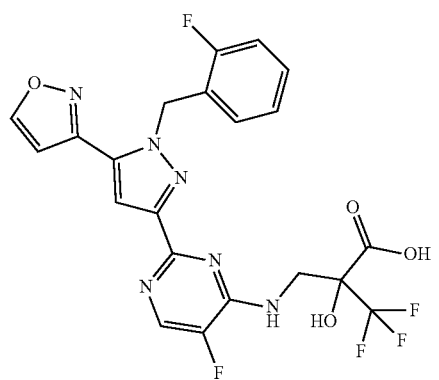
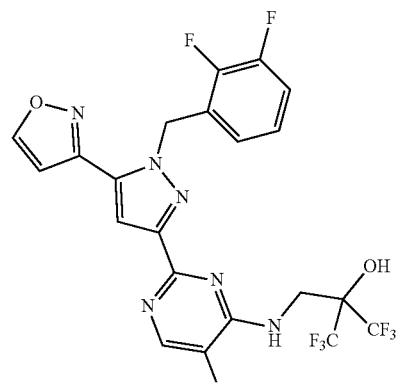
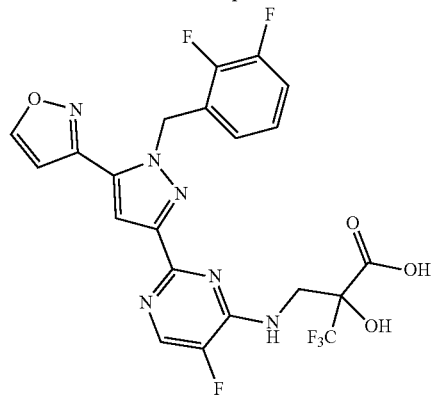
194
-continued
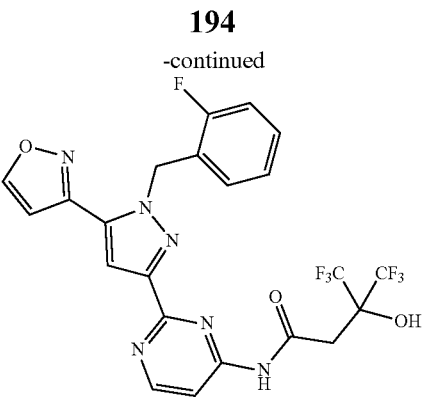
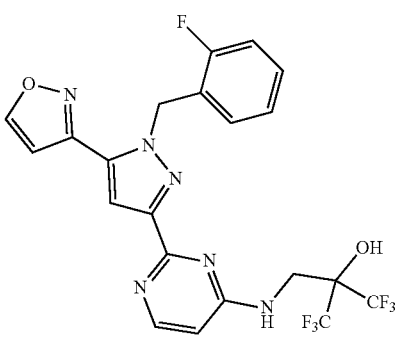
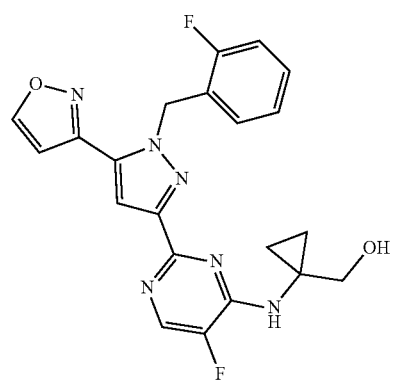
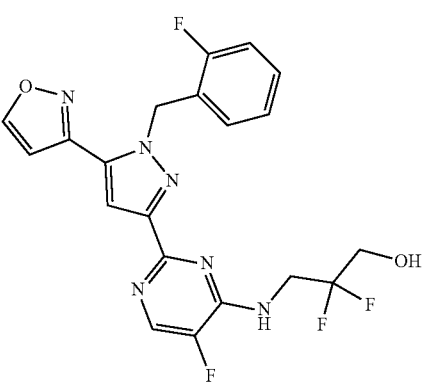

-continued

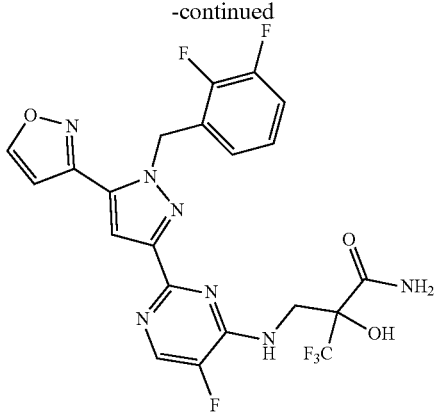

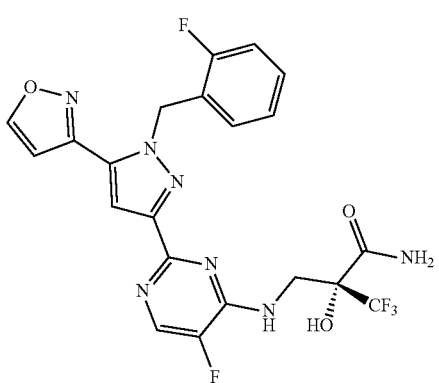

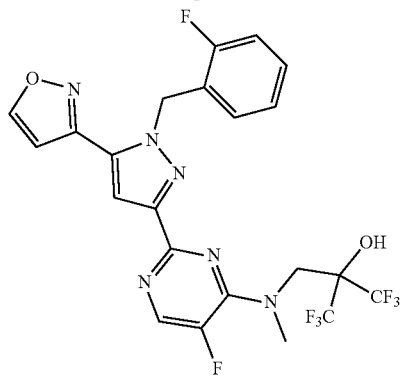

-continued

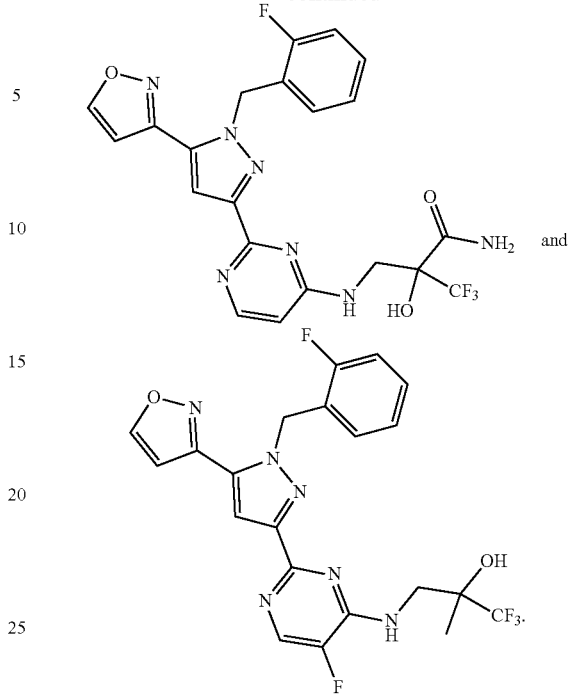

[41.] A method of any one of [1] to [36] above, or according to other embodiments of the invention, wherein the sGC stimulator is selected from one depicted in any one of Tables X, XX, XXX, IV or XIV. [42] A pharmaceutical composition comprising an sGC stimulator, or a pharmaceutically acceptable salt thereof, for use in the treatment of NASH in a patient in need thereof.

[43.] A pharmaceutical composition of [42] above, or according to other embodiments of the invention, wherein said sGC stimulator is selected from one depicted in any one of [37], [38], [39], [40], or [41] above, or according to other embodiments of the invention.

[44.] A pharmaceutical composition comprising an sGC stimulator, or a pharmaceutically acceptable salt thereof, and one or more additional therapeutic agents, for use in the treatment of NASH in a patient in need thereof.

[45.] A pharmaceutical composition of [44] above, or according to other embodiments of the invention, wherein said sGC stimulator is selected from one depicted in any one of [37], [38], [39], [40], or [41] above, or according to other embodiments of the invention.

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

We claim:

1. A method of treating NASH in a patient in need thereof, comprising administering to said patient a therapeutically effective amount of an sGC stimulator or a pharmaceutically acceptable salt thereof.

2. The method of claim 1, wherein said sGC stimulator or pharmaceutically acceptable salt thereof is administered as a monotherapy.

3. The method of claim 1, wherein said sGC stimulator or pharmaceutically acceptable salt thereof is administered in combination with a therapeutically or prophylactically effective amount of one or more additional therapeutic agents.

4. The method of claim 3, wherein said additional therapeutic agent known to up-regulate the NO-pathway is selected from arginine, nitric oxide, a NO-donor, an sGC stimulator, an sGC activator or a PDE5 inhibitor.

5. The method of claim 4, wherein said additional therapeutic agent is an NO-donor.

6. The method of claim 5, wherein the NO-donor is selected from a nitrate, a nitrite a NONOate or a nitrosothiol.

7. The method of claim 1, wherein the patient in need thereof is an adult or of a child.

8. The method of claim 1, wherein the sGC stimulator is administered prior to, at the same time as, or after the initiation of treatment with another therapeutic agent.

9. The method of claim 1, wherein the patient in need thereof is clinically obese, a patient who is clinically overweight, a patient who has been diagnosed with diabetes or pre-diabetes, a patient who has been diagnosed with metabolic syndrome, or a patient having insulin resistance.

10. The method of claim 1, wherein the administration of an sGC stimulator or pharmaceutically acceptable salt thereof, alone or in combination with another therapeutic agent, results in (i) an observable or measurable decrease in the level of steatosis or abnormal fat accumulation in the liver, (ii) an observable or measurable decrease in the degree of inflammation of the liver or hepatitis, (iii) an observable or measurable decrease in the degree of fibrosis, cirrhosis, or sclerosis of the liver, (iv) an observable or measurable simultaneous reduction in the levels of steatosis, inflammation and fibrosis of the liver, (v) an observable or measurable reduction in fatigue, (vi) an observable or measurable reduction in weakness; (vii) an observable or measurable reduction in the elevation of liver enzyme levels, (viii) an observable or measurable reduction in the elevation of inflammatory cytokine levels, or (ix) an observable or measurable inhibition of weight loss.

11. The method of claim 1, wherein the administration of an sGC stimulator or a pharmaceutically acceptable salt thereof, alone or in combination with another therapeutic agent, to a patient in need thereof, is aimed at or results in slowing down or halting the progression of NASH into cirrhosis; or is aimed at or results in increasing the survival time of a patient diagnosed with NASH.

12. The method of claim 1, wherein the sGC stimulator is one of Formula IA, or a pharmaceutically acceptable salt thereof,

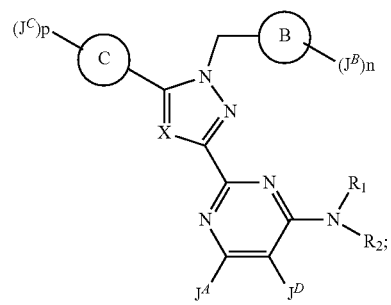

Formula IA wherein:

X is selected from N, CH, C($C_{1-4}$ alkyl), C($C_{1-4}$ haloalkyl), CCl and CF;

ring B is a phenyl or a 6-membered heteroaryl ring containing 1 or 2 ring nitrogen atoms, or ring B is a thiophene;

n is 0 or an integer selected from 1 to 3;

each $J^B$ is independently selected from halogen, —CN, a $C_{1-6}$ aliphatic, —$OR^B$ or a $C_{3-8}$ cycloaliphatic ring; wherein each of said $C_{1-6}$ aliphatic and each of said $C_{3-8}$ cycloaliphatic group is optionally substituted with up to 3 instances of halogen;

each $R^B$ is independently selected from hydrogen, a $C_{1-6}$ aliphatic or a $C_{3-8}$ cycloaliphatic ring;

wherein each of said $R^B$ that is a $C_{1-6}$ aliphatic and each of said $R^B$ that is a $C_{3-8}$ cycloaliphatic ring is optionally substituted with up to 3 instances of halogen;

$J^A$ is selected from hydrogen, halogen, methyl, methoxy, trifluoromethyl, trifluoromethoxy or —$NR^aR^b$, wherein $R^a$ and $R^b$ are each independently selected from hydrogen, $C_{1-6}$ alkyl or a 3-6 cycloalkyl ring;

$J^D$ is hydrogen or selected from halogen, —CN, —$CF_3$, methoxy, trifluoromethoxy, nitro, amino or methyl;

$R^1$ and $R^2$, together with the nitrogen atom to which they are attached, form a 4 to 8-membered heterocyclic ring or 5 or 6-membered heteroaryl ring; wherein said 4 to 8-membered heterocyclic ring or said 5 or 6-membered heteroaryl ring optionally contains in addition to the nitrogen atom to which $R^1$ and $R^2$ are attached, up to 3 ring heteroatoms independently selected from N, O or S, and is optionally substituted by up to 5 instances of $R^5$; or alternatively, $R^1$ and $R^2$ are each independently selected from hydrogen, $C_{1-6}$ alkyl, a $C_{3-8}$ cycloalkyl ring, a 4 to 8-membered heterocyclic ring, a 5 or 6-membered heteroaryl or a $C_{1-6}$ alkyl-$R^Y$;

wherein each of said 4 to 8-membered heterocyclic ring and each of said 5 or 6-membered heteroaryl ring contains up to 3 ring heteroatoms independently selected from N, O and S;

and wherein each of said $C_{1-6}$ alkyl, each of said $C_{3-8}$ cycloalkyl ring, each of said 4 to 8-membered heterocyclic ring group, each of said 5 or 6-membered heteroaryl and each of said $C_{1-6}$ alkyl portion of each said $C_{1-6}$ alkyl-$R^Y$ is optionally and independently substituted with up to 5 instances of $R^{5a}$; provided that $R^1$ and $R^2$ are not simultaneously hydrogen; and provided than when X is one of CH, C($C_{1-4}$ alkyl), C($C_{1-4}$ haloalkyl), CCl or CF, neither of $R^1$ and $R^2$ is a pyridine or a pyrimidine; or alternatively, $J^D$ and one of $R^1$ or $R^2$ can form a 5-6 membered heterocyclic ring containing up to two heteroatoms selected from O, N and S and optionally substituted with up to 3 instances of oxo or —(Y)—$R^9$;

wherein Y is either absent or is a linkage in the form of a $C_{1-6}$ alkyl chain optionally substituted by up to 6 instances of fluoro;

each $R^9$ is independently selected from hydrogen, fluoro, —CN, —OR$^{10}$, —SR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —C(=O)NHOR$^{10}$, a $C_{3-6}$ cycloalkyl ring, a 4-8-membered heterocyclic ring or a 5-6 membered heteroaryl ring;

wherein each said 4 to 8-membered heterocyclic ring and each said 5 to 6-membered heteroaromatic ring contains up to 4 ring heteroatoms independently selected from N, O or S; and wherein each said $C_{3-6}$ cycloalkyl ring, each said 4 to 8-membered heterocyclic ring and each said 5 to 6-membered heteroaromatic ring is optionally substituted with up to 3 instances of $R^{11}$;

each $R^{11}$ is independently selected from halogen, $C_{1-6}$ alkyl, —CN, —OR$^{12}$, —SR$^{12}$, —COR$^{12}$, —OC(O)R$^{12}$, —C(O)OR$^{12}$, —C(O)N(R$^{12}$)$_2$, —C(O)N(R$^{12}$)SO$_2$R$^{12}$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$, —SO$_2$N(R$^{12}$)COOR$^{12}$, —SO$_2$N(R$^{12}$)C(O)R$^{12}$, —N(R$^{12}$)SO$_2$R$^{12}$ and —N=OR$^{12}$; wherein each of said $C_{1-6}$ alkyl is optionally and independently substituted by up to 3 instances of fluoro, —OH, —O($C_{1-4}$ alkyl), phenyl or —O($C_{1-4}$ fluoroalkyl)

wherein each $R^{10}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and each said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo; and wherein each $R^{12}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and each said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo;

$R^Y$ is selected from a $C_{3-8}$ cycloalkyl ring, a 4 to 8-membered heterocyclic ring, phenyl, or a 5 to 6-membered heteroaromatic ring; wherein each of said 4 to 8-membered heterocyclic ring and each of said 5 to 6-membered heteroaromatic ring contains up to 4 ring heteroatoms independently selected from N, O or S; and wherein each of said $C_{3-8}$ cycloalkyl ring, each of said 4 to 8-membered heterocyclic ring, each of said phenyl, and each of said 5 to 6-membered heteroaromatic ring is optionally substituted with up to 5 instances of $R^{5c}$;

each $R^{5c}$ is independently selected from halogen, —CN, $C_{1-6}$ alkyl, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, N(R$^{6b}$)C(O)R$^{6b}$, —N(R$^{6b}$)C(O)OR$^{6b}$, —N(R$^{6b}$)C(O)N (R$^{6b}$)$_2$, —N(R$^{6b}$)$_2$, —SO$_2$R$^{6b}$, —SO$_2$N(R$^{6b}$)$_2$, —SO$_2$N (R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S;

and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and each of said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; or two instances of $R^{5c}$ attached to the same or different ring atoms of $R^Y$, together with said ring atom or atoms, may form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said $C_{3-8}$ cycloalkyl ring, 4 to 6-membered heterocyclic ring, phenyl or a 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O) OH, —NR"(CO)CO($C_{1-4}$ alkyl), —OH or halogen; wherein R" is hydrogen or a $C_{1-2}$ alkyl;

each $R^{5a}$ is independently selected from halogen, —CN, $C_{1-6}$ alkyl, —OR$^{6a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$—N (R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$N(R$^{6a}$)$_2$, —SO$_2$N(R$^{6a}$) COOR$^{6a}$, —SO$_2$N(R$^{6a}$)C(O)R$^{6a}$, —N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring and each of said 4 to 7-membered heterocyclic ring contains up to 4 ring heteroatoms independently selected from N, O and S, wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —C(O)$NH_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-6}$ alkyl), —O($C_{1-6}$ haloalkyl) or oxo, wherein each of said 5 or 6-membered heteroaryl ring or 4 to 7-membered heterocyclic ring contains up to 4 ring heteroatoms independently selected from N, O and S; or when one of $R^1$ or $R^2$ is the $C_{3-8}$ cycloalkyl ring, 4 to 8-membered heterocyclic ring or 5 or 6-membered heteroaryl substituted with up to 5 instances of $R^{5a}$, two of the instances of $R^{5a}$ attached to the same or different ring atoms of said $R^1$ or $R^2$, together with said atom or atoms, may optionally form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)CO($C_{1-4}$ alkyl), —NR'(CO)CO($C_{1-4}$ alkyl) or halogen; wherein R' is hydrogen or a $C_{1-2}$ alkyl;

each $R^5$ is independently selected from halogen, —CN, $C_{1-6}$ alkyl, —$OR^6$, —$SR^6$, —$COR^6$, —$OC(O)R^6$, —$C(O)OR^6$, —$C(O)N(R^6)_2$, —$C(O)N(R^6)SO_2R^6$, —$N(R^6)C(O)R^6$, —$N(R^6)C(O)OR^6$, —$N(R^6)C(O)N(R^6)_2$, —$N(R^6)_2$, —$SO_2R^6$, —$SO_2N(R^6)_2$, —$SO_2N(R^6)COOR^6$, —$SO_2N(R^6)C(O)R^6$, —$N(R^6)SO_2R^6$, —(C=O)$NHOR^6$, a $C_{3-8}$ cycloalkyl ring, a 4 to 7-membered heterocyclic ring, a 5 or 6-membered heteroaryl ring, phenyl, benzyl, an oxo group or a bicyclic group;

wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said $C_{3-8}$ cycloalkyl ring, each of said 4 to 7-membered heterocyclic ring, each of said 5 or 6-membered heteroaryl ring, each said benzyl or each said phenyl group is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^6$ is independently selected from hydrogen, a $C_{1-6}$ alkyl, phenyl, benzyl, a $C_{3-8}$ cycloalkyl ring or a 4 to 7-membered heterocyclic ring, a 5 or 6-membered heteroaryl ring; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; or when $R^1$ and $R^2$ attached to the nitrogen atom form the 4 to 8-membered heterocyclic ring or 5 or 6-membered heteroaryl ring substituted with up to 5 instances of $R^5$, two of the instances of $R^5$ attached to the same or different atoms of said ring, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, said 4 to 6-membered heterocyclic ring, said phenyl or said 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen; wherein R is hydrogen or a $C_{1-2}$ alkyl;

p is an integer selected from 0, 1 or 2;

ring C is a monocyclic 5-membered heteroaryl ring containing up to 4 ring heteroatoms selected from N, O or S; wherein said monocyclic 5-membered heteroaryl ring is not a 1,3,5-triazinyl ring;

each $J^C$ is independently selected from halogen or a $C_{1-4}$ aliphatic optionally and independently substituted by up to 3 instances of $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen.

13. The method of claim 12, wherein the sGC stimulator is one of Formula IB, or a pharmaceutically acceptable salt thereof:

Formula IB

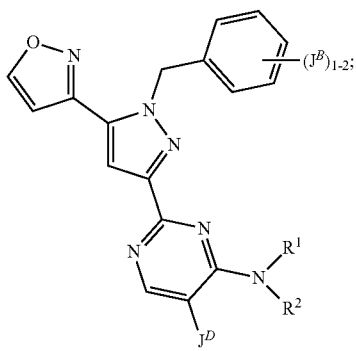

wherein:
$J^D$ is selected from hydrogen or halogen; $J^B$ is halogen and $R^1$ and $R^2$, together with the nitrogen atom to which they are attached, form a 4 to 8-membered heterocyclic ring or 5-membered heteroaryl ring; wherein said 4 to 8-membered heterocyclic ring or said 5-membered heteroaryl ring optionally contains, in addition to the nitrogen atom to which $R^1$ and $R^2$ are attached, up to 3 ring heteroatoms independently selected from N, O or S, and is optionally substituted by up to 5 instances of $R^{5e}$;

each $R^{5e}$ is independently selected from halogen, —CN, $C_{1-6}$ alkyl, —($C_{1-4}$ alkyl)-$R^6$, a $C_{3-8}$ cycloalkyl ring, $C_{1-4}$ cyanoalkyl, —$OR^6$, —$SR^6$, —$OCOR^6$, —$COR^6$, —$C(O)OR^6$, —$C(O)N(R^6)_2$, —$N(R^6)C(O)R^6$, —$N(R^6)_2$, —$SO_2R^6$, —$SO_2OH$, —$SO_2NHOH$, —$SO_2N(R^6)COR^6$, —$SO_2N(R^6)_2$, —$N(R^6)SO_2R^6$, benzyl, phenyl or an oxo group; wherein each said phenyl ring and each said benzyl group, is optionally and independently substituted with up to 3 instances of halogen, —OH, —$NH_2$, —NH($C_{1-4}$ alkyl), —N($C_{1-4}$ alkyl)$_2$, —CN, $C_{1-4}$ alkyl, $C_{1-4}$ haloalkyl, —O($C_{1-4}$ alkyl) or —O($C_{1-4}$ haloalkyl); and wherein each said $C_{1-6}$ alkyl, each $C_{1-4}$ alkyl portion of said —($C_{1-4}$ alkyl)-$R^6$ moiety, and each said $C_{3-8}$ cycloalkyl ring is optionally and independently substituted with up to 3 instances of halogen; wherein each $R^6$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

two of the instances of $R^{5e}$ attached to the same or different atoms of said ring formed by $R^1$, $R^2$ and the nitrogen to which $R^1$ and $R^2$ are attached, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)$NH_2$, —NR(CO)O($C_{1-4}$ alkyl), —OH or halogen; wherein R is hydrogen or a $C_{1-2}$ alkyl;

alternatively, $R^1$ and $R^2$ are each independently selected from hydrogen, $C_{1-6}$ alkyl, a $C_{3-8}$ cycloalkyl ring, a 4 to 10-membered heterocyclic ring, a 5 or 6-membered heteroaryl, phenyl or a $C_{1-6}$ alkyl-$R^Y$; wherein each of said 4 to 10-membered heterocyclic ring and each of said 5 or 6-membered heteroaryl ring contains up to 3 ring heteroatoms independently selected from N, O and S; and wherein each of said $C_{1-6}$ alkyl, each of said $C_{1-6}$ alkyl portion of each said $C_{1-6}$ alkyl-$R^Y$ moiety, each of said $C_{3-8}$ cycloalkyl ring, each of said 4 to 10-membered heterocyclic ring group, each of said 5 or 6-membered heteroaryl, each of said phenyl is optionally and independently substituted with up to 5 instances of $R^5$; provided that neither of $R^1$ or $R^2$ are pyridine or pyrimidine;

$R^Y$ is selected from a $C_{3-8}$ cycloalkyl ring, a 4 to 8-membered heterocyclic ring, phenyl, or a 5 to 6-membered heteroaryl ring; wherein each of said 4 to 8-membered heterocyclic ring and each of said 5 to 6-membered heteroaromatic ring contains between 1 and 4 ring heteroatoms independently selected from N, O or S; and wherein each of said $C_{3-8}$ cycloalkyl ring, each of said 4 to 8-membered heterocyclic ring, each of said phenyl, and each of said 5 to 6-membered heteroaryl ring is optionally substituted with up to 5 instances of $R^{5g}$;

each $R^{5f}$ is independently selected from halogen, —CN, $C_{1-6}$ alkyl, —($C_{1-4}$ alkyl)-$R^{6a}$, a $C_{7-12}$ aralkyl, $C_{3-8}$ cycloalkyl ring, $C_{1-4}$ cyanoalkyl, —$OR^{6a}$, —$SR^{6a}$, —$OCOR^{6a}$, —$COR^{6a}$, —$C(O)OR^{6a}$, —$C(O)N(R^{6a})_2$, —$N(R^{6a})C(O)R^{6a}$—$N(R^{6a})_2$, —$SO_2R^{6a}$, —$SO_2N(R^{6a})_2$, —$N(R^{6a})SO_2R^{6a}$, —$SO_2OH$, —$SO_2NHOH$, —$SO_2N(R^{6a})COR^{6a}$, phenyl or an oxo group; wherein each said phenyl group is optionally and independently substituted with up to 3 instances of halogen, —OH, —$NH_2$, —NH($C_{1-4}$ alkyl), —N($C_{1-4}$ alkyl)$_2$, —$NO_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl, each said $C_{1-6}$ alkyl, each said $C_{1-4}$ alkyl portion of each said —($C_{1-4}$ alkyl)-$R^{6a}$ and each said $C_{3-8}$ cycloalkyl group is optionally and independently substituted with up to three instances of halogen;

each $R^{6a}$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

when one of $R^1$ or $R^2$ is the $C_{3-8}$ cycloalkyl ring, 4 to 8-membered heterocyclic ring or 5 or 6-membered heteroaryl substituted with up to 5 instances of $R^{5f}$, two of the instances of $R^{5f}$ attached to the same or different ring atoms of said $R^1$ or $R^2$, together with said atom or atoms, form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)

O($C_{1-4}$ alkyl), —NR'(CO)O($C_{1-4}$ alkyl) or halogen; wherein R' is hydrogen or a $C_{1-2}$ alkyl;

each $R^{5g}$ is independently selected from halogen, —CN, $C_{1-6}$ alkyl, —($C_{1-4}$ alkyl)-$R^{6b}$, a benzyl, $C_{3-8}$ cycloalkyl ring, $C_{1-4}$ cyanoalkyl, —$OR^{6b}$, —$SR^{6b}$, —$OCOR^{6b}$, —$COR^{6b}$, —C(O)$OR^{6b}$, —C(O)N($R^{6b})_2$, —N($R^{6b}$)C(O)$R^{6b}$, —N($R^{6b})_2$, —$SO_2R^{6b}$, —$SO_2N(R^{6b})_2$, —N($R^{6b}$)$SO_2R^{6b}$, —$SO_2OH$, —$SO_2NHOH$, —$SO_2N(R^{6b})COR^{6b}$, phenyl or an oxo group; wherein each said phenyl and each said benzyl group is optionally and independently substituted with up to 3 instances of halogen, —OH, —$NH_2$, —NH($C_{1-4}$ alkyl), —N($C_{1-4}$ alkyl)$_2$, —$NO_2$, —CN, $C_{1-4}$ alkyl, $C_{1-4}$ haloalkyl, —O($C_{1-4}$ alkyl) or —O($C_{1-4}$ haloalkyl); and wherein each said $C_{1-6}$ alkyl, $C_{1-4}$ alkyl portion of each said ($C_{1-4}$ alkyl)-$R^{6b}$ moiety and each said $C_{3-8}$ cycloalkyl group is optionally and independently substituted with up to 3 instances of halogen;

each $R^{6b}$ is independently selected from hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

alternatively, two instances of $R^{5g}$ attached to the same or different ring atoms of $R^Y$, together with said ring atom or atoms, form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)$NH_2$, —NR"(CO)O($C_{1-4}$ alkyl), —OH or halogen; and R" is hydrogen or a $C_{1-2}$ alkyl.

14. The method of claim 13, wherein the sGC stimulator is one of Formula IC, or a pharmaceutically acceptable salt thereof:

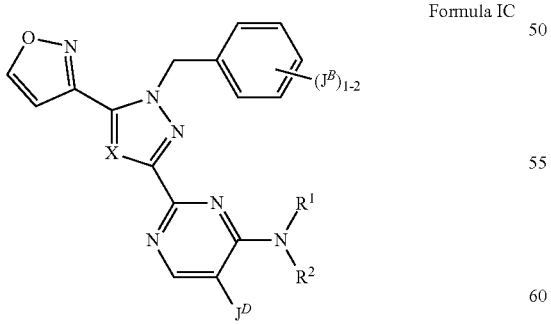

Formula IC wherein $J^B$ is halogen;
$R^1$ is hydrogen or $C_{1-6}$ alkyl; and
$R^2$ is a $C_{1-6}$ alkyl group optionally and independently substituted by up to three instances of $R^{5a}$.

15. The method of claim 14, wherein the sGC stimulator is selected from one depicted below or a pharmaceutically acceptable salt thereof:

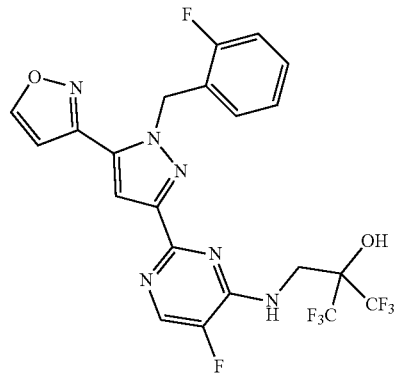

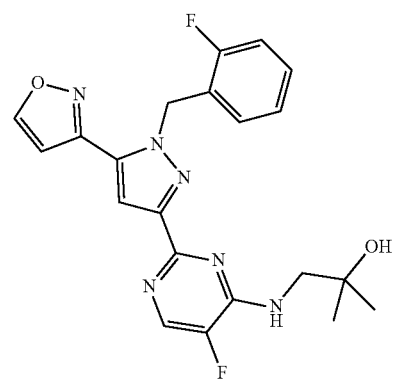

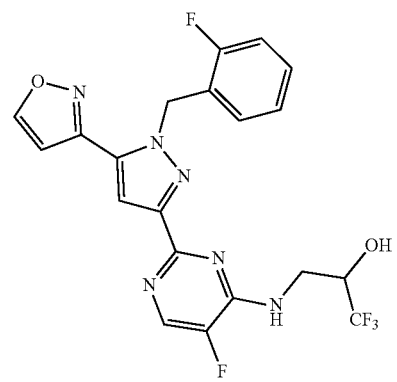

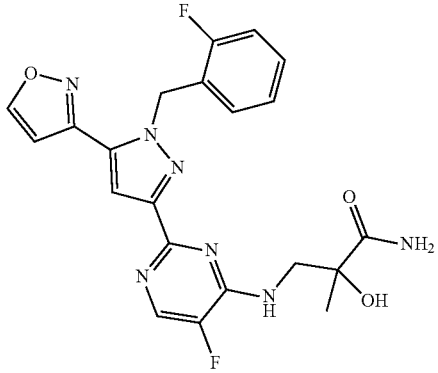

207
-continued
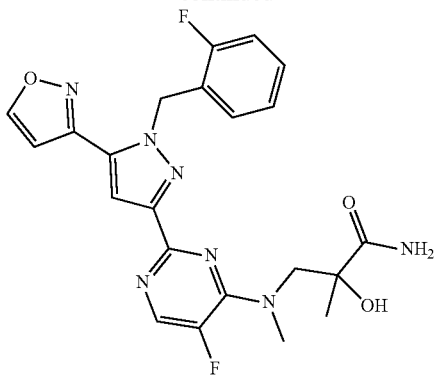
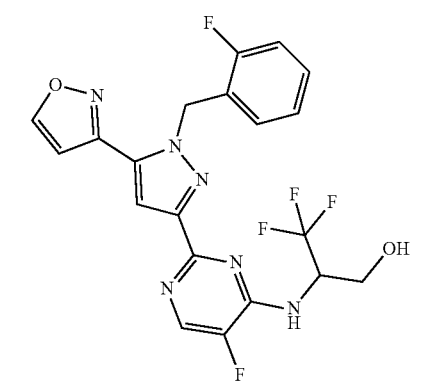
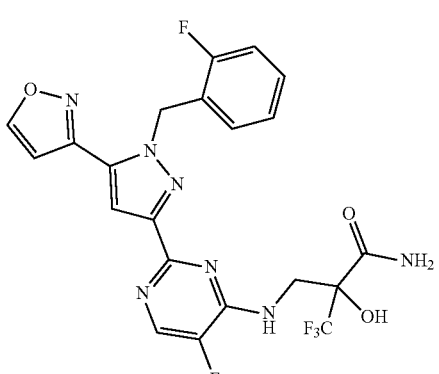
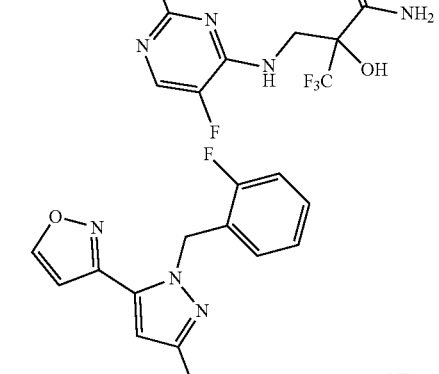
208
-continued
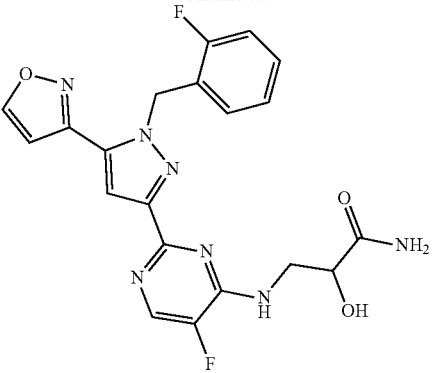
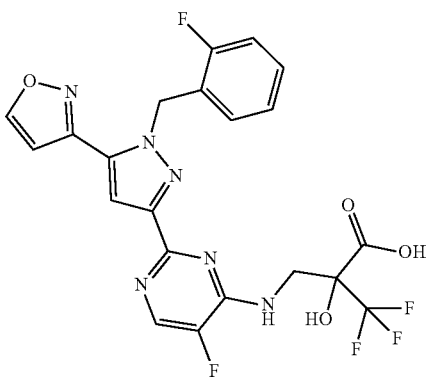
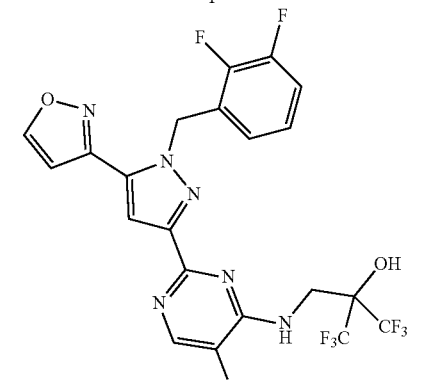
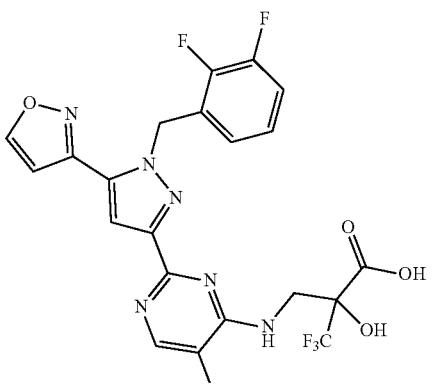

209
-continued
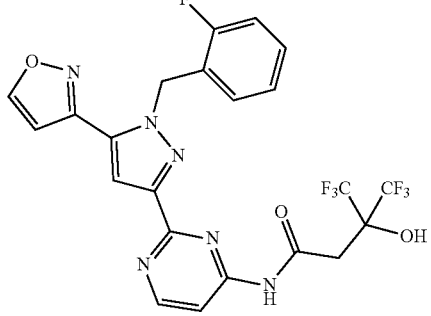
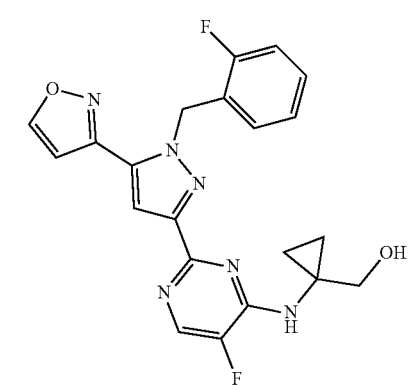
210
-continued
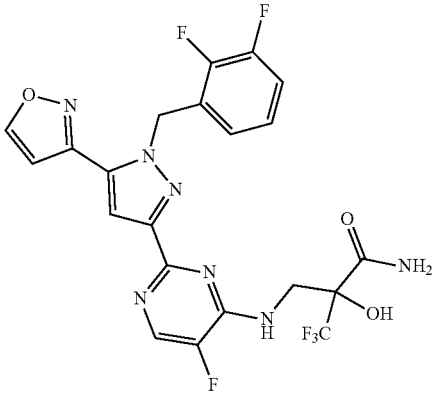
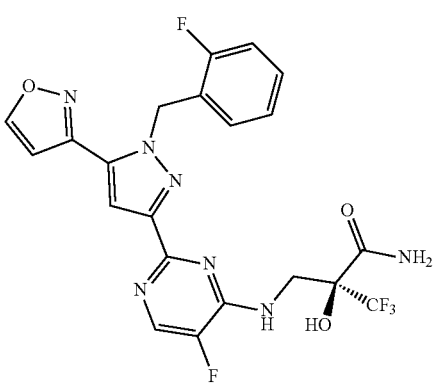
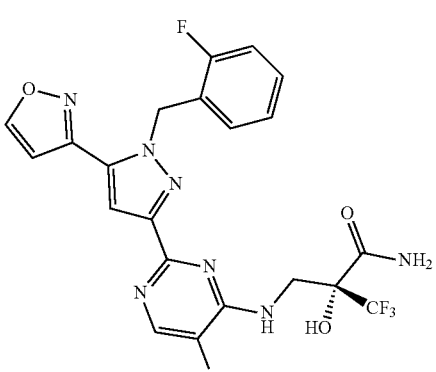
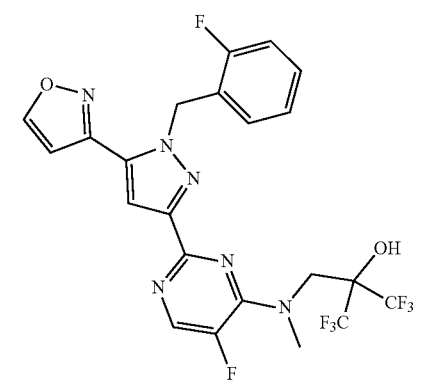

-continued

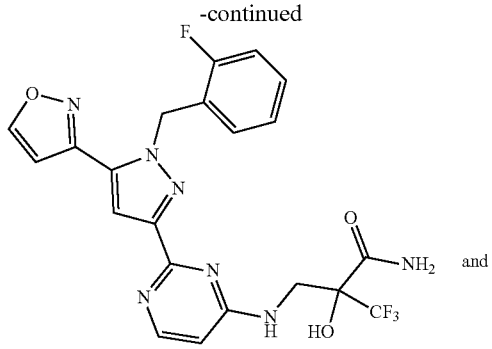

and

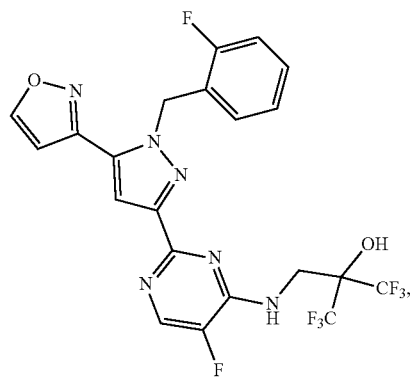

or (Compound B)

(Compound C)

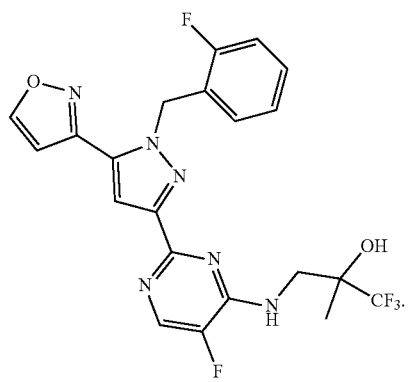

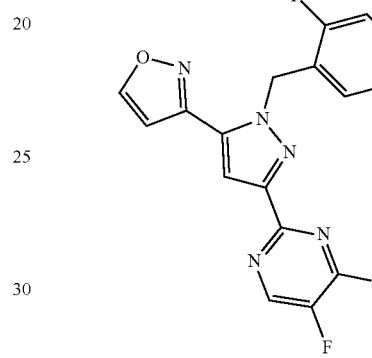

16. The method of claim 1, wherein the sGC stimulator is selected from one depicted in any one of Tables X, XX, XXX, IV or XIV.

17. The method of claim 1, wherein said sGC stimulator or pharmaceutically acceptable salt thereof is administered in combination with one or more additional therapeutic agents; wherein the additional therapeutic agent is an antidiabetic agent or an antiobesity drug.

18. The method of claim 1, wherein said sGC stimulator is or pharmaceutically acceptable salt thereof.

19. The method of claim 1, wherein said sGC stimulator is a compound represented by Formula XY, or a pharmaceutically acceptable salt thereof,

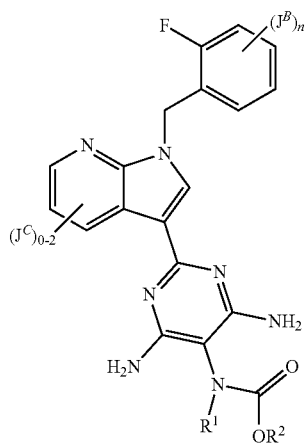

Formula XY wherein:
n is 0 or an integer selected from 1 to 3;
each $J^B$ is independently selected from halogen, —CN, a $C_{1-6}$ aliphatic, —$OR^B$ or a $C_{3-8}$ cycloaliphatic ring; wherein each of said $C_{1-6}$ aliphatic and each of said $C_{3-8}$ cycloaliphatic group is optionally substituted with up to 3 instances of halogen;
each $R^B$ is independently selected from hydrogen, a $C_{1-6}$ aliphatic or a $C_{3-8}$ cycloaliphatic ring; wherein each of (Compound A)

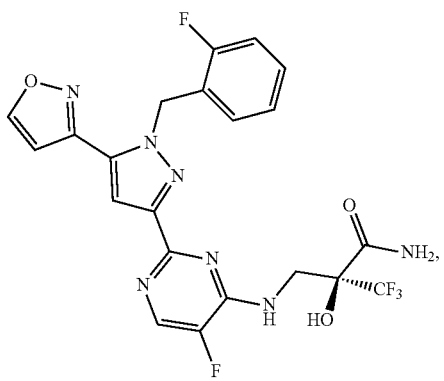

said $R^B$ that is a $C_{1-6}$ aliphatic and each of said $R^B$ that is a $C_{3-8}$ cycloaliphatic ring is optionally substituted with up to 3 instances of halogen;

each $J^C$, if present, is independently selected from halogen;

$R^1$ is hydrogen or $C_{1-6}$ alkyl; and $R^2$ is a $C_{1-6}$ alkyl.

20. The method of claim 19, wherein the sGC stimulator is riociguat or vericiguat:

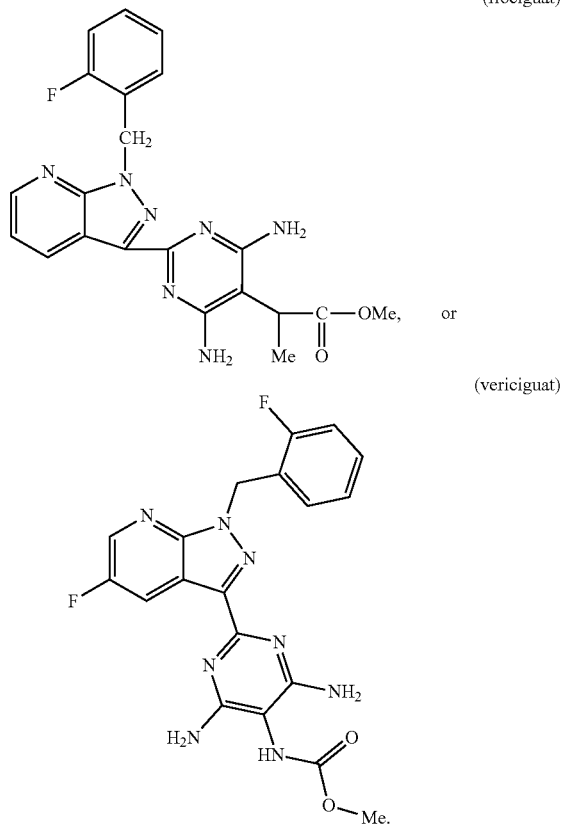

21. The method of claim 17, wherein the anti-diabetic agent is selected from the group consisting of insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®); α-glucosidase inhibitors such as acarbose, epalrestat, voglibose, miglitol; thiazolidinone compounds such as rosiglitazone (Avandia®), troglitazone (Rezulin®), ciglitazone, pioglitazone (Actos®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; DPP-IV inhibitors such as sitagliptin (Januvia®), vildagliptin (Galvus®), saxagliptin (Onglyza®), linagliptin (Tradjenta®), anagliptin (Sanwa®), teneligliptin, alogliptin, trelagliptin, gemigliptin, dutogliptin and omarigliptin (MK-3102); GLP-1 agonists such as: exenatide (Byetta®/Bydureon®), liraglutide (Victoza®, Saxenda®), lixisenatide (Lyxumia®), albiglutide (Tanzeum®), dulaglutide (Trulicity®); and the antiobesity drug is canaglifozin.

22. The method of claim 3, wherein the additional therapeutic agent is one known to up-regulate the NO-pathway.

23. The method of claim 3, wherein the additional therapeutic agent is selected from: a statin, a PPAR agonist, a FXR agonist, a DPP-IV inhibitor, a Caspase inhibitor, a GLP-1 agonist, a LOXL2 monoclonal antibody, an Acetyl Co-A Carboxylase (ACC) inhibitor, a CCR2/CCR5 antagonist, a Fatty acid/bile acid conjugate, a Galectin-3 inhibitors, ursodeoxycholic acid (UDCA), a DGAT1 inhibitor, IMM-124E, a neprilysin inhibitor, an angiotensin receptor blocker (ARB), an angiotensin converting enzyme (ACE) inhibitor, and an endothelin receptor antagonist (ERA).

* * * * *

UNITED STATES PATENT AND TRADEMARK OFFICE
CERTIFICATE OF CORRECTION

PATENT NO. : 11,357,777 B2
APPLICATION NO. : 16/074357
DATED : June 14, 2022
INVENTOR(S) : G-Yoon Jamie Im et al.

Page 1 of 2

It is certified that error appears in the above-identified patent and that said Letters Patent is hereby corrected as shown below:

In the Claims

At Column 205, Claim number 14, Line number 47, please replace the formula:

"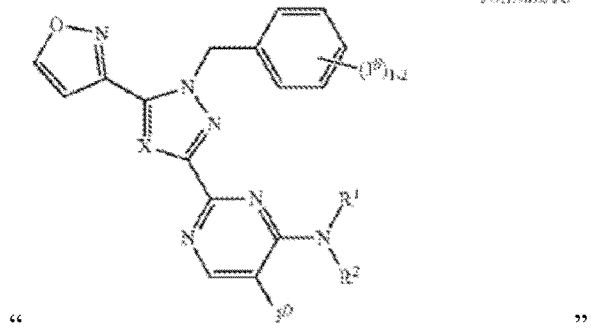"

With formula:

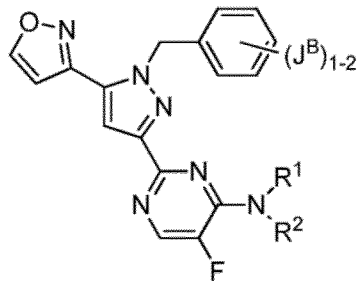

Formula IC

--.

Signed and Sealed this
Twenty-eighth Day of February, 2023

Katherine Kelly Vidal
*Director of the United States Patent and Trademark Office*

//CERTIFICATE OF CORRECTION (continued)//
//U.S. Pat. No. 11,357,777 B2//

At Column 212, Claim number 19, Line number 40, please replace the formula:

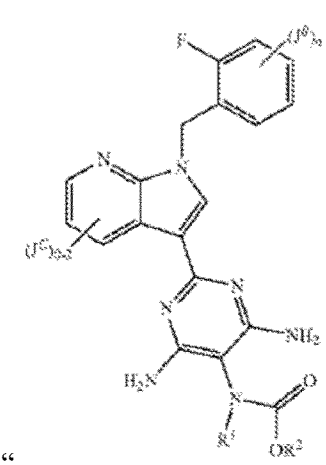

"  "

With formula:

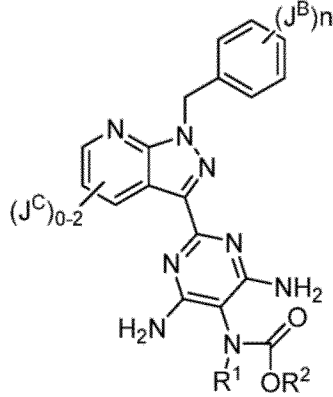

-- Formula XY --.